US011578309B2

(12) United States Patent
Rezania et al.

(10) Patent No.: US 11,578,309 B2
(45) Date of Patent: Feb. 14, 2023

(54) UNIVERSAL DONOR CELLS

(71) Applicant: CRISPR THERAPEUTICS AG, Zug (CH)

(72) Inventors: Alireza Rezania, Cambridge, MA (US); Valentin Sluch, Cambridge, MA (US)

(73) Assignee: CRISPR THERAPEUTICS AG, Zug (CH)

( * ) Notice: Subject to any disclaimer, the term of this patent is extended or adjusted under 35 U.S.C. 154(b) by 0 days.

(21) Appl. No.: 17/566,924

(22) Filed: Dec. 31, 2021

(65) Prior Publication Data

US 2022/0204940 A1 Jun. 30, 2022

Related U.S. Application Data

(60) Provisional application No. 63/288,356, filed on Dec. 10, 2021, provisional application No. 63/234,997, filed on Aug. 19, 2021, provisional application No. 63/132,890, filed on Dec. 31, 2020.

(51) Int. Cl.

| | |
|---|---|
| ***C12N 5/071*** | (2010.01) |
| ***A61P 1/18*** | (2006.01) |
| ***A61K 35/39*** | (2015.01) |
| ***C07K 14/475*** | (2006.01) |
| ***C07K 14/525*** | (2006.01) |
| ***C07K 14/705*** | (2006.01) |
| ***C07K 14/74*** | (2006.01) |
| ***A61K 35/545*** | (2015.01) |
| ***C12N 5/0735*** | (2010.01) |
| ***C12N 5/074*** | (2010.01) |
| ***C12N 9/22*** | (2006.01) |
| ***C12N 15/85*** | (2006.01) |
| ***C12N 15/90*** | (2006.01) |
| ***A61K 38/00*** | (2006.01) |

(52) U.S. Cl.

CPC ............ *C12N 5/0676* (2013.01); *A61K 35/39* (2013.01); *A61K 35/545* (2013.01); *A61P 1/18* (2018.01); *C07K 14/475* (2013.01); *C07K 14/525* (2013.01); *C07K 14/70532* (2013.01); *C07K 14/70539* (2013.01); *C12N 5/0606* (2013.01); *C12N 5/0696* (2013.01); *C12N 9/22* (2013.01); *C12N 15/85* (2013.01); *C12N 15/907* (2013.01); *A61K 38/00* (2013.01); *C07K 2319/02* (2013.01); *C07K 2319/035* (2013.01); *C07K 2319/09* (2013.01); *C12N 2506/02* (2013.01); *C12N 2506/03* (2013.01); *C12N 2506/45* (2013.01); *C12N 2510/00* (2013.01)

(58) Field of Classification Search

CPC .................................................... C12N 5/0676

See application file for complete search history.

(56) References Cited

U.S. PATENT DOCUMENTS

| | | | |
|---|---|---|---|
| 1,724,052 | A | 8/1929 | Swearengin |
| 5,034,506 | A | 7/1991 | Summerton et al. |
| 7,101,543 | B2 | 9/2006 | Fakhrai |
| 7,432,104 | B2 | 10/2008 | Mitalipova et al. |
| 7,510,876 | B2 | 3/2009 | D'Amour et al. |
| 7,541,185 | B2 | 6/2009 | D'Amour et al. |
| 7,695,963 | B2 | 4/2010 | Agulnick et al. |
| 7,695,965 | B2 | 4/2010 | Martinson et al. |
| 7,964,402 | B2 | 6/2011 | Terskikh et al. |
| 7,985,585 | B2 | 7/2011 | D'Amour et al. |
| 8,008,075 | B2 | 8/2011 | Green et al. |
| 8,129,182 | B2 | 3/2012 | D'Amour et al. |
| 8,153,429 | B2 | 4/2012 | Robins et al. |
| 8,187,878 | B2 | 5/2012 | Dalton et al. |
| 8,211,699 | B2 | 7/2012 | Robins et al. |
| 8,278,106 | B2 | 10/2012 | Martinson et al. |
| 8,334,138 | B2 | 12/2012 | Robins et al. |
| 8,338,170 | B2 | 12/2012 | Kelly et al. |
| 8,586,357 | B2 | 11/2013 | D'Amour et al. |
| 8,633,024 | B2 | 1/2014 | D'Amour et al. |
| 8,685,726 | B2 | 4/2014 | Schulz et al. |

(Continued)

FOREIGN PATENT DOCUMENTS

| | | | |
|---|---|---|---|
| EP | 3886759 | A1 | 10/2021 |
| WO | 9204033 | A1 | 3/1992 |

(Continued)

OTHER PUBLICATIONS

Wang et al., 2020, PNAS, vol. 117(12), pp. 6640-6650 (Year: 2020).* de Campo et al. (2014, Int. J. Caner, vol. 134, pp. 102-113) (Year: 2014).*

Joosten et al. (2016, J. Immunol. Res., Article ID 2695396, pp. 1-11) (Year: 2016).*

Katsu-Jimenez et al. (2019, Diabetes, vol. 68, pp. 709-723) (Year: 2019).*

(Continued)

*Primary Examiner* — Ram R Shukla
*Assistant Examiner* — David A Montanari
(74) *Attorney, Agent, or Firm* — Sheppard, Mullin, Richter & Hampton LLP

(57) ABSTRACT

Genetically modified cells that are compatible with multiple subjects, e.g., universal donor cells, and methods of generating said genetic modified cells are provided herein. The universal donor cells comprise at least one genetic modification within or near a gene that encodes one or more MHC-I or MHC-II human leukocyte antigens or a component or a transcriptional regulator of a MHC-I or MHC-II complex, wherein genetic modification comprises an insertion of a polynucleotide encoding a tolerogenic factor and/or survival factor. The universal donor cells may further comprise at least one genetic modification within or near a gene that encodes a survival factor, wherein said genetic modification comprises an insertion of a polynucleotide encoding a second tolerogenic factor and/or a different survival factor.

16 Claims, 28 Drawing Sheets

Specification includes a Sequence Listing.

(56) References Cited

U.S. PATENT DOCUMENTS

| | | | |
|---|---|---|---|
| 8,859,286 | B2 | 10/2014 | Agulnick |
| 8,895,300 | B2 | 11/2014 | Schulz |
| 8,906,616 | B2 | 12/2014 | Zhang et al. |
| 8,999,944 | B2 | 4/2015 | Berk |
| 9,109,245 | B2 | 8/2015 | Agulnick et al. |
| 9,365,830 | B2 | 6/2016 | Schulz et al. |
| 10,030,229 | B2 | 7/2018 | Peterson et al. |
| 10,391,156 | B2 | 8/2019 | Bhoumik et al. |
| 10,724,052 | B2 | 7/2020 | Rezania et al. |
| 10,865,424 | B2 | 12/2020 | Rezania et al. |
| 11,008,586 | B2 | 5/2021 | Rezania et al. |
| 11,008,587 | B2 | 5/2021 | Rezania et al. |
| 11,104,918 | B2 | 8/2021 | Rezania et al. |
| 11,116,797 | B2 | 9/2021 | Rezania et al. |
| 11,118,195 | B2 | 9/2021 | Rezania et al. |
| 11,118,196 | B2 | 9/2021 | Rezania et al. |
| 2005/0266554 | A1 | 12/2005 | D'Amour et al. |
| 2006/0222633 | A1 | 10/2006 | Shlomchik et al. |
| 2007/0122905 | A1 | 5/2007 | D'Amour et al. |
| 2009/0170198 | A1 | 7/2009 | Rezania |
| 2009/0269845 | A1 | 10/2009 | Rezania |
| 2010/0015100 | A1 | 1/2010 | Xu |
| 2010/0112692 | A1 | 5/2010 | Rezania |
| 2010/0112693 | A1 | 5/2010 | Rezania et al. |
| 2010/0233755 | A1 | 9/2010 | D'Amour et al. |
| 2010/0272695 | A1 | 10/2010 | Agulnick et al. |
| 2011/0014702 | A1 | 1/2011 | Xu |
| 2011/0014703 | A1 | 1/2011 | Xu et al. |
| 2011/0151560 | A1 | 6/2011 | Xu |
| 2011/0151561 | A1 | 6/2011 | Davis et al. |
| 2012/0052575 | A1 | 3/2012 | Rezania |
| 2012/0052576 | A1 | 3/2012 | Rezania |
| 2013/0189777 | A1 | 7/2013 | Rezania |
| 2013/0330823 | A1 | 12/2013 | Rezania |
| 2014/0068797 | A1 | 3/2014 | Doudna et al. |
| 2014/0134195 | A1 | 5/2014 | Russell |
| 2014/0162359 | A1 | 6/2014 | Rezania |
| 2014/0186305 | A1 | 7/2014 | Rezina |
| 2014/0186953 | A1 | 7/2014 | Rezania |
| 2014/0242693 | A1 | 8/2014 | Fryer et al. |
| 2014/0271580 | A1 | 9/2014 | Garry et al. |
| 2014/0295552 | A1 | 10/2014 | Fryer et al. |
| 2015/0218522 | A1 | 8/2015 | Peterson et al. |
| 2015/0329828 | A1 | 11/2015 | Rezania |
| 2016/0175462 | A1 | 6/2016 | Zhang et al. |
| 2016/0215268 | A1 | 7/2016 | Fryer et al. |
| 2017/0029778 | A1 | 2/2017 | Peterson et al. |
| 2017/0274048 | A1 | 9/2017 | Neves et al. |
| 2018/0100158 | A1 | 4/2018 | Del'Guidice et al. |
| 2019/0015487 | A1 | 1/2019 | Bhoumik et al. |
| 2019/0223416 | A1 | 7/2019 | Lesko |
| 2019/0309259 | A1 | 10/2019 | Meissner et al. |
| 2020/0080107 | A1 | 3/2020 | Rezania |
| 2020/0080114 | A1 | 3/2020 | Rezania |
| 2020/0347403 | A1 | 11/2020 | Rezania et al. |
| 2020/0407713 | A1 | 12/2020 | Lim et al. |
| 2021/0015859 | A1 | 1/2021 | Valamehr et al. |
| 2021/0069256 | A1 | 3/2021 | Rezania et al. |
| 2021/0070835 | A1 | 3/2021 | Rezania et al. |
| 2021/0070836 | A1 | 3/2021 | Rezania et al. |
| 2021/0070837 | A1 | 3/2021 | Rezania et al. |
| 2021/0071201 | A1 | 3/2021 | Rezania et al. |
| 2021/0161971 | A1 | 6/2021 | Nagy et al. |
| 2021/0260117 | A1 | 8/2021 | Moriarity et al. |
| 2021/0275541 | A1 | 9/2021 | Dietz et al. |
| 2022/0016181 | A1 | 1/2022 | Nagy et al. |

FOREIGN PATENT DOCUMENTS

| | | | |
|---|---|---|---|
| WO | 0183692 | A2 | 11/2001 |
| WO | 2009155669 | A1 | 12/2009 |
| WO | 2013090648 | A1 | 6/2013 |
| WO | 2013159879 | A1 | 10/2013 |
| WO | 2013192005 | A2 | 12/2013 |
| WO | 2014200180 | A1 | 12/2014 |
| WO | 2015065524 | A2 | 5/2015 |
| WO | 2016183041 | A2 | 11/2016 |
| WO | 2017079673 | A1 | 5/2017 |
| WO | 2018035387 | A1 | 2/2018 |
| WO | 2018089011 | A1 | 5/2018 |
| WO | 2018132783 | A1 | 7/2018 |
| WO | 2019076486 | A1 | 4/2019 |
| WO | 2020049535 | A1 | 3/2020 |
| WO | 2020206055 | A1 | 10/2020 |
| WO | 2020228039 | A1 | 11/2020 |

OTHER PUBLICATIONS

Chutkow et al., 2010, Diabetes, vol. 59, pp. 1424-1434 (Year: 2010).*

Devi T.S., et al., "TXNIP Regulates Mitophagy in Retinal Muller Cells Under High-Glucose Conditions: Implications for Diabetic Retinopathy," Cell Death and Disease, 2017, Supplementary Data, pp. 1-15.

Dreier B., et al., "Development of Zinc Finger Domains for Recognition of the 5'-ANN-3' Family of DNA Sequences and Their Use in the Construction of Artificial Transcription Factors," The Journal of Biological Chemistry, 2001, vol. 276(31), pp. 29466-29478.

Dreier B., et al., "Development of Zinc Finger Domains for Recognition of the 5'-CNN-3' Family DNA Sequences and Their Use in the Construction of Artificial Transcription Factors," The Journal of Biological Chemistry, Oct. 21, 2005, vol. 280(42), pp. 35588-35597.

Dreier B., et al., "Insights into the Molecular Recognition of the 5'-GNN-3' Family of DNA Sequences by Zinc Finger Domains," Journal of Molecular Biology, 2000, vol. 303, pp. 489-502.

Duan Y., et al., "Differentiation and Characterization of Metabolically Functioning Hepatocytes from Human Embryonic Stem Cells," Stem Cells, Apr. 2010, vol. 28(4), pp. 674-686.

Dulberger, C.L., et al., "Human Leukocyte Antigen F Presents Peptides and Regulates Immunity through Interactions with NK Cell Receptors," Immunity, Jun. 20, 2017, vol. 46, No. 6, pp. 1018-1029.

Dwyer K.M., et al., "The Transgenic Expression of Human CD39 on Murine Islets Inhibits Clotting of Human Blood," Transplantation, 2006, vol. 82, No. 3, pp. 428-432.

El Khatib M., et al., "β-Cell-Targeted Blockage of PD1 and CTLA4 Pathways Prevents Development of Autoimmune Diabetes and Acute Allogeneic Islets Rejection," Gene Therapy, May 2015, vol. 22, No. 5, pp. 430-438.

Fife B.T., et al., "Control of Peripheral T-Cell Tolerance and Autoimmunity via the CTLA-4 and PD-1 Pathways," Immunological Reviews, Aug. 2008, vol. 224, pp. 166-182.

Fink D.W. Jr., "FDA Regulation of Stem Cell-Based Products," Science, Jun. 26, 2009, vol. 324, No. 5935, pp. 1662-1663.

Fiorina P., et al., "The Clinical Impact of Islet Transplantation," American Journal of Transplantation, Oct. 2008, vol. 8, No. 10, pp. 1990-1997.

Fleischhauer K., et al. "Bone Marrow-Allograft Rejection by T Lymphocytes Recognizing a Single Amino Acid Difference in HLA-B44," The New England Journal of Medicine, Dec. 27, 1990, vol. 323(26), pp. 1818-1822.

Fonfara I., et al., "Phylogeny of Cas9 Determines Functional Exchangeability of Dual-RNA and Cas9 Among Orthologous Type II CRISPR-Cas Systems," Nucleic Acids Research, 2014, vol. 42(4), pp. 2577-2590.

Gadi V.K., et al., "Soluble Donor DNA and Islet Injury After Transplantation," Transplantation, Sep. 15, 2011, vol. 92, No. 5, pp. 607-611.

Gebeyehu G., et al., "Novel Biotinylated Nucleotide-Analogs for Labeling and Colorimetric Detection of DNA," Nucleic Acids Research, 1987, vol. 15(11), pp. 4513-4534.

GenEmbl Accession No. AY254342 PD-L1, *Homo sapiens* programmed death ligand 1 (PDL1) mRNA, Apr. 3, 2003; 3 pages.

Gerasimovskaya E.V., et al., "Extracellular ATP-induced Proliferation of Adventitial Fibroblasts Requires Phosphoinositide 3-Kinase,

(56) References Cited

OTHER PUBLICATIONS

Akt, Mammalian Target of Rapamycin, and p70 S6 Kinase Signaling Pathways," The Journal of Biological Chemistry, 2005, vol. 280, No. 3, pp. 1838-1848.
Gillard P., et al., "Minimal Functional Beta-Cell Mass in Intraportal Implants That Reduces Glycemic Variability in Type 1 Diabetic Recipients," Diabetes Care, Nov. 2013, vol. 36, No. 11, pp. 3483-3488.
Goeckel E., et al., "Modulating CRISPR gene drive activity through nucleocytoplasmic localization of Cas9 in *S. cerevisiae*," Fungal Biology and Biotechnology, Year 2019, vol. 6(2), pp. 1-11.
Gonzalez F., et al., "An iCRISPR Platform for Rapid, Multiplexable, and Inducible Genome Editing in Human Pluripotent Stem Cells," Cell Stem Cell, Aug. 7, 2014, vol. 15, No. 02, pp. 215-226.
Gornalusse G.G., et al., "HLA-E-Expressing Pluripotent Stem Cells Escape Allogeneic Responses and Lysis by NK Cells," Nature Biotechnology, XP055754630, Aug. 2017, vol. 35(8), pp. 765-773, ISSN: 1087-0156, DOI:10.1038/nbt.3860.
Gould D.S., et al., "Direct and Indirect Recognition: The Role of MHC Antigens in Graft Rejection," Immunology Today, Feb. 1999, vol. 20, No. 02, pp. 77-82.
Grau J., et al., "TALENoffer: Genome-Wide TALEN Off-Target Prediction," Bioinformatics, 2013, vol. 29(22), pp. 2931-2932.
Gray S.J., et al., "Optimizing Promoters for Recombinant Adeno-Associated Virus-Mediated Gene Expression in the Peripheral and Central Nervous System using Self-Complementary Vectors," Human Gene Therapy, Sep. 2011, vol. 22, No. 09, pp. 1143-1153.
Grey S.T., et al., "A20 Inhibits Cytokine-induced Apoptosis and Nuclear Factor kappaB-dependent Gene Activation in Islets," Journal of Experimental Medicine, 1999, vol. 190, No. 8, pp. 1135-1145.
Grey S.T., et al., "Genetic Engineering of a Suboptimal Islet Graft with A20 Preserves Beta Cell Mass and Function," Journal of Immunology, Jun. 15, 2003, vol. 170, No. 12, pp. 6250-6256.
Grierson I., et al., "Wound Repair: The Fibroblast and the Inhibition of Scar Formation," Eye, 1988, vol. 2, pp. 135-148.
Gross R., et al., "Pertussis Toxin Promoter Sequences Involved in Modulation," Journal of Bacteriology, Jul. 1989, vol. 171(7), pp. 4026-4030.
Guilinger et al., "Fusion of Catalytically Inactive Cas9 to Fokl Nuclease Improves the Specificity of Genome Modification", Nature Biotechnology, Jun. 2014, vol. 32(6), pp. 577-582.
Guilinger J.P., et al., "Broad Specificity Profiling of TALENs Results in Engineered Nucleases With Improved DNA Cleavage Specificity," Nature Methods, Apr. 2014, vol. 11(4), pp. 429-435.
Guo T., et al., "Stem Cells to Pancreatic Beta-Cells: New Sources for Diabetes Cell Therapy," Endocrine Reviews, May 2009, vol. 30, No. 03, pp. 214-227.
Haeussler M., et al., "Evaluation of Off-target and On-target Scoring Algorithms and Integration into the Guide RNA Selection Tool CRISPOR," Genome Biology, Jul. 5, 2016, vol. 17, No. 01, pp. 148.
Hafez M., et al., "Homing Endonucleases: DNA Scissors on a Mission," Genome, 2012, vol. 55, pp. 553-569.
Hakonen E., et al., "MANF Protects Human Pancreatic Beta Cells Against Stress-Induced Cell Death," Diabetologia, Oct. 2018, vol. 61, No. 10, pp. 2202-2214.
Hale C.R., et al., "RNA-Guided RNA Cleavage by a CRISPR RNA-Cas Protein Complex," Cell, Nov. 25, 2009, vol. 139, No. 5, pp. 945-956.
Han X., et al., "Generation of Hypoimmunogenic Human Pluripotent Stem cells," Proceedings of the National Academy of Sciences of the United States of America, May 21, 2019, vol. 116(21), pp. 10441-10446.
Heasman J., "Morpholino Oligos: Making Sense of Antisense?," Developmental Biology, 2002, vol. 243, pp. 209-214.
Hering B.J., et al., "Clinical Islet Transplantation Consortium Phase 3 Trial of Transplantation of Human Islets in Type 1 Diabetes Complicated by Severe Hypoglycemia," Diabetes Care, Jul. 2016, vol. 39, No. 7, pp. 1230-1240.
Hill C., et al., "Transforming Growth Factor-β2 Antibody Attenuates Fibrosis in the Experimental Diabetic Rat Kidney," Journal of Endocrinology, 2001, vol. 170(3), pp. 647-651.
Hindson B.J., et al., "High-Throughput Droplet Digital PCR System for Absolute Quantitation of DNA Copy Number," Analytical Chemistry, Nov. 15, 2011, vol. 83, No. 22, pp. 8604-8610.
Hindson C.M, et al., "Absolute Quantification by Droplet Digital PCR versus Analog Real-Time PCR," Nature Methods, Oct. 2013, vol. 10, No. 10, pp. 1003-1005.
Hong K., et al., "Cytokines Regulate B-Cell Thioredoxin-Interacting Protein (TXNIP) via Distinct Mechanisms and Pathways," Journal of Biological Chemistry, Apr. 15, 2016, vol. 291, No. 16, pp. 8428-8439.
Hong S.G., et al., "Rhesus iPSC Safe Harbor Gene-Editing Platform for Stable Expression of Transgenes in Differentiated Cells of All Germ Layers," Molecular Therapy, Jan. 2017, vol. 25(1), pp. 44-53.
Horvath P., et al., "Diversity, Activity, and Evolution of CRISPR Loci in *Streptococcus thermophiles*," Journal of Bacteriology, Feb. 2008, vol. 190, No. 4, pp. 1401-1412.
Hsu J., et al., "Contribution of NK Cells to Immunotherapy Mediated by PD-1/PD-L1 Blockade," Journal of Clinical Investigation, Oct. 1, 2018, vol. 128, No. 10, pp. 4654-4668.
International Preliminary Report on Patentability for International Application No. PCT/IB2019/057555, dated Mar. 18, 2021, 9 pages.
International Search Report and Written Opinion for International Application No. PCT/IB2019/057555, dated Nov. 21, 2019, 13 pages.
International Search Report and Written Opinion for International Application No. PCT/IB2020/058281, dated Dec. 11, 2020, 14 pages.
International Search Report and Written Opinion for International Application No. PCT/IB2020/058279, dated Nov. 20, 2020, 11 Pages.
Ito E., et al., "Tumorigenicity Assay Essential for Facilitating Safety Studies of Hipsc-Derived Cardiomyocytes for Clinical Application," Scientific Reports, Feb. 13, 2019, vol. 9, No. 1, 10 pages.
Nasr M.B., et al., "PD-L1 Genetic Overexpression or Pharmacological Restoration in Hematopoietic Stem and Progenitor Cells Reverses Autoimmune Diabetes," Science Translational Medicine, Nov. 15, 2017, vol. 9, No. 416, 28 pages.
Niwa H., et al., "Efficient Selection for High-Expression Transfectants with a Novel Eukaryotic Vector," Gene, Dec. 15, 1991, vol. 108, No. 2, pp. 193-199.
Office Action dated Dec. 21, 2020 for U.S. Appl. No. 17/013,208, 18 Pages.
Office Action dated Feb. 12, 2021 for U.S. Appl. No. 17/013,135, 18 pages.
Office Action dated Feb. 16, 2021 for U.S. Appl. No. 17/013,162, 11 pages.
Office Action dated Feb. 27, 2020 for U.S. Appl. No. 16/563,553, 31 pages.
Office Action dated Jan. 13, 2021 for U.S. Appl. No. 17/013,154, 26 pages.
Office Action from U.S. Appl. No. 17/013,143, dated Jan. 28, 2021, 10 pages.
Opipari A.W., Jr., et al., "The A20 cDNA Induced by Tumor Necrosis Factor Alpha Encodes a Novel Type of Zinc Finger Protein," Journal of Biological Chemistry, Sep. 5, 1990, vol. 265, No. 25, pp. 14705-14708.
Orive G., et al., "Engineering a Clinically Translatable Bioartificial Pancreas to Treat Type I Diabetes," Trends in Biotechnology, Apr. 2018, vol. 36, No. 4, pp. 445-456.
Ovalle F., et al., "Verapamil and Beta Cell Function in Adults with Recent-Onset Type 1 Diabetes," Nature Medicine, Aug. 2018, vol. 24, No. 8, pp. 1108-1112.
Pagliuca F.W., et al., "Generation of Functional Human Pancreatic beta Cells In Vitro," Cell, Oct. 9, 2014, vol. 159, pp. 428-439.
Pan F.C., et al., "Pancreas Organogenesis: From Bud to Plexus to Gland," Developmental Dynamics, Mar. 2011, vol. 240, No. 3, pp. 530-565.
Parham P., "MHC Class I Molecules and KIRS in Human History, Health and Survival," Nature Reviews, Immunology, Mar. 2005, vol. 5, pp. 201-214.

(56) References Cited

OTHER PUBLICATIONS

Pearl J.I., et al., "Short-Term Immunosuppression Promotes Engraftment of Embryonic and Induced Pluripotent Stem Cells," Cell Stem Cell, Mar. 4, 2011, vol. 8, No. 3, pp. 309-317.
Peer D., et al., "Special Delivery: Targeted Therapy with Small RNAs," Gene Therapy, 2011, vol. 18, pp. 1127-1133.
Pegram H.J., et al., "Activating and Inhibitory Receptors of Natural Killer Cells," Immunology and Cell Biology, Feb. 2011, vol. 89(2), pp. 216-224.
Pellenz S., et al., "New Human Chromosomal Sites with Safe Harbor Potential for Targeted Transgene Insertion," Human Gene Therapy, Year 2019, vol. 30(7), pp. 814-828.
Perera L.M.B., et al., "The Regulation of Skin Fibrosis in Systemic Sclerosis by Extracellular ATP via P2Y2 Purinergic Receptor," Journal of Investigative Dermatology, 2019, vol. 139, pp. 890-899.
Pinheiro L., et al., "Basic Concepts and Validation of Digital PCR Measurements," Methods in Molecular Biology, 2018, vol. 1768, pp. 11-24.
Pipeleers D., et al., "Restoring A Functional Beta-Cell Mass in Diabetes," Diabetes, Obesity and Metabolism, Nov. 2008, vol. 10, No. 4, pp. 54-62.
Plesner A., et al., "Islet Remodeling in Female Mice With Spontaneous Autoimmune and Streptozotocin-Induced Diabetes," PLoS ONE, Aug. 7, 2014, vol. 9, No. 8, 13 pages.
Polastri L., et al., "Secretory Defects Induced by Immunosuppressive Agents on Human Pancreatic Beta-Cells," Acta Diabetologica, Dec. 2002, vol. 39, No. 4, pp. 229-233.
Pommey S., et al., "Liver Grafts from CD39-Overexpressing Rodents Are Protected From Ischemia Reperfusion Injury Due to Reduced Numbers of Resident CD4+ T Cells", Hepatology, 2013, vol. 57, No. 4, pp. 1597-1606.
Qian et al., "Impact of donor MHC class I or class II antigen deficiency on first- and second-set rejection of mouse heart or liver allografts", Immunology, 1996, pp. 124-129, vol. 88.
Ramzy A., et al., "Implanted Pluripotent Stem-Cell-Derived Pancreatic Endoderm Cells Secrete Glucose-Responsive C-Peptide in Patients with Type 1 Diabetes," Cell Stem Cell, Dec. 2, 2021, vol. 28, No. 12, pp. 2047-2061.
Ratajczak W., et al., "A20 Controls Expression of Beta Cell Regulatory Genes and Transcription Factors," Journal of Molecular Endocrinology, 2021, vol. 67, pp. 1-40.
Rezania A., et al., "Enrichment of Human Embryonic Stem Cell-Derived NKX6.1—Expressing Pancreatic Progenitor Cells Accelerates the Maturation of Insulin-Secreting Cells In Vivo," Stem Cells, Nov. 2013, vol. 31 (11), pp. 2432-2442.
Rezania A., et al., "Maturation of Human Embryonic Stem Cell-Derived Pancreatic Progenitors Into Functional Islets Capable of Treating Pre-existing Diabetes in Mice," Diabetes, Aug. 2012, vol. 61(8), pp. 2016-2029.
Rezania A., et al., "Production of Functional Glucagon-Secreting α-Cells From Human Embryonic Stem Cells," Diabetes, Jan. 2011, vol. 60(1), pp. 239-247.
Rezania A., et al., "Reversal of Diabetes with Insulin-Producing Cells Derived in Vitro from Human Pluripotent Stem Cells," Nature Biotechnology, Nov. 2014, vol. 32(11), pp. 1121-1133.
Robert T., et al., "Functional Beta Cell Mass From Device-Encapsulated hESC-Derived Pancreatic Endoderm Achieving Metabolic Control," Stem Cell Reports, Mar. 13, 2018, vol. 10, No. 3, pp. 739-750.
Roberts et al., "The role of ectonucleotidases CD39 and CD73 and adenosine signaling in solid organ transplantation", Frontiers in Immunology, 2014, pp. 1-7, vol. 5, No. 64.
Robertson N.J., et al., "Embryonic Stem Cell-Derived Tissues Are Immunogenic But Their Inherent Immune Privilege Promotes the Induction of Tolerance," Proceedings of the National Academy of Sciences, Dec. 26, 2007, vol. 104, No. 52, pp. 20920-20925.
Rong Z., et al., "An Effective Approach to Prevent Immune Rejection of Human ESC-Derived Allografts," Cell Stem Cell, Jan. 2, 2014, vol. 14, No. 1, pp. 121-130.
Rubinstein P., "HLA Matching for Bone Marrow Transplantation—How Much is Enough?," The New England Journal of Medicine, Dec. 20, 2001, vol. 345(25), pp. 1842-1844.
Russ H.A., et al., "Controlled Induction of Human Pancreatic Progenitors Produces Functional Beta-like Cells in Vitro," The EMBO Journal, Jul. 2, 2015, vol. 34(13), pp. 1759-1772.
Ryan E.A., et al., "Five-Year Follow-Up After Clinical Islet Transplantation," Diabetes, Jul. 2005, vol. 54, No. 7, pp. 2060-2069.
Sadelain M., et al., "Safe Harbours for the Integration of New DNA in the Human Genome," Nature Reviews Cancer, Jan. 2012, vol. 12, pp. 51-58.
Sandvig I., et al., "Strategies to Enhance Implantation and Survival of Stem Cells After Their Injection in Ischemic Neural Tissue," Stem Cells and Development, Apr. 15, 2017, vol. 26, No. 8, pp. 554-565.
Sapranauskas R., et al., "The *Streptococcus thermophilus* Crispr/Cas System Provides Immunity in *Escherichia coli*," Nucleic Acids Research, Nov. 2011, vol. 39(21), pp. 9275-9282.
Sato Y., et al., "Tumorigenicity Assessment of Cell Therapy Products: The Need for Global Consensus and Points to Consider," Cytotherapy, Nov. 2019, vol. 21, No. 11, pp. 1095-1111.
Sawitza I., et al., "Bile Acids Induce Hepatic Differentiation of Mesenchymal Stem Cells," Scientific Reports, Aug. 25, 2015, vol. 5(13320), pp. 1-15.
Schmitt J., et al., "Human Parthenogenetic Embryonic Stem Cell-Derived Neural Stem Cells Express HLA-G and Show Unique Resistance to NK Cell-Mediated Killing," Molecular Medicine, Mar. 23, 2015, vol. 21, No. 1, pp. 185-196.
Scholpp S., et al., "Morpholino-Induced Knockdown of Zebrafish Engrailed Genes eng2 and eng3 Reveals Redundant and Unique Functions in Midbrain-Hindbrain Boundary Development," Genesis, Jul. 23, 2001, vol. 30(3), pp. 129-133.
Schuldiner M., et al., "Selective Ablation of Human Embryonic Stem Cells Expressing a "Suicide" Gene," Stem Cells, May 2003, vol. 21(3), pp. 257-265.
Schulz T.C., et al., "A Scalable System for Production of Functional Pancreatic Progenitors from Human Embryonic Stem Cells," PLoS One, 2012, vol. 7(5), pp. 1-17, e37004.
Segal D.J., et al., "Toward Controlling Gene Expression at Will: Selection and Design of Zinc Finger Domains Recognizing Each of the 5'-GNN-3' DNA Target Sequences," Proceedings of the National Academy of Sciences of the United States of America, Mar. 1999, vol. 96, pp. 2758-2763.
Shah S.A., et al., "Protospacer Recognition Motifs: Mixed Identities and Functional Diversity," RNA Biology, May 2013, vol. 10, No. 5, pp. 891-899.
Shalev A.," Lack of TXNIP Protects Beta-Cells against Glucotoxicity," Biochemical Society Transactions, Oct. 2008, vol. 36, No. 5, pp. 963-965.
Adair T. H., "Growth Regulation of the Vascular System: An Emerging Role for Adenosine," The American Journal of Physiology Regulatory, Integrative and Comparative Physiology, 2005, vol. 289, pp. R283-R296.
Adams A.B., et al., "Costimulation Blockade in Autoimmunity and Transplantation: The CD28 pathway," Journal of Immunology, Sep. 15, 2016, vol. 197, No. 6, pp. 2045-2050.
Agulnick A.D., et al., "Insulin-Producing Endocrine Cells Differentiated In Vitro From Human Embryonic Stem Cells Function in Macroencapsulation Devices In Vivo," Stem Cells Translational Medicine, 2015, vol. 4(10), pp. 1-9.
Almehthel M., et al., "Progress of Islet Transplantation Over the Last 15 Years," US Endocrinology, Oct. 28, 2015, vol. 11, No. 2, pp. 70-74.
Andrade S., et al., "Evidence for premature aging due to oxidative stress in iPSCs from Cockayne syndrome," Human Molecular Genetics, Year 2012, vol. 21(17), pp. 3825-3834.
Andre P., et al., "Anti-NKG2A mAb is a Checkpoint Inhibitor that Promotes Anti-Tumor Immunity by Unleashing Both T and NK Cells," Cell, Dec. 13, 2018, vol. 175, No. 7, pp. 1731-1743.
Antonioli L., et al., "CD39 and CD73 in Immunity and Inflammation," Trends in Molecular Medicine, 2013, vol. 19, 26 pages.
Aquino-Lopez A., et al., "Interferon Gamma Induces Changes in Natural Killer (NK) Cell Ligand Expression and Alters NK Cell-

(56) References Cited

OTHER PUBLICATIONS

Mediated Lysis of Pediatric Cancer Cell Lines," Frontiers in Immunology, Apr. 6, 2017, vol. 8(391), pp. 1-12.
Arce-Gomez B., et al.,"The Genetic Control of HLA-A and B Antigens in Somatic Cell Hybrids: Requirement for Beta2 Microglobulin," Tissue Antigens, Feb. 1978, vol. 11, No. 2, pp. 96-112.
Barrangou R., et al., "CRISPR Provides Acquired Resistance Against Viruses in Prokaryotes," Science, Mar. 23, 2007, vol. 315, No. 5819, pp. 1709-1712.
Bastid J., et al., "ENTPD1/CD39 is a Promising Therapeutic Target in Oncology," Oncogene, 2013, vol. 32, pp. 1743-1751.
Bauche C., et al., Geneseq Accession No. BBQ97661, Computer printout, Year 2014 pp. 5-7.
Belfort M., et al., "Homing Endonucleases: From Genetic Anomalies to Programmable Genomic Clippers," Methods in Molecular Biology, May 19, 2015, vol. 1123, pp. 1-27.
Biarnes M., et al., "Beta-Cell Death and Mass in Syngeneically Transplanted Islets Exposed to Short- and Long-Term Hyperglycemia," Diabetes, Jan. 2002, vol. 51, No. 1, pp. 66-72.
Biassoni R., et al., "Human Natural Killer Cell Receptors and Co-Receptors," Immunological Reviews, Jun. 2001, vol. 181, No. 1, pp. 203-214.
Biernacka A., et al., "TGF-β Signaling in Fibrosis," Growth Factors, 2011, vol. 29, 12 pages.
Bix M., et al., "Rejection of Class I MHC-Deficient Haemopoietic Cells by Irradiated MHC-Matched Mice," Nature, Jan. 24, 1991, vol. 349, pp. 329-331.
Boch J., et al., "Breaking the Code of DNA Binding Specificity of TAL-Type III Effectors," Science, Dec. 11, 2009, vol. 326, pp. 1509-1512.
Boissel S., et al., "Assembly and Characterization of MegaTALs for Hyperspecific Genome Engineering Applications," Chromosomal Mutagenesis, Methods in Molecular Biology, Second Edition, Chapter 9, 2015, vol. 1239, pp. 171-196.
Boissel S., et al., "MegaTALs: A Rare-Cleaving Nuclease Architecture for Therapeutic Genome Engineering," Nucleic Acids Research, Feb. 2014, vol. 42(4), pp. 2591-2601.
Bolton E.M., et al., "Avoiding Immunological Rejection in Regenerativemedicine," Regenerative Medicine, 2015, vol. 10, No. 3, pp. 287-304.
Bonini C., et al., "HSV-TK Gene Transfer into Donor Lymphocytes for Control of Allogeneic Graft-Versus-Leukemia," Science, Jun. 13, 1997, vol. 276, pp. 1719-1724.
Bordignon C., et al., "Transfer of the HSV-tk Gene into Donor Peripheral Blood Lymphocytes for In Vivo Modulation of Donor Anti-Tumor Immunity after Allogeneic Bone Marrow Transplantation," Human Gene Therapy, Jun. 27, 1995, vol. 6(6), pp. 813-819.
Borowicz S., et al., "The Soft Agar Colony Formation Assay," Journal of Visualized Experiments, Oct. 27, 2014, Issue. 92, 6 pages.
Braasch D.A., et al., "Novel Antisense and Peptide Nucleic Acid Strategies for Controlling Gene Expression," Biochemistry, Apr. 9, 2002, vol. 41(14), pp. 4503-4510.
Braud V.M., et al., "HLA-E Binds to Natural Killer Cell Receptors CD94/NKG2A, B and C," Nature, Feb. 1998, vol. 391, No. 6669, pp. 795-799.
Brinkman E.K., et al., "Easy Quantitative Assessment of Genome Editing by Sequence Trace Decomposition," Nucleic Acids Research, Dec. 16, 2014, vol. 42, No. 22, 8 pages.
Bruin, J.E., et al., "Maturation and Function of Human Embryonic Stem Cell-Derived Pancreatic Progenitors in Microencapsulation Devices Following Transplant into Mice," Diabetologia, Sep. 2013, vol. 56, No. 9, pp. 1987-1998.
Callewaert H.L, et al., "Deletion of STAT-1 Pancreatic Islets Protects against Streptozotocin-Induced Diabetes and Early Graft Failure but not Against Late Rejection," Diabetes, Aug. 2007, vol. 56, No. 8, pp. 2169-2173.
Ceccaldi R., et al., "Homologous Recombination-deficient Tumors are Hyper-dependent on POLQ-mediated Repair," Nature, Feb. 12, 2015, vol. 518(7538), pp. 258-262 and Supplementary Material.
Cermak T., et al., "Efficient Design and Assembly of Custom TALEN and Other TAL Effector-Based Constructs for DNA Targeting," Nucleic Acids Research, Jul. 2011, e82, vol. 39(12), pp. 1-11.
Cermak T., et al., "Efficient Design and Assembly of Custom TALENs Using the Golden Gate Platform," Methods in Molecular Biology, 2015, vol. 1239, pp. 133-159.
Chen J., et al., "Thioredoxin-Interacting Protein Deficiency Induces Akt/Bcl-xL Signaling and Pancreatic Beta-Cell Mass and Protects Against Diabetes," Federation of American Societies for Experimental Biology, Oct. 2008, vol. 22, No. 10, pp. 3581-3594.
Chia J.S.J., et al., "The Protective Effects of CD39 Overexpression in Multiple Low-Dose Streptozotocin-Induced Diabetes in Mice", Diabetes, 2013, vol. 62, pp. 2026-2035.
Cho N.W., et al., "DNA Repair: Familiar Ends With Alternative Endings," Nature, Feb. 12, 2015, vol. 518, No. 7538, pp. 174-176.
Cho N.W., et al., "Familiar Ends with Alternative Endings," Nature, Feb. 12, 2015, vol. 518, pp. 174-176.
Cong L., et al., "Multiplex Genome Engineering using CRISPR/Cas Systems," Science, 2013, vol. 339, pp. 819-823.
Cowan C.A ., et al., N_Geneseq_201922, Accession No. BDA08012, computer printout, Year 2016, pp. 6-7.
Cowan C.A ., et al.,Geneseq Accession No. BDA07999 Computer printout, Year 2016, pp. 5-7.
Cox D.B.T., et al., "Therapeutic Genome Editing: Prospects and Challenges," Nature Medicine, Feb. 2015, vol. 21(2), pp. 121-131.
Cradick T.J., et al., "COSMID: A Web-Based Tool for Identifying and Validating CRISPR/Cas off-Target Sites," Molecular Therapy Nucleic Acids, Dec. 2, 2014, vol. 3, No. 12, 10 pages.
Crew M.D., et al., "An HLA-E Single Chain Trimer Inhibits Human NK Cell Reactivity towards Porcine Cells," Molecular Immunology, 2005, vol. 42, pp. 1205-1214.
Crooke S.T., et al., "Antisense Research and Applications," CRC Press, May 27, 1993, pp. 276-278.
D'Amour K.A, et al., "Production of Pancreatic Hormone-Expressing Endocrine Cells from Human Embryonic Stem Cells," Nature Biotechnology, Nov. 2006, vol. 24(11), pp. 1392-1401.
Danilova T., et al., "MANF is Required for the Postnatal Expansion and Maintenance of Pancreatic β-Cell Mass in Mice," Diabetes, 2019, vol. 68, pp. 66-80.
DeKelver R.C., et al., "Functional Genomics, Proteomics, and Regulatory DNA Analysis in Isogenic Settings using Zinc Inger Nuclease-Driven Transgenesis into a Safe Harbor Locus in the Human Genome," Genome Research, Aug. 2010, vol. 20, pp. 1133-1142.
Deltcheva E., et al., "CRISPR RNA maturation by trans-encoded small RNA and host factor RNase III," Nature, Mar. 31, 2011, vol. 471(7340), pp. 602-607.
Denu R.A., et al., "Effects of Oxidative Stress on Mesenchymal Stem Cell Biology," Oxidative Medicine and Cellular Longevity, Jun. 2016, vol. 2016(1), pp. 1-9.
Deuse T., et al., "Hypoimmunogenic Derivatives of Induced Pluripotent Stem Cells Evade Immune Rejection in Fully Immunocompetent Allogeneic Recipients," Nature Biotechnology, 2019, vol. 37, 29 pages.
Devi T.S., et al., "TXNIP Regulates Mitophagy in Retinal Muller Cells Under High-Glucose Conditions: Implications for Diabetic Retinopathy," Cell Death and Disease, May 11, 2017, vol. 8(5), e2777, pp. 1-12.
Shalev A., "Minireview: Thioredoxin-Interacting Protein: Regulation and Function in the Pancreatic β-Cell," Molecular Endocrinology, Aug. 2014, vol. 28, No. 8, pp. 1211-1220.
Sharpiro A.M., et al., "Islet Transplantation in Seven Patients With Type 1 Diabetes Mellitus Using A Glucocorticoid-Free Immunosuppressive Regimen," The New England Journal of Medicine, Jul. 27, 2000, vol. 343, No. 4, pp. 230-238.
Sharpiro A.M.J., et al., "Insulin Expression and C-Peptide in Type 1 Diabetes Subjects Implanted With Stem Cell-Derived Pancreatic Endoderm Cells in An Encapsulation Device," Cell Reports Medicine, Dec. 21, 2021, vol. 2, No. 100466, 17 pages.

(56) References Cited

OTHER PUBLICATIONS

Sluch V.M., et al., "CRISPR-Editing of hESCs Allows for Production of Immune Evasive Cells Capable of Differentiation to Pancreatic Progenitors for Future Type 1 Diabetes Therapy," Sep. 17, 2019, 6 pages. Retrieved from the Internet URL: https://crisprtx.gcs-web.com/static-files/af584c8b-5264-4bdd-a409-fec52e06d365.

Sluch V.M., et al., "CRISPR-Editing of hESCS Allows for Production of Immune Evasive Cells Capable of Differentiation to Pancreatic Progenitors for Future Type 1 Diabetes Therapy," Dated Sep. 1, 2019, 1 Page. Retrieved from the Internet: URL: https://27funs395cqh24ygs02Iso4j-wpengine.netdna-ssl.com/wp-content/uploads/2019/09/ViaCyte-CRISPR-EASD-Abstract-September-2019.pdf [retrieved on Nov. 8, 2019, ] abstract Steentoft C., et al., "Precision Genome Editing: A Small Revolution for Glycobiology," Glycobiology, Aug. 2014, vol. 24(8), pp. 663-680.

Sutherland D.E., et al., "Islet Autotransplant Outcomes after Total Pancreatectomy: A Contrast to Islet Allograft Outcomes," Transplantation, Dec. 27, 2008, vol. 86, No. 12, pp. 1799-1802.

Takahashi K., et al., "Induction of Pluripotent Stem Cells from Mouse Embryonic and Adult Fibroblast Cultures by Defined Factors," Cell, Aug. 2006, vol. 126(4), pp. 663-676.

Thielen L.A., et al., "Identification of an Anti-diabetic, Orally Available Small Molecule that Regulates TXNIP Expression and Glucagon Action," Cell Metabolism, 2020, vol. 32, pp. 1-13.

Tibell A., et al., "Survival of Macroencapsulated Allogeneic Parathyroid Tissue One Year after Transplantation in Non-Immunosuppressed Humans," Cell Transplantation, 2001, vol. 10, No. 7, pp. 591-599.

Tsai S.Q., et al., "Dimeric CRISPR RNA-Guided Fokl Nucleases for Highly Specific Genome Editing," Nature Biotechnology, Jun. 2014, vol. 32(6), pp. 569-576.

Tsai S.Q., et al., "GUIDE-Seq Enables Genome-Wide Profiling of Off-Target Cleavage by CRISPR-Cas Nucleases," HHS Public Access Author Manuscript, Aug. 1, 2015, pp. 1-23, published in final edited form as: Nat. Biotech., Feb. 2015, vol. 33, No. 2, pp. 187-197.

Verma N., et al., "CRISPR/Cas-Mediated Knockin in Human Pluripotent Stem Cells," Methods in Molecular Biology, Year 2017, vol. 1513, pp. 119-140.

Wahoff D.C., et al., "Autologous Islet Transplantation to Prevent Diabetes after Pancreatic Resection," Annals of Surgery, Oct. 1995, vol. 222, No. 4, pp. 562-579.

Wang C.J., et al., "Protective Role of Programmed Death 1 Ligand 1 (PD-L1) in Nonobese Diabetic Mice: The Paradox in Transgenic Models," Diabetes, Jul. 2008, vol. 57, No. 7, pp. 1861-1869.

Wang D., et al., "Targeted Disruption of the β2-Microglobulin Gene Minimizes the Immunogenicity of Human Embryonic Stem Cells," Stem Cells Translational Medicine, Oct. 2015, vol. 4(10), pp. 1234-1245.

Wang J., et al., "Cyclohexene Nucleic Acids (CeNA): Serum Stable Oligonucleotides that Activate RNase H and Increase Duplex Stability with Complementary RNA," Journal of the American Chemical Society, 2000, vol. 122(36), pp. 8595-8602.

Wang S., et al., "Rapid and Efficient Assembly of Transcription Activator-Like Effector Genes by USER Cloning," Journal of Genetics and Genomics, 2014, vol. 41, pp. 339-347.

Weber E., et al., "A Modular Cloning System for Standardized Assembly of Multigene Constructs," PLoS One, 2011, vol. 6(2), e16765, pp. 1-11.

Winkler H., et al., "The Chromogranins A and B: The First 25 Years and Future Perspectives," Neuroscience, Aug. 1992, vol. 49, No. 3, pp. 497-528.

Wolfs J.M., et al., "MegaTevs: Single-chain Dual Nucleases for Efficient Gene Disruption," Nucleic Acids Research, 2014, vol. 42(13), pp. 8816-8829.

Wondafrash D.Z., et al., "Thioredoxin-Interacting Protein as a Novel Potential Therapeutic Target in Diabetes Meilitus and its Underlying Complications," Diabetes, Metabolic Syndrome and Obesity: Targets and Therapy, Jan. 7, 2020, vol. 13, pp. 43-51.

Xiao, X., et al., "Endogenous Reprogramming of Alpha Cells into Beta Cells, Induced by Viral Gene Therapy, Reverses Autoimmune Diabetes," Cell Stem Cell, Jan. 4, 2018, vol. 22, No. 1, pp. 78-90.

Yoshihara E., et al., "Immune-Evasive Human Islet-Like Organoids Ameliorate Diabetes," Nature, Oct. 2020, vol. 586, No. 7830, pp. 606-611.

Yu, Y., et al., "MANF: A Novel Endoplasmic Reticulum Stress Response Protein—The Role in Neurological and Metabolic Disorders," Oxidative Medicine and Cellular Longevity, Oct. 28, 2021, pp. 1-10.

Zammit N.W., et al., "A20 as an Immune Tolerance Factor Can Determine Islet Transplant Outcomes," JCI Insight, Nov. 1, 2019, vol. 4, No. 21, 16 pages.

Zarcone D., et al., "Human Leukemia-derived Cell Lines and Clones as Models for Mechanistic Analysis of Natural Killer Cell-mediated Cytotoxicity," Cancer Research, May 15, 1987, vol. 47, pp. 2674-2682.

Zhang H-H., et al., "Efficient Preparation of a TXNIP Knockout Mouse Model by Transcription Activator-like Effect or Nucleases (TALEN)," Chinese Journal of Comparative Medicine, Jun. 2015, vol. 25(6), pp. 9-13.

Zhao H.X., et al., "Enhanced Immunological Tolerance by HLA-G1 from Neural Progenitor Cells (NPCs) Derived from Human Embryonic Stem Cells (hESCs)," Cellular Physiology and Biochemistry, 2017, vol. 44, No. 4, pp. 1435-1444.

Zhao L., et al., "Heterelogous Expression of Mutated HLA-G Decreases Immunogenicity of Human Embryonic Stem Cells and Their Epidermal Derivatives," Stem Cell Research, Sep. 2014, vol. 13, No. 2, pp. 342-354.

Jackson S.W., et al., "Disordered Purinergic Signaling Inhibits Pathological Angiogenesis in Cd39/Entpd1-Null Mice," The American Journal of Pathology, 2007, vol. 171, No. 4, pp. 1395-1404.

Jinek M., et al., "A Programmable Dual RNA-guided DNA Endonuclease in Adaptive Bacterial Immunity," Science, Aug. 17, 2012, vol. 337(6069), pp. 816-821.

Karabekian Z., et al., "HLA Class I Depleted hESC as a Source of Hypoimmunogenic Cells for Tissue Engineering Applications," Tissue Engineering: Part A, Oct. 1, 2015, vol. 21(19&20), pp. 2559-2571.

Kelly O.G., et al., "Cell-Surface Markers for the Isolation of Pancreatic Cell Types Derived from Human Embryonic Stem Cells," Nature Biotechnology, Jul. 31, 2011, vol. 29, No. 8, pp. 750-756.

Kent T., et al., "Mechanism of Microhomology-Mediated End-Joining Promoted by Human DNA Polymerase Theta," Nature Structural and Molecular Biology, Mar. 2015, vol. 22(3), pp. 230-237.

Kieffer T.J., et al., "Beta-Cell Replacement Strategies for Diabetes," Journal of Diabetes Investigation, Oct. 6, 2017, vol. 9, No. 3, pp. 457-463.

Kimelman M., et al., "Trends in Immunosuppression after Pancreas Transplantation: What is in the Pipeline?," Current Opinion in Organ Transplantation, Feb. 2013, vol. 18, No. 1, pp. 76-82.

Kirk K., et al., "Human Embryonic Stem Cell Derived Islet Progenitors Mature Inside an Encapsulation Device without Evidence of Increased Biomass or Cell Escape," Stem Cell Research, May 2014, vol. 12, No. 3, pp. 807-814.

Kleinstiver B.P., et al., "Genome-Wide Specificities of CRISPR-Cas Cpf1 Nucleases in Human Cells," Nature Biotechnology, Aug. 2016, vol. 34, No. 8, pp. 869-875.

Kleinstiver B.P., et al., "The I-Tevl Nuclease and Linker Domains Contribute to the Specificity of Monomeric TALENs," Genes, Genomes, Genetics, 2014, vol. 4(6), pp. 1155-1165.

Klinke D. J., II., "Age-Corrected Beta Cell Mass Following Onset of Type 1 Diabetes Mellitus Correlates with Plasma C-Peptide in Humans," PLoS One, 2011, vol. 6, No. 11, 7 pages.

Knoepfler P.S., "Deconstructing Stem Cell Tumorigenicity: A Roadmap to Safe Regenerative Medicine," Stem Cells, May 2009, vol. 27(5), pp. 1050-1056.

Kondo Y., et al., "Identification of a Small Molecule that Facilitates the Differentiation of Human iPSCS/ESCs and Mouse Embryonic Pancreatic Explants into Pancreatic Endocrine Cells," Diabetologia, Aug. 2017, vol. 60, No. 8, pp. 1454-1466.

(56) References Cited

OTHER PUBLICATIONS

Kooreman N.G., et al., "Alloimmune Responses of Humanized Mice to Human Pluripotent Stem Cell Therapeutics" Cell Reports, Aug. 22, 2017, vol. 20, No. 8, pp. 1978-1990.
Korsgren O., et al., "Current Status of Clinical Islet Transplantation," Transplantation, May 27, 2005, vol. 79, No. 10, pp. 1289-1293.
Kotini A.G., et al., "LiPS-A3S, a Human Genomic Site for Robust Expression of Inserted Transgenes," Molecular Therapy—Nucleic Acids, Nov. 29, 2016, vol. 5(11), e394, pp. 1-8.
Kroon E., et al., "Pancreatic Endoderm Derived from Human Embryonic Stem Cells Generates Glucose-Responsive Insulin-Secreting Cells in Vivo," Nat Biotechnology, Apr. 2008, vol. 26, No. 4, pp. 443-452.
Kuroda T., et al., "Highly Sensitive in Vitro Methods for Detection of Residual Undifferentiated Cells in Retinal Pigment Epithelial Cells Derived from Human Ips Cells," PLoS One, May 17, 2012, vol. 7, No. 5, 9 pages.
Kuypers D.R.J., et al., "Consensus Report on Therapeutic Drug Monitoring of Mycophenolic Acid in Solid Organ Transplantation," Clinical Journal of the American Society of Nephrology, Feb. 2010, vol. 5, No. 2, pp. 341-358.
Kwon D.J., et al., "Generation of Alpha-1,3-Galactosyltransferase Knocked-Out Transgenic Cloned Pigs With Knocked-in Five Human Genes," Transgenic Research, Aug. 23, 2016, vol. 26, pp. 153-163.
Lablanche S., et al., "Islet Transplantation Versus Insulin Therapy in Patients with Type 1 Diabetes with Severe Hypoglycaemia or Poorly Controlled Glycaemia After Kidney Transplantation (TRIMECO): A Multicentre, Randomised Controlled Trial," Lancet Diabetes Endocrinology, Jul. 2018, vol. 6, No. 7, pp. 527-537.
Lacerra G., et al., "Restoration of Hemoglobin a Synthesis in Erythroid Cells from Peripheral Blood of Thalassemic Patients," Proceedings of the National Academy of Sciences of the United States of America, Aug. 15, 2000, vol. 97 (17), pp. 9591-9596.
Langmead B., et al., "Ultrafast and Memory-Efficient Alignment of Short DNA Sequences to the Human Genome," Genome Biology, Mar. 4, 2009, vol. 10, No. 3, 10 pages.
Li H., "Toward Better Understanding of Artifacts in Variant Calling from High Coverage Samples," Bioinformatics, Oct. 15, 2014, vol. 30, No. 20, pp. 2843-2851.
Li T., et al., "Modularly Assembled Designer TAL Effector Nucleases for Targeted Gene Knockout and Gene Replacement in Eukaryotes," Nucleic Acids Research, 2011, vol. 39(14), pp. 6315-6325.
Lin S.C., et al., "Molecular Basis for the Unique Deubiquitinating Activity of the Nf-KappaB Inhibitor A20," Journal of Molecular Biology, Feb. 15, 2008, vol. 376, No. 2, pp. 526-540.
Lindahl M., et al., "MANF is Indispensable for the Proliferation and Survival of Pancreatic β Cells," Cell Reports, Apr. 24, 2014, vol. 7, No. 2, pp. 366-375.
Liu J.S.E., et al., "All Mixed up: Defining Roles for p-Cell Subtypes in Mature Islets," Genes & Development, Feb. 1, 2017, vol. 31, pp. 228-240.
Liu Q., et al., "Validated Zinc Finger Protein Designs for All 16 GNN DNA Triplet Targets," The Journal of Biological Chemistry, 2002, vol. 277(6), pp. 3850-3856.
Liu X., et al., "The Immunogenicity and Immune Tolerance of Pluripotent Stem Cell Derivatives," Frontiers in Immunology, Jun. 2017, vol. 8(645), pp. 1-6.
Liuwantara D., et al., "Nuclear Factor-KappaB Regulates Beta-Cell Death: A Critical Role for A20 in Beta-Cell Protection," Diabetes, Sep. 2006, vol. 55, No. 9, p. 2491-2501.
Lu P., et al., "Generating Hypoimmunogenic Human Embryonic Stem Cells by the Disruption of Beta 2-Microglobulin," Stem Cell Reviews and Reports, 2013, vol. 9, pp. 806-813.
Ludwig B., et al., "Favorable Outcome of Experimental Islet Xenotransplantation without Immunosuppression in a Nonhuman Primate Model of Diabetes," Proceedings of the National Academy of Sciences, Oct. 31, 2017, vol. 114, No. 44, p. 11745-11750.
Ludwig B., et al., "Transplantation of Human Islets Without Immunosuppression," Proceedings of the National Academy of Sciences, Nov. 19, 2013, vol. 110, No. 47, pp. 19054-19058.
Ma X., et al., "Highly Efficient Differentiation of Functional Hepatocytes From Human Induced Pluripotent Stem Cells," Stem Cells Translational Medicine, 2013, vol. 2, pp. 409-419.
Mak A.N-S., et al., "The Crystal Structure of TAL Effector PthXol Bound to its DNA Target," Science, Feb. 10, 2012, vol. 335, pp. 716-719.
Makhlouf et al., "Allorecognition and Effector Pathways of Islet Allograft Rejection in Normal versus Nonobese Diabetic Mice", Journal of the American Society of Nephrology, 2003, pp. 2168-2175, vol. 14.
Markmann J.F., et al., "Indefinite Survival of MHC Class I-Deficient Murine Pancreatic Islet Allografts," Transplantation, 1992, vol. 54, No. 6, pp. 1085-1089.
Mateos-Gomez P.A., et al., "Mammalian Polymerase Theta Promotes Alternative-NHEJ and Suppresses Recombination," Nature, Feb. 12, 2015, vol. 518(7538), pp. 254-257.
Matsumoto S., et al., "Clinical Benefit of Islet Xenotransplantation for the Treatment of Type 1 Diabetes," EBioMedicine, Oct. 2016, vol. 12, pp. 255-262.
Matveyenko A.V., et al., "Relationship between Beta-Cell Mass and Diabetes Onset," Diabetes, Obesity and Metabolism, Nov. 2008, vol. 10, No. 4, pp. 23-31.
Meier-Kriescha H.U., et al., "Lack of Improvement in Renal Allograft Survival Despite a Marked Decrease in Acute Rejection Rates Over the Most Recent Era," American Journal of Transplantation, Mar. 2004, vol. 4, No. 3, pp. 378-383.
Merkle F.T., et al., "Human Pluripotent Stem Cells Recurrently Acquire and Expand Dominant Negative P53 Mutations," Nature, May 2017, vol. 545, No. 7653, pp. 229-233.
Mojica F.J.M., et al., "Short Motif Sequences Determine the Targets of the Prokaryotic CRISPR Defence System," Microbiology, Mar. 2009, vol. 155, No. 3, pp. 733-740.
Moore F., et al., "STAT1 is a Master Regulator of Pancreatic Beta-Cell Apoptosis and Islet Inflammation," Journal of Biological Chemistry, Jan. 14, 2011, vol. 286, No. 2, pp. 929-941.
Moscou M.J., et al., "A Simple Cipher Governs DNA Recognition by TAL Effectors," Science, Dec. 11, 2009, vol. 326, pp. 1501.
Motte E., et al., "Composition and Function of Macroencapsulated Human Embryonic Stem Cell-Derived Implants: Comparison with Clinical Human Islet Cell Grafts," American Journal of Physiology, Endocrinology and Metabolism, Nov. 1, 2014, vol. 307, No. 9, pp. E838-E846.
Nabavi S.M., et al., "Anti-Inflammatory Effects of Melatonin: a Mechanistic Review," Critical Reviews in Food Science and Nutrition, Jun. 2018, vol. 59(1), pp. 1-63.
Nagaraj K., et al., "Identification of Thioredoxin-Interacting Protein (TXNIP) as a Downstream Target for IGF1 Action," Proceedings of the National Academy of Sciences of the United States of America, Jan. 30, 2018, vol. 115 (5), pp. 1045-1050.
Nasevicius A., et al., "Effective Targeted Gene 'Knockdown' in Zebrafish," Nature Genetics, Oct. 2000, vol. 26, pp. 216-220.

* cited by examiner

FIG. 4
X1-1 B2M-CAGGS-TNFAIP3-P2A-PDL1
9569 bp
AAV2 ITR
LHA-800
1000
CMV enhancer
chicken β-actin promoter
2000
chimeric intron
Kozak sequence
3000
TNFAIP3 CDS
4000
5000
P2A
GSG tag
PD-L1
6000
bGH poly(A) signal
RHA-800
7000
AAV2 ITR
f1 ori
8000
KanR
9000
ori

SEQUENCE LISTING

```
<160> NUMBER OF SEQ ID NOS: 60

<210> SEQ ID NO 1
<211> LENGTH: 20
<212> TYPE: DNA
<213> ORGANISM: Homo sapiens

<400> SEQUENCE: 1

gctactctct ctttctggcc                                                20


<210> SEQ ID NO 2
<211> LENGTH: 20
<212> TYPE: DNA
<213> ORGANISM: Homo sapiens

<400> SEQUENCE: 2

ggccgagatg tctcgctccg                                                20


<210> SEQ ID NO 3
<211> LENGTH: 20
<212> TYPE: DNA
<213> ORGANISM: Homo sapiens

<400> SEQUENCE: 3

cgcgagcaca gctaaggcca                                                20


<210> SEQ ID NO 4
<211> LENGTH: 20
<212> TYPE: DNA
<213> ORGANISM: Homo sapiens

<400> SEQUENCE: 4

tataagtgga ggcgtcgcgc                                                20


<210> SEQ ID NO 5
<211> LENGTH: 20
<212> TYPE: DNA
<213> ORGANISM: Homo sapiens

<400> SEQUENCE: 5

gagtagcgcg agcacagcta                                                20


<210> SEQ ID NO 6
<211> LENGTH: 20
<212> TYPE: DNA
```

<213> ORGANISM: Homo sapiens

<400> SEQUENCE: 6
actggacgcg tcgcgctggc 20

<210> SEQ ID NO 7
<211> LENGTH: 20
<212> TYPE: DNA
<213> ORGANISM: Homo sapiens

<400> SEQUENCE: 7
aagtggaggc gtcgcgctgg 20

<210> SEQ ID NO 8
<211> LENGTH: 20
<212> TYPE: DNA
<213> ORGANISM: Homo sapiens

<400> SEQUENCE: 8
ggccacggag cgagacatct 20

<210> SEQ ID NO 9
<211> LENGTH: 20
<212> TYPE: DNA
<213> ORGANISM: Homo sapiens

<400> SEQUENCE: 9
gcccgaatgc tgtcagcttc 20

<210> SEQ ID NO 10
<211> LENGTH: 20
<212> TYPE: DNA
<213> ORGANISM: Homo sapiens

<400> SEQUENCE: 10
ctcgcgctac tctctctttc 20

<210> SEQ ID NO 11
<211> LENGTH: 20
<212> TYPE: DNA
<213> ORGANISM: Homo sapiens

<400> SEQUENCE: 11
tcctgaagct gacagcattc 20

<210> SEQ ID NO 12
<211> LENGTH: 20
<212> TYPE: DNA
<213> ORGANISM: Homo sapiens

<400> SEQUENCE: 12
ttcctgaagc tgacagcatt 20

<210> SEQ ID NO 13
<211> LENGTH: 20
<212> TYPE: DNA
<213> ORGANISM: Homo sapiens

<400> SEQUENCE: 13
actctctctt tctggcctgg 20

<210> SEQ ID NO 14
<211> LENGTH: 130

<212> TYPE: DNA
<213> ORGANISM: Homo sapiens

<400> SEQUENCE: 14
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct 130

<210> SEQ ID NO 15
<211> LENGTH: 800
<212> TYPE: DNA
<213> ORGANISM: Homo sapiens

<400> SEQUENCE: 15
gttctagggt ggaaactaag agaatgatgt acctagaggg cgctggaagc tctaaagccc 60
tagcagttac tgcttttact attagtggtc gtttttttct cccccccgcc ccccgacaaa 120
tcaacagaac aaagaaaatt acctaaacag caaggacata gggaggaact tcttggcaca 180
gaactttcca aacacttttt cctgaaggga tacaagaagc aagaaaggta ctctttcact 240
aggaccttct ctgagctgtc ctcaggatgc ttttgggact atttttctta cccagagaat 300
ggagaaaccc tgcagggaat tcccaagctg tagttataaa cagaagttct ccttctgcta 360
ggtagcattc aaagatctta atcttctggg tttccgtttt ctcgaatgaa aaatgcaggt 420
ccgagcagtt aactggctgg ggcaccatta gcaagtcact tagcatctct ggggccagtc 480
tgcaaagcga gggggcagcc ttaatgtgcc tccagcctga agtcctagaa tgagcgcccg 540
gtgtcccaag ctggggcgcg caccccagat cggagggcgc cgatgtacag acagcaaact 600
cacccagtct agtgcatgcc ttcttaaaca tcacgagact ctaagaaaag gaaactgaaa 660
acgggaaagt ccctctctct aacctggcac tgcgtcgctg gcttggagac aggtgacggt 720
ccctgcgggc cttgtcctga ttggctgggc acgcgtttaa tataagtgga ggcgtcgcgc 780
tggcgggcat tcctgaagct 800

<210> SEQ ID NO 16
<211> LENGTH: 1667
<212> TYPE: DNA
<213> ORGANISM: Artificial Sequence
<220> FEATURE:
<223> OTHER INFORMATION: Synthetic

<400> SEQUENCE: 16
gacattgatt attgactagt tattaatagt aatcaattac ggggtcatta gttcatagcc 60
catatatgga gttccgcgtt acataactta cggtaaatgg cccgcctggc tgaccgccca 120
acgacccccg cccattgacg tcaataatga cgtatgttcc catagtaacg ccaataggga 180
ctttccattg acgtcaatgg gtggactatt tacggtaaac tgcccacttg gcagtacatc 240
aagtgtatca tatgccaagt acgcccccta ttgacgtcaa tgacggtaaa tggcccgcct 300
ggcattatgc ccagtacatg accttatggg actttcctac ttggcagtac atctacgtat 360
tagtcatcgc tattaccatg ggtcgaggtg agccccacgt tctgcttcac tctccccatc 420
tcccccccct ccccaccccc aattttgtat ttatttattt tttaattatt ttgtgcagcg 480
atgggggcgg gggggggggg ggcgcgcgcc aggcggggcg gggcggggcg aggggcgggg 540
cggggcgagg cggagaggtg cggcggcagc caatcagagc ggcgcgctcc gaaagtttcc 600
ttttatggcg aggcggcggc ggcggcggcc ctataaaaag cgaagcgcgc ggcgggcggg 660

```
agtcgctgcg ttgccttcgc cccgtgcccc gctccgcgcc gcctcgcgcc gcccgccccg    720

gctctgactg accgcgttac tcccacaggt gagcgggcgg gacggccctt ctcctccggg    780

ctgtaattag cgcttggttt aatgacggct cgtttctttt ctgtggctgc gtgaaagcct    840

taaagggctc cgggagggcc ctttgtgcgg gggggagcgg ctcggggggt gcgtgcgtgt    900

gtgtgtgcgt ggggagcgcc gcgtgcggcc cgcgctgccc ggcggctgtg agcgctgcgg    960

gcgcggcgcg gggctttgtg cgctccgcgt gtgcgcgagg ggagcgcggc cgggggcggt   1020

gccccgcggt gcgggggggc tgcgagggga acaaaggctg cgtgcggggt gtgtgcgtgg   1080

gggggtgagc agggggtgtg ggcgcggcgg tcgggctgta acccccccct gcaccccccct  1140

ccccgagttg ctgagcacgg cccggcttcg ggtgcggggc tccgtgcggg gcgtggcgcg   1200

gggctcgccg tgccgggcgg ggggtggcgg caggtggggg tgccgggcgg ggcggggccg   1260

cctcgggccg gggagggctc gggggagggg cgcggcggcc ccggagcgcc ggcggctgtc   1320

gaggcgcggc gagccgcagc cattgccttt tatggtaatc gtgcgagagg gcgcagggac   1380

ttcctttgtc ccaaatctgg cggagccgaa atctgggagg cgccgccgca ccccctctag   1440

cgggcgcggg cgaagcggtg cggcgccggc aggaaggaaa tgggcgggga gggccttcgt   1500

gcgtcgccgc gccgccgtcc ccttctccat ctccagcctc ggggctgccg caggggggacg  1560

gctgccttcg ggggggacgg ggcagggcgg ggttcggctt ctggcgtgtg accggcggct   1620

ctagagcctc tgctaaccat gttcatgcct tcttcttttt cctacag                 1667
```

<210> SEQ ID NO 17
<211> LENGTH: 546
<212> TYPE: DNA
<213> ORGANISM: Homo sapiens

<400> SEQUENCE: 17

```
atgaggagga tgtgggccac gcaggggctg gcggtggcgc tggctctgag cgtgctgccg     60

ggcagccggg cgctgcggcc gggcgactgc gaagtttgta tttcttatct gggaagattt    120

taccaggacc tcaaagacag agatgtcaca ttctcaccag ccactattga aaacgaactt    180

ataaagttct gccgggaagc aagaggcaaa gagaatcggt tgtgctacta tatcggggcc    240

acagatgatg cagccaccaa aatcatcaat gaggtatcaa agcctctggc ccaccacatc    300

cctgtggaga agatctgtga gaagcttaag aagaaggaca gccagatatg tgagcttaag    360

tatgacaagc agatcgacct gagcacagtg gacctgaaga agctccgagt taaagagctg    420

aagaagattc tggatgactg gggggagaca tgcaaaggct gtgcagaaaa gtctgactac    480

atccggaaga taaatgaact gatgcctaaa tatgccccca aggcagccag tgcacggacc    540

gatttg                                                               546
```

<210> SEQ ID NO 18
<211> LENGTH: 57
<212> TYPE: DNA
<213> ORGANISM: Artificial Sequence
<220> FEATURE:
<223> OTHER INFORMATION: Synthetic

<400> SEQUENCE: 18

```
gctactaact tcagcctgct gaagcaggct ggagacgtgg aggagaaccc tggacct        57
```

<210> SEQ ID NO 19
<211> LENGTH: 2370
<212> TYPE: DNA
<213> ORGANISM: Homo sapiens

<400> SEQUENCE: 19

```
atggctgaac aagtccttcc tcaggctttg tatttgagca atatgcggaa agctgtgaag     60
atacgggaga gaactccaga agacattttt aaacctacta atgggatcat tcatcatttt    120
aaaaccatgc accgatacac actggaaatg ttcagaactt gccagttttg tcctcagttt    180
cgggagatca tccacaaagc cctcatcgac agaaacatcc aggccaccct ggaaagccag    240
aagaaactca actggtgtcg agaagtccgg aagcttgtgg cgctgaaaac gaacggtgac    300
ggcaattgcc tcatgcatgc cacttctcag tacatgtggg gcgttcagga cacagacttg    360
gtactgagga aggcgctgtt cagcacgctc aaggaaacag acacacgcaa ctttaaattc    420
cgctggcaac tggagtctct caaatctcag gaatttgttg aaacggggct ttgctatgat    480
actcggaact ggaatgatga atgggacaat cttatcaaaa tggcttccac agacacaccc    540
atggcccgaa gtggacttca gtacaactca ctggaagaaa tacacatatt tgtcctttgc    600
aacatcctca gaaggccaat cattgtcatt tcagacaaaa tgctaagaag tttggaatca    660
ggttccaatt tcgccccttt gaaagtgggt ggaatttact tgcctctcca ctggcctgcc    720
caggaatgct acagataccc cattgttctc ggctatgaca gccatcattt tgtacccttg    780
gtgaccctga aggacagtgg gcctgaaatc cgagctgttc cacttgttaa cagagaccgg    840
ggaagatttg aagacttaaa agttcacttt ttgacagatc ctgaaaatga gatgaaggag    900
aagctcttaa aagagtactt aatggtgata gaaatccccg tccaaggctg ggaccatggc    960
acaactcatc tcatcaatgc cgcaaagttg gatgaagcta acttaccaaa agaaatcaat   1020
ctggtagatg attactttga acttgttcag catgagtaca agaaatggca ggaaaacagc   1080
gagcagggga ggagagaggg gcacgcccag aatcccatgg aaccttccgt gccccagctt   1140
tctctcatgg atgtaaaatg tgaaacgccc aactgcccct tcttcatgtc tgtgaacacc   1200
cagcctttat gccatgagtg ctcagagagg cggcaaaaga atcaaaacaa actcccaaag   1260
ctgaactcca agccgggccc tgaggggctc cctggcatgg cgctcggggc ctctcgggga   1320
gaagcctatg agcccttggc gtggaaccct gaggagtcca ctgggggggcc tcattcggcc   1380
ccaccgacag cacccagccc ttttctgttc agtgagacca ctgccatgaa gtgcaggagc   1440
cccggctgcc ccttcacact gaatgtgcag cacaacggat tttgtgaacg ttgccacaac   1500
gcccggcaac ttcacgccag ccacgcccca gaccacacaa ggcacttgga tcccgggaag   1560
tgccaagcct gcctccagga tgttaccagg acatttaatg ggatctgcag tacttgcttc   1620
aaaaggacta cagcagaggc ctcctccagc ctcagcacca gcctccctcc ttcctgtcac   1680
cagcgttcca agtcagatcc ctcgcggctc gtccggagcc cctccccgca ttcttgccac   1740
agagctggaa acgacgcccc tgctggctgc ctgtctcaag ctgcacggac tcctggggac   1800
aggacgggga cgagcaagtg cagaaaagcc ggctgcgtgt attttgggac tccagaaaac   1860
aagggctttt gcacactgtg tttcatcgag tacagagaaa acaaacattt tgctgctgcc   1920
tcagggaaag tcagtcccac agcgtccagg ttccagaaca ccattccgtg cctggggagg   1980
gaatgcggca cccttggaag caccatgttt gaaggatact gccagaagtg tttcattgaa   2040
gctcagaatc agagatttca tgaggccaaa aggacagaag agcaactgag atcgagccag   2100
cgcagagatg tgcctcgaac cacacaaagc acctcaaggc ccaagtgcgc ccgggcctcc   2160
tgcaagaaca tcctggcctg ccgcagcgag gagctctgca tggagtgtca gcatcccaac   2220
cagaggatgg gccctggggc ccaccggggt gagcctgccc ccgaagaccc ccccaagcag   2280
```

cgttgccggg cccccgcctg tgatcatttt ggcaatgcca agtgcaacgg ctactgcaac 2340
gaatgctttc agttcaagca gatgtatggc 2370

<210> SEQ ID NO 20
<211> LENGTH: 873
<212> TYPE: DNA
<213> ORGANISM: Homo sapiens

<400> SEQUENCE: 20
atgaggatat ttgctgtctt tatattcatg acctactggc atttgctgaa cgcatttact 60
gtcacggttc ccaaggacct atatgtggta gagtatggta gcaatatgac aattgaatgc 120
aaattcccag tagaaaaaca attagacctg gctgcactaa ttgtctattg ggaaatggag 180
gataagaaca ttattcaatt tgtgcatgga gaggaagacc tgaaggttca gcatagtagc 240
tacagacaga gggcccggct gttgaaggac cagctctccc tgggaaatgc tgcacttcag 300
atcacagatg tgaaattgca ggatgcaggg gtgtaccgct gcatgatcag ctatggtggt 360
gccgactaca agcgaattac tgtgaaagtc aatgccccat acaacaaaat caaccaaaga 420
attttggttg tggatccagt cacctctgaa catgaactga catgtcaggc tgagggctac 480
cccaaggccg aagtcatctg gacaagcagt gaccatcaag tcctgagtgg taagaccacc 540
accaccaatt ccaagagaga ggagaaactt ttcaatgtga ccagcacact gagaatcaac 600
acaacaacta atgagatttt ctactgcact tttaggagat tagatcctga ggaaaaccat 660
acagctgaat tggtcatccc agaactacct ctggcacatc ctccaaatga aaggactcac 720
ttggtaattc tgggagccat cttattatgc cttggtgtag cactgacatt catcttccgt 780
ttaagaaaag ggagaatgat ggatgtgaaa aaatgtggca tccaagatac aaactcaaag 840
aagcaaagtg atacacattt ggaggagacg taa 873

<210> SEQ ID NO 21
<211> LENGTH: 225
<212> TYPE: DNA
<213> ORGANISM: Bos taurus

<400> SEQUENCE: 21
gtgccttcta gttgccagcc atctgttgtt tgcccctccc ccgtgccttc cttgaccctg 60
gaaggtgcca ctcccactgt cctttcctaa taaaatgagg aaattgcatc gcattgtctg 120
agtaggtgtc attctattct ggggggtggg gtggggcagg acagcaaggg ggaggattgg 180
gaagacaata gcaggcatgc tggggatgcg gtgggctcta tgggt 225

<210> SEQ ID NO 22
<211> LENGTH: 800
<212> TYPE: DNA
<213> ORGANISM: Homo sapiens

<400> SEQUENCE: 22
ccagcgtgag tctctcctac cctcccgctc tggtccttcc tctcccgctc tgcaccctct 60
gtggccctcg ctgtgctctc tcgctccgtg acttcccttc tccaagttct ccttggtggc 120
ccgccgtggg gctagtccag ggctggatct cggggaagcg gcggggtggc ctgggagtgg 180
ggaagggggt gcgcacccgg gacgcgcgct acttgcccct ttcggcgggg agcaggggag 240
acctttggcc tacggcgacg ggagggtcgg gacaaagttt agggcgtcga taagcgtcag 300
agcgccgagg ttgggggagg gtttctcttc cgctctttcg cggggcctct ggctccccca 360
gcgcagctgg agtgggggac gggtaggctc gtcccaaagg cgcggcgctg aggtttgtga 420
acgcgtggag gggcgcttgg ggtctggggg aggcgtcgcc cgggtaagcc tgtctgctgc 480
ggctctgctt cccttagact ggagagctgt ggacttcgtc taggcgcccg ctaagttcgc 540
atgtcctagc acctctgggt ctatgtgggg ccacaccgtg gggaggaaac agcacgcgac 600
gtttgtagaa tgcttggctg tgatacaaag cggtttcgaa taattaactt atttgttccc 660
atcacatgtc acttttaaaa aattataaga actacccgtt attgacatct ttctgtgtgc 720
caaggacttt atgtgctttg cgtcatttaa ttttgaaaac agttatcttc cgccatagat 780
aactactatg gttatcttct 800

<210> SEQ ID NO 23
<211> LENGTH: 141
<212> TYPE: DNA
<213> ORGANISM: Artificial Sequence
<220> FEATURE:
<223> OTHER INFORMATION: Synthetic

<400> SEQUENCE: 23
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgcag ctgcctgcag g 141

<210> SEQ ID NO 24
<211> LENGTH: 10181
<212> TYPE: DNA
<213> ORGANISM: Artificial Sequence
<220> FEATURE:
<223> OTHER INFORMATION: Synthetic

<400> SEQUENCE: 24
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtgttcta gggtggaaac taagagaatg atgtacctag 180
agggcgctgg aagctctaaa gccctagcag ttactgcttt tactattagt ggtcgttttt 240 ttctccccc cgcccccga caaatcaaca gaacaaagaa aattacctaa acagcaagga 300
catagggagg aacttcttgg cacagaactt tccaaacact ttttcctgaa gggatacaag 360
aagcaagaaa ggtactcttt cactaggacc ttctctgagc tgtcctcagg atgcttttgg 420
gactattttt cttacccaga gaatggagaa accctgcagg gaattcccaa gctgtagtta 480
taaacagaag ttctccttct gctaggtagc attcaaagat cttaatcttc tgggtttccg 540
ttttctcgaa tgaaaaatgc aggtccgagc agttaactgg ctggggcacc attagcaagt 600
cacttagcat ctctggggcc agtctgcaaa gcgagggggc agccttaatg tgcctccagc 660
ctgaagtcct agaatgagcg cccggtgtcc caagctgggg cgcgcacccc agatcggagg 720
gcgccgatgt acagacagca aactcaccca gtctagtgca tgccttctta aacatcacga 780
gactctaaga aaaggaaact gaaaacggga aagtccctct ctctaacctg gcactgcgtc 840
gctggcttgg agacaggtga cggtccctgc gggccttgtc ctgattggct gggcacgcgt 900
ttaatataag tggaggcgtc gcgctggcgg gcattcctga agctaagctt gtggacgata 960
tcgaattcgc acgacattga ttattgacta gttattaata gtaatcaatt acggggtcat 1020
tagttcatag cccatatatg gagttccgcg ttacataact tacggtaaat ggcccgcctg 1080
gctgaccgcc caacgacccc cgcccattga cgtcaataat gacgtatgtt cccatagtaa 1140
cgccaatagg gactttccat tgacgtcaat gggtggacta tttacggtaa actgcccact 1200
tggcagtaca tcaagtgtat catatgccaa gtacgccccc tattgacgtc aatgacggta 1260
aatggcccgc ctggcattat gcccagtaca tgaccttatg ggactttcct acttggcagt 1320
acatctacgt attagtcatc gctattacca tgggtcgagg tgagccccac gttctgcttc 1380
actctcccca tctccccccc ctccccaccc ccaattttgt atttatttat tttttaatta 1440
ttttgtgcag cgatgggggc gggggggggg ggggcgcgcg ccaggcgggg cggggcgggg 1500
cgaggggcgg ggcggggcga ggcggagagg tgcggcggca gccaatcaga gcggcgcgct 1560
ccgaaagttt ccttttatgg cgaggcggcg gcggcggcgg ccctataaaa agcgaagcgc 1620
gcggcgggcg ggagtcgctg cgttgccttc gccccgtgcc ccgctccgcg ccgcctcgcg 1680
ccgcccgccc cggctctgac tgaccgcgtt actcccacag gtgagcgggc gggacggccc 1740
ttctcctccg ggctgtaatt agcgcttggt ttaatgacgg ctcgtttctt ttctgtggct 1800
gcgtgaaagc cttaaagggc tccgggaggg ccctttgtgc ggggggggagc ggctcggggg 1860 gtgcgtgcgt gtgtgtgtgc gtggggagcg ccgcgtgcgg cccgcgctgc ccggcggctg 1920
tgagcgctgc gggcgcggcg cggggctttg tgcgctccgc gtgtgcgcga ggggagcgcg 1980
gccgggggcg gtgccccgcg gtgcgggggg gctgcgaggg gaacaaaggc tgcgtgcggg 2040
gtgtgtgcgt gggggggtga gcagggggtg tgggcgcggc ggtcgggctg taaccccccc 2100
ctgcaccccc ctccccgagt tgctgagcac ggcccggctt cgggtgcggg gctccgtgcg 2160
gggcgtggcg cggggctcgc cgtgccgggc ggggggtggc ggcaggtggg ggtgccgggc 2220
ggggcggggc cgcctcgggc cggggagggc tcgggggagg ggcgcggcgg ccccggagcg 2280
ccggcggctg tcgaggcgcg gcgagccgca gccattgcct tttatggtaa tcgtgcgaga 2340
gggcgcaggg acttcctttg tcccaaatct ggcggagccg aaatctggga ggcgccgccg 2400
caccccctct agcgggcgcg ggcgaagcgg tgcggcgccg gcaggaagga aatgggcggg 2460
gagggccttc gtgcgtcgcc gcgccgccgt ccccttctcc atctccagcc tcggggctgc 2520 cgcagggggga cggctgcctt cggggggggac ggggcagggc ggggttcggc ttctggcgtg 2580
tgaccggcgg ctctagagcc tctgctaacc atgttcatgc cttcttcttt ttcctacagg 2640
ggggatccgt ttatctgcag aattcgccct tgacgtcgcc accatgagga ggatgtgggc 2700
cacgcagggg ctggcggtgg cgctggctct gagcgtgctg ccgggcagcc gggcgctgcg 2760
gccgggcgac tgcgaagttt gtatttctta tctgggaaga ttttaccagg acctcaaaga 2820
cagagatgtc acattctcac cagccactat tgaaaacgaa cttataaagt tctgccggga 2880
agcaagaggc aaagagaatc ggttgtgcta ctatatcggg gccacagatg atgcagccac 2940
caaaatcatc aatgaggtat caaagcctct ggcccaccac atccctgtgg agaagatctg 3000
tgagaagctt aagaagaagg acagccagat atgtgagctt aagtatgaca agcagatcga 3060
cctgagcaca gtggacctga agaagctccg agttaaagag ctgaagaaga ttctggatga 3120
ctggggggag acatgcaaag gctgtgcaga aaagtctgac tacatccgga agataaatga 3180
actgatgcct aaatatgccc ccaaggcagc cagtgcacgg accgatttgg gaagcggagc 3240
tactaacttc agcctgctga agcaggctgg agacgtggag gagaaccctg gacctatggc 3300
tgaacaagtc cttcctcagg ctttgtattt gagcaatatg cggaaagctg tgaagatacg 3360
ggagagaact ccagaagaca tttttaaacc tactaatggg atcattcatc attttaaaac 3420
catgcaccga tacacactgg aaatgttcag aacttgccag ttttgtcctc agtttcggga 3480
gatcatccac aaagccctca tcgacagaaa catccaggcc accctggaaa gccagaagaa 3540

-continued actcaactgg tgtcgagaag tccggaagct tgtggcgctg aaaacgaacg gtgacggcaa 3600
ttgcctcatg catgccactt ctcagtacat gtggggcgtt caggacacag acttggtact 3660
gaggaaggcg ctgttcagca cgctcaagga aacagacaca cgcaacttta aattccgctg 3720
gcaactggag tctctcaaat ctcaggaatt tgttgaaacg gggctttgct atgatactcg 3780
gaactggaat gatgaatggg acaatcttat caaaatggct tccacagaca cacccatggc 3840
ccgaagtgga cttcagtaca actcactgga agaaatacac atatttgtcc tttgcaacat 3900
cctcagaagg ccaatcattg tcatttcaga caaaatgcta agaagtttgg aatcaggttc 3960
caatttcgcc cctttgaaag tgggtggaat ttacttgcct ctccactggc ctgcccagga 4020
atgctacaga taccccattg ttctcggcta tgacagccat cattttgtac ccttggtgac 4080
cctgaaggac agtgggcctg aaatccgagc tgttccactt gttaacagag accggggaag 4140
atttgaagac ttaaaagttc actttttgac agatcctgaa aatgagatga aggagaagct 4200
cttaaaagag tacttaatgg tgatagaaat ccccgtccaa ggctgggacc atggcacaac 4260
tcatctcatc aatgccgcaa agttggatga agctaactta ccaaaagaaa tcaatctggt 4320
agatgattac tttgaacttg ttcagcatga gtacaagaaa tggcaggaaa acagcgagca 4380
ggggaggaga gaggggcacg cccagaatcc catggaacct tccgtgcccc agctttctct 4440
catggatgta aaatgtgaaa cgcccaactg ccccttcttc atgtctgtga acacccagcc 4500
tttatgccat gagtgctcag agaggcggca aaagaatcaa aacaaactcc caaagctgaa 4560
ctccaagccg ggccctgagg ggctccctgg catggcgctc ggggcctctc ggggagaagc 4620
ctatgagccc ttggcgtgga accctgagga gtccactggg gggcctcatt cggccccacc 4680
gacagcaccc agccctttc tgttcagtga gaccactgcc atgaagtgca ggagccccgg 4740
ctgccccttc acactgaatg tgcagcacaa cggattttgt gaacgttgcc acaacgcccg 4800
gcaacttcac gccagccacg ccccagacca cacaaggcac ttggatcccg ggaagtgcca 4860
agcctgcctc caggatgtta ccaggacatt taatgggatc tgcagtactt gcttcaaaag 4920
gactacagca gaggcctcct ccagcctcag caccagcctc cctccttcct gtcaccagcg 4980
ttccaagtca gatccctcgc ggctcgtccg gagcccctcc ccgcattctt gccacagagc 5040
tggaaacgac gcccctgctg gctgcctgtc tcaagctgca cggactcctg ggacaggac 5100
ggggacgagc aagtgcagaa aagccggctg cgtgtatttt gggactccag aaaacaaggg 5160
cttttgcaca ctgtgtttca tcgagtacag agaaaacaaa cattttgctg ctgcctcagg 5220
gaaagtcagt cccacagcgt ccaggttcca gaacaccatt ccgtgcctgg ggagggaatg 5280
cggcaccctt ggaagcacca tgtttgaagg atactgccag aagtgtttca ttgaagctca 5340
gaatcagaga tttcatgagg ccaaaaggac agaagagcaa ctgagatcga gccagcgcag 5400
agatgtgcct cgaaccacac aaagcacctc aaggcccaag tgcgcccggg cctcctgcaa 5460
gaacatcctg gcctgccgca gcgaggagct ctgcatggag tgtcagcatc ccaaccagag 5520
gatgggccct ggggcccacc ggggtgagcc tgcccccgaa gacccccca agcagcgttg 5580
ccgggccccc gcctgtgatc attttggcaa tgccaagtgc aacggctact gcaacgaatg 5640
ctttcagttc aagcagatgt atggcggaag cggagctact aacttcagcc tgctgaagca 5700
ggctggagac gtggaggaga accctggacc tatgaggata tttgctgtct ttatattcat 5760
gacctactgg catttgctga acgcatttac tgtcacggtt cccaaggacc tatatgtggt 5820
agagtatggt agcaatatga caattgaatg caaattccca gtagaaaaac aattagacct 5880

-continued ggctgcacta attgtctatt gggaaatgga ggataagaac attattcaat ttgtgcatgg 5940
agaggaagac ctgaaggttc agcatagtag ctacagacag agggcccggc tgttgaagga 6000
ccagctctcc ctgggaaatg ctgcacttca gatcacagat gtgaaattgc aggatgcagg 6060
ggtgtaccgc tgcatgatca gctatggtgg tgccgactac aagcgaatta ctgtgaaagt 6120
caatgcccca tacaacaaaa tcaaccaaag aattttggtt gtggatccag tcacctctga 6180
acatgaactg acatgtcagg ctgagggcta ccccaaggcc gaagtcatct ggacaagcag 6240
tgaccatcaa gtcctgagtg gtaagaccac caccaccaat tccaagagag aggagaaact 6300
tttcaatgtg accagcacac tgagaatcaa cacaacaact aatgagattt tctactgcac 6360
ttttaggaga ttagatcctg aggaaaacca tacagctgaa ttggtcatcc cagaactacc 6420
tctggcacat cctccaaatg aaaggactca cttggtaatt ctgggagcca tcttattatg 6480
ccttggtgta gcactgacat tcatcttccg tttaagaaaa gggagaatga tggatgtgaa 6540
aaaatgtggc atccaagata caaactcaaa gaagcaaagt gatacacatt tggaggagac 6600
gtaaccgctg atcagcctcg actgtgcctt ctagttgcca gccatctgtt gtttgcccct 6660
cccccgtgcc ttccttgacc ctggaaggtg ccactcccac tgtcctttcc taataaaatg 6720
aggaaattgc atcgcattgt ctgagtaggt gtcattctat tctggggggt ggggtggggc 6780
aggacagcaa gggggaggat tgggaagaca atagcaggca tgctggggat gcggtgggct 6840
ctatgggtcg acccagcgtg agtctctcct accctcccgc tctggtcctt cctctcccgc 6900
tctgcaccct ctgtggccct cgctgtgctc tctcgctccg tgacttccct tctccaagtt 6960
ctccttggtg gcccgccgtg ggctagtccc agggctggat ctcggggaag cggcggggtg 7020
gcctgggagt ggggaagggg gtgcgcaccc gggacgcgcg ctacttgccc ctttcggcgg 7080
ggagcagggg agacctttgg cctacggcga cgggagggtc gggacaaagt ttagggcgtc 7140
gataagcgtc agagcgccga ggttggggga gggtttctct tccgctcttt cgcggggcct 7200
ctggctcccc cagcgcagct ggagtggggg acgggtaggc tcgtcccaaa ggcgcggcgc 7260
tgaggtttgt gaacgcgtgg aggggcgctt ggggtctggg ggaggcgtcg cccgggtaag 7320
cctgtctgct gcggctctgc ttcccttaga ctggagagct gtggacttcg tctaggcgcc 7380
cgctaagttc gcatgtccta gcacctctgg gtctatgtgg ggccacaccg tggggaggaa 7440
acagcacgcg acgtttgtag aatgcttggc tgtgatacaa agcggtttcg aataattaac 7500
ttatttgttc ccatcacatg tcacttttaa aaaattataa gaactacccg ttattgacat 7560
ctttctgtgt gccaaggact ttatgtgctt tgcgtcattt aattttgaaa acagttatct 7620
tccgccatag ataactacta tggttatctt ctggtaacca cgtgcggacc gaggctgcag 7680
cgtcgtcctc cctaggaacc cctagtgatg gagttggcca ctccctctct gcgcgctcgc 7740
tcgctcactg aggccgggcg accaaaggtc gcccgacgcc cgggctttgc ccgggcggcc 7800
tcagtgagcg agcgagcgcg cagctgcctg caggggcgcc tgatgcggta ttttctcctt 7860
acgcatctgt gcggtatttc acaccgcata cgtcaaagca accatagtac gcgccctgta 7920
gcggcgcatt aagcgcggcg ggtgtggtgg ttacgcgcag cgtgaccgct acacttgcca 7980
gcgccctagc gcccgctcct ttcgctttct tcccttcctt tctcgccacg ttcgccggct 8040
ttccccgtca agctctaaat cgggggctcc ctttagggtt ccgatttagt gctttacggc 8100
acctcgaccc caaaaaactt gatttgggtg atggttcacg tagtgggcca tcgccctgat 8160
agacggtttt tcgccctttg acgttggagt ccacgttctt taatagtgga ctcttgttcc 8220
aaactggaac aacactcaac cctatctcgg gctattcttt tgatttataa gggattttgc 8280
cgatttcggc ctattggtta aaaaatgagc tgatttaaca aaaatttaac gcgaatttta 8340
acaaaatatt aacgtttaca attttatggt gcactctcag tacaatctgc tctgatgccg 8400
catagttaag ccagccccga cacccgccaa cacccgctga cgcgccctga cgggcttgtc 8460
tgctcccggc atccgcttac agacaagctg tgaccgtctc cgggagctgc atgtgtcaga 8520
ggttttcacc gtcatcaccg aaacgcgcga gacgaaaggg cctcgtgata cgcctatttt 8580
tataggttaa tgtcatgaac aataaaactg tctgcttaca taaacagtaa tacaaggggt 8640
gttatgagcc atattcaacg ggaaacgtcg aggccgcgat taaattccaa catggatgct 8700
gatttatatg ggtataaatg ggctcgcgat aatgtcgggc aatcaggtgc gacaatctat 8760
cgcttgtatg ggaagcccga tgcgccagag ttgtttctga aacatggcaa aggtagcgtt 8820
gccaatgatg ttacagatga gatggtcaga ctaaactggc tgacggaatt tatgcctctt 8880
ccgaccatca agcattttat ccgtactcct gatgatgcat ggttactcac cactgcgatc 8940
cccggaaaaa cagcattcca ggtattagaa gaatatcctg attcaggtga aaatattgtt 9000
gatgcgctgg cagtgttcct gcgccggttg cattcgattc ctgtttgtaa ttgtcctttt 9060
aacagcgatc gcgtatttcg tctcgctcag gcgcaatcac gaatgaataa cggtttggtt 9120
gatgcgagtg attttgatga cgagcgtaat ggctggcctg ttgaacaagt ctggaaagaa 9180
atgcataaac ttttgccatt ctcaccggat tcagtcgtca ctcatggtga tttctcactt 9240
gataacctta tttttgacga ggggaaatta ataggttgta ttgatgttgg acgagtcgga 9300
atcgcagacc gataccagga tcttgccatc ctatggaact gcctcggtga gttttctcct 9360
tcattacaga aacggctttt tcaaaaatat ggtattgata atcctgatat gaataaattg 9420
cagtttcatt tgatgctcga tgagtttttc taatctcatg accaaaatcc cttaacgtga 9480
gttttcgttc cactgagcgt cagaccccgt agaaaagatc aaaggatctt cttgagatcc 9540
tttttttctg cgcgtaatct gctgcttgca aacaaaaaaa ccaccgctac cagcggtggt 9600
ttgtttgccg gatcaagagc taccaactct ttttccgaag gtaactggct tcagcagagc 9660
gcagatacca aatactgtcc ttctagtgta gccgtagtta ggccaccact tcaagaactc 9720
tgtagcaccg cctacatacc tcgctctgct aatcctgtta ccagtggctg ctgccagtgg 9780
cgataagtcg tgtcttaccg ggttggactc aagacgatag ttaccggata aggcgcagcg 9840
gtcgggctga acggggggtt cgtgcacaca gcccagcttg gagcgaacga cctacaccga 9900
actgagatac ctacagcgtg agctatgaga aagcgccacg cttcccgaag ggagaaaggc 9960
ggacaggtat ccggtaagcg gcagggtcgg aacaggagag cgcacgaggg agcttccagg 10020
gggaaacgcc tggtatcttt atagtcctgt cgggtttcgc cacctctgac ttgagcgtcg 10080
atttttgtga tgctcgtcag gggggcggag cctatggaaa aacgccagca acgcggcctt 10140
tttacggttc ctggcctttt gctggccttt tgctcacatg t 10181

<210> SEQ ID NO 25
<211> LENGTH: 20
<212> TYPE: DNA
<213> ORGANISM: Homo sapiens

<400> SEQUENCE: 25
ggtccatctg gtcatagaag 20

<210> SEQ ID NO 26
<211> LENGTH: 800
<212> TYPE: DNA

<213> ORGANISM: Homo sapiens

<400> SEQUENCE: 26
catatttatg gggtatatgt gaatatttat tacatgcata gaaggtataa tgatcatgtc 60
aggatatttg aggtatccac atttgggatt gtttaaagat taaatgaaat agtgttaaaa 120
gtatttaata tgcccttcaa caaatgatga ggaaatctta gaatctgctc agactccttc 180
agtttacata ttaggaaact gaggcacaga aaggagcaga gacttgctca agtccaccca 240
aagcagtaga gcattgtggt taaatgcagg acttcagtca gactgtctgg gttcaaatcc 300
tggttccact tggacatggg tttccttaca taaatcactt cacctctctg agcctcagtt 360
ttctcatatg caaagtgagg ataataataa taccttcctt acatggttac tgatatgagt 420
attaaatgtg ccagctcatg tgcctggcgt ataggaggtg ctttataaac cttagctgtt 480
accactcatg gcattgccaa atgtgggacg ggtctcctga ctctctggtg tgagattgat 540
ggaatccaca ctttccagtt ccctttttcta cctcctgggt atcttctcat atggttgtaa 600
gttccttgga ggaagggaat gtggcttgct ctctccacca cgctgagcat ataagaggtg 660
ctgaatgagc gcttttattc actcctctca tccccagccc tcaccagctg ggagttgttg 720
taggtgtcaa ttttctgcct ctttccaaca ccctgtgagg tgactgagca ttgtcttccc 780
tcccaggcag ctcacagtgt 800

<210> SEQ ID NO 27
<211> LENGTH: 1530
<212> TYPE: DNA
<213> ORGANISM: Homo sapiens

<400> SEQUENCE: 27
atggaagata caaaggagtc taacgtgaag acattttgct ccaagaatat cctagccatc 60
cttggcttct cctctatcat agctgtgata gctttgcttg ctgtggggtt gacccagaac 120
aaagcattgc cagaaaacgt taagtatggg attgtgctgg atgcgggttc ttctcacaca 180
agtttataca tctataagtg gccagcagaa aaggagaatg acacaggcgt ggtgcatcaa 240
gtagaagaat gcagggttaa aggtcctgga atctcaaaat ttgttcagaa agtaaatgaa 300
ataggcattt acctgactga ttgcatggaa agagctaggg aagtgattcc aaggtcccag 360
caccaagaga cacccgttta cctgggagcc acggcaggca tgcggttgct caggatggaa 420
agtgaagagt tggcagacag ggttctggat gtggtggaga ggagcctcag caactacccc 480
tttgacttcc agggtgccag gatcattact ggccaagagg aaggtgccta tggctggatt 540
actatcaact atctgctggg caaattcagt cagaaaacaa ggtggttcag catagtccca 600
tatgaaacca ataatcagga aacctttgga gctttggacc ttgggggagc ctctacacaa 660
gtcacttttg taccccaaaa ccagactatc gagtccccag ataatgctct gcaatttcgc 720
ctctatggca aggactacaa tgtctacaca catagcttct tgtgctatgg gaaggatcag 780
gcactctggc agaaactggc caaggacatt caggttgcaa gtaatgaaat tctcagggac 840
ccatgctttc atcctggata taagaaggta gtgaacgtaa gtgaccttta caagaccccc 900
tgcaccaaga gatttgagat gactcttcca ttccagcagt ttgaaatcca gggtattgga 960
aactatcaac aatgccatca aagcatcctg gagctcttca acaccagtta ctgcccttac 1020
tcccagtgtg ccttcaatgg gattttcttg ccaccactcc agggggattt tggggcattt 1080
tcagcttttt actttgtgat gaagttttta aacttgacat cagagaaagt ctctcaggaa 1140
aaggtgactg agatgatgaa aaagttctgt gctcagcctt gggaggagat aaaaacatct 1200

```
tacgctggag taaaggagaa gtacctgagt gaatactgct tttctggtac ctacattctc   1260

tccctccttc tgcaaggcta tcatttcaca gctgattcct gggagcacat ccatttcatt   1320

ggcaagatcc agggcagcga cgccggctgg actttgggct acatgctgaa cctgaccaac   1380

atgatcccag ctgagcaacc attgtccaca cctctctccc actccaccta tgtcttcctc   1440

atggttctat tctccctggt ccttttcaca gtggccatca taggcttgct tatctttcac   1500

aagccttcat atttctggaa agatatggta                                    1530


<210> SEQ ID NO 28
<211> LENGTH: 800
<212> TYPE: DNA
<213> ORGANISM: Homo sapiens

<400> SEQUENCE: 28

tgaccagatg gacctggctg gagaagaaga gattgagctc tactcaggtg ggccctcctc     60

cctctggtct cttccggtat cccccacccc tcagcttgct gtagagacgg caatcagggg    120

aaattctggt ccctgccctc ccgtcagcac cacggacagc tcccacgtct gtgggacgct    180

ctctgcagat ggggatgatc tcccagccct gccccgcctc tccctcgttc cccaccagcc    240

ctctttccag aaatttcctt cttcatccaa gggacttttc ctcccagaac ccgacacaga    300

caccatcaac tgcgaccagt tcagcaggct gttgtgtgac atggaaggtg atgaagagac    360

cagggaggct tatgccaata tcggtgagga agcacctgag cccagaaaag gacaatcaag    420

ggcaagagtt ctttgctgcc acttgtcaat atcacccatt catcatgagc cacgtcagtc    480

ccctcccaca gaaatcattg caagggggat gcggagcaat ggctggagga acggagactc    540

cagggaagag aggggagatg gaggccagtg ggggaaatag gccccttcac taatgaccac    600

caagaaaaca aaatctcatg tttacatcct ccacctccat ttctatacgc atttctgctt    660

cttgctcttc tgtccatcct ttctacaaag cccataccat acaccccttt ccctttttcct    720

cccagctcct tagccaagct actctagtat ttgtaataac tagcatttac tggatactca    780

tagtatgctc attgctgtcc                                                800


<210> SEQ ID NO 29
<211> LENGTH: 7799
<212> TYPE: DNA
<213> ORGANISM: Artificial Sequence
<220> FEATURE:
<223> OTHER INFORMATION: Synthetic

<400> SEQUENCE: 29

cctgcaggca gctgcgcgct cgctcgctca ctgaggccgc ccgggcgtcg ggcgaccttt     60

ggtcgcccgg cctcagtgag cgagcgagcg cgcagagagg gagtggccaa ctccatcact    120

aggggttcct gcggccgcac gcgtcatatt tatggggtat atgtgaatat ttattacatg    180

catagaaggt ataatgatca tgtcaggata tttgaggtat ccacatttgg gattgtttaa    240

agattaaatg aaatagtgtt aaaagtattt aatatgccct tcaacaaatg atgaggaaat    300

cttagaatct gctcagactc cttcagttta catattagga aactgaggca cagaaaggag    360

cagagacttg ctcaagtcca cccaaagcag tagagcattg tggttaaatg caggacttca    420

gtcagactgt ctgggttcaa atcctggttc cacttggaca tgggtttcct tacataaatc    480

acttcacctc tctgagcctc agttttctca tatgcaaagt gaggataata ataatacctt    540

ccttacatgg ttactgatat gagtattaaa tgtgccagct catgtgcctg gcgtatagga    600
```

-continued

```
ggtgctttat aaaccttagc tgttaccact catggcattg ccaaatgtgg gacgggtctc    660
ctgactctct ggtgtgagat tgatggaatc cacactttcc agttcccttt tctacctcct    720
gggtatcttc tcatatggtt gtaagttcct tggaggaagg gaatgtggct tgctctctcc    780
accacgctga gcatataaga ggtgctgaat gagcgctttt attcactcct ctcatcccca    840
gccctcacca gctgggagtt gttgtaggtg tcaattttct gcctctttcc aacaccctgt    900
gaggtgactg agcattgtct tccctcccag gcagctcaca gtgtaagctt gtggacgata    960
tcgaattcgc acgacattga ttattgacta gttattaata gtaatcaatt acggggtcat   1020
tagttcatag cccatatatg gagttccgcg ttacataact tacggtaaat ggcccgcctg   1080
gctgaccgcc caacgacccc cgcccattga cgtcaataat gacgtatgtt cccatagtaa   1140
cgccaatagg gactttccat tgacgtcaat gggtggacta tttacggtaa actgcccact   1200
tggcagtaca tcaagtgtat catatgccaa gtacgccccc tattgacgtc aatgacggta   1260
aatggcccgc ctggcattat gcccagtaca tgaccttatg ggactttcct acttggcagt   1320
acatctacgt attagtcatc gctattacca tgggtcgagg tgagccccac gttctgcttc   1380
actctcccca tctccccccc ctccccaccc ccaattttgt atttatttat tttttaatta   1440
ttttgtgcag cgatgggggc gggggggggg ggggcgcgcg ccaggcgggg cggggcgggg   1500
cgaggggcgg ggcggggcga ggcggagagg tgcggcggca gccaatcaga gcggcgcgct   1560
ccgaaagttt ccttttatgg cgaggcggcg gcggcggcgg ccctataaaa agcgaagcgc   1620
gcggcgggcg ggagtcgctg cgttgccttc gccccgtgcc ccgctccgcg ccgcctcgcg   1680
ccgcccgccc cggctctgac tgaccgcgtt actcccacag gtgagcgggc gggacggccc   1740
ttctcctccg ggctgtaatt agcgcttggt ttaatgacgg ctcgtttctt ttctgtggct   1800
gcgtgaaagc cttaaagggc tccgggaggg ccctttgtgc ggggggggagc ggctcggggg   1860
gtgcgtgcgt gtgtgtgtgc gtggggagcg ccgcgtgcgg cccgcgctgc ccggcggctg   1920
tgagcgctgc gggcgcggcg cggggctttg tgcgctccgc gtgtgcgcga ggggagcgcg   1980
gccgggggcg gtgccccgcg gtgcgggggg gctgcgaggg gaacaaaggc tgcgtgcggg   2040
gtgtgtgcgt gggggggtga gcagggggtg tgggcgcggc ggtcgggctg taaccccccc   2100
ctgcaccccc ctccccgagt tgctgagcac ggcccggctt cgggtgcggg gctccgtgcg   2160
gggcgtggcg cggggctcgc cgtgccgggc ggggggtggc ggcaggtggg ggtgccgggc   2220
ggggcggggc cgcctcgggc cggggagggc tcgggggagg ggcgcggcgg ccccggagcg   2280
ccggcggctg tcgaggcgcg gcgagccgca gccattgcct tttatggtaa tcgtgcgaga   2340
gggcgcaggg acttcctttg tcccaaatct ggcggagccg aaatctggga ggcgccgccg   2400
caccccctct agcgggcgcg ggcgaagcgg tgcggcgccg gcaggaagga aatgggcggg   2460
gagggccttc gtgcgtcgcc gcgccgccgt ccccttctcc atctccagcc tcggggctgc   2520
cgcagggggga cggctgcctt cgggggggac ggggcagggc ggggttcggc ttctggcgtg   2580
tgaccggcgg ctctagagcc tctgctaacc atgttcatgc cttcttcttt ttcctacagg   2640
ggggatccgt ttatctgcag aattcgccct tgacgtcgcc accatggaag atacaaagga   2700
gtctaacgtg aagacatttt gctccaagaa tatcctagcc atccttggct tctcctctat   2760
catagctgtg atagctttgc ttgctgtggg gttgacccag aacaaagcat tgccagaaaa   2820
cgttaagtat gggattgtgc tggatgcggg ttcttctcac acaagtttat acatctataa   2880
gtggccagca gaaaaggaga atgacacagg cgtggtgcat caagtagaag aatgcagggt   2940
taaaggtcct ggaatctcaa aatttgttca gaaagtaaat gaaataggca tttacctgac   3000
```

```
tgattgcatg gaaagagcta gggaagtgat tccaaggtcc cagcaccaag agacacccgt   3060
ttacctggga gccacggcag gcatgcggtt gctcaggatg gaaagtgaag agttggcaga   3120
cagggttctg gatgtggtgg agaggagcct cagcaactac ccctttgact tccagggtgc   3180
caggatcatt actggccaag aggaaggtgc ctatggctgg attactatca actatctgct   3240
gggcaaattc agtcagaaaa caaggtggtt cagcatagtc ccatatgaaa ccaataatca   3300
ggaaaccttt ggagctttgg accttggggg agcctctaca caagtcactt ttgtacccca   3360
aaaccagact atcgagtccc cagataatgc tctgcaattt cgcctctatg gcaaggacta   3420
caatgtctac acacatagct tcttgtgcta tgggaaggat caggcactct ggcagaaact   3480
ggccaaggac attcaggttg caagtaatga aattctcagg gacccatgct ttcatcctgg   3540
atataagaag gtagtgaacg taagtgacct ttacaagacc ccctgcacca agagatttga   3600
gatgactctt ccattccagc agtttgaaat ccagggtatt ggaaactatc aacaatgcca   3660
tcaaagcatc ctggagctct tcaacaccag ttactgccct tactcccagt gtgccttcaa   3720
tgggattttc ttgccaccac tccaggggga ttttggggca ttttcagctt tttactttgt   3780
gatgaagttt ttaaacttga catcagagaa agtctctcag gaaaaggtga ctgagatgat   3840
gaaaaagttc tgtgctcagc cttgggagga gataaaaaca tcttacgctg gagtaaagga   3900
gaagtacctg agtgaatact gcttttctgg tacctacatt ctctccctcc ttctgcaagg   3960
ctatcatttc acagctgatt cctgggagca catccatttc attggcaaga tccagggcag   4020
cgacgccggc tggactttgg gctacatgct gaacctgacc aacatgatcc cagctgagca   4080
accattgtcc acacctctct cccactccac ctatgtcttc ctcatggttc tattctccct   4140
ggtccttttc acagtggcca tcataggctt gcttatcttt cacaagcctt catatttctg   4200
gaaagatatg gtataatgat agccgctgat cagcctcgac tgtgccttct agttgccagc   4260
catctgttgt ttgcccctcc cccgtgcctt ccttgaccct ggaaggtgcc actcccactg   4320
tcctttccta ataaaatgag gaaattgcat cgcattgtct gagtaggtgt cattctattc   4380
tggggggtgg ggtggggcag gacagcaagg gggaggattg ggaagacaat agcaggcatg   4440
ctggggatgc ggtgggctct atgggtcgac tgaccagatg gacctggctg gagaagaaga   4500
gattgagctc tactcaggtg ggccctcctc cctctggtct cttccggtat cccccacccc   4560
tcagcttgct gtagagacgg caatcagggg aaattctggt ccctgccctc ccgtcagcac   4620
cacggacagc tcccacgtct gtgggacgct ctctgcagat ggggatgatc tcccagccct   4680
gccccgcctc tccctcgttc cccaccagcc ctctttccag aaatttcctt cttcatccaa   4740
gggacttttc ctcccagaac ccgacacaga caccatcaac tgcgaccagt tcagcaggct   4800
gttgtgtgac atggaaggtg atgaagagac cagggaggct tatgccaata tcggtgagga   4860
agcacctgag cccagaaaag gacaatcaag ggcaagagtt ctttgctgcc acttgtcaat   4920
atcacccatt catcatgagc cacgtcagtc ccctcccaca gaaatcattg caagggggat   4980
gcggagcaat ggctggagga acggagactc cagggaagag aggggagatg gaggccagtg   5040
ggggaaatag gcccccttcac taatgaccac caagaaaaca aaatctcatg tttacatcct   5100
ccacctccat ttctatacgc atttctgctt cttgctcttc tgtccatcct ttctacaaag   5160
cccataccat acacccccttt cccttttcct cccagctcct tagccaagct actctagtat   5220
ttgtaataac tagcatttac tggatactca tagtatgctc attgctgtcc ggtaaccacg   5280
tgcggaccga ggctgcagcg tcgtcctccc taggaacccc tagtgatgga gttggccact   5340
```

```
ccctctctgc gcgctcgctc gctcactgag gccgggcgac caaaggtcgc ccgacgcccg   5400
ggctttgccc gggcggcctc agtgagcgag cgagcgcgca gctgcctgca ggggcgcctg   5460
atgcggtatt ttctccttac gcatctgtgc ggtatttcac accgcatacg tcaaagcaac   5520
catagtacgc gccctgtagc ggcgcattaa gcgcggcggg tgtggtggtt acgcgcagcg   5580
tgaccgctac acttgccagc gccctagcgc ccgctccttt cgctttcttc ccttcctttc   5640
tcgccacgtt cgccggcttt ccccgtcaag ctctaaatcg ggggctccct ttagggttcc   5700
gatttagtgc tttacggcac ctcgacccca aaaaacttga tttgggtgat ggttcacgta   5760
gtgggccatc gccctgatag acggtttttc gccctttgac gttggagtcc acgttcttta   5820
atagtggact cttgttccaa actggaacaa cactcaaccc tatctcgggc tattcttttg   5880
atttataagg gattttgccg atttcggcct attggttaaa aaatgagctg atttaacaaa   5940
aatttaacgc gaattttaac aaaatattaa cgtttacaat tttatggtgc actctcagta   6000
caatctgctc tgatgccgca tagttaagcc agccccgaca cccgccaaca cccgctgacg   6060
cgccctgacg ggcttgtctg ctcccggcat ccgcttacag acaagctgtg accgtctccg   6120
ggagctgcat gtgtcagagg ttttcaccgt catcaccgaa acgcgcgaga cgaaagggcc   6180
tcgtgatacg cctattttta taggttaatg tcatgaacaa taaaactgtc tgcttacata   6240
aacagtaata caaggggtgt tatgagccat attcaacggg aaacgtcgag gccgcgatta   6300
aattccaaca tggatgctga tttatatggg tataaatggg ctcgcgataa tgtcgggcaa   6360
tcaggtgcga caatctatcg cttgtatggg aagcccgatg cgccagagtt gtttctgaaa   6420
catggcaaag gtagcgttgc caatgatgtt acagatgaga tggtcagact aaactggctg   6480
acggaattta tgcctcttcc gaccatcaag cattttatcc gtactcctga tgatgcatgg   6540
ttactcacca ctgcgatccc cggaaaaaca gcattccagg tattagaaga atatcctgat   6600
tcaggtgaaa atattgttga tgcgctggca gtgttcctgc gccggttgca ttcgattcct   6660
gtttgtaatt gtccttttaa cagcgatcgc gtatttcgtc tcgctcaggc gcaatcacga   6720
atgaataacg gtttggttga tgcgagtgat tttgatgacg agcgtaatgg ctggcctgtt   6780
gaacaagtct ggaaagaaat gcataaactt ttgccattct caccggattc agtcgtcact   6840
catggtgatt tctcacttga taaccttatt tttgacgagg ggaaattaat aggttgtatt   6900
gatgttggac gagtcggaat cgcagaccga taccaggatc ttgccatcct atggaactgc   6960
ctcggtgagt tttctccttc attacagaaa cggctttttc aaaaatatgg tattgataat   7020
cctgatatga ataaattgca gtttcatttg atgctcgatg agtttttcta atctcatgac   7080
caaaatccct taacgtgagt tttcgttcca ctgagcgtca gaccccgtag aaaagatcaa   7140
aggatcttct tgagatcctt tttttctgcg cgtaatctgc tgcttgcaaa caaaaaaacc   7200
accgctacca gcggtggttt gtttgccgga tcaagagcta ccaactcttt ttccgaaggt   7260
aactggcttc agcagagcgc agataccaaa tactgtcctt ctagtgtagc cgtagttagg   7320
ccaccacttc aagaactctg tagcaccgcc tacatacctc gctctgctaa tcctgttacc   7380
agtggctgct gccagtggcg ataagtcgtg tcttaccggg ttggactcaa gacgatagtt   7440
accggataag gcgcagcggt cgggctgaac ggggggttcg tgcacacagc ccagcttgga   7500
gcgaacgacc tacaccgaac tgagatacct acagcgtgag ctatgagaaa gcgccacgct   7560
tcccgaaggg agaaaggcgg acaggtatcc ggtaagcggc agggtcggaa caggagagcg   7620
cacgagggag cttccagggg gaaacgcctg gtatctttat agtcctgtcg ggtttcgcca   7680
```

cctctgactt gagcgtcgat ttttgtgatg ctcgtcaggg gggcggagcc tatggaaaaa 7740
cgccagcaac gcggcctttt tacggttcct ggccttttgc tggccttttg ctcacatgt 7799

<210> SEQ ID NO 30
<211> LENGTH: 8729
<212> TYPE: DNA
<213> ORGANISM: Artificial Sequence
<220> FEATURE:
<223> OTHER INFORMATION: Synthetic

<400> SEQUENCE: 30
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtgttcta gggtggaaac taagagaatg atgtacctag 180
agggcgctgg aagctctaaa gccctagcag ttactgcttt tactattagt ggtcgttttt 240
ttctcccccc cgcccccccga caaatcaaca gaacaaagaa aattacctaa acagcaagga 300
catagggagg aacttcttgg cacagaactt tccaaacact tttcctgaa gggatacaag 360 aagcaagaaa ggtactcttt cactaggacc ttctctgagc tgtcctcagg atgcttttgg 420
gactattttt cttacccaga gaatggagaa accctgcagg gaattcccaa gctgtagtta 480
taaacagaag ttctccttct gctaggtagc attcaaagat cttaatcttc tgggtttccg 540
ttttctcgaa tgaaaaatgc aggtccgagc agttaactgg ctggggcacc attagcaagt 600
cacttagcat ctctggggcc agtctgcaaa gcgagggggc agccttaatg tgcctccagc 660
ctgaagtcct agaatgagcg cccggtgtcc caagctgggg cgcgcacccc agatcggagg 720
gcgccgatgt acagacagca aactcaccca gtctagtgca tgccttctta aacatcacga 780
gactctaaga aaaggaaact gaaaacggga aagtccctct ctctaacctg gcactgcgtc 840
gctggcttgg agacaggtga cggtccctgc gggccttgtc ctgattggct gggcacgcgt 900
ttaatataag tggaggcgtc gcgctggcgg gcattcctga agctaagctt gtggacgata 960
tcgaattcgc acgacattga ttattgacta gttattaata gtaatcaatt acggggtcat 1020
tagttcatag cccatatatg gagttccgcg ttacataact tacggtaaat ggcccgcctg 1080
gctgaccgcc caacgacccc cgcccattga cgtcaataat gacgtatgtt cccatagtaa 1140
cgccaatagg gactttccat tgacgtcaat gggtggacta tttacggtaa actgcccact 1200
tggcagtaca tcaagtgtat catatgccaa gtacgccccc tattgacgtc aatgacggta 1260
aatggcccgc ctggcattat gcccagtaca tgaccttatg ggactttcct acttggcagt 1320
acatctacgt attagtcatc gctattacca tgggtcgagg tgagccccac gttctgcttc 1380
actctcccca tctccccccc ctccccaccc ccaattttgt atttatttat tttttaatta 1440
ttttgtgcag cgatgggggc gggggggggg ggggcgcgcg ccaggcgggg cggggcgggg 1500
cgaggggcgg ggcggggcga ggcggagagg tgcggcggca gccaatcaga gcggcgcgct 1560
ccgaaagttt ccttttatgg cgaggcggcg gcggcggcgg ccctataaaa agcgaagcgc 1620
gcggcgggcg ggagtcgctg cgttgccttc gccccgtgcc ccgctccgcg ccgcctcgcg 1680
ccgcccgccc cggctctgac tgaccgcgtt actcccacag gtgagcgggc gggacggccc 1740
ttctcctccg ggctgtaatt agcgcttggt ttaatgacgg ctcgtttctt ttctgtggct 1800
gcgtgaaagc cttaaagggc tccgggaggg ccctttgtgc ggggggggagc ggctcggggg 1860 gtgcgtgcgt gtgtgtgtgc gtggggagcg ccgcgtgcgg cccgcgctgc ccggcggctg 1920

-continued

```
tgagcgctgc gggcgcggcg cggggctttg tgcgctccgc gtgtgcgcga ggggagcgcg   1980
gccgggggcg gtgccccgcg gtgcgggggg gctgcgaggg gaacaaaggc tgcgtgcggg   2040
gtgtgtgcgt gggggggtga gcagggggtg tgggcgcggc ggtcgggctg taaccccccc   2100
ctgcaccccc ctccccgagt tgctgagcac ggcccggctt cgggtgcggg gctccgtgcg   2160
gggcgtggcg cggggctcgc cgtgccgggc ggggggtggc ggcaggtggg ggtgccgggc   2220
ggggcggggc cgcctcgggc cggggagggc tcgggggagg ggcgcggcgg ccccggagcg   2280
ccggcggctg tcgaggcgcg gcgagccgca gccattgcct tttatggtaa tcgtgcgaga   2340
gggcgcaggg acttcctttg tcccaaatct ggcggagccg aaatctggga ggcgccgccg   2400
caccccctct agcgggcgcg ggcgaagcgg tgcggcgccg gcaggaagga aatgggcggg   2460
gagggccttc gtgcgtcgcc gcgccgccgt ccccttctcc atctccagcc tcggggctgc   2520
cgcagggggga cggctgcctt cgggggggac ggggcagggc ggggttcggc ttctggcgtg   2580
tgaccggcgg ctctagagcc tctgctaacc atgttcatgc cttcttcttt ttcctacagg   2640
ggggatccgt ttatctgcag aattcgccct tgacgtcgcc accatggaag atacaaagga   2700
gtctaacgtg aagacatttt gctccaagaa tatcctagcc atccttggct tctcctctat   2760
catagctgtg atagctttgc ttgctgtggg gttgacccag aacaaagcat tgccagaaaa   2820
cgttaagtat gggattgtgc tggatgcggg ttcttctcac acaagtttat acatctataa   2880
gtggccagca gaaaaggaga atgacacagg cgtggtgcat caagtagaag aatgcagggt   2940
taaaggtcct ggaatctcaa aatttgttca gaaagtaaat gaaataggca tttacctgac   3000
tgattgcatg gaaagagcta gggaagtgat tccaaggtcc cagcaccaag agacacccgt   3060
ttacctggga gccacggcag gcatgcggtt gctcaggatg gaaagtgaag agttggcaga   3120
cagggttctg gatgtggtgg agaggagcct cagcaactac ccctttgact tccagggtgc   3180
caggatcatt actggccaag aggaaggtgc ctatggctgg attactatca actatctgct   3240
gggcaaattc agtcagaaaa caaggtggtt cagcatagtc ccatatgaaa ccaataatca   3300
ggaaaccttt ggagctttgg accttggggg agcctctaca caagtcactt ttgtacccca   3360
aaaccagact atcgagtccc cagataatgc tctgcaattt cgcctctatg gcaaggacta   3420
caatgtctac acacatagct tcttgtgcta tgggaaggat caggcactct ggcagaaact   3480
ggccaaggac attcaggttg caagtaatga aattctcagg gacccatgct ttcatcctgg   3540
atataagaag gtagtgaacg taagtgacct ttacaagacc ccctgcacca agagatttga   3600
gatgactctt ccattccagc agtttgaaat ccagggtatt ggaaactatc aacaatgcca   3660
tcaaagcatc ctggagctct tcaacaccag ttactgccct tactcccagt gtgccttcaa   3720
tgggattttc ttgccaccac tccaggggga ttttggggca ttttcagctt tttactttgt   3780
gatgaagttt ttaaacttga catcagagaa agtctctcag gaaaaggtga ctgagatgat   3840
gaaaaagttc tgtgctcagc cttgggagga gataaaaaca tcttacgctg gagtaaagga   3900
gaagtacctg agtgaatact gcttttctgg tacctacatt ctctccctcc ttctgcaagg   3960
ctatcatttc acagctgatt cctgggagca catccatttc attggcaaga tccagggcag   4020
cgacgccggc tggactttgg gctacatgct gaacctgacc aacatgatcc cagctgagca   4080
accattgtcc acacctctct cccactccac ctatgtcttc ctcatggttc tattctccct   4140
ggtccttttc acagtggcca tcataggctt gcttatcttt cacaagcctt catatttctg   4200
gaaagatatg gtaggaagcg gagctactaa cttcagcctg ctgaagcagg ctggagacgt   4260
ggaggagaac cctggaccta tgaggatatt tgctgtcttt atattcatga cctactggca   4320
```

-continued tttgctgaac gcatttactg tcacggttcc caaggaccta tatgtggtag agtatggtag 4380
caatatgaca attgaatgca aattcccagt agaaaaacaa ttagacctgg ctgcactaat 4440
tgtctattgg gaaatggagg ataagaacat tattcaattt gtgcatggag aggaagacct 4500
gaaggttcag catagtagct acagacagag ggcccggctg ttgaaggacc agctctccct 4560
gggaaatgct gcacttcaga tcacagatgt gaaattgcag gatgcagggg tgtaccgctg 4620
catgatcagc tatggtggtg ccgactacaa gcgaattact gtgaaagtca atgccccata 4680
caacaaaatc aaccaaagaa ttttggttgt ggatccagtc acctctgaac atgaactgac 4740
atgtcaggct gagggctacc ccaaggccga agtcatctgg acaagcagtg accatcaagt 4800
cctgagtggt aagaccacca ccaccaattc caagagagag gagaaacttt tcaatgtgac 4860
cagcacactg agaatcaaca caacaactaa tgagattttc tactgcactt ttaggagatt 4920
agatcctgag gaaaaccata cagctgaatt ggtcatccca gaactacctc tggcacatcc 4980
tccaaatgaa aggactcact tggtaattct gggagccatc ttattatgcc ttggtgtagc 5040
actgacattc atcttccgtt taagaaaagg gagaatgatg gatgtgaaaa aatgtggcat 5100
ccaagataca aactcaaaga agcaaagtga tacacatttg gaggagacgt aaccgctgat 5160
cagcctcgac tgtgccttct agttgccagc catctgttgt ttgcccctcc cccgtgcctt 5220
ccttgaccct ggaaggtgcc actcccactg tcctttccta ataaaatgag gaaattgcat 5280
cgcattgtct gagtaggtgt cattctattc tggggggtgg ggtggggcag gacagcaagg 5340
gggaggattg ggaagacaat agcaggcatg ctggggatgc ggtgggctct atgggtcgac 5400
ccagcgtgag tctctcctac cctcccgctc tggtccttcc tctcccgctc tgcaccctct 5460
gtggccctcg ctgtgctctc tcgctccgtg acttcccttc tccaagttct ccttggtggc 5520
ccgccgtggg gctagtccag ggctggatct cggggaagcg gcggggtggc ctgggagtgg 5580
ggaagggggt gcgcacccgg gacgcgcgct acttgcccct ttcggcgggg agcaggggag 5640
acctttggcc tacggcgacg ggagggtcgg gacaaagttt agggcgtcga taagcgtcag 5700
agcgccgagg ttgggggagg gtttctcttc cgctctttcg cggggcctct ggctcccccca 5760
gcgcagctgg agtgggggac gggtaggctc gtcccaaagg cgcggcgctg aggtttgtga 5820
acgcgtggag gggcgcttgg ggtctggggg aggcgtcgcc cgggtaagcc tgtctgctgc 5880
ggctctgctt cccttagact ggagagctgt ggacttcgtc taggcgcccg ctaagttcgc 5940
atgtcctagc acctctgggt ctatgtgggg ccacaccgtg ggggaggaaac agcacgcgac 6000
gtttgtagaa tgcttggctg tgatacaaag cggtttcgaa taattaactt atttgttccc 6060
atcacatgtc acttttaaaa aattataaga actacccgtt attgacatct ttctgtgtgc 6120
caaggacttt atgtgctttg cgtcatttaa ttttgaaaac agttatcttc cgccatagat 6180
aactactatg gttatcttct ggtaaccacg tgcggaccga ggctgcagcg tcgtcctccc 6240
taggaacccc tagtgatgga gttggccact ccctctctgc gcgctcgctc gctcactgag 6300
gccgggcgac caaaggtcgc ccgacgcccg ggctttgccc gggcggcctc agtgagcgag 6360
cgagcgcgca gctgcctgca ggggcgcctg atgcggtatt ttctccttac gcatctgtgc 6420
ggtatttcac accgcatacg tcaaagcaac catagtacgc gccctgtagc ggcgcattaa 6480
gcgcggcggg tgtggtggtt acgcgcagcg tgaccgctac acttgccagc gccctagcgc 6540
ccgctccttt cgctttcttc ccttcctttc tcgccacgtt cgccggcttt ccccgtcaag 6600
ctctaaatcg ggggctccct ttagggttcc gatttagtgc tttacggcac ctcgacccca 6660
aaaaacttga tttgggtgat ggttcacgta gtgggccatc gccctgatag acggtttttc 6720
gccctttgac gttggagtcc acgttcttta atagtggact cttgttccaa actggaacaa 6780
cactcaaccc tatctcgggc tattcttttg atttataagg gattttgccg atttcggcct 6840
attggttaaa aaatgagctg atttaacaaa aatttaacgc gaattttaac aaaatattaa 6900
cgtttacaat tttatggtgc actctcagta caatctgctc tgatgccgca tagttaagcc 6960
agccccgaca cccgccaaca cccgctgacg cgccctgacg ggcttgtctg ctcccggcat 7020
ccgcttacag acaagctgtg accgtctccg ggagctgcat gtgtcagagg ttttcaccgt 7080
catcaccgaa acgcgcgaga cgaaagggcc tcgtgatacg cctattttta taggttaatg 7140
tcatgaacaa taaaactgtc tgcttacata aacagtaata caaggggtgt tatgagccat 7200
attcaacggg aaacgtcgag gccgcgatta aattccaaca tggatgctga tttatatggg 7260
tataaatggg ctcgcgataa tgtcgggcaa tcaggtgcga caatctatcg cttgtatggg 7320
aagcccgatg cgccagagtt gtttctgaaa catggcaaag gtagcgttgc caatgatgtt 7380
acagatgaga tggtcagact aaactggctg acggaattta tgcctcttcc gaccatcaag 7440
cattttatcc gtactcctga tgatgcatgg ttactcacca ctgcgatccc cggaaaaaca 7500
gcattccagg tattagaaga atatcctgat tcaggtgaaa atattgttga tgcgctggca 7560
gtgttcctgc gccggttgca ttcgattcct gtttgtaatt gtccttttaa cagcgatcgc 7620
gtatttcgtc tcgctcaggc gcaatcacga atgaataacg gtttggttga tgcgagtgat 7680
tttgatgacg agcgtaatgg ctggcctgtt gaacaagtct ggaaagaaat gcataaactt 7740
ttgccattct caccggattc agtcgtcact catggtgatt tctcacttga taaccttatt 7800
tttgacgagg ggaaattaat aggttgtatt gatgttggac gagtcggaat cgcagaccga 7860
taccaggatc ttgccatcct atggaactgc ctcggtgagt tttctccttc attacagaaa 7920
cggctttttc aaaaatatgg tattgataat cctgatatga ataaattgca gtttcatttg 7980
atgctcgatg agtttttcta atctcatgac caaaatccct taacgtgagt tttcgttcca 8040
ctgagcgtca gaccccgtag aaaagatcaa aggatcttct tgagatcctt tttttctgcg 8100
cgtaatctgc tgcttgcaaa caaaaaaacc accgctacca gcggtggttt gtttgccgga 8160
tcaagagcta ccaactcttt ttccgaaggt aactggcttc agcagagcgc agataccaaa 8220
tactgtcctt ctagtgtagc cgtagttagg ccaccacttc aagaactctg tagcaccgcc 8280
tacatacctc gctctgctaa tcctgttacc agtggctgct gccagtggcg ataagtcgtg 8340
tcttaccggg ttggactcaa gacgatagtt accggataag gcgcagcggt cgggctgaac 8400
ggggggttcg tgcacacagc ccagcttgga gcgaacgacc tacaccgaac tgagatacct 8460
acagcgtgag ctatgagaaa gcgccacgct tcccgaaggg agaaaggcgg acaggtatcc 8520
ggtaagcggc agggtcggaa caggagagcg cacgagggag cttccagggg gaaacgcctg 8580
gtatctttat agtcctgtcg ggtttcgcca cctctgactt gagcgtcgat ttttgtgatg 8640
ctcgtcaggg gggcggagcc tatggaaaaa cgccagcaac gcggcctttt tacggttcct 8700
ggccttttgc tggccttttg ctcacatgt 8729

<210> SEQ ID NO 31
<211> LENGTH: 9569
<212> TYPE: DNA
<213> ORGANISM: Artificial Sequence
<220> FEATURE:
<223> OTHER INFORMATION: Synthetic

<400> SEQUENCE: 31

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggccgcac gcgtgttcta gggtggaaac taagagaatg atgtacctag    180
agggcgctgg aagctctaaa gccctagcag ttactgcttt tactattagt ggtcgttttt    240
ttctcccccc cgccccccga caaatcaaca gaacaaagaa aattacctaa acagcaagga    300
catagggagg aacttcttgg cacagaactt tccaaacact tttcctgaa gggatacaag     360
aagcaagaaa ggtactcttt cactaggacc ttctctgagc tgtcctcagg atgcttttgg    420
gactattttt cttacccaga gaatggagaa accctgcagg gaattcccaa gctgtagtta    480
taaacagaag ttctccttct gctaggtagc attcaaagat cttaatcttc tgggtttccg    540
ttttctcgaa tgaaaaatgc aggtccgagc agttaactgg ctggggcacc attagcaagt    600
cacttagcat ctctggggcc agtctgcaaa gcgagggggc agccttaatg tgcctccagc    660
ctgaagtcct agaatgagcg cccggtgtcc caagctgggg cgcgcacccc agatcggagg    720
gcgccgatgt acagacagca aactcaccca gtctagtgca tgccttctta aacatcacga    780
gactctaaga aaaggaaact gaaaacggga aagtccctct ctctaacctg gcactgcgtc    840
gctggcttgg agacaggtga cggtccctgc gggccttgtc ctgattggct gggcacgcgt    900
ttaatataag tggaggcgtc gcgctggcgg gcattcctga agctaagctt gtggacgata    960
tcgaattcgc acgacattga ttattgacta gttattaata gtaatcaatt acggggtcat   1020
tagttcatag cccatatatg gagttccgcg ttacataact tacggtaaat ggcccgcctg   1080
gctgaccgcc caacgacccc cgcccattga cgtcaataat gacgtatgtt cccatagtaa   1140
cgccaatagg gactttccat tgacgtcaat gggtggacta tttacggtaa actgcccact   1200
tggcagtaca tcaagtgtat catatgccaa gtacgccccc tattgacgtc aatgacggta   1260
aatggcccgc ctggcattat gcccagtaca tgaccttatg ggactttcct acttggcagt   1320
acatctacgt attagtcatc gctattacca tgggtcgagg tgagccccac gttctgcttc   1380
actctcccca tctccccccc ctccccaccc ccaattttgt atttatttat tttttaatta   1440
ttttgtgcag cgatgggggc gggggggggg ggggcgcgcg ccaggcgggg cggggcgggg   1500
cgaggggcgg ggcggggcga ggcggagagg tgcggcggca gccaatcaga gcggcgcgct   1560
ccgaaagttt ccttttatgg cgaggcggcg gcggcggcgg ccctataaaa agcgaagcgc   1620
gcggcgggcg ggagtcgctg cgttgccttc gccccgtgcc ccgctccgcg ccgcctcgcg   1680
ccgcccgccc cggctctgac tgaccgcgtt actcccacag gtgagcgggc gggacggccc   1740
ttctcctccg ggctgtaatt agcgcttggt ttaatgacgg ctcgtttctt ttctgtggct   1800
gcgtgaaagc cttaaagggc tccgggaggg ccctttgtgc ggggggggagc ggctcggggg   1860
gtgcgtgcgt gtgtgtgtgc gtggggagcg ccgcgtgcgg cccgcgctgc ccggcggctg   1920
tgagcgctgc gggcgcggcg cggggctttg tgcgctccgc gtgtgcgcga ggggagcgcg   1980
gccgggggcg gtgccccgcg gtgcgggggg gctgcgaggg gaacaaaggc tgcgtgcggg   2040
gtgtgtgcgt gggggggtga gcagggggtg tgggcgcggc ggtcgggctg taaccccccc   2100
ctgcaccccc ctccccgagt tgctgagcac ggcccggctt cgggtgcggg gctccgtgcg   2160
gggcgtggcg cggggctcgc cgtgccgggc ggggggtggc ggcaggtggg ggtgccgggc   2220
ggggcggggc cgcctcgggc cggggagggc tcgggggagg ggcgcggcgg ccccggagcg   2280
```

ccggcggctg tcgaggcgcg gcgagccgca gccattgcct tttatggtaa tcgtgcgaga 2340
gggcgcaggg acttcctttg tcccaaatct ggcggagccg aaatctggga ggcgccgccg 2400
cacccccctct agcgggcgcg ggcgaagcgg tgcggcgccg gcaggaagga aatgggcggg 2460
gagggccttc gtgcgtcgcc gcgccgccgt ccccttctcc atctccagcc tcggggctgc 2520
cgcaggggga cggctgcctt cgggggggac ggggcagggc ggggttcggc ttctggcgtg 2580
tgaccggcgg ctctagagcc tctgctaacc atgttcatgc cttcttcttt ttcctacagg 2640
ggggatccgt ttatctgcag aattcgccct tgacgtcgcc accatggctg aacaagtcct 2700
tcctcaggct ttgtatttga gcaatatgcg gaaagctgtg aagatacggg agagaactcc 2760
agaagacatt tttaaaccta ctaatgggat cattcatcat tttaaaacca tgcaccgata 2820
cacactggaa atgttcagaa cttgccagtt ttgtcctcag tttcgggaga tcatccacaa 2880
agccctcatc gacagaaaca tccaggccac cctggaaagc cagaagaaac tcaactggtg 2940
tcgagaagtc cggaagcttg tggcgctgaa aacgaacggt gacggcaatt gcctcatgca 3000
tgccacttct cagtacatgt ggggcgttca ggacacagac ttggtactga ggaaggcgct 3060
gttcagcacg ctcaaggaaa cagacacacg caactttaaa ttccgctggc aactggagtc 3120
tctcaaatct caggaatttg ttgaaacggg gctttgctat gatactcgga actggaatga 3180
tgaatgggac aatcttatca aaatggcttc cacagacaca cccatggccc gaagtggact 3240
tcagtacaac tcactggaag aaatacacat atttgtcctt tgcaacatcc tcagaaggcc 3300
aatcattgtc atttcagaca aaatgctaag aagtttggaa tcaggttcca atttcgcccc 3360
tttgaaagtg ggtggaattt acttgcctct ccactggcct gcccaggaat gctacagata 3420
ccccattgtt ctcggctatg acagccatca ttttgtaccc ttggtgaccc tgaaggacag 3480
tgggcctgaa atccgagctg ttccacttgt taacagagac cggggaagat ttgaagactt 3540
aaaagttcac tttttgacag atcctgaaaa tgagatgaag gagaagctct taaaagagta 3600
cttaatggtg atagaaatcc ccgtccaagg ctgggaccat ggcacaactc atctcatcaa 3660
tgccgcaaag ttggatgaag ctaacttacc aaaagaaatc aatctggtag atgattactt 3720
tgaacttgtt cagcatgagt acaagaaatg gcaggaaaac agcgagcagg ggaggagaga 3780
ggggcacgcc cagaatccca tggaaccttc cgtgccccag ctttctctca tggatgtaaa 3840
atgtgaaacg cccaactgcc ccttcttcat gtctgtgaac acccagcctt tatgccatga 3900
gtgctcagag aggcggcaaa agaatcaaaa caaactccca aagctgaact ccaagccggg 3960
ccctgagggg ctccctggca tggcgctcgg ggcctctcgg ggagaagcct atgagccctt 4020
ggcgtggaac cctgaggagt ccactggggg gcctcattcg gccccaccga cagcacccag 4080
cccttttctg ttcagtgaga ccactgccat gaagtgcagg agccccggct gccccttcac 4140
actgaatgtg cagcacaacg gattttgtga acgttgccac aacgcccggc aacttcacgc 4200
cagccacgcc ccagaccaca caaggcactt ggatcccggg aagtgccaag cctgcctcca 4260
ggatgttacc aggacattta atgggatctg cagtacttgc ttcaaaagga ctacagcaga 4320
ggcctcctcc agcctcagca ccagcctccc tccttcctgt caccagcgtt ccaagtcaga 4380
tccctcgcgg ctcgtccgga gcccctcccc gcattcttgc cacagagctg gaaacgacgc 4440
ccctgctggc tgcctgtctc aagctgcacg gactcctggg gacaggacgg ggacgagcaa 4500
gtgcagaaaa gccggctgcg tgtattttgg gactccagaa aacaagggct tttgcacact 4560
gtgtttcatc gagtacagag aaaacaaaca ttttgctgct gcctcaggga aagtcagtcc 4620
cacagcgtcc aggttccaga acaccattcc gtgcctgggg agggaatgcg gcacccttgg 4680
aagcaccatg tttgaaggat actgccagaa gtgtttcatt gaagctcaga atcagagatt 4740
tcatgaggcc aaaaggacag aagagcaact gagatcgagc cagcgcagag atgtgcctcg 4800
aaccacacaa agcacctcaa ggcccaagtg cgcccgggcc tcctgcaaga acatcctggc 4860
ctgccgcagc gaggagctct gcatggagtg tcagcatccc aaccagagga tgggccctgg 4920
ggcccaccgg ggtgagcctg cccccgaaga cccccccaag cagcgttgcc gggcccccgc 4980
ctgtgatcat tttggcaatg ccaagtgcaa cggctactgc aacgaatgct ttcagttcaa 5040
gcagatgtat ggcggaagcg gagctactaa cttcagcctg ctgaagcagg ctggagacgt 5100
ggaggagaac cctggaccta tgaggatatt tgctgtcttt atattcatga cctactggca 5160
tttgctgaac gcatttactg tcacggttcc caaggaccta tatgtggtag agtatggtag 5220
caatatgaca attgaatgca aattcccagt agaaaaacaa ttagacctgg ctgcactaat 5280
tgtctattgg gaaatggagg ataagaacat tattcaattt gtgcatggag aggaagacct 5340
gaaggttcag catagtagct acagacagag ggcccggctg ttgaaggacc agctctccct 5400
gggaaatgct gcacttcaga tcacagatgt gaaattgcag gatgcagggg tgtaccgctg 5460
catgatcagc tatggtggtg ccgactacaa gcgaattact gtgaaagtca atgccccata 5520
caacaaaatc aaccaaagaa ttttggttgt ggatccagtc acctctgaac atgaacttac 5580
atgtcaggct gagggctacc ccaaggccga agtcatctgg acaagcagtg accatcaagt 5640
cctgagtggt aagaccacca ccaccaattc caagagagag gagaaacttt tcaatgtgac 5700
cagcacactg agaatcaaca caacaactaa tgagattttc tactgcactt ttaggagatt 5760
agatcctgag gaaaaccata cagctgaatt ggtcatccca gaactacctc tggcacatcc 5820
tccaaatgaa aggactcact tggtaattct gggagccatc ttattatgcc ttggtgtagc 5880
actgacattc atcttccgtt taagaaaagg gagaatgatg gatgtgaaaa aatgtggcat 5940
ccaagataca aactcaaaga agcaaagtga tacacatttg gaggagacgt aaccgctgat 6000
cagcctcgac tgtgccttct agttgccagc catctgttgt ttgcccctcc cccgtgcctt 6060
ccttgaccct ggaaggtgcc actcccactg tcctttccta ataaaatgag gaaattgcat 6120
cgcattgtct gagtaggtgt cattctattc tggggggtgg ggtggggcag gacagcaagg 6180
gggaggattg ggaagacaat agcaggcatg ctggggatgc ggtgggctct atgggtcgac 6240
ccagcgtgag tctctcctac cctcccgctc tggtccttcc tctcccgctc tgcaccctct 6300
gtggccctcg ctgtgctctc tcgctccgtg acttcccttc tccaagttct ccttggtggc 6360
ccgccgtggg gctagtccag ggctggatct cggggaagcg gcggggtggc ctgggagtgg 6420
ggaagggggt gcgcacccgg gacgcgcgct acttgcccct ttcggcgggg agcaggggag 6480
acctttggcc tacggcgacg ggagggtcgg gacaaagttt agggcgtcga taagcgtcag 6540
agcgccgagg ttgggggagg gtttctcttc cgctctttcg cggggcctct ggctcccccca 6600
gcgcagctgg agtgggggac gggtaggctc gtcccaaagg cgcggcgctg aggtttgtga 6660
acgcgtggag ggcgcttgg ggtctggggg aggcgtcgcc cgggtaagcc tgtctgctgc 6720
ggctctgctt cccttagact ggagagctgt ggacttcgtc taggcgcccg ctaagttcgc 6780
atgtcctagc acctctgggt ctatgtgggg ccacaccgtg gggaggaaac agcacgcgac 6840
gtttgtagaa tgcttggctg tgatacaaag cggtttcgaa taattaactt atttgttccc 6900
atcacatgtc acttttaaaa aattataaga actacccgtt attgacatct ttctgtgtgc 6960
caaggacttt atgtgctttg cgtcatttaa ttttgaaaac agttatcttc cgccatagat 7020

-continued

```
aactactatg gttatcttct ggtaaccacg tgcggaccga ggctgcagcg tcgtcctccc   7080
taggaacccc tagtgatgga gttggccact ccctctctgc gcgctcgctc gctcactgag   7140
gccgggcgac caaaggtcgc ccgacgcccg ggctttgccc gggcggcctc agtgagcgag   7200
cgagcgcgca gctgcctgca ggggcgcctg atgcggtatt ttctccttac gcatctgtgc   7260
ggtatttcac accgcatacg tcaaagcaac catagtacgc gccctgtagc ggcgcattaa   7320
gcgcggcggg tgtggtggtt acgcgcagcg tgaccgctac acttgccagc gccctagcgc   7380
ccgctccttt cgctttcttc ccttcctttc tcgccacgtt cgccggcttt ccccgtcaag   7440
ctctaaatcg ggggctccct ttagggttcc gatttagtgc tttacggcac ctcgacccca   7500
aaaaacttga tttgggtgat ggttcacgta gtgggccatc gccctgatag acggtttttc   7560
gccctttgac gttggagtcc acgttcttta atagtggact cttgttccaa actggaacaa   7620
cactcaaccc tatctcgggc tattcttttg atttataagg gattttgccg atttcggcct   7680
attggttaaa aaatgagctg atttaacaaa aatttaacgc gaattttaac aaaatattaa   7740
cgtttacaat tttatggtgc actctcagta caatctgctc tgatgccgca tagttaagcc   7800
agccccgaca cccgccaaca cccgctgacg cgccctgacg ggcttgtctg ctcccggcat   7860
ccgcttacag acaagctgtg accgtctccg ggagctgcat gtgtcagagg ttttcaccgt   7920
catcaccgaa acgcgcgaga cgaaagggcc tcgtgatacg cctattttta taggttaatg   7980
tcatgaacaa taaaactgtc tgcttacata aacagtaata caaggggtgt tatgagccat   8040
attcaacggg aaacgtcgag gccgcgatta aattccaaca tggatgctga tttatatggg   8100
tataaatggg ctcgcgataa tgtcgggcaa tcaggtgcga caatctatcg cttgtatggg   8160
aagcccgatg cgccagagtt gtttctgaaa catggcaaag gtagcgttgc caatgatgtt   8220
acagatgaga tggtcagact aaactggctg acggaattta tgcctcttcc gaccatcaag   8280
cattttatcc gtactcctga tgatgcatgg ttactcacca ctgcgatccc cggaaaaaca   8340
gcattccagg tattagaaga atatcctgat tcaggtgaaa atattgttga tgcgctggca   8400
gtgttcctgc gccggttgca ttcgattcct gtttgtaatt gtccttttaa cagcgatcgc   8460
gtatttcgtc tcgctcaggc gcaatcacga atgaataacg gtttggttga tgcgagtgat   8520
tttgatgacg agcgtaatgg ctggcctgtt gaacaagtct ggaaagaaat gcataaactt   8580
ttgccattct caccggattc agtcgtcact catggtgatt tctcacttga taaccttatt   8640
tttgacgagg ggaaattaat aggttgtatt gatgttggac gagtcggaat cgcagaccga   8700
taccaggatc ttgccatcct atggaactgc ctcggtgagt tttctccttc attacagaaa   8760
cggctttttc aaaaatatgg tattgataat cctgatatga ataaattgca gtttcatttg   8820
atgctcgatg agtttttcta atctcatgac caaaatccct taacgtgagt tttcgttcca   8880
ctgagcgtca gaccccgtag aaaagatcaa aggatcttct tgagatcctt tttttctgcg   8940
cgtaatctgc tgcttgcaaa caaaaaaacc accgctacca gcggtggttt gtttgccgga   9000
tcaagagcta ccaactcttt ttccgaaggt aactggcttc agcagagcgc agataccaaa   9060
tactgtcctt ctagtgtagc cgtagttagg ccaccacttc aagaactctg tagcaccgcc   9120
tacatacctc gctctgctaa tcctgttacc agtggctgct gccagtggcg ataagtcgtg   9180
tcttaccggg ttggactcaa gacgatagtt accggataag gcgcagcggt cgggctgaac   9240
ggggggttcg tgcacacagc ccagcttgga gcgaacgacc tacaccgaac tgagatacct   9300
acagcgtgag ctatgagaaa gcgccacgct tcccgaaggg agaaaggcgg acaggtatcc   9360
ggtaagcggc agggtcggaa caggagagcg cacgagggag cttccagggg gaaacgcctg   9420
```

gtatctttat agtcctgtcg ggtttcgcca cctctgactt gagcgtcgat ttttgtgatg 9480
ctcgtcaggg gggcggagcc tatggaaaaa cgccagcaac gcggcctttt tacggttcct 9540
ggccttttgc tggccttttg ctcacatgt 9569

<210> SEQ ID NO 32
<211> LENGTH: 20
<212> TYPE: DNA
<213> ORGANISM: Homo sapiens

<400> SEQUENCE: 32
gaagcgtgtc ttcatagcgc 20

<210> SEQ ID NO 33
<211> LENGTH: 20
<212> TYPE: DNA
<213> ORGANISM: Homo sapiens

<400> SEQUENCE: 33
ttactcgtgt caaagccgtt 20

<210> SEQ ID NO 34
<211> LENGTH: 20
<212> TYPE: DNA
<213> ORGANISM: Homo sapiens

<400> SEQUENCE: 34
tgtcaaagcc gttaggatcc 20

<210> SEQ ID NO 35
<211> LENGTH: 20
<212> TYPE: DNA
<213> ORGANISM: Homo sapiens

<400> SEQUENCE: 35
gccgttagga tcctggcttg 20

<210> SEQ ID NO 36
<211> LENGTH: 20
<212> TYPE: DNA
<213> ORGANISM: Homo sapiens

<400> SEQUENCE: 36
gcggagtggc taaagtgctt 20

<210> SEQ ID NO 37
<211> LENGTH: 20
<212> TYPE: DNA
<213> ORGANISM: Homo sapiens

<400> SEQUENCE: 37
tccgcaagcc aggatcctaa 20

<210> SEQ ID NO 38
<211> LENGTH: 20
<212> TYPE: DNA
<213> ORGANISM: Homo sapiens

<400> SEQUENCE: 38
gttcggcttt gagcttcctc 20

<210> SEQ ID NO 39

<211> LENGTH: 20
<212> TYPE: DNA
<213> ORGANISM: Homo sapiens

<400> SEQUENCE: 39
gagatggtga tcatgagacc 20

<210> SEQ ID NO 40
<211> LENGTH: 20
<212> TYPE: DNA
<213> ORGANISM: Homo sapiens

<400> SEQUENCE: 40
ttgtactcat atttgtttcc 20

<210> SEQ ID NO 41
<211> LENGTH: 20
<212> TYPE: DNA
<213> ORGANISM: Homo sapiens

<400> SEQUENCE: 41
aacaaatatg agtacaagtt 20

<210> SEQ ID NO 42
<211> LENGTH: 800
<212> TYPE: DNA
<213> ORGANISM: Homo sapiens

<400> SEQUENCE: 42
accgctctca gaccagaaac gtccacaccc gccctccgat ggcctgtcgc cctggctagg 60
ttttagggtc agtgggatcc tccttccact ggacccggga gaagacgctc aacagccccc 120
tccttcccct ccttcctctc cttcctctcc ttccccccctc cctgcgccgc tccagagcgc 180
aacaaccatt ttcccagcca ggagcacacc gtgtccacgc gccacagcga tctcactgat 240
tggtcgggct cctggtaaac aaggaccggg cagccaatgg gagggatgtg cacgagggca 300
gcacgagcct ccgggccagc gctcgcgtgg ctcttctggc ccgggctact atatagagac 360
gtttccgcct cctgcttgaa actaacccct ctttttctcc aaaggagtgc ttgtggagat 420
cggatctttt ctccagcaat tgggggaaag aaggcttttt ctctgaatta gcttagtgta 480
accagcggcg tatatttttt aggcgccttt tcgaaaacct agtagttaat attcatttgt 540
ttaaatctta ttttattttt aagctcaaac tgcttaagaa taccttaatt ccttaaagtg 600
aaataatttt ttgcaaaggg gtttcctcga tttggagctt ttttttcttt ccaccgtcat 660
ttctaactct taaaaccaac tcagttccat catggtgatg ttcaagaaga tcaagtcttt 720
tgaggtggtc tttaacgacc ctgaaaaggt gtacggcagt ggcgagaagg tggctggccg 780
ggtgatagtg gaggtgtgtg 800

<210> SEQ ID NO 43
<211> LENGTH: 1500
<212> TYPE: DNA
<213> ORGANISM: Artificial Sequence
<220> FEATURE:
<223> OTHER INFORMATION: Synthetic

<400> SEQUENCE: 43
atgtctcgct ccgttgcctt agctgtgctc gcgctactct ctctttctgg attagaggct 60
gtcatggcgc cccgaaccct cttcctgggt ggaggcggtt caggcggagg tggctctggc 120
ggtggcggat cgatccagcg tactccaaag attcaggttt actcacgtca tccagcagag 180

```
aatggaaagt caaatttcct gaattgctat gtgtctgggt ttcatccatc cgacattgaa    240

gttgacttac tgaagaatgg agagagaatt gaaaaagtgg agcattcaga cttgtctttc    300

agcaaggact ggtctttcta tctcttgtac tacactgaat tcaccccac tgaaaaagat    360

gagtatgcct gccgtgtgaa ccatgtgact ttgtcacagc ccaagatagt taagtgggat    420

cgagacatgg gtggtggtgg ttctggtggt ggtggttctg gcggcggcgg ctccggtggt    480

ggtggatccg gctcccactc cttgaagtat ttccacactt ccgtgtcccg gcccggccgc    540

ggggagcccc gcttcatctc tgtgggctac gtggacgaca cccagttcgt gcgcttcgac    600

aacgacgccg cgagtccgag gatggtgccg cgggcgccgt ggatggagca ggaggggtca    660

gagtattggg accgggagac acggagcgcc agggacaccg cacagatttt ccgagtgaat    720

ctgcggacgc tgcgcggcta ctacaatcag agcgaggccg ggtctcacac cctgcagtgg    780

atgcatggct gcgagctggg gcccgacggg cgcttcctcc gcgggtatga acagttcgcc    840

tacgacggca aggattatct caccctgaat gaggacctgc gctcctggac cgcggtggac    900

acggcggctc agatctccga gcaaaagtca aatgatgcct ctgaggcgga gcaccagaga    960

gcctacctgg aagacacatg cgtggagtgg ctccacaaat acctggagaa ggggaaggag   1020

acgctgcttc acctggagcc cccaaagaca cacgtgactc accaccccat ctctgaccat   1080

gaggccaccc tgaggtgctg ggccctgggc ttctaccctg cggagatcac actgacctgg   1140

cagcaggatg gggagggcca tacccaggac acggagctcg tggagaccag gcctgcaggg   1200

gatggaacct tccagaagtg ggcagctgtg gtggtgcctt ctggagagga gcagagatac   1260

acgtgccatg tgcagcatga ggggctaccc gagcccgtca ccctgagatg gaagccggct   1320

tcccagccca ccatccccat cgtgggcatc attgctggcc tggttctcct tggatctgtg   1380

gtctctggag ctgtggttgc tgctgtgata tggaggaaga agagctcagg tggaaaagga   1440

gggagctact ctaaggctga gtggagcgac agtgcccagg ggtctgagtc tcacagcttg   1500
```

<210> SEQ ID NO 44
<211> LENGTH: 800
<212> TYPE: DNA
<213> ORGANISM: Homo sapiens

<400> SEQUENCE: 44

```
cagggatccc agcagtgcaa acagacttcg gagtacctgc gctatgaaga cacgcttctt     60

ctggaagacc agccaacagg taagcggccc aattcattgt tggagggtga aagctgatta    120

gagaagagaa ttgaatacac aaaacctgta cgaaatgttt taagttgctc agtttgagtg    180

gtttgaatta cgtgttgttg cttccttttt tctgttttaa tttgcagaca ttctcctccc    240

cccccaaaaa aaagggtgat ttgtacaatt ttttatggtg ctgtgtccta aaggggatcc    300

tgaggggcgt tgcctcgggt agttaaagtc ttatgtgtgc ataagttgct tattctttgt    360

ctacttccta tttgagatgt tagtagagaa ctgtcctggg tgaatctttc agtattgcag    420

ggcttggcaa cttgctgccc gacaaaatac atcagaattt ctctttaaga acaatatggg    480

atggattaaa aaatatatat atgggatgaa attgggggta cttcaatacc ttgcatgcca    540

cccaagcatt ccttatcaca cagatgcatt ttaagtgtaa cagcaagcct aatggctact    600

cgattttctt tcccttcagg tgagaatgag atggtgatca tgagacctgg aaacaaatat    660

gagtacaagt tcggctttga gcttcctcag ggtaaatat cagctaaatg catctttgaa    720
```

ctttctgtc taaaatatct tgccctcctt tgatcactta ctgttcttgg agagcgtttt 780
aaaattttca ttttcttgac 800

<210> SEQ ID NO 45
<211> LENGTH: 8381
<212> TYPE: DNA
<213> ORGANISM: Artificial Sequence
<220> FEATURE:
<223> OTHER INFORMATION: Synthetic

<400> SEQUENCE: 45
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtaccgct ctcagaccag aaacgtccac acccgccctc 180
cgatggcctg tcgccctggc taggttttag ggtcagtggg atcctccttc cactggaccc 240
gggagaagac gctcaacagc cccctccttc ccctccttcc tctccttcct ctccttcccc 300
cctccctgcg ccgctccaga gcgcaacaac cattttccca gccaggagca caccgtgtcc 360
acgcgccaca gcgatctcac tgattggtcg ggctcctggt aaacaaggac cgggcagcca 420
atgggaggga tgtgcacgag ggcagcacga gcctccgggc cagcgctcgc gtggctcttc 480
tggcccgggc tactatatag agacgtttcc gcctcctgct tgaaactaac ccctcttttt 540
ctccaaagga gtgcttgtgg agatcggatc ttttctccag caattggggg aaagaaggct 600
ttttctctga attagcttag tgtaaccagc ggcgtatatt ttttaggcgc cttttcgaaa 660
acctagtagt taatattcat ttgtttaaat cttattttat ttttaagctc aaactgctta 720
agaatacctt aattccttaa agtgaaataa ttttttgcaa aggggtttcc tcgatttgga 780
gctttttttt tcttccaccg tcatttctaa ctcttaaaac caactcagtt ccatcatggt 840
gatgttcaag aagatcaagt cttttgaggt ggtctttaac gaccctgaaa aggtgtacgg 900
cagtggcgag aaggtggctg gccgggtgat agtggaggtg tgtgaagctt gtggacgata 960
tcgaattcgc acgacattga ttattgacta gttattaata gtaatcaatt acggggtcat 1020
tagttcatag cccatatatg gagttccgcg ttacataact tacggtaaat ggcccgcctg 1080
gctgaccgcc caacgacccc cgcccattga cgtcaataat gacgtatgtt cccatagtaa 1140
cgccaatagg gactttccat tgacgtcaat gggtggacta tttacggtaa actgcccact 1200
tggcagtaca tcaagtgtat catatgccaa gtacgccccc tattgacgtc aatgacggta 1260
aatggcccgc ctggcattat gcccagtaca tgaccttatg ggactttcct acttggcagt 1320
acatctacgt attagtcatc gctattacca tgggtcgagg tgagccccac gttctgcttc 1380
actctcccca tctccccccc ctccccaccc ccaattttgt atttatttat tttttaatta 1440
ttttgtgcag cgatgggggc gggggggggg ggggcgcgcg ccaggcgggg cggggcgggg 1500
cgaggggcgg ggcggggcga ggcggagagg tgcggcggca gccaatcaga gcggcgcgct 1560
ccgaaagttt ccttttatgg cgaggcggcg gcggcggcgg ccctataaaa agcgaagcgc 1620
gcggcgggcg ggagtcgctg cgttgccttc gccccgtgcc ccgctccgcg ccgcctcgcg 1680
ccgcccgccc cggctctgac tgaccgcgtt actcccacag gtgagcgggc gggacggccc 1740
ttctcctccg ggctgtaatt agcgcttggt ttaatgacgg ctcgtttctt ttctgtggct 1800
gcgtgaaagc cttaaagggc tccgggaggg ccctttgtgc ggggggggagc ggctcggggg 1860 gtgcgtgcgt gtgtgtgtgc gtggggagcg ccgcgtgcgg cccgcgctgc ccggcggctg 1920

-continued

```
tgagcgctgc gggcgcggcg cggggctttg tgcgctccgc gtgtgcgcga ggggagcgcg   1980
gccgggggcg gtgccccgcg gtgcgggggg gctgcgaggg gaacaaaggc tgcgtgcggg   2040
gtgtgtgcgt gggggggtga gcagggggtg tgggcgcggc ggtcgggctg taaccccccc   2100
ctgcaccccc ctccccgagt tgctgagcac ggcccggctt cgggtgcggg gctccgtgcg   2160
gggcgtggcg cggggctcgc cgtgccgggc ggggggtggc ggcaggtggg ggtgccgggc   2220
ggggcggggc cgcctcgggc cggggagggc tcgggggagg ggcgcggcgg ccccggagcg   2280
ccggcggctg tcgaggcgcg gcgagccgca gccattgcct tttatggtaa tcgtgcgaga   2340
gggcgcaggg acttcctttg tcccaaatct ggcggagccg aaatctggga ggcgccgccg   2400
caccccctct agcgggcgcg ggcgaagcgg tgcggcgccg gcaggaagga aatgggcggg   2460
gagggccttc gtgcgtcgcc gcgccgccgt ccccttctcc atctccagcc tcggggctgc   2520
cgcaggggga cggctgcctt cgggggggac ggggcagggc ggggttcggc ttctggcgtg   2580
tgaccggcgg ctctagagcc tctgctaacc atgttcatgc cttcttcttt ttcctacagg   2640
ggggatccgt ttatctgcag aattcgccct tgacgtcgcc accatgagga ggatgtgggc   2700
cacgcagggg ctggcggtgg cgctggctct gagcgtgctg ccgggcagcc gggcgctgcg   2760
gccgggcgac tgcgaagttt gtatttctta tctgggaaga ttttaccagg acctcaaaga   2820
cagagatgtc acattctcac cagccactat tgaaaacgaa cttataaagt tctgccggga   2880
agcaagaggc aaagagaatc ggttgtgcta ctatatcggg gccacagatg atgcagccac   2940
caaaatcatc aatgaggtat caaagcctct ggcccaccac atccctgtgg agaagatctg   3000
tgagaagctt aagaagaagg acagccagat atgtgagctt aagtatgaca agcagatcga   3060
cctgagcaca gtggacctga agaagctccg agttaaagag ctgaagaaga ttctggatga   3120
ctggggggag acatgcaaag gctgtgcaga aaagtctgac tacatccgga agataaatga   3180
actgatgcct aaatatgccc ccaaggcagc cagtgcacgg accgatttgg gaagcggagc   3240
tactaacttc agcctgctga agcaggctgg agacgtggag gagaaccctg gacctatgtc   3300
tcgctccgtt gccttagctg tgctcgcgct actctctctt tctggattag aggctgtcat   3360
ggcgccccga accctcttcc tgggtggagg cggttcaggc ggaggtggct ctggcggtgg   3420
cggatcgatc cagcgtactc caaagattca ggtttactca cgtcatccag cagagaatgg   3480
aaagtcaaat ttcctgaatt gctatgtgtc tgggtttcat ccatccgaca ttgaagttga   3540
cttactgaag aatggagaga gaattgaaaa agtggagcat tcagacttgt ctttcagcaa   3600
ggactggtct ttctatctct tgtactacac tgaattcacc cccactgaaa aagatgagta   3660
tgcctgccgt gtgaaccatg tgactttgtc acagcccaag atagttaagt gggatcgaga   3720
catgggtggt ggtggttctg gtggtggtgg ttctggcggc ggcggctccg gtggtggtgg   3780
atccggctcc cactccttga agtatttcca cacttccgtg tcccggcccg gccgcgggga   3840
gccccgcttc atctctgtgg gctacgtgga cgacacccag ttcgtgcgct tcgacaacga   3900
cgccgcgagt ccgaggatgg tgccgcgggc gccgtggatg gagcaggagg ggtcagagta   3960
ttgggaccgg gagacacgga gcgccaggga caccgcacag attttccgag tgaatctgcg   4020
gacgctgcgc ggctactaca atcagagcga ggccgggtct cacaccctgc agtggatgca   4080
tggctgcgag ctggggcccg acgggcgctt cctccgcggg tatgaacagt tcgcctacga   4140
cggcaaggat tatctcaccc tgaatgagga cctgcgctcc tggaccgcgg tggacacggc   4200
ggctcagatc tccgagcaaa agtcaaatga tgcctctgag gcggagcacc agagagccta   4260
cctggaagac acatgcgtgg agtggctcca caaatacctg gagaagggga aggagacgct   4320
```

gcttcacctg gagcccccaa agacacacgt gactcaccac cccatctctg accatgaggc 4380
caccctgagg tgctgggccc tgggcttcta ccctgcggag atcacactga cctggcagca 4440
ggatggggag ggccataccc aggacacgga gctcgtggag accaggcctg caggggatgg 4500
aaccttccag aagtgggcag ctgtggtggt gccttctgga gaggagcaga gatacacgtg 4560
ccatgtgcag catgaggggc tacccgagcc cgtcaccctg agatggaagc cggcttccca 4620
gcccaccatc cccatcgtgg gcatcattgc tggcctggtt ctccttggat ctgtggtctc 4680
tggagctgtg gttgctgctg tgatatggag gaagaagagc tcaggtggaa aaggagggag 4740
ctactctaag gctgagtgga gcgacagtgc ccaggggtct gagtctcaca gcttgtaatg 4800
atagccgctg atcagcctcg actgtgcctt ctagttgcca gccatctgtt gtttgcccct 4860
cccccgtgcc ttccttgacc ctggaaggtg ccactcccac tgtcctttcc taataaaatg 4920
aggaaattgc atcgcattgt ctgagtaggt gtcattctat tctggggggt ggggtggggc 4980
aggacagcaa gggggaggat tgggaagaca atagcaggca tgctggggat gcggtgggct 5040
ctatgggtcg accagggatc ccagcagtgc aaacagactt cggagtacct gcgctatgaa 5100
gacacgcttc ttctggaaga ccagccaaca ggtaagcggc ccaattcatt gttggagggt 5160
gaaagctgat tagagaagag aattgaatac acaaaacctg tacgaaatgt tttaagttgc 5220
tcagtttgag tggtttgaat tacgtgttgt tgcttccttt tttctgtttt aatttgcaga 5280
cattctcctc cccccccaaa aaaaagggtg atttgtacaa ttttttatgg tgctgtgtcc 5340
taaaggggat cctgaggggc gttgcctcgg gtagttaaag tcttatgtgt gcataagttg 5400
cttattcttt gtctacttcc tatttgagat gttagtagag aactgtcctg ggtgaatctt 5460
tcagtattgc agggcttggc aacttgctgc ccgacaaaat acatcagaat ttctctttaa 5520
gaacaatatg ggatggatta aaaaatatat atatgggatg aaattggggg tacttcaata 5580
ccttgcatgc cacccaagca ttccttatca cacagatgca ttttaagtgt aacagcaagc 5640
ctaatggcta ctcgatttc tttcccttca ggtgagaatg agatggtgat catgagacct 5700
ggaaacaaat atgagtacaa gttcggcttt gagcttcctc aggggtaaat atcagctaaa 5760
tgcatctttg aacttttctg tctaaaatat cttgccctcc tttgatcact tactgttctt 5820
ggagagcgtt ttaaaatttt cattttcttg acggtaacca cgtgcggacc gaggctgcag 5880
cgtcgtcctc cctaggaacc cctagtgatg gagttggcca ctccctctct gcgcgctcgc 5940
tcgctcactg aggccgggcg accaaaggtc gcccgacgcc cgggctttgc ccgggcggcc 6000
tcagtgagcg agcgagcgcg cagctgcctg caggggcgcc tgatgcggta ttttctcctt 6060
acgcatctgt gcggtatttc acaccgcata cgtcaaagca accatagtac gcgccctgta 6120
gcggcgcatt aagcgcggcg ggtgtggtgg ttacgcgcag cgtgaccgct acacttgcca 6180
gcgccctagc gcccgctcct ttcgctttct tcccttcctt tctcgccacg ttcgccggct 6240
ttccccgtca agctctaaat cgggggctcc ctttagggtt ccgatttagt gctttacggc 6300
acctcgaccc caaaaaactt gatttgggtg atggttcacg tagtgggcca tcgccctgat 6360
agacggtttt tcgccctttg acgttggagt ccacgttctt taatagtgga ctcttgttcc 6420
aaactggaac aacactcaac cctatctcgg gctattcttt tgatttataa gggattttgc 6480
cgatttcggc ctattggtta aaaaatgagc tgatttaaca aaaatttaac gcgaatttta 6540
acaaaatatt aacgtttaca attttatggt gcactctcag tacaatctgc tctgatgccg 6600
catagttaag ccagccccga cacccgccaa cacccgctga cgcgccctga cgggcttgtc 6660

-continued

```
tgctcccggc atccgcttac agacaagctg tgaccgtctc cgggagctgc atgtgtcaga   6720
ggttttcacc gtcatcaccg aaacgcgcga gacgaaaggg cctcgtgata cgcctatttt   6780
tataggttaa tgtcatgaac aataaaactg tctgcttaca taaacagtaa tacaaggggt   6840
gttatgagcc atattcaacg ggaaacgtcg aggccgcgat taaattccaa catggatgct   6900
gatttatatg ggtataaatg ggctcgcgat aatgtcgggc aatcaggtgc gacaatctat   6960
cgcttgtatg ggaagcccga tgcgccagag ttgtttctga aacatggcaa aggtagcgtt   7020
gccaatgatg ttacagatga gatggtcaga ctaaactggc tgacggaatt tatgcctctt   7080
ccgaccatca agcattttat ccgtactcct gatgatgcat ggttactcac cactgcgatc   7140
cccggaaaaa cagcattcca ggtattagaa gaatatcctg attcaggtga aaatattgtt   7200
gatgcgctgg cagtgttcct gcgccggttg cattcgattc ctgtttgtaa ttgtcctttt   7260
aacagcgatc gcgtatttcg tctcgctcag gcgcaatcac gaatgaataa cggtttggtt   7320
gatgcgagtg attttgatga cgagcgtaat ggctggcctg ttgaacaagt ctggaaagaa   7380
atgcataaac ttttgccatt ctcaccggat tcagtcgtca ctcatggtga tttctcactt   7440
gataacctta tttttgacga ggggaaatta ataggttgta ttgatgttgg acgagtcgga   7500
atcgcagacc gataccagga tcttgccatc ctatggaact gcctcggtga gttttctcct   7560
tcattacaga aacggctttt tcaaaaatat ggtattgata atcctgatat gaataaattg   7620
cagtttcatt tgatgctcga tgagtttttc taatctcatg accaaaatcc cttaacgtga   7680
gttttcgttc cactgagcgt cagaccccgt agaaaagatc aaaggatctt cttgagatcc   7740
tttttttctg cgcgtaatct gctgcttgca aacaaaaaaa ccaccgctac cagcggtggt   7800
ttgtttgccg gatcaagagc taccaactct ttttccgaag gtaactggct tcagcagagc   7860
gcagatacca aatactgtcc ttctagtgta gccgtagtta ggccaccact tcaagaactc   7920
tgtagcaccg cctacatacc tcgctctgct aatcctgtta ccagtggctg ctgccagtgg   7980
cgataagtcg tgtcttaccg ggttggactc aagacgatag ttaccggata aggcgcagcg   8040
gtcgggctga acggggggtt cgtgcacaca gcccagcttg gagcgaacga cctacaccga   8100
actgagatac ctacagcgtg agctatgaga aagcgccacg cttcccgaag ggagaaaggc   8160
ggacaggtat ccggtaagcg gcagggtcgg aacaggagag cgcacgaggg agcttccagg   8220
gggaaacgcc tggtatcttt atagtcctgt cgggtttcgc cacctctgac ttgagcgtcg   8280
atttttgtga tgctcgtcag gggggcggag cctatggaaa aacgccagca acgcggcctt   8340
tttacggttc ctggcctttt gctggccttt tgctcacatg t                        8381
```

<210> SEQ ID NO 46
<211> LENGTH: 1722
<212> TYPE: DNA
<213> ORGANISM: Homo sapiens

<400> SEQUENCE: 46

```
atgtgtcccc gagccgcgcg ggcgcccgcg acgctactcc tcgccctggg cgcggtgctg     60
tggcctgcgg ctggcgcctg ggagcttacg attttgcaca ccaacgacgt gcacagccgg    120
ctggagcaga ccagcgagga ctccagcaag tgcgtcaacg ccagccgctg catgggtggc    180
gtggctcggc tcttcaccaa ggttcagcag atccgccgcg ccgaacccaa cgtgctgctg    240
ctggacgccg gcgaccagta ccagggcact atctggttca ccgtgtacaa gggcgccgag    300
gtggcgcact tcatgaacgc cctgcgctac gatgccatgg cactgggaaa tcatgaattt    360
gataatggtg tggaaggact gatcgagcca ctcctcaaag aggccaaatt tccaattctg    420
```

```
agtgcaaaca ttaaagcaaa ggggccacta gcatctcaaa tatcaggact ttatttgcca    480
tataaagttc ttcctgttgg tgatgaagtt gtgggaatcg ttggatacac ttccaaagaa    540
accccttttc tctcaaatcc agggacaaat ttagtgtttg aagatgaaat cactgcatta    600
caacctgaag tagataagtt aaaaactcta aatgtgaaca aaattattgc actgggacat    660
tcgggttttg aaatggataa actcatcgct cagaaagtga ggggtgtgga cgtcgtggtg    720
ggaggacact ccaacacatt tctttacaca ggcaatccac cttccaaaga ggtgcctgct    780
gggaagtacc cattcatagt cacttctgat gatgggcgga aggttcctgt agtccaggcc    840
tatgcttttg gcaaatacct aggctatctg aagatcgagt ttgatgaaag aggaaacgtc    900
atctcttccc atggaaatcc cattcttcta aacagcagca ttcctgaaga tccaagcata    960
aaagcagaca ttaacaaatg gaggataaaa ttggataatt attctaccca ggaattaggg   1020
aaaacaattg tctatctgga tggctcctct caatcatgcc gctttagaga atgcaacatg   1080
ggcaacctga tttgtgatgc aatgattaac aacaacctga gacacacgga tgaaatgttc   1140
tggaaccacg tatccatgtg cattttaaat ggaggtggta tccggtcgcc cattgatgaa   1200
cgcaacaatg gcacaattac ctgggagaac ctggctgctg tattgccctt tggaggcaca   1260
tttgacctag tccagttaaa aggttccacc ctgaagaagg cctttgagca tagcgtgcac   1320
cgctacggcc agtccactgg agagttcctg caggtgggcg gaatccatgt ggtgtatgat   1380
ctttcccgaa aacctggaga cagagtagtc aaattagatg ttctttgcac caagtgtcga   1440
gtgcccagtt atgaccctct caaaatggac gaggtatata aggtgatcct cccaaacttc   1500
ctggccaatg gtggagatgg gttccagatg ataaaagatg aattattaag acatgactct   1560
ggtgaccaag atatcaacgt ggtttctaca tatatctcca aaatgaaagt aatttatcca   1620
gcagttgaag gtcggatcaa gttttccaca ggaagtcact gccatggaag cttttcttta   1680
atatttcttt cactttgggc agtgatcttt gttttatacc aa                      1722
```

<210> SEQ ID NO 47
<211> LENGTH: 10517
<212> TYPE: DNA
<213> ORGANISM: Artificial Sequence
<220> FEATURE:
<223> OTHER INFORMATION: Synthetic

<400> SEQUENCE: 47

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggccgcac gcgtgttcta gggtggaaac taagagaatg atgtacctag    180
agggcgctgg aagctctaaa gccctagcag ttactgcttt tactattagt ggtcgttttt    240
ttctccccccc cgccccccga caaatcaaca gaacaaagaa aattacctaa acagcaagga    300
catagggagg aacttcttgg cacagaactt tccaaacact ttttcctgaa gggatacaag    360
aagcaagaaa ggtactcttt cactaggacc ttctctgagc tgtcctcagg atgcttttgg    420
gactattttt cttacccaga gaatggagaa accctgcagg gaattcccaa gctgtagtta    480
taaacagaag ttctccttct gctaggtagc attcaaagat cttaatcttc tgggtttccg    540
ttttctcgaa tgaaaaatgc aggtccgagc agttaactgg ctggggcacc attagcaagt    600
cacttagcat ctctggggcc agtctgcaaa gcgagggggc agccttaatg tgcctccagc    660
ctgaagtcct agaatgagcg cccggtgtcc caagctgggg cgcgcacccc agatcggagg    720
```

-continued

```
gcgccgatgt acagacagca aactcaccca gtctagtgca tgccttctta aacatcacga    780
gactctaaga aaaggaaact gaaaacggga aagtccctct ctctaacctg gcactgcgtc    840
gctggcttgg agacaggtga cggtccctgc gggccttgtc ctgattggct gggcacgcgt    900
ttaatataag tggaggcgtc gcgctggcgg gcattcctga agctaagctt gtggacgata    960
tcgaattcgc acgacattga ttattgacta gttattaata gtaatcaatt acggggtcat   1020
tagttcatag cccatatatg gagttccgcg ttacataact tacggtaaat ggcccgcctg   1080
gctgaccgcc caacgacccc cgcccattga cgtcaataat gacgtatgtt cccatagtaa   1140
cgccaatagg gactttccat tgacgtcaat gggtggacta tttacggtaa actgcccact   1200
tggcagtaca tcaagtgtat catatgccaa gtacgccccc tattgacgtc aatgacggta   1260
aatggcccgc ctggcattat gcccagtaca tgaccttatg ggactttcct acttggcagt   1320
acatctacgt attagtcatc gctattacca tgggtcgagg tgagccccac gttctgcttc   1380
actctcccca tctccccccc ctccccaccc ccaattttgt atttatttat tttttaatta   1440
ttttgtgcag cgatgggggc gggggggggg ggggcgcgcg ccaggcgggg cggggcgggg   1500
cgaggggcgg ggcggggcga ggcggagagg tgcggcggca gccaatcaga gcggcgcgct   1560
ccgaaagttt ccttttatgg cgaggcggcg gcggcggcgg ccctataaaa agcgaagcgc   1620
gcggcgggcg ggagtcgctg cgttgccttc gccccgtgcc ccgctccgcg ccgcctcgcg   1680
ccgcccgccc cggctctgac tgaccgcgtt actcccacag gtgagcgggc gggacggccc   1740
ttctcctccg ggctgtaatt agcgcttggt ttaatgacgg ctcgtttctt ttctgtggct   1800
gcgtgaaagc cttaaagggc tccgggaggg ccctttgtgc ggggggggagc ggctcggggg   1860
gtgcgtgcgt gtgtgtgtgc gtggggagcg ccgcgtgcgg cccgcgctgc ccggcggctg   1920
tgagcgctgc gggcgcggcg cggggctttg tgcgctccgc gtgtgcgcga ggggagcgcg   1980
gccgggggcg gtgccccgcg gtgcgggggg gctgcgaggg gaacaaaggc tgcgtgcggg   2040
gtgtgtgcgt gggggggtga gcagggggtg tgggcgcggc ggtcgggctg taaccccccc   2100
ctgcaccccc ctccccgagt tgctgagcac ggcccggctt cgggtgcggg gctccgtgcg   2160
gggcgtggcg cggggctcgc cgtgccgggc ggggggtggc ggcaggtggg ggtgccgggc   2220
ggggcggggc cgcctcgggc cggggagggc tcgggggagg ggcgcggcgg ccccggagcg   2280
ccggcggctg tcgaggcgcg gcgagccgca gccattgcct tttatggtaa tcgtgcgaga   2340
gggcgcaggg acttcctttg tcccaaatct ggcggagccg aaatctggga ggcgccgccg   2400
caccccctct agcgggcgcg ggcgaagcgg tgcggcgccg gcaggaagga aatgggcggg   2460
gagggccttc gtgcgtcgcc gcgccgccgt ccccttctcc atctccagcc tcggggctgc   2520
cgcagggggga cggctgcctt cgggggggac ggggcagggc ggggttcggc ttctggcgtg   2580
tgaccggcgg ctctagagcc tctgctaacc atgttcatgc cttcttcttt ttcctacagg   2640
ggggatccgt ttatctgcag aattcgccct tgacgtcgcc accatggaag atacaaagga   2700
gtctaacgtg aagacatttt gctccaagaa tatcctagcc atccttggct tctcctctat   2760
catagctgtg atagctttgc ttgctgtggg gttgacccag aacaaagcat tgccagaaaa   2820
cgttaagtat gggattgtgc tggatgcggg ttcttctcac acaagtttat acatctataa   2880
gtggccagca gaaaaggaga atgacacagg cgtggtgcat caagtagaag aatgcagggt   2940
taaaggtcct ggaatctcaa aatttgttca gaaagtaaat gaaataggca tttacctgac   3000
tgattgcatg gaaagagcta gggaagtgat tccaaggtcc cagcaccaag agacacccgt   3060
ttacctggga gccacggcag gcatgcggtt gctcaggatg gaaagtgaag agttggcaga   3120
```

cagggttctg gatgtggtgg agaggagcct cagcaactac ccctttgact tccagggtgc 3180
caggatcatt actggccaag aggaaggtgc ctatggctgg attactatca actatctgct 3240
gggcaaattc agtcagaaaa caaggtggtt cagcatagtc ccatatgaaa ccaataatca 3300
ggaaaccttt ggagctttgg accttggggg agcctctaca caagtcactt ttgtacccca 3360
aaaccagact atcgagtccc cagataatgc tctgcaattt cgcctctatg gcaaggacta 3420
caatgtctac acacatagct tcttgtgcta tgggaaggat caggcactct ggcagaaact 3480
ggccaaggac attcaggttg caagtaatga aattctcagg gacccatgct ttcatcctgg 3540
atataagaag gtagtgaacg taagtgacct ttacaagacc ccctgcacca agagatttga 3600
gatgactctt ccattccagc agtttgaaat ccagggtatt ggaaactatc aacaatgcca 3660
tcaaagcatc ctggagctct tcaacaccag ttactgccct tactcccagt gtgccttcaa 3720
tgggattttc ttgccaccac tccaggggga ttttggggca ttttcagctt tttactttgt 3780
gatgaagttt ttaaacttga catcagagaa agtctctcag gaaaaggtga ctgagatgat 3840
gaaaaagttc tgtgctcagc cttgggagga gataaaaaca tcttacgctg gagtaaagga 3900
gaagtacctg agtgaatact gcttttctgg tacctacatt ctctccctcc ttctgcaagg 3960
ctatcatttc acagctgatt cctgggagca catccatttc attggcaaga tccagggcag 4020
cgacgccggc tggactttgg gctacatgct gaacctgacc aacatgatcc cagctgagca 4080
accattgtcc acacctctct cccactccac ctatgtcttc ctcatggttc tattctccct 4140
ggtccttttc acagtggcca tcataggctt gcttatcttt cacaagcctt catatttctg 4200
gaaagatatg gtaggaagcg gagctactaa cttcagcctg ctgaagcagg ctggagacgt 4260
ggaggagaac cctggaccta tgtgtccccg agccgcgcgg gcgcccgcga cgctactcct 4320
cgccctgggc gcggtgctgt ggcctgcggc tggcgcctgg gagcttacga ttttgcacac 4380
caacgacgtg cacagccggc tggagcagac cagcgaggac tccagcaagt gcgtcaacgc 4440
cagccgctgc atgggtggcg tggctcggct cttcaccaag gttcagcaga tccgccgcgc 4500
cgaacccaac gtgctgctgc tggacgccgg cgaccagtac cagggcacta tctggttcac 4560
cgtgtacaag ggcgccgagg tggcgcactt catgaacgcc ctgcgctacg atgccatggc 4620
actgggaaat catgaatttg ataatggtgt ggaaggactg atcgagccac tcctcaaaga 4680
ggccaaattt ccaattctga gtgcaaacat taaagcaaag ggccactag catctcaaat 4740 atcaggactt tatttgccat ataaagttct tcctgttggt gatgaagttg tgggaatcgt 4800
tggatacact tccaaagaaa ccccttttct ctcaaatcca gggacaaatt tagtgtttga 4860
agatgaaatc actgcattac aacctgaagt agataagtta aaaactctaa atgtgaacaa 4920
aattattgca ctgggacatt cgggttttga aatggataaa ctcatcgctc agaaagtgag 4980
gggtgtggac gtcgtggtgg gaggacactc caacacattt ctttacacag gcaatccacc 5040
ttccaaagag gtgcctgctg ggaagtaccc attcatagtc acttctgatg atgggcggaa 5100
ggttcctgta gtccaggcct atgcttttgg caaataccta ggctatctga agatcgagtt 5160
tgatgaaaga ggaaacgtca tctcttccca tggaaatccc attcttctaa acagcagcat 5220
tcctgaagat ccaagcataa aagcagacat taacaaatgg aggataaaat tggataatta 5280
ttctacccag gaattaggga aaacaattgt ctatctggat ggctcctctc aatcatgccg 5340
ctttagagaa tgcaacatgg gcaacctgat ttgtgatgca atgattaaca acaacctgag 5400
acacacggat gaaatgttct ggaaccacgt atccatgtgc attttaaatg gaggtggtat 5460

-continued

```
ccggtcgccc attgatgaac gcaacaatgg cacaattacc tgggagaacc tggctgctgt   5520
attgcccttt ggaggcacat ttgacctagt ccagttaaaa ggttccaccc tgaagaaggc   5580
ctttgagcat agcgtgcacc gctacggcca gtccactgga gagttcctgc aggtgggcgg   5640
aatccatgtg gtgtatgatc tttcccgaaa acctggagac agagtagtca aattagatgt   5700
tctttgcacc aagtgtcgag tgcccagtta tgaccctctc aaaatggacg aggtatataa   5760
ggtgatcctc ccaaacttcc tggccaatgg tggagatggg ttccagatga taaaagatga   5820
attattaaga catgactctg gtgaccaaga tatcaacgtg gtttctacat atatctccaa   5880
aatgaaagta atttatccag cagttgaagg tcggatcaag ttttccacag gaagtcactg   5940
ccatggaagc ttttctttaa tatttctttc actttgggca gtgatctttg ttttatacca   6000
aggaagcgga gctactaact tcagcctgct gaagcaggct ggagacgtgg aggagaaccc   6060
tggacctatg aggatatttg ctgtctttat attcatgacc tactggcatt tgctgaacgc   6120
atttactgtc acggttccca aggacctata tgtggtagag tatggtagca atatgacaat   6180
tgaatgcaaa ttcccagtag aaaaacaatt agacctggct gcactaattg tctattggga   6240
aatggaggat aagaacatta ttcaatttgt gcatggagag gaagacctga aggttcagca   6300
tagtagctac agacagaggg cccggctgtt gaaggaccag ctctccctgg gaaatgctgc   6360
acttcagatc acagatgtga aattgcagga tgcaggggtg taccgctgca tgatcagcta   6420
tggtggtgcc gactacaagc gaattactgt gaaagtcaat gccccataca acaaaatcaa   6480
ccaaagaatt ttggttgtgg atccagtcac ctctgaacat gaactgacat gtcaggctga   6540
gggctacccc aaggccgaag tcatctggac aagcagtgac catcaagtcc tgagtggtaa   6600
gaccaccacc accaattcca agagagagga gaaacttttc aatgtgacca gcacactgag   6660
aatcaacaca acaactaatg agattttcta ctgcactttt aggagattag atcctgagga   6720
aaaccataca gctgaattgg tcatcccaga actacctctg gcacatcctc caaatgaaag   6780
gactcacttg gtaattctgg gagccatctt attatgcctt ggtgtagcac tgacattcat   6840
cttccgttta agaaaaggga gaatgatgga tgtgaaaaaa tgtggcatcc aagatacaaa   6900
ctcaaagaag caaagtgata cacatttgga ggagacgtaa ccgctgatca gcctcgactg   6960
tgccttctag ttgccagcca tctgttgttt gcccctcccc cgtgccttcc ttgaccctgg   7020
aaggtgccac tcccactgtc ctttcctaat aaaatgagga aattgcatcg cattgtctga   7080
gtaggtgtca ttctattctg gggggtgggg tggggcagga cagcaagggg gaggattggg   7140
aagacaatag caggcatgct ggggatgcgg tgggctctat gggtcgaccc agcgtgagtc   7200
tctcctaccc tcccgctctg gtccttcctc tcccgctctg caccctctgt ggccctcgct   7260
gtgctctctc gctccgtgac ttcccttctc caagttctcc ttggtggccc gccgtggggc   7320
tagtccaggg ctggatctcg gggaagcggc ggggtggcct gggagtgggg aagggggtgc   7380
gcacccggga cgcgcgctac ttgccccttt cggcggggag caggggagac ctttggccta   7440
cggcgacggg agggtcggga caaagtttag ggcgtcgata agcgtcagag cgccgaggtt   7500
gggggagggt ttctcttccg ctctttcgcg gggcctctgg ctcccccagc gcagctggag   7560
tgggggacgg gtaggctcgt cccaaaggcg cggcgctgag gtttgtgaac gcgtggaggg   7620
gcgcttgggg tctgggggag gcgtcgcccg ggtaagcctg tctgctgcgg ctctgcttcc   7680
cttagactgg agagctgtgg acttcgtcta ggcgcccgct aagttcgcat gtcctagcac   7740
ctctgggtct atgtggggcc acaccgtggg gaggaaacag cacgcgacgt ttgtagaatg   7800
cttggctgtg atacaaagcg gtttcgaata attaacttat ttgttcccat cacatgtcac   7860
```

ttttaaaaaa ttataagaac tacccgttat tgacatcttt ctgtgtgcca aggactttat 7920
gtgctttgcg tcatttaatt ttgaaaacag ttatcttccg ccatagataa ctactatggt 7980
tatcttctgg taaccacgtg cggaccgagg ctgcagcgtc gtcctcccta ggaacccccta 8040
gtgatggagt tggccactcc ctctctgcgc gctcgctcgc tcactgaggc cgggcgacca 8100
aaggtcgccc gacgcccggg ctttgcccgg gcggcctcag tgagcgagcg agcgcgcagc 8160
tgcctgcagg ggcgcctgat gcggtatttt ctccttacgc atctgtgcgg tatttcacac 8220
cgcatacgtc aaagcaacca tagtacgcgc cctgtagcgg cgcattaagc gcggcgggtg 8280
tggtggttac gcgcagcgtg accgctacac ttgccagcgc cctagcgccc gctcctttcg 8340
ctttcttccc ttcctttctc gccacgttcg ccggctttcc ccgtcaagct ctaaatcggg 8400
ggctcccttt agggttccga tttagtgctt tacggcacct cgaccccaaa aaacttgatt 8460
tgggtgatgg ttcacgtagt gggccatcgc cctgatagac ggtttttcgc cctttgacgt 8520
tggagtccac gttctttaat agtggactct tgttccaaac tggaacaaca ctcaacccta 8580
tctcgggcta ttcttttgat ttataaggga ttttgccgat ttcggcctat tggttaaaaa 8640
atgagctgat ttaacaaaaa tttaacgcga attttaacaa aatattaacg tttacaattt 8700
tatggtgcac tctcagtaca atctgctctg atgccgcata gttaagccag ccccgacacc 8760
cgccaacacc cgctgacgcg ccctgacggg cttgtctgct cccggcatcc gcttacagac 8820
aagctgtgac cgtctccggg agctgcatgt gtcagaggtt ttcaccgtca tcaccgaaac 8880
gcgcgagacg aaagggcctc gtgatacgcc tatttttata ggttaatgtc atgaacaata 8940
aaactgtctg cttacataaa cagtaataca aggggtgtta tgagccatat tcaacgggaa 9000
acgtcgaggc cgcgattaaa ttccaacatg gatgctgatt tatatgggta taaatgggct 9060
cgcgataatg tcgggcaatc aggtgcgaca atctatcgct tgtatgggaa gcccgatgcg 9120
ccagagttgt ttctgaaaca tggcaaaggt agcgttgcca atgatgttac agatgagatg 9180
gtcagactaa actggctgac ggaatttatg cctcttccga ccatcaagca ttttatccgt 9240
actcctgatg atgcatggtt actcaccact gcgatccccg gaaaaacagc attccaggta 9300
ttagaagaat atcctgattc aggtgaaaat attgttgatg cgctggcagt gttcctgcgc 9360
cggttgcatt cgattcctgt ttgtaattgt ccttttaaca gcgatcgcgt atttcgtctc 9420
gctcaggcgc aatcacgaat gaataacggt ttggttgatg cgagtgattt tgatgacgag 9480
cgtaatggct ggcctgttga acaagtctgg aaagaaatgc ataaactttt gccattctca 9540
ccggattcag tcgtcactca tggtgatttc tcacttgata accttatttt tgacgagggg 9600
aaattaatag gttgtattga tgttggacga gtcggaatcg cagaccgata ccaggatctt 9660
gccatcctat ggaactgcct cggtgagttt tctccttcat tacagaaacg gctttttcaa 9720
aaatatggta ttgataatcc tgatatgaat aaattgcagt ttcatttgat gctcgatgag 9780
tttttctaat ctcatgacca aaatccctta acgtgagttt tcgttccact gagcgtcaga 9840
ccccgtagaa aagatcaaag gatcttcttg agatcctttt tttctgcgcg taatctgctg 9900
cttgcaaaca aaaaaaccac cgctaccagc ggtggtttgt ttgccggatc aagagctacc 9960
aactcttttt ccgaaggtaa ctggcttcag cagagcgcag ataccaaata ctgtccttct 10020
agtgtagccg tagttaggcc accacttcaa gaactctgta gcaccgccta catacctcgc 10080
tctgctaatc ctgttaccag tggctgctgc cagtggcgat aagtcgtgtc ttaccgggtt 10140
ggactcaaga cgatagttac cggataaggc gcagcggtcg ggctgaacgg ggggttcgtg 10200
cacacagccc agcttggagc gaacgaccta caccgaactg agatacctac agcgtgagct 10260
atgagaaagc gccacgcttc ccgaagggag aaaggcggac aggtatccgg taagcggcag 10320
ggtcggaaca ggagagcgca cgagggagct tccaggggga aacgcctggt atctttatag 10380
tcctgtcggg tttcgccacc tctgacttga gcgtcgattt ttgtgatgct cgtcaggggg 10440
gcggagccta tggaaaaacg ccagcaacgc ggccttttta cggttcctgg ccttttgctg 10500
gccttttgct cacatgt 10517

<210> SEQ ID NO 48
<211> LENGTH: 20
<212> TYPE: DNA
<213> ORGANISM: Homo sapiens

<400> SEQUENCE: 48
gctccaggta gccaccttct 20

<210> SEQ ID NO 49
<211> LENGTH: 20
<212> TYPE: DNA
<213> ORGANISM: Homo sapiens

<400> SEQUENCE: 49
taggggcccc aactccatgg 20

<210> SEQ ID NO 50
<211> LENGTH: 20
<212> TYPE: DNA
<213> ORGANISM: Homo sapiens

<400> SEQUENCE: 50
ggcttatgcc aatatcggtg 20

<210> SEQ ID NO 51
<211> LENGTH: 20
<212> TYPE: DNA
<213> ORGANISM: Homo sapiens

<400> SEQUENCE: 51
aggtgatgaa gagaccaggg 20

<210> SEQ ID NO 52
<211> LENGTH: 3921
<212> TYPE: DNA
<213> ORGANISM: Artificial Sequence
<220> FEATURE:
<223> OTHER INFORMATION: Synthetic

<400> SEQUENCE: 52
atgaggagga tgtgggccac gcaggggctg gcggtggcgc tggctctgag cgtgctgccg 60
ggcagccggg cgctgcggcc gggcgactgc gaagtttgta tttcttatct gggaagattt 120
taccaggacc tcaaagacag agatgtcaca ttctcaccag ccactattga aaacgaactt 180
ataaagttct gccgggaagc aagaggcaaa gagaatcggt tgtgctacta tatcggggcc 240
acagatgatg cagccaccaa aatcatcaat gaggtatcaa agcctctggc ccaccacatc 300
cctgtggaga agatctgtga gaagcttaag aagaaggaca gccagatatg tgagcttaag 360
tatgacaagc agatcgacct gagcacagtg gacctgaaga agctccgagt taaagagctg 420
aagaagattc tggatgactg gggggagaca tgcaaaggct gtgcagaaaa gtctgactac 480
atccggaaga taaatgaact gatgcctaaa tatgccccca aggcagccag tgcacggacc 540

```
gatttgggaa gcggagctac taacttcagc ctgctgaagc aggctggaga cgtggaggag    600
aaccctggac ctatggctga acaagtcctt cctcaggctt tgtatttgag caatatgcgg    660
aaagctgtga agatacggga gagaactcca gaagacattt ttaaacctac taatgggatc    720
attcatcatt ttaaaaccat gcaccgatac acactggaaa tgttcagaac ttgccagttt    780
tgtcctcagt ttcgggagat catccacaaa gccctcatcg acagaaacat ccaggccacc    840
ctggaaagcc agaagaaact caactggtgt cgagaagtcc ggaagcttgt ggcgctgaaa    900
acgaacggtg acggcaattg cctcatgcat gccacttctc agtacatgtg ggcgttcag    960
gacacagact tggtactgag gaaggcgctg ttcagcacgc tcaaggaaac agacacacgc   1020
aactttaaat tccgctggca actggagtct ctcaaatctc aggaatttgt tgaaacgggg   1080
ctttgctatg atactcggaa ctggaatgat gaatgggaca atcttatcaa aatggcttcc   1140
acagacacac ccatggcccg aagtggactt cagtacaact cactggaaga aatacacata   1200
tttgtccttt gcaacatcct cagaaggcca atcattgtca tttcagacaa aatgctaaga   1260
agtttggaat caggttccaa tttcgcccct ttgaaagtgg gtggaattta cttgcctctc   1320
cactggcctg cccaggaatg ctacagatac cccattgttc tcggctatga cagccatcat   1380
tttgtaccct tggtgaccct gaaggacagt gggcctgaaa tccgagctgt tccacttgtt   1440
aacagagacc ggggaagatt tgaagactta aaagttcact tttgacaga tcctgaaaat   1500
gagatgaagg agaagctctt aaaagagtac ttaatggtga tagaaatccc cgtccaaggc   1560
tgggaccatg gcacaactca tctcatcaat gccgcaaagt tggatgaagc taacttacca   1620
aaagaaatca atctggtaga tgattacttt gaacttgttc agcatgagta caagaaatgg   1680
caggaaaaca gcgagcaggg gaggagagag gggcacgccc agaatcccat ggaaccttcc   1740
gtgccccagc tttctctcat ggatgtaaaa tgtgaaacgc ccaactgccc cttcttcatg   1800
tctgtgaaca cccagccttt atgccatgag tgctcagaga ggcggcaaaa gaatcaaaac   1860
aaactcccaa agctgaactc caagccgggc cctgaggggc tccctggcat ggcgctcggg   1920
gcctctcggg gagaagccta tgagcccttg gcgtggaacc ctgaggagtc cactgggggg   1980
cctcattcgg ccccaccgac agcacccagc ccttttctgt tcagtgagac cactgccatg   2040
aagtgcagga gccccggctg ccccttcaca ctgaatgtgc agcacaacgg attttgtgaa   2100
cgttgccaca acgcccggca acttcacgcc agccacgccc cagaccacac aaggcacttg   2160
gatcccggga agtgccaagc ctgcctccag gatgttacca ggacatttaa tgggatctgc   2220
agtacttgct tcaaaaggac tacagcagag gcctcctcca gcctcagcac cagcctccct   2280
ccttcctgtc accagcgttc caagtcagat ccctcgcggc tcgtccggag cccctccccg   2340
cattcttgcc acagagctgg aaacgacgcc cctgctggct gcctgtctca agctgcacgg   2400
actcctgggg acaggacggg gacgagcaag tgcagaaaag ccggctgcgt gtattttggg   2460
actccagaaa acaagggctt ttgcacactg tgtttcatcg agtacagaga aaacaaacat   2520
tttgctgctg cctcagggaa agtcagtccc acagcgtcca ggttccagaa caccattccg   2580
tgcctgggga gggaatgcgg caccccttgga agcaccatgt ttgaaggata ctgccagaag   2640
tgtttcattg aagctcagaa tcagagattt catgaggcca aaaggacaga agagcaactg   2700
agatcgagcc agcgcagaga tgtgcctcga accacacaaa gcacctcaag gcccaagtgc   2760
gcccgggcct cctgcaagaa catcctggcc tgccgcagcg aggagctctg catggagtgt   2820
cagcatccca accagaggat gggccctggg gcccaccggg gtgagcctgc ccccgaagac   2880
```

cccccaagc agcgttgccg ggcccccgcc tgtgatcatt ttggcaatgc caagtgcaac 2940
ggctactgca acgaatgctt tcagttcaag cagatgtatg gcggaagcgg agctactaac 3000
ttcagcctgc tgaagcaggc tggagacgtg gaggagaacc ctggacctat gaggatattt 3060
gctgtcttta tattcatgac ctactggcat ttgctgaacg catttactgt cacggttccc 3120
aaggacctat atgtggtaga gtatggtagc aatatgacaa ttgaatgcaa attcccagta 3180
gaaaaacaat tagacctggc tgcactaatt gtctattggg aaatggagga taagaacatt 3240
attcaatttg tgcatggaga ggaagacctg aaggttcagc atagtagcta cagacagagg 3300
gcccggctgt tgaaggacca gctctccctg ggaaatgctg cacttcagat cacagatgtg 3360
aaattgcagg atgcaggggt gtaccgctgc atgatcagct atggtggtgc cgactacaag 3420
cgaattactg tgaaagtcaa tgccccatac aacaaaatca accaaagaat tttggttgtg 3480
gatccagtca cctctgaaca tgaactgaca tgtcaggctg agggctaccc caaggccgaa 3540
gtcatctgga caagcagtga ccatcaagtc ctgagtggta agaccaccac caccaattcc 3600
aagagagagg agaaactttt caatgtgacc agcacactga gaatcaacac aacaactaat 3660
gagattttct actgcacttt taggagatta gatcctgagg aaaaccatac agctgaattg 3720
gtcatcccag aactacctct ggcacatcct ccaaatgaaa ggactcactt ggtaattctg 3780
ggagccatct tattatgcct tggtgtagca ctgacattca tcttccgttt aagaaaaggg 3840
agaatgatgg atgtgaaaaa atgtggcatc caagatacaa actcaaagaa gcaaagtgat 3900
acacatttgg aggagacgta a 3921

<210> SEQ ID NO 53
<211> LENGTH: 2469
<212> TYPE: DNA
<213> ORGANISM: Artificial Sequence
<220> FEATURE:
<223> OTHER INFORMATION: Synthetic

<400> SEQUENCE: 53
atggaagata caaaggagtc taacgtgaag acattttgct ccaagaatat cctagccatc 60
cttggcttct cctctatcat agctgtgata gctttgcttg ctgtggggtt gacccagaac 120
aaagcattgc cagaaaacgt taagtatggg attgtgctgg atgcgggttc ttctcacaca 180
agtttataca tctataagtg gccagcagaa aaggagaatg acacaggcgt ggtgcatcaa 240
gtagaagaat gcagggttaa aggtcctgga atctcaaaat ttgttcagaa agtaaatgaa 300
ataggcattt acctgactga ttgcatggaa agagctaggg aagtgattcc aaggtcccag 360
caccaagaga cacccgttta cctgggagcc acggcaggca tgcggttgct caggatggaa 420
agtgaagagt tggcagacag ggttctggat gtggtggaga ggagcctcag caactacccc 480
tttgacttcc agggtgccag gatcattact ggccaagagg aaggtgccta tggctggatt 540
actatcaact atctgctggg caaattcagt cagaaaacaa ggtggttcag catagtccca 600
tatgaaacca ataatcagga aacctttgga gctttggacc ttgggggagc ctctacacaa 660
gtcacttttg taccccaaaa ccagactatc gagtccccag ataatgctct gcaatttcgc 720
ctctatggca aggactacaa tgtctacaca catagcttct tgtgctatgg gaaggatcag 780
gcactctggc agaaactggc caaggacatt caggttgcaa gtaatgaaat tctcagggac 840
ccatgctttc atcctggata taagaaggta gtgaacgtaa gtgaccttta caagaccccc 900
tgcaccaaga gatttgagat gactcttcca ttccagcagt ttgaaatcca gggtattgga 960
aactatcaac aatgccatca aagcatcctg gagctcttca acaccagtta ctgcccttac 1020
tcccagtgtg ccttcaatgg gattttcttg ccaccactcc agggggattt tggggcattt 1080
tcagcttttt actttgtgat gaagttttta aacttgacat cagagaaagt ctctcaggaa 1140
aaggtgactg agatgatgaa aaagttctgt gctcagcctt gggaggagat aaaaacatct 1200
tacgctggag taaaggagaa gtacctgagt gaatactgct tttctggtac ctacattctc 1260
tccctccttc tgcaaggcta tcatttcaca gctgattcct gggagcacat ccatttcatt 1320
ggcaagatcc agggcagcga cgccggctgg actttgggct acatgctgaa cctgaccaac 1380
atgatcccag ctgagcaacc attgtccaca cctctctccc actccaccta tgtcttcctc 1440
atggttctat tctccctggt ccttttcaca gtggccatca taggcttgct tatctttcac 1500
aagccttcat atttctggaa agatatggta ggaagcggag ctactaactt cagcctgctg 1560
aagcaggctg gagacgtgga ggagaaccct ggacctatga ggatatttgc tgtctttata 1620
ttcatgacct actggcattt gctgaacgca tttactgtca cggttcccaa ggacctatat 1680
gtggtagagt atggtagcaa tatgacaatt gaatgcaaat tcccagtaga aaaacaatta 1740
gacctggctg cactaattgt ctattgggaa atggaggata agaacattat tcaatttgtg 1800
catggagagg aagacctgaa ggttcagcat agtagctaca gacagagggc ccggctgttg 1860
aaggaccagc tctccctggg aaatgctgca cttcagatca cagatgtgaa attgcaggat 1920
gcaggggtgt accgctgcat gatcagctat ggtggtgccg actacaagcg aattactgtg 1980
aaagtcaatg ccccatacaa caaaatcaac caaagaattt tggttgtgga tccagtcacc 2040
tctgaacatg aactgacatg tcaggctgag ggctacccca aggccgaagt catctggaca 2100
agcagtgacc atcaagtcct gagtggtaag accaccacca ccaattccaa gagagaggag 2160
aaacttttca atgtgaccag cacactgaga atcaacacaa caactaatga gattttctac 2220
tgcactttta ggagattaga tcctgaggaa aaccatacag ctgaattggt catcccagaa 2280
ctacctctgg cacatcctcc aaatgaaagg actcacttgg taattctggg agccatctta 2340
ttatgccttg gtgtagcact gacattcatc ttccgtttaa gaaaagggag aatgatggat 2400
gtgaaaaaat gtggcatcca agatacaaac tcaaagaagc aaagtgatac acatttggag 2460
gagacgtaa 2469

<210> SEQ ID NO 54
<211> LENGTH: 3309
<212> TYPE: DNA
<213> ORGANISM: Artificial Sequence
<220> FEATURE:
<223> OTHER INFORMATION: Synthetic

<400> SEQUENCE: 54
atggctgaac aagtccttcc tcaggctttg tatttgagca atatgcggaa agctgtgaag 60
atacgggaga gaactccaga agacattttt aaacctacta atgggatcat tcatcatttt 120
aaaaccatgc accgatacac actggaaatg ttcagaactt gccagttttg tcctcagttt 180
cgggagatca tccacaaagc cctcatcgac agaaacatcc aggccaccct ggaaagccag 240
aagaaactca actggtgtcg agaagtccgg aagcttgtgg cgctgaaaac gaacggtgac 300
ggcaattgcc tcatgcatgc cacttctcag tacatgtggg gcgttcagga cacagacttg 360
gtactgagga aggcgctgtt cagcacgctc aaggaaacag acacacgcaa ctttaaattc 420
cgctggcaac tggagtctct caaatctcag gaatttgttg aaacggggct ttgctatgat 480
actcggaact ggaatgatga atgggacaat cttatcaaaa tggcttccac agacacaccc 540

-continued

```
atggcccgaa gtggacttca gtacaactca ctggaagaaa tacacatatt tgtcctttgc    600
aacatcctca gaaggccaat cattgtcatt tcagacaaaa tgctaagaag tttggaatca    660
ggttccaatt tcgccccttt gaaagtgggt ggaatttact tgcctctcca ctggcctgcc    720
caggaatgct acagataccc cattgttctc ggctatgaca gccatcattt tgtacccttg    780
gtgaccctga aggacagtgg gcctgaaatc cgagctgttc cacttgttaa cagagaccgg    840
ggaagatttg aagacttaaa agttcacttt ttgacagatc ctgaaaatga gatgaaggag    900
aagctcttaa aagagtactt aatggtgata gaaatccccg tccaaggctg ggaccatggc    960
acaactcatc tcatcaatgc cgcaaagttg gatgaagcta acttaccaaa agaaatcaat   1020
ctggtagatg attactttga acttgttcag catgagtaca agaaatggca ggaaaacagc   1080
gagcagggga ggagagaggg gcacgcccag aatcccatgg aaccttccgt gccccagctt   1140
tctctcatgg atgtaaaatg tgaaacgccc aactgcccct tcttcatgtc tgtgaacacc   1200
cagcctttat gccatgagtg ctcagagagg cggcaaaaga atcaaaacaa actcccaaag   1260
ctgaactcca agccgggccc tgaggggctc cctggcatgg cgctcggggc ctctcgggga   1320
gaagcctatg agcccttggc gtggaaccct gaggagtcca ctgggggggcc tcattcggcc   1380
ccaccgacag cacccagccc ttttctgttc agtgagacca ctgccatgaa gtgcaggagc   1440
cccggctgcc ccttcacact gaatgtgcag cacaacggat tttgtgaacg ttgccacaac   1500
gcccggcaac ttcacgccag ccacgcccca gaccacacaa ggcacttgga tcccgggaag   1560
tgccaagcct gcctccagga tgttaccagg acatttaatg ggatctgcag tacttgcttc   1620
aaaaggacta cagcagaggc ctcctccagc ctcagcacca gcctccctcc ttcctgtcac   1680
cagcgttcca agtcagatcc ctcgcggctc gtccggagcc cctccccgca ttcttgccac   1740
agagctggaa acgacgcccc tgctggctgc ctgtctcaag ctgcacggac tcctggggac   1800
aggacgggga cgagcaagtg cagaaaagcc ggctgcgtgt attttgggac tccagaaaac   1860
aagggctttt gcacactgtg tttcatcgag tacagagaaa acaaacattt tgctgctgcc   1920
tcagggaaag tcagtcccac agcgtccagg ttccagaaca ccattccgtg cctggggagg   1980
gaatgcggca cccttggaag caccatgttt gaaggatact gccagaagtg tttcattgaa   2040
gctcagaatc agagatttca tgaggccaaa aggacagaag agcaactgag atcgagccag   2100
cgcagagatg tgcctcgaac cacacaaagc acctcaaggc ccaagtgcgc ccgggcctcc   2160
tgcaagaaca tcctggcctg ccgcagcgag gagctctgca tggagtgtca gcatcccaac   2220
cagaggatgg gccctggggc ccaccggggt gagcctgccc ccgaagaccc ccccaagcag   2280
cgttgccggg cccccgcctg tgatcatttt ggcaatgcca agtgcaacgg ctactgcaac   2340
gaatgctttc agttcaagca gatgtatggc ggaagcggag ctactaactt cagcctgctg   2400
aagcaggctg gagacgtgga ggagaaccct ggacctatga ggatatttgc tgtctttata   2460
ttcatgacct actggcattt gctgaacgca tttactgtca cggttcccaa ggacctatat   2520
gtggtagagt atggtagcaa tatgacaatt gaatgcaaat tcccagtaga aaaacaatta   2580
gacctggctg cactaattgt ctattgggaa atggaggata agaacattat tcaatttgtg   2640
catggagagg aagacctgaa ggttcagcat agtagctaca gacagagggc ccggctgttg   2700
aaggaccagc tctccctggg aaatgctgca cttcagatca cagatgtgaa attgcaggat   2760
gcaggggtgt accgctgcat gatcagctat ggtggtgccg actacaagcg aattactgtg   2820
aaagtcaatg ccccatacaa caaaatcaac caaagaattt tggttgtgga tccagtcacc   2880
tctgaacatg aacttacatg tcaggctgag ggctacccca aggccgaagt catctggaca   2940
```

```
agcagtgacc atcaagtcct gagtggtaag accaccacca ccaattccaa gagagaggag   3000

aaacttttca atgtgaccag cacactgaga atcaacacaa caactaatga gattttctac   3060

tgcactttta ggagattaga tcctgaggaa aaccatacag ctgaattggt catcccagaa   3120

ctacctctgg cacatcctcc aaatgaaagg actcacttgg taattctggg agccatctta   3180

ttatgccttg gtgtagcact gacattcatc ttccgtttaa gaaaagggag aatgatggat   3240

gtgaaaaaat gtggcatcca agatacaaac tcaaagaagc aaagtgatac acatttggag   3300

gagacgtaa                                                            3309
```

<210> SEQ ID NO 55
<211> LENGTH: 2112
<212> TYPE: DNA
<213> ORGANISM: Artificial Sequence
<220> FEATURE:
<223> OTHER INFORMATION: Synthetic

<400> SEQUENCE: 55

```
atgaggagga tgtgggccac gcaggggctg gcggtggcgc tggctctgag cgtgctgccg     60

ggcagccggg cgctgcggcc gggcgactgc gaagtttgta tttcttatct gggaagattt    120

taccaggacc tcaaagacag agatgtcaca ttctcaccag ccactattga aaacgaactt    180

ataaagttct gccgggaagc aagaggcaaa gagaatcggt tgtgctacta tatcggggcc    240

acagatgatg cagccaccaa aatcatcaat gaggtatcaa agcctctggc ccaccacatc    300

cctgtggaga agatctgtga gaagcttaag aagaaggaca gccagatatg tgagcttaag    360

tatgacaagc agatcgacct gagcacagtg gacctgaaga agctccgagt taaagagctg    420

aagaagattc tggatgactg gggggagaca tgcaaaggct gtgcagaaaa gtctgactac    480

atccggaaga taaatgaact gatgcctaaa tatgccccca aggcagccag tgcacggacc    540

gatttgggaa gcggagctac taacttcagc ctgctgaagc aggctggaga cgtggaggag    600

aaccctggac ctatgtctcg ctccgttgcc ttagctgtgc tcgcgctact ctctctttct    660

ggattagagg ctgtcatggc gccccgaacc ctcttcctgg gtggaggcgg ttcaggcgga    720

ggtggctctg gcggtggcgg atcgatccag cgtactccaa agattcaggt ttactcacgt    780

catccagcag agaatggaaa gtcaaatttc ctgaattgct atgtgtctgg gtttcatcca    840

tccgacattg aagttgactt actgaagaat ggagagagaa ttgaaaaagt ggagcattca    900

gacttgtctt tcagcaagga ctggtctttc tatctcttgt actacactga attcaccccc    960

actgaaaaag atgagtatgc ctgccgtgtg aaccatgtga ctttgtcaca gcccaagata   1020

gttaagtggg atcgagacat gggtggtggt ggttctggtg gtggtggttc tggcggcggc   1080

ggctccggtg gtggtggatc cggctcccac tccttgaagt atttccacac ttccgtgtcc   1140

cggcccggcc gcggggagcc ccgcttcatc tctgtgggct acgtggacga cacccagttc   1200

gtgcgcttcg acaacgacgc cgcgagtccg aggatggtgc cgcgggcgcc gtggatggag   1260

caggaggggt cagagtattg ggaccgggag acacggagcg ccagggacac cgcacagatt   1320

ttccgagtga atctgcggac gctgcgcggc tactacaatc agagcgaggc cgggtctcac   1380

accctgcagt ggatgcatgg ctgcgagctg gggcccgacg ggcgcttcct ccgcgggtat   1440

gaacagttcg cctacgacgg caaggattat ctcaccctga atgaggacct gcgctcctgg   1500

accgcggtgg acacggcggc tcagatctcc gagcaaaagt caaatgatgc ctctgaggcg   1560

gagcaccaga gagcctacct ggaagacaca tgcgtggagt ggctccacaa atacctggag   1620
```

-continued

```
aaggggaagg agacgctgct tcacctggag cccccaaaga cacacgtgac tcaccacccc   1680

atctctgacc atgaggccac cctgaggtgc tgggccctgg gcttctaccc tgcggagatc   1740

acactgacct ggcagcagga tggggagggc catacccagg acacggagct cgtggagacc   1800

aggcctgcag gggatggaac cttccagaag tgggcagctg tggtggtgcc ttctggagag   1860

gagcagagat acacgtgcca tgtgcagcat gaggggctac ccgagcccgt caccctgaga   1920

tggaagccgg cttcccagcc caccatcccc atcgtgggca tcattgctgg cctggttctc   1980

cttggatctg tggtctctgg agctgtggtt gctgctgtga tatggaggaa gaagagctca   2040

ggtggaaaag gagggagcta ctctaaggct gagtggagcg acagtgccca ggggtctgag   2100

tctcacagct tg                                                         2112
```

<210> SEQ ID NO 56
<211> LENGTH: 4257
<212> TYPE: DNA
<213> ORGANISM: Artificial Sequence
<220> FEATURE:
<223> OTHER INFORMATION: Synthetic

<400> SEQUENCE: 56

```
atggaagata caaaggagtc taacgtgaag acattttgct ccaagaatat cctagccatc     60

cttggcttct cctctatcat agctgtgata gctttgcttg ctgtggggtt gacccagaac    120

aaagcattgc cagaaaacgt taagtatggg attgtgctgg atgcgggttc ttctcacaca    180

agtttataca tctataagtg gccagcagaa aaggagaatg acacaggcgt ggtgcatcaa    240

gtagaagaat gcagggttaa aggtcctgga atctcaaaat ttgttcagaa agtaaatgaa    300

ataggcattt acctgactga ttgcatggaa agagctaggg aagtgattcc aaggtcccag    360

caccaagaga cacccgttta cctgggagcc acggcaggca tgcggttgct caggatggaa    420

agtgaagagt tggcagacag ggttctggat gtggtggaga ggagcctcag caactacccc    480

tttgacttcc agggtgccag gatcattact ggccaagagg aaggtgccta tggctggatt    540

actatcaact atctgctggg caaattcagt cagaaaacaa ggtggttcag catagtccca    600

tatgaaacca ataatcagga aacctttgga gctttggacc ttgggggagc ctctacacaa    660

gtcacttttg taccccaaaa ccagactatc gagtccccag ataatgctct gcaatttcgc    720

ctctatggca aggactacaa tgtctacaca catagcttct tgtgctatgg gaaggatcag    780

gcactctggc agaaactggc caaggacatt caggttgcaa gtaatgaaat tctcagggac    840

ccatgctttc atcctggata taagaaggta gtgaacgtaa gtgaccttta caagaccccc    900

tgcaccaaga gatttgagat gactcttcca ttccagcagt ttgaaatcca gggtattgga    960

aactatcaac aatgccatca aagcatcctg gagctcttca acaccagtta ctgcccttac   1020

tcccagtgtg ccttcaatgg gattttcttg ccaccactcc aggggggattt tggggcattt   1080

tcagcttttt actttgtgat gaagttttta aacttgacat cagagaaagt ctctcaggaa   1140

aaggtgactg agatgatgaa aaagttctgt gctcagcctt gggaggagat aaaaaacatct   1200

tacgctggag taaaggagaa gtacctgagt gaatactgct tttctggtac ctacattctc   1260

tccctccttc tgcaaggcta tcatttcaca gctgattcct gggagcacat ccatttcatt   1320

ggcaagatcc agggcagcga cgccggctgg actttgggct acatgctgaa cctgaccaac   1380

atgatcccag ctgagcaacc attgtccaca cctctctccc actccaccta tgtcttcctc   1440

atggttctat tctccctggt ccttttcaca gtggccatca taggcttgct tatctttcac   1500

aagccttcat atttctggaa agatatggta ggaagcggag ctactaactt cagcctgctg   1560
```

-continued

```
aagcaggctg gagacgtgga ggagaaccct ggacctatgt gtccccgagc cgcgcgggcg   1620
cccgcgacgc tactcctcgc cctgggcgcg gtgctgtggc ctgcggctgg cgcctgggag   1680
cttacgattt tgcacaccaa cgacgtgcac agccggctgg agcagaccag cgaggactcc   1740
agcaagtgcg tcaacgccag ccgctgcatg ggtggcgtgg ctcggctctt caccaaggtt   1800
cagcagatcc gccgcgccga acccaacgtg ctgctgctgg acgccggcga ccagtaccag   1860
ggcactatct ggttcaccgt gtacaagggc gccgaggtgg cgcacttcat gaacgccctg   1920
cgctacgatg ccatggcact gggaaatcat gaatttgata atggtgtgga aggactgatc   1980
gagccactcc tcaaagaggc caaatttcca attctgagtg caaacattaa agcaaagggg   2040
ccactagcat ctcaaatatc aggactttat ttgccatata aagttcttcc tgttggtgat   2100
gaagttgtgg gaatcgttgg atacacttcc aaagaaaccc cttttctctc aaatccaggg   2160
acaaatttag tgtttgaaga tgaaatcact gcattacaac ctgaagtaga taagttaaaa   2220
actctaaatg tgaacaaaat tattgcactg ggacattcgg gttttgaaat ggataaactc   2280
atcgctcaga aagtgagggg tgtggacgtc gtggtgggag gacactccaa cacatttctt   2340
tacacaggca atccaccttc caaagaggtg cctgctggga agtacccatt catagtcact   2400
tctgatgatg ggcggaaggt tcctgtagtc caggcctatg cttttggcaa atacctaggc   2460
tatctgaaga tcgagtttga tgaaagagga aacgtcatct cttcccatgg aaatcccatt   2520
cttctaaaca gcagcattcc tgaagatcca agcataaaag cagacattaa caaatggagg   2580
ataaaattgg ataattattc tacccaggaa ttagggaaaa caattgtcta tctggatggc   2640
tcctctcaat catgccgctt tagagaatgc aacatgggca acctgatttg tgatgcaatg   2700
attaacaaca acctgagaca cacggatgaa atgttctgga accacgtatc catgtgcatt   2760
ttaaatggag gtggtatccg gtcgcccatt gatgaacgca acaatggcac aattacctgg   2820
gagaacctgg ctgctgtatt gccctttgga ggcacatttg acctagtcca gttaaaaggt   2880
tccaccctga agaaggcctt tgagcatagc gtgcaccgct acggccagtc cactggagag   2940
ttcctgcagg tgggcggaat ccatgtggtg tatgatcttt cccgaaaacc tggagacaga   3000
gtagtcaaat tagatgttct ttgcaccaag tgtcgagtgc ccagttatga ccctctcaaa   3060
atggacgagg tatataaggt gatcctccca aacttcctgg ccaatggtgg agatgggttc   3120
cagatgataa aagatgaatt attaagacat gactctggtg accaagatat caacgtggtt   3180
tctacatata tctccaaaat gaaagtaatt tatccagcag ttgaaggtcg gatcaagttt   3240
tccacaggaa gtcactgcca tggaagcttt tctttaatat ttctttcact ttgggcagtg   3300
atctttgttt tataccaagg aagcggagct actaacttca gcctgctgaa gcaggctgga   3360
gacgtggagg agaaccctgg acctatgagg atatttgctg tctttatatt catgacctac   3420
tggcatttgc tgaacgcatt tactgtcacg gttcccaagg acctatatgt ggtagagtat   3480
ggtagcaata tgacaattga atgcaaattc ccagtagaaa aacaattaga cctggctgca   3540
ctaattgtct attgggaaat ggaggataag aacattattc aatttgtgca tggagaggaa   3600
gacctgaagg ttcagcatag tagctacaga cagagggccc ggctgttgaa ggaccagctc   3660
tccctgggaa atgctgcact tcagatcaca gatgtgaaat tgcaggatgc aggggtgtac   3720
cgctgcatga tcagctatgg tggtgccgac tacaagcgaa ttactgtgaa agtcaatgcc   3780
ccatacaaca aaatcaacca aagaattttg gttgtggatc cagtcacctc tgaacatgaa   3840
ctgacatgtc aggctgaggg ctaccccaag gccgaagtca tctggacaag cagtgaccat   3900
```

```
caagtcctga gtggtaagac caccaccacc aattccaaga gagaggagaa acttttcaat   3960

gtgaccagca cactgagaat caacacaaca actaatgaga ttttctactg cacttttagg   4020

agattagatc ctgaggaaaa ccatacagct gaattggtca tcccagaact acctctggca   4080

catcctccaa atgaaaggac tcacttggta attctgggag ccatcttatt atgccttggt   4140

gtagcactga cattcatctt ccgtttaaga aaagggagaa tgatggatgt gaaaaaatgt   4200

ggcatccaag atacaaactc aaagaagcaa agtgatacac atttggagga gacgtaa      4257
```

<210> SEQ ID NO 57
<211> LENGTH: 20
<212> TYPE: DNA
<213> ORGANISM: Homo sapiens

<400> SEQUENCE: 57

```
gttcatgcgc aagaggatcg                                                 20
```

<210> SEQ ID NO 58
<211> LENGTH: 3318
<212> TYPE: DNA
<213> ORGANISM: Artificial Sequence
<220> FEATURE:
<223> OTHER INFORMATION: Synthetic

<400> SEQUENCE: 58

```
atggaagata caaaggagtc taacgtgaag acattttgct ccaagaatat cctagccatc     60

cttggcttct cctctatcat agctgtgata gctttgcttg ctgtggggtt gacccagaac    120

aaagcattgc cagaaaacgt taagtatggg attgtgctgg atgcgggttc ttctcacaca    180

agtttataca tctataagtg gccagcagaa aaggagaatg acacaggcgt ggtgcatcaa    240

gtagaagaat gcagggttaa aggtcctgga atctcaaaat ttgttcagaa agtaaatgaa    300

ataggcattt acctgactga ttgcatggaa agagctaggg aagtgattcc aaggtcccag    360

caccaagaga cacccgttta cctgggagcc acggcaggca tgcggttgct caggatggaa    420

agtgaagagt tggcagacag ggttctggat gtggtggaga ggagcctcag caactacccc    480

tttgacttcc agggtgccag gatcattact ggccaagagg aaggtgccta tggctggatt    540

actatcaact atctgctggg caaattcagt cagaaaacaa ggtggttcag catagtccca    600

tatgaaacca ataatcagga aacctttgga gctttggacc ttgggggagc ctctacacaa    660

gtcacttttg taccccaaaa ccagactatc gagtccccag ataatgctct gcaatttcgc    720

ctctatggca aggactacaa tgtctacaca catagcttct tgtgctatgg gaaggatcag    780

gcactctggc agaaactggc caaggacatt caggttgcaa gtaatgaaat tctcagggac    840

ccatgctttc atcctggata taagaaggta gtgaacgtaa gtgaccttta caagaccccc    900

tgcaccaaga gatttgagat gactcttcca ttccagcagt ttgaaatcca gggtattgga    960

aactatcaac aatgccatca aagcatcctg gagctcttca acaccagtta ctgcccttac   1020

tcccagtgtg ccttcaatgg gattttcttg ccaccactcc agggggattt tggggcattt   1080

tcagcttttt actttgtgat gaagttttta aacttgacat cagagaaagt ctctcaggaa   1140

aaggtgactg agatgatgaa aaagttctgt gctcagcctt gggaggagat aaaaaacatct   1200

tacgctggag taaaggagaa gtacctgagt gaatactgct tttctggtac ctacattctc   1260

tccctccttc tgcaaggcta tcatttcaca gctgattcct gggagcacat ccatttcatt   1320

ggcaagatcc agggcagcga cgccggctgg actttgggct acatgctgaa cctgaccaac   1380

atgatcccag ctgagcaacc attgtccaca cctctctccc actccaccta tgtcttcctc   1440
```

atggttctat tctccctggt ccttttcaca gtggccatca taggcttgct tatctttcac 1500
aagccttcat atttctggaa agatatggta ggaagcggag ctactaactt cagcctgctg 1560
aagcaggctg gagacgtgga ggagaaccct ggacctatgt gtccccgagc cgcgcgggcg 1620
cccgcgacgc tactcctcgc cctgggcgcg gtgctgtggc ctgcggctgg cgcctgggag 1680
cttacgattt tgcacaccaa cgacgtgcac agccggctgg agcagaccag cgaggactcc 1740
agcaagtgcg tcaacgccag ccgctgcatg ggtggcgtgg ctcggctctt caccaaggtt 1800
cagcagatcc gccgcgccga acccaacgtg ctgctgctgg acgccggcga ccagtaccag 1860
ggcactatct ggttcaccgt gtacaagggc gccgaggtgg cgcacttcat gaacgccctg 1920
cgctacgatg ccatggcact gggaaatcat gaatttgata atggtgtgga aggactgatc 1980
gagccactcc tcaaagaggc caaatttcca attctgagtg caaacattaa agcaaagggg 2040
ccactagcat ctcaaatatc aggactttat ttgccatata aagttcttcc tgttggtgat 2100
gaagttgtgg gaatcgttgg atacacttcc aaagaaaccc cttttctctc aaatccaggg 2160
acaaatttag tgtttgaaga tgaaatcact gcattacaac ctgaagtaga taagttaaaa 2220
actctaaatg tgaacaaaat tattgcactg ggacattcgg gttttgaaat ggataaactc 2280
atcgctcaga aagtgagggg tgtggacgtc gtggtgggag gacactccaa cacatttctt 2340
tacacaggca atccaccttc caaagaggtg cctgctggga agtacccatt catagtcact 2400
tctgatgatg ggcggaaggt tcctgtagtc caggcctatg cttttggcaa atacctaggc 2460
tatctgaaga tcgagtttga tgaaagagga aacgtcatct cttcccatgg aaatcccatt 2520
cttctaaaca gcagcattcc tgaagatcca agcataaaag cagacattaa caaatggagg 2580
ataaaattgg ataattattc tacccaggaa ttagggaaaa caattgtcta tctggatggc 2640
tcctctcaat catgccgctt tagagaatgc aacatgggca acctgatttg tgatgcaatg 2700
attaacaaca acctgagaca cacggatgaa atgttctgga accacgtatc catgtgcatt 2760
ttaaatggag gtggtatccg gtcgcccatt gatgaacgca acaatggcac aattacctgg 2820
gagaacctgg ctgctgtatt gccctttgga ggcacatttg acctagtcca gttaaaaggt 2880
tccaccctga agaaggcctt tgagcatagc gtgcaccgct acggccagtc cactggagag 2940
ttcctgcagg tgggcggaat ccatgtggtg tatgatcttt cccgaaaacc tggagacaga 3000
gtagtcaaat tagatgttct ttgcaccaag tgtcgagtgc ccagttatga ccctctcaaa 3060
atggacgagg tatataaggt gatcctccca aacttcctgg ccaatggtgg agatgggttc 3120
cagatgataa aagatgaatt attaagacat gactctggtg accaagatat caacgtggtt 3180
tctacatata tctccaaaat gaaagtaatt tatccagcag ttgaaggtcg gatcaagttt 3240
tccacaggaa gtcactgcca tggaagcttt tctttaatat ttctttcact ttgggcagtg 3300
atctttgttt tataccaa 3318

<210> SEQ ID NO 59
<211> LENGTH: 22
<212> TYPE: DNA
<213> ORGANISM: Homo sapiens

<400> SEQUENCE: 59
aggatacgtt tttctgttgg gc 22

<210> SEQ ID NO 60
<211> LENGTH: 20
<212> TYPE: DNA

-continued

```
<213> ORGANISM: Homo sapiens

<400> SEQUENCE: 60

ggagaacggg aaaagagcga                                              20
```

UNIVERSAL DONOR CELLS

CROSS-REFERENCE TO RELATED APPLICATION

This application claims the benefit of U.S. Provisional Application No. 63/132,890, filed Dec. 31, 2020, U.S. Provisional Application No. 63/234,997, filed Aug. 19, 2021, and U.S. Provisional Application No. 63/288,356, filed Dec. 10, 2021, the disclosure of each is hereby incorporated by reference in its entirety.

INCORPORATION BY REFERENCE OF SEQUENCE LISTING

This application contains a Sequence Listing that has been submitted in ASCII format via EFS-Web and is hereby incorporated by reference in its entirety. The ASCII copy, created on Dec. 22, 2021, is named 711615-CT154_Sequence_Listing_ST25.txt, and is about 131,000 bytes in size.

FIELD OF THE INVENTION

The invention relates to the field of gene editing and, in some embodiments, to genetic modifications for the purposes of generating cells that are compatible with multiple subjects, e.g., universal donor cells.

BACKGROUND

Various approaches have been proposed to overcome allogeneic rejection of transplanted or engrafted cells including HLA-matching, blocking pathways that trigger T-cell activation with antibodies, use of a cocktail of immune suppressive drugs, and autologous cell therapy. Another strategy to dampen graft rejection involves minimization of allogenic differences between transplanted or engrafted cells and the recipient. The cell surface-expressed human leukocyte antigens (HLAs), molecules encoded by genes located in the human major histocompatibility complex on chromosome 6, are the major mediators of immune rejection. Mismatch of a single HLA gene between the donor and subject can cause a robust immune response (Fleischhauer K. et al. "Bone marrow-allograft rejection by T lymphocytes recognizing a single amino acid difference in HLA-B44," N Engl J Med., 1990, 323:1818-1822). HLA genes are divided into MHC class I (MHC-I) and MHC class II (MHC-II). MHC-I genes (HLA-A, HLA-B, and HLA-C) are expressed in almost all tissue cell types, presenting "non-self" antigen-processed peptides to CD8+ T cells, thereby promoting their activation to cytolytic CD8+ T cells. Transplanted or engrafted cells expressing "non-self" MHC-I molecules will cause a robust cellular immune response directed at these cells and ultimately resulting in their demise by activated cytolytic CD8+ T cells. MHC-I proteins are intimately associated with beta-2-microglobulin (B2M) in the endoplasmic reticulum, which is essential for forming functional MHC-I molecules on the cell surface.

In contrast to the wide cellular expression of MHC-I genes, expression of MHC-II genes is restricted to antigen-presenting cells such as dendritic cells, macrophages, and B cells. HLA antigen genes are the most polymorphic genes observed in the human genome (Rubinstein P., "HLA matching for bone marrow transplantation—how much is enough?" N Engl J Med., 2001, 345:1842-1844). The generation of a "universal donor" cell that is compatible with any HLA genotype provides an alternative strategy that could resolve the immune rejection and associated economical costs of current methodologies for immune evasion.

To generate such a line of universal donor cell(s), one previous approach has been to functionally disrupt the expression of MHC-I and MHC-II class genes. This could be achieved through genetic disruption, e.g., of both genetic alleles encoding the MHC-I light chain, B2M. The resulting B2M-null cell line and its derivatives would be expected to exhibit greatly reduced surface MHC-I and thus, reduced immunogenicity to allogeneic CD8+ T cells. The transcription activator-like effector nuclease (TALEN) targeting approach has been used to generate B2M-deficient hESC lines by deletion of a few nucleotides in exon 2 of the B2M gene (Lu, P. et al., "Generating hypoimmunogenic human embryonic stem cells by the disruption of beta 2-microglobulin," Stem Cell Rev. 2013, 9:806-813). Although the B2M-targeted hESC lines appeared to be surface HLA-I deficient, they were found to still contain mRNAs specific for B2M and MHC-I. The B2M and MHC-I mRNAs were expressed at levels equivalent to those of untargeted hESCs (both constitutive and IFN-g induced). Thus, concern exists that these TALEN B2M-targeted hESC lines might express residual cell surface MHC-I that would be sufficient to cause immune rejection, such as has been observed with B2M2/2 mouse cells that also express B2M mRNA (Gross, R. and Rappuoli, R. "Pertussis toxin promoter sequences involved in modulation," Proc Natl Acad Sci, 1993, 90:3913-3917). Although the TALEN B2M targeted hESC lines were not examined for off-target cleavage events, the occurrence of nonspecific cleavage when using TALENs remains a significant issue that would impose a major safety concern on their clinical use (Grau, J. et al. "TALENoffer: genome-wide TALEN off-target prediction," Bioinformatics, 2013, 29:2931-2932; Guilinger J. P. et al. "Broad specificity profiling of TALENs results in engineered nucleases with improved DNA-cleavage specificity," Nat Methods 2014, 11:429-435). Further, another report generated IPS cells that escaped allogeneic recognition by knocking out a first B2M allele and knocking in a HLA-E gene at a second B2M allele, which resulted in surface expression of HLA-E dimers or trimers in the absence of surface expression of HLA-A, HLA-B, or HLA-C (Gornalusse, G. G. et al., "HLA-E-expressing pluripotent stem cells escape allogeneic responses and lysis by NK cells," Nature Biotechnology, 2017, 35, 765-773).

A potential limitation of some of the above strategies is that MHC class I-negative cells are susceptible to lysis by natural killer (NK) cells as HLA molecules serve as major ligand inhibitors to natural killer (NK) cells. Host NK cells have been shown to eliminate transplanted or engrafted B2M−/− donor cells, and a similar phenomenon occurs in vitro with MHC class-I-negative human leukemic lines (Bix, M. et al., "Rejection of class I MHC-deficient haemopoietic cells by irradiated MHC-matched mice," Nature, 1991, 349, 329-331; Zarcone, D. et al., "Human leukemia-derived cell lines and clones as models for mechanistic analysis of natural killer cell-mediated cytotoxicity," Cancer Res. 1987, 47, 2674-2682). Thus, there exists a need to improve upon previous methods to generate universal donor cells that can evade the immune response as well as a need to generate cells that can survive post-engraftment. As described herein, cell survival post-engraftment or post-transplantation may be mediated by a host of other pathways independent of allogeneic rejection e.g., hypoxia, reactive oxygen species, nutrient deprivation, and oxidative stress. Also as described herein, genetic introduction of survival factors (genes and/or proteins) may help cells to survive post-engraftment. As described herein, a universal donor cell line may combine properties that address both allogeneic rejection and survival post-engraftment.

SUMMARY

In some aspects, the present disclosure encompasses a genetically modified cell comprising (a) a first exogenous polynucleotide insertion encoding mesencephalic astrocyte derived neurotrophic factor (MANF), a second exogenous polynucleotide insertion encoding tumor necrosis factor alpha induced protein 3 (TNFAIP3), a third exogenous polynucleotide insertion encoding cluster of differentiation 39 (CD39), and/or a fourth exogenous polynucleotide insertion encoding cluster of differentiation 73 (CD73), wherein the genetically modified cell expresses CD39, MANF, TNFAIP3, and/or CD73; and/or (b) a disrupted gene encoding a transforming growth factor beta (TGFβ) protein, a beta-2-microglobulin (B2M) protein, a thioredoxin interacting protein (TXNIP) protein, and/or a class II transactivator (CIITA) protein wherein the genetically modified cell has disrupted expression of the TGFβ protein, the B2M protein, the TXNIP protein, and/or the CIITA protein.

In some aspects, the genetically modified cell of the present disclosure is a stem cell, a hematopoietic stem cell, a lineage-restricted progenitor cell and/or a fully differentiated somatic cell.

In some aspects, the present disclosure encompasses a plurality of genetically modified cells comprising one or more of the exogenous polynucleotide insertions comprising MANF, TNFAIP3, CD39, CD73 and/or one or more of disrupted genes encoding transforming growth factor beta (TGFβ), protein, a beta-2-microglobulin (B2M) protein, a thioredoxin interacting protein (TXNIP) protein, and/or a class II transactivator (CIITA) protein wherein the genetically modified cell has disrupted expression of the TGFβ protein, the B2M protein, the TXNIP protein, and/or the CIITA protein. In some aspects, the present disclosure encompasses a plurality of genetically modified cells wherein at least about 50% of the cells express MANF, HLA-E, TNFAIP3, PD-L-1, CD39 and/or CD73.

In some further aspects, the present disclosure encompasses population of lineage-restricted progenitor cells (including but not restricted to endoderm cell, primitive gut tube cell, posterior foregut cell, pancreatic endoderm progenitor cell, pancreatic endocrine progenitor cell, pancreatic endocrine cell, or immature beta cell, and the fully differentiated somatic cell is a pancreatic beta cell) or fully differentiated somatic cells derived from the plurality of genetically modified cells. In some aspects, the present disclosure further encompasses a population of lineage-restricted progenitor cells (including but not restricted to endoderm cell, primitive gut tube cell, posterior foregut cell, pancreatic endoderm progenitor cell, pancreatic endocrine progenitor cell, pancreatic endocrine cell, or immature beta cell, and the fully differentiated somatic cell is a pancreatic beta cell) or fully differentiated somatic cells derived from the plurality of genetically modified cells wherein at least about 50% of the cells express MANF, HLA-E, TNFAIP3, PD-L-1, CD39 and/or CD73.

In some aspects, the present disclosure encompasses compositions comprising a plurality of genetically modified cells or populations of cells of genetically modified cells comprising (a) a first exogenous polynucleotide insertion encoding mesencephalic astrocyte derived neurotrophic factor (MANF), a second exogenous polynucleotide insertion encoding tumor necrosis factor alpha induced protein 3 (TNFAIP3), a third exogenous polynucleotide insertion encoding cluster of differentiation 39 (CD39), and/or a fourth exogenous polynucleotide insertion encoding cluster of differentiation 73 (CD73), wherein the genetically modified cell expresses CD39, MANF, TNFAIP3, and/or CD73; and/or (b) a disrupted gene encoding a transforming growth factor beta (TGFβ) protein, a beta-2-microglobulin (B2M) protein, a thioredoxin interacting protein (TXNIP) protein, and/or a class II transactivator (CIITA) protein wherein the genetically modified cell has disrupted expression of the TGFβ protein, the B2M protein, the TXNIP protein, and/or the CIITA protein.

In some aspects, the present disclosure also encompasses methods for treating a subject in need thereof, the method comprising: (a) obtaining or having obtained the plurality of genetically modified cells disclosed herein, wherein the plurality of genetically modified cells comprises stem cells; (b) differentiating the genetically modified cells into pancreatic endoderm cells, pancreatic endocrine precursor cells, immature beta cells, and/or pancreatic beta cells; and (c) administering the pancreatic endoderm cells, pancreatic endocrine precursor cells, immature beta cells, and/or pancreatic beta cells to the subject.

In further aspects the present disclosure encompasses method for treating a subject in need thereof, the method comprising: (a) obtaining or having obtained the population of lineage restricted progenitor cells or fully differentiated somatic cells derived from the plurality of genetically modified cells disclosed herein, wherein the lineage restricted progenitor cells or fully differentiated somatic cells comprise pancreatic endoderm cells, pancreatic endocrine precursor cells, immature beta cells, and/or pancreatic beta cells; and (b) administering the pancreatic endoderm cells, pancreatic endocrine cells, immature beta cells, and/or beta cells to the subject.

In some aspects the present disclosure encompasses methods for treating a subject in need thereof, the method comprising: (a) obtaining or having obtained the plurality of genetically modified cells, wherein the plurality of genetically modified cells disclosed herein comprises stem cells; (b) differentiating the genetically modified cells into pancreatic endoderm cells, pancreatic endocrine precursor cells, immature beta cells, and/or pancreatic beta cells; and (c) administering the pancreatic endoderm cells, pancreatic endocrine precursor cells, immature beta cells, and/or pancreatic beta cells to the subject.

While the disclosure is susceptible to various modifications and alternative forms, specific embodiments thereof are shown by way of example in the drawings and will herein be described in detail. It should be understood, however, that the drawings and detailed description presented herein are not intended to limit the disclosure to the particular embodiments disclosed, but on the contrary, the intention is to cover all modifications, equivalents, and alternatives falling within the spirit and scope of the present disclosure as defined by the appended claims.

Other features and advantages of this disclosure will become apparent in the following detailed description of embodiments of this invention, taken with reference to the accompanying drawings.

DETAILED DESCRIPTION

I. Definitions

Figure 1:
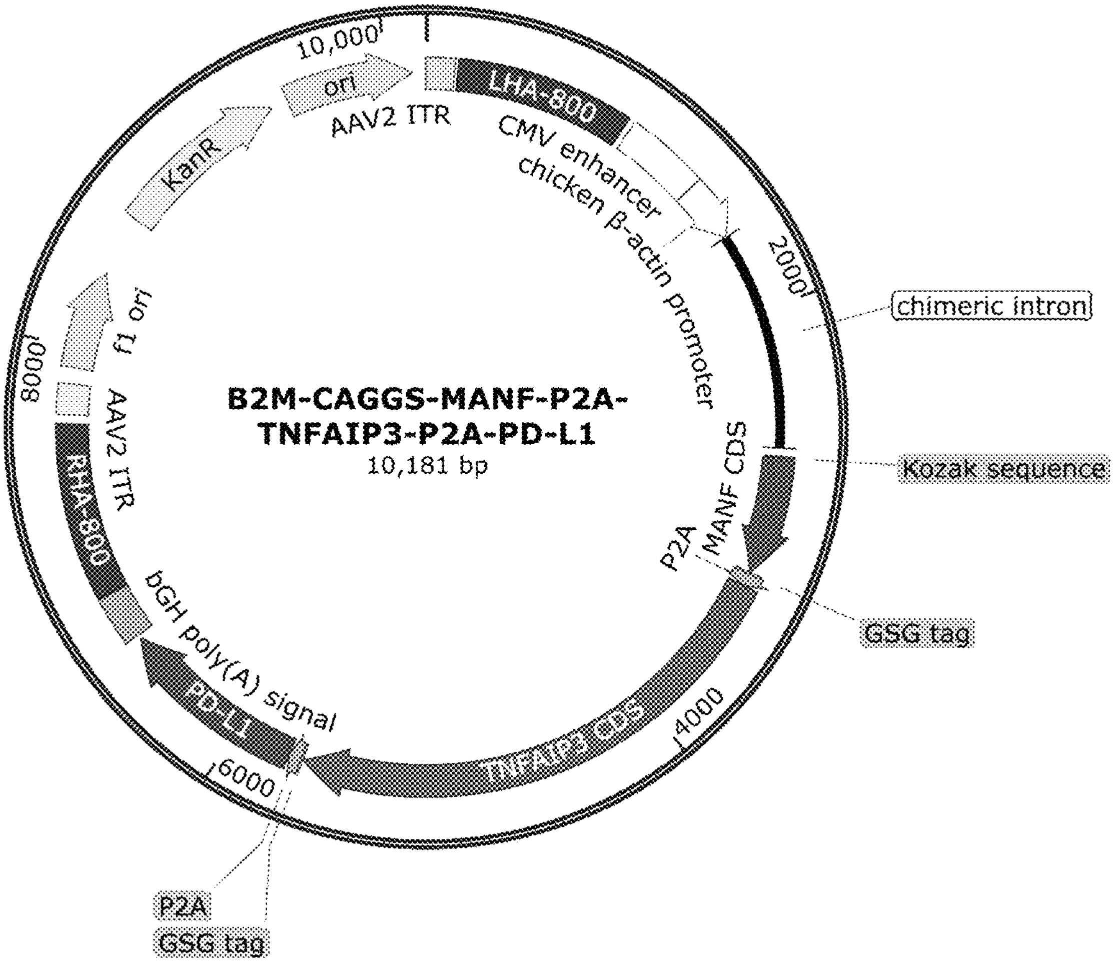
FIG. 1 presents the plasmid map of B2M-CAGGS-MANF-P2A-TNFAIP3-P2A-PD-L-1 donor vector.

Deletion: As used herein, the term "deletion", which may be used interchangeably with the terms "genetic deletion" or "knock-out", generally refers to a genetic modification wherein a site or region of genomic DNA is removed by any molecular biology method, e.g., methods described herein, e.g., by delivering to a site of genomic DNA an endonuclease and at least one gRNA. Any number of nucleotides can be deleted. In some embodiments, a deletion involves the removal of at least one, at least two, at least three, at least four, at least five, at least ten, at least fifteen, at least twenty, or at least 25 nucleotides. In some embodiments, a deletion involves the removal of 10-50, 25-75, 50-100, 50-200, or more than 100 nucleotides. In some embodiments, a deletion involves the removal of part or all of one target gene, e.g., a B2M gene, a TXNIP gene, a CIITA gene, or TGF-β2 gene. In some embodiments, a deletion involves the removal of part or all of two target genes, three target gene, or four target genes. In some embodiments, the removal of part of a target gene refers to removal of all or part of a promoter and/or coding sequence of a gene. In some embodiments, a deletion involves the removal of a transcriptional regulator, e.g., a promoter region, of a target gene. In some embodiments, a deletion involves the removal of all or part of a coding region such that the product normally expressed by the coding region is no longer expressed, is expressed as a truncated form, or expressed at a reduced level. In some embodiments, a deletion leads to a decrease in expression of a gene relative to an unmodified cell. In some embodiments, a deletion leads to a loss of expression of a gene relative to an unmodified cell.

Disruption: As used herein the terms "disruption," "disrupting," or "disrupted" refer to genetic modifications that alter the level of expression of a target gene. In some aspects, the disruption can be due to a deletion of at least one nucleotide within or near the target gene or a deletion of part or all of a target gene, as described above. In other aspects, the disruption also can be due to a substitution of at least one nucleotide and/or an insertion of at least one nucleotide within or near the target gene. In further aspects, the disruption can be due to an insertion of one or more exogenous polynucleotides within or near the target gene. In general, as used herein, disrupted expression refers to reduced or eliminated expression of the target gene. In some embodiments, the disruption can be a reduced level of expression (e.g., express less than 30%, less than 25%, less than 20%, less than 10%, or less than 5% of the level of an unmodified cell). In some embodiments, the disruption can be eliminated expression (e.g., no expression or an undetectable level of RNA and/or protein expression). Expression can be measured using any standard RNA-based, protein-based, and/or antibody-based detection method (e.g., RT-PCR, ELISA, flow cytometry, immunocytochemistry, and the like). Detectable levels are defined as being higher that the limit of detection (LOD), which is the lowest concentration that can be measured (detected) with statistical significance by means of a given detection method.

Endonuclease: As used herein, the term "endonuclease" generally refers to an enzyme that cleaves phosphodiester bonds within a polynucleotide. In some embodiments, an endonuclease specifically cleaves phosphodiester bonds within a DNA polynucleotide. In some embodiments, an endonuclease is a zinc finger nuclease (ZFN), transcription activator like effector nuclease (TALEN), homing endonuclease (HE), meganuclease, MegaTAL, or a CRISPR-associated endonuclease. In some embodiments, an endonuclease is a RNA-guided endonuclease. In certain aspects, the RNA-guided endonuclease is a CRISPR nuclease, e.g., a Type II CRISPR Cas9 endonuclease or a Type V CRISPR Cpf1 endonuclease. In some embodiments, an endonuclease is a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, or a homolog thereof, a recombination of the naturally occurring molecule thereof, a codon-optimized version thereof, or a modified version thereof, or combinations thereof. In some embodiments, an endonuclease may introduce one or more single-stranded breaks (SSBs) and/or one or more double-stranded breaks (DSBs).

Exogenous: The term "exogenous" as used herein refers to a polynucleotide sequence originating outside the recipient cell or organism, a polynucleotide sequence assembled outside the recipient cell or organism, or a polynucleotide sequence originating from the recipient cell or organism but integrated into the recipient genome at a location other than the naturally occurring location. An exogenous polynucleotide sequence may comprise a gene sequence, may comprise a coding sequence (CDS) of a gene, may comprise coding sequences from more than one gene, may comprise promoter sequences, enhancer sequences, and/or other regulatory elements, may comprise ribosome skip sequences, and/or may comprise artificial sequences. An exogenous polynucleotide may be codon optimized to ensure efficient translation in the recipient cell or organism.

Genetic modification: As used herein, the term "genetic modification" generally refers to a site of genomic DNA that has been genetically edited or manipulated using any molecular biological method, e.g., methods described herein, e.g., by delivering to a site of genomic DNA an endonuclease and at least one gRNA. Example genetic modifications include insertions, deletions, duplications, inversions, and translocations, and combinations thereof. In some embodiments, a genetic modification is a deletion. In some embodiments, a genetic modification is an insertion. In other embodiments, a genetic modification is an insertion-deletion mutation (or indel), such that the reading frame of the target gene is shifted leading to an altered gene product or no gene product.

Guide RNA (gRNA): As used herein, the term "guide RNA" or "gRNA" generally refers to short ribonucleic acid that can interact with, e.g., bind to, to an endonuclease and bind, or hybridize to a target genomic site or region. In some embodiments, a gRNA is a single-molecule guide RNA (sgRNA). In some embodiments, a gRNA may comprise a spacer extension region. In some embodiments, a gRNA may comprise a tracrRNA extension region. In some embodiments, a gRNA is single-stranded. In some embodiments, a gRNA comprises naturally occurring nucleotides. In some embodiments, a gRNA is a chemically modified gRNA. In some embodiments, a chemically modified gRNA is a gRNA that comprises at least one nucleotide with a chemical modification, e.g., a 2'-O-methyl sugar modification. In some embodiments, a chemically modified gRNA comprises a modified nucleic acid backbone. In some embodiments, a chemically modified gRNA comprises a 2'-O-methyl-phosphorothioate residue. In some embodiments, a gRNA may be pre-complexed with a DNA endonuclease.

Insertion: As used herein, the term "insertion" which may be used interchangeably with the terms "genetic insertion" or "knock-in", generally refers to a genetic modification wherein a polynucleotide is introduced or added into a site or region of genomic DNA by any molecular biological method, e.g., methods described herein, e.g., by delivering to a site of genomic DNA an endonuclease and at least one gRNA. In some embodiments, an insertion of an exogenous polynucleotide occurs within or near a target gene. In some embodiments, an insertion of an exogenous polynucleotide may occur within or near a site of genomic DNA that has been the site of a prior genetic modification, e.g., a deletion or insertion-deletion mutation. In some embodiments, an insertion occurs at a site of genomic DNA that partially overlaps, completely overlaps, or is contained within a site of a prior genetic modification, e.g., a deletion or insertion-deletion mutation. In some embodiments, an insertion simultaneously leads to a disruption of the gene at the targeted site of the insertion. In some embodiments, an insertion occurs at a safe harbor locus. In some embodiments, an insertion involves the introduction of a polynucleotide that encodes a protein of interest. In some embodiments, an insertion involves the introduction of a polynucleotide that encodes a tolerogenic factor. In some embodiments, an insertion involves the introduction of a polynucleotide that encodes a survival factor. In some embodiments, the insertion involves the introduction of a polynucleotide that encodes MANF, TNFAIP3, CD39, CD73, PD-L-1, and/or HLA-E. In some embodiments, an insertion involves the introduction of an exogenous promoter, e.g., a constitutive promoter, e.g., a CAG or CAGGS promoter. In some embodiments, an insertion involves the introduction of a polynucleotide that encodes a noncoding gene. In general, a polynucleotide to be inserted is flanked by sequences (e.g., homology arms) having substantial sequence homology with genomic DNA at or near the site of insertion.

Major histocompatibility complex class I (MHC-I): As used herein, the terms "Major histocompatibility complex class I" or "MHC-I" generally refer to a class of biomolecules that are found on the cell surface of all nucleated cells in vertebrates, including mammals, e.g., humans; and function to display peptides of non-self or foreign antigens, e.g., proteins, from within the cell (i.e. cytosolic) to cytotoxic T cells, e.g., CD8+ T cells, in order to stimulate an immune response. In some embodiments, a MHC-I biomolecule is a MHC-I gene or a MHC-I protein. Complexation of MHC-I proteins with beta-2 microglobulin (B2M) protein is required for the cell surface expression of all MHC-I proteins. In some embodiments, decreasing the expression of a MHC-I human leukocyte antigen (HLA) relative to an unmodified cell involves a decrease (or reduction) in the expression of a MHC-I gene. In some embodiments, decreasing the expression of a MHC-I human leukocyte antigen (HLA) relative to an unmodified cell involves a decrease (or reduction) in the cell surface expression of a MHC-I protein. In some embodiments, a MHC-I biomolecule is HLA-A (NCBI Gene ID No: 3105), HLA-B (NCBI Gene ID No: 3106), HLA-C(NCBI Gene ID No: 3107), or B2M (NCBI Gene ID No: 567).

Major histocompatibility complex class H (MHC-II): As used herein, the term "Major histocompatibility complex class II" or "MHC-II" generally refer to a class of biomolecules that are typically found on the cell surface of antigen-presenting cells in vertebrates, including mammals, e.g., humans; and function to display peptides of non-self or foreign antigens, e.g., proteins, from outside of the cell (extracellular) to cytotoxic T cells, e.g., CD8+ T cells, in order to stimulate an immune response. In some embodiments, an antigen-presenting cell is a dendritic cell, macrophage, or a B cell. In some embodiments, a MHC-II biomolecule is a MHC-II gene or a MHC-II protein. In some embodiments, decreasing the expression of a MHC-II human leukocyte antigen (HLA) relative to an unmodified cell involves a decrease (or reduction) in the expression of a MHC-II gene. In some embodiments, decreasing the expression of a MHC-II human leukocyte antigen (HLA) relative to an unmodified cell involves a decrease (or reduction) in the cell surface expression of a MHC-II protein. In some embodiments, a MHC-II biomolecule is HLA-DPA (NCBI Gene ID No: 3113), HLA-DPB (NCBI Gene ID No: 3115), HLA-DMA (NCBI Gene ID No: 3108), HLA-DMB (NCBI Gene ID No: 3109), HLA-DOA (NCBI Gene ID No: 3111), HLA-DOB (NCBI Gene ID No: 3112), HLA-DQA (NCBI Gene ID No: 3117), HLA-DQB (NCBI Gene ID No: 3119), HLA-DRA (NCBI Gene ID No: 3122), or HLA-DRB (NCBI Gene ID No: 3123).

Polynucleotide: As used herein, the term "polynucleotide", which may be used interchangeably with the term "nucleic acid" generally refers to a biomolecule that comprises two or more nucleotides. In some embodiments, a polynucleotide comprises at least two, at least five at least ten, at least twenty, at least 30, at least 40, at least 50, at least 100, at least 200, at least 250, at least 500, or any number of nucleotides. For example, the polynucleotides may include at least 500 nucleotides, at least about 600 nucleotides, at least about 700 nucleotides, at least about 800 nucleotides, at least about 900 nucleotides, at least about 1000 nucleotides, at least about 2000 nucleotides, at least about 3000 nucleotides, at least about 4000 nucleotides, at least about 4500 nucleotides, or at least about 5000 nucleotides. A polynucleotide may be a DNA or RNA molecule or a hybrid DNA/RNA molecule. A polynucleotide may be single-stranded or double-stranded. In some embodiments, a polynucleotide is a site or region of genomic DNA. In some embodiments, a polynucleotide is an endogenous gene that is comprised within the genome of an unmodified cell or universal donor cell. In some embodiments, a polynucleotide is an exogenous polynucleotide that is not integrated into genomic DNA. In some embodiments, a polynucleotide is an exogenous polynucleotide that is integrated into genomic DNA. In some embodiments, a polynucleotide is a plasmid or an adeno-associated viral vector. In some embodiments, a polynucleotide is a circular or linear molecule.

Safe harbor locus: As used herein, the term "safe harbor locus" generally refers to any location, site, or region of genomic DNA that may be able to accommodate a genetic insertion into said location, site, or region without adverse effects on a cell. In some embodiments, a safe harbor locus is an intragenic or extragenic region. In some embodiments, a safe harbor locus is a region of genomic DNA that is typically transcriptionally silent. In some embodiments, a safe harbor locus is a AAVS1 (PPP1 R12C), ALB, Angptl3, ApoC3, ASGR2, CCR5, FIX (F9), G6PC, Gys2, HGD, Lp(a), Pcsk9, Serpinal, TF, or TTR locus. In some embodiments, a safe harbor locus is described in Sadelain, M. et al., "Safe harbours for the integration of new DNA in the human genome," Nature Reviews Cancer, 2012, Vol 12, pages 51-58.

Safety switch: As used herein, the term "safety switch" generally refers to a biomolecule that leads a cell to undergo apoptosis. In some embodiments, a safety switch is a protein or gene. In some embodiments, a safety switch is a suicide gene. In some embodiments, a safety switch, e.g., herpes simplex virus thymidine kinase (HSV-tk), leads a cell to undergo apoptosis by metabolizing a prodrug, e.g., ganciclovir. In some embodiments, the overexpressed presence of a safety switch on its own leads a cell to undergo apoptosis. In some embodiments, a safety switch is a p53-based molecule, HSV-tk, or inducible caspase-9.

Subject: As used herein, the term "subject" refers to a mammal. In some embodiments, a subject is non-human primate or rodent. In some embodiments, a subject is a human. In some embodiments, a subject has, is suspected of having, or is at risk for, a disease or disorder. In some embodiments, a subject has one or more symptoms of a disease or disorder.

Survival factor: As used herein, the term "survival factor" generally refers to a protein (e.g., expressed by a polynucleotide as described herein) that, when increased or decreased in a cell, enables the cell, e.g., a universal donor cell, to survive after transplantation or engraftment into a host subject at higher survival rates relative to an unmodified cell.

In some embodiments, a survival factor is a human survival factor. In some embodiments, a survival factor is a member of a critical pathway involved in cell survival. In some embodiments, a critical pathway involved in cell survival has implications on hypoxia, reactive oxygen species, nutrient deprivation, and/or oxidative stress. In some embodiments, the genetic modification, e.g., deletion or insertion, of at least one survival factor enables a universal donor cell to survive for a longer time period, e.g., at least 1.05, at least 1.1, at least 1.25, at least 1.5, at least 2, at least 3, at least 4, at least 5, at least 10, at least 20, or at least 50 times longer time period, than an unmodified cell following engraftment. In some embodiments, a survival factor is MANF (NCBI Gene ID No: 7873), ZNF143 (NCBI Gene ID No: 7702), TXNIP (NCBI Gene ID No: 10628), FOXO1 (NCBI Gene ID No: 2308), or JNK (NCBI Gene ID No: 5599). In some embodiments, a survival factor is inserted into a cell, e.g., a universal donor cell. In some embodiments, a survival factor is deleted from a cell, e.g., a universal donor cell. In some embodiments, an insertion of a polynucleotide that encodes MANF enables a cell, e.g., a universal donor cell, to survive after transplantation or engraftment into a host subject at higher survival rates relative to an unmodified cell. In some embodiments, a deletion or insertion-deletion mutation within or near a TXNIP gene enables a cell, e.g., a universal donor cell, to survive after transplantation or engraftment into a host subject at higher survival rates relative to an unmodified cell.

Tolerogenic factor: As used herein, the term "tolerogenic factor" generally refers to a protein (e.g., expressed by a polynucleotide as described herein) that, when increased or decreased in a cell, enables the cell, e.g., a universal donor cell, to inhibit or evade immune rejection after transplantation or engraftment into a host subject at higher rates relative to an unmodified cell. In some embodiments, a tolerogenic factor is a human tolerogenic factor. In some embodiments, the genetic modification of at least one tolerogenic factor (e.g., the insertion or deletion of at least one tolerogenic factor) enables a cell, e.g., a universal donor cell. to inhibit or evade immune rejection with rates at least 1.05, at least 1.1, at least 1.25, at least 1.5, at least 2, at least 3, at least 4, at least 5, at least 10, at least 20, or at least 50 times higher than an unmodified cell following engraftment. In some embodiments, a tolerogenic factor is TNFAIP3 (NCBI Gene ID No: 7128), CD39 (NCBI Gene ID No: 953), CD73 (NCBI Gene ID No. 4907), PD-L-1 (NCBI Gene ID No: 29126), HLA-E (NCBI Gene ID No: 3133), HLA-G (NCBI Gene ID No: 3135), CTLA-4 (NCBI Gene ID No: 1493), or CD47 (NCBI Gene ID No: 961). In some embodiments, a tolerogenic factor is inserted into a cell, e.g., a universal donor cell. In some embodiments, a tolerogenic factor is deleted from a cell, e.g., a universal donor cell. In some embodiments, an insertion of a polynucleotide that encodes TNFAIP3, CD39, CD73, HLA-E, PD-L-1, HLA-G, CTLA-4, and/or CD47 enables a cell, e.g., a universal donor cell, to inhibit or evade immune rejection after transplantation or engraftment into a host subject.

Transcriptional regulator of MHC-I or MHC-I: As used herein, the term "transcriptional regulator of MHC-I or MHC-II" generally refers to a biomolecule that modulates, e.g., increases or decreases, the expression of a MHC-I and/or MHC-II human leukocyte antigen. In some embodiments, a biomolecule is a polynucleotide, e.g., a gene, or a protein. In some embodiments, a transcriptional regulator of MHC-I or MHC-II will increase or decrease the cell surface expression of at least one MHC-I or MHC-II protein. In some embodiments, a transcriptional regulator of MHC-I or MHC-II will increase or decrease the expression of at least one MHC-I or MHC-II gene. In some embodiments, the transcriptional regulator is CIITA (NCBI Gene ID No: 4261) or NLRC5 (NCBI Gene ID No: 84166). In some embodiments, a deletion or reduction of expression of CIITA or NLRC5 decreases expression of at least one MHC-I or MHC-II gene.

Universal donor cell: As used herein, the term "universal donor cell" generally refers to a genetically modified cell that is less susceptible to allogeneic rejection during a cellular transplant and/or demonstrates increased survival after transplantation, relative to an unmodified cell. In some embodiments, a genetically modified cell as described herein is a universal donor cell. In some embodiments, the universal donor cell has increased immune evasion and/or post-transplantation survival compared to an unmodified cell. In some embodiments, the universal donor cell has increased cell survival compared to an unmodified cell. In some embodiments, a universal donor cell may be a stem cell. In some embodiments, a universal donor cell may be an embryonic stem cell (ESC), an adult stem cell (ASC), an induced pluripotent stem cell (iPSC), or a hematopoietic stem or progenitor cell (HSPC) (also called a hematopoietic stem cell (HSC)). In some embodiments, a universal donor cell may be a differentiated cell. In some embodiments, a universal donor cell may be a somatic cell (e.g., immune system cells). In some embodiments, a universal donor cell is administered to a subject. In some embodiments, a universal donor cell is administered to a subject who has, is suspected of having, or is at risk for a disease. In some embodiments, the universal donor cell is capable of being differentiated into lineage-restricted progenitor cells or fully differentiated somatic cells. In some embodiments, the lineage-restricted progenitor cells are pancreatic endoderm progenitors, pancreatic endocrine progenitors, mesenchymal progenitor cells, muscle progenitor cells, blast cells, hematopoietic progenitor cells, or neural progenitor cells. In some embodiments, the fully differentiated somatic cells are endocrine secretory cells such as pancreatic beta cells, epithelial cells, endodermal cells, macrophages, hepatocytes, adipocytes, kidney cells, blood cells, or immune system cells. In some embodiments, the fully differentiated somatic cells are cardiomyocytes.

Unmodified cell: As used herein, the term "unmodified cell" refers to a cell that has not been subjected to a genetic modification involving a polynucleotide or gene that encodes a MHC-I, MHC-I, transcriptional regulator of MHC-I or MHC-II, survival factor, and/or tolerogenic factor. In some embodiments, an unmodified cell may be a stem cell. In some embodiments, an unmodified cell may be an embryonic stem cell (ESC), an adult stem cell (ASC), an induced pluripotent stem cell (iPSC), or a hematopoietic stem or progenitor cell (HSPC) (also called a hematopoietic stem cell (HSC)). In some embodiments, an unmodified cell may be a differentiated cell. In some embodiments, an unmodified cell may be selected from somatic cells (e.g., immune system cells, e.g., a T cell, e.g., a CD8+ T cell). If a universal donor cell is compared "relative to an unmodified cell", the universal donor cell and the unmodified cell are the same cell type or share a common parent cell line, e.g., a universal donor iPSC is compared relative to an unmodified iPSC.

Within or near a gene: As used herein, the term "within or near a gene" refers to a site or region of genomic DNA that is an intronic or exonic component of said gene or is located proximal to said gene. In some embodiments, a site of genomic DNA is within a gene if it comprises at least a portion of an intron or exon of said gene. In some embodiments, a site of genomic DNA located near a gene may be at the 5' or 3' end of said gene (e.g., the 5' or 3' end of the coding region of said gene). In some embodiments, a site of genomic DNA located near a gene may be a promoter region or repressor region that modulates the expression of said gene. In some embodiments, a site of genomic DNA located near a gene may be on the same chromosome as said gene. In some embodiments, a site or region of genomic DNA is near a gene if it is within 50 Kb, 40 Kb, 30 Kb, 20 Kb, 10 Kb, 5 Kb, 1 Kb, or closer to the 5' or 3' end of said gene (e.g., the 5' or 3' end of the coding region of said gene).

As used herein, the term "comprising" or "comprises" is inclusive or open-ended and does not exclude additional, unrecited elements, ingredients, or method steps; the phrase "consisting of" or "consists of" is closed and excludes any element, step, or ingredient not specified; and the phrase "consisting essentially of" or "consists essentially" means that specific further components can be present, namely those not materially affecting the essential characteristics of the compound, composition, or method. When used in the context of a sequence, the phrase "consisting essentially of" or "consists essentially" means that the sequence can comprise substitutions and/or additional sequences that do not change the essential function or properties of the sequence.

II. Strategies to Evade Immune Response and Increase Survival

Described herein are strategies to enable genetically modified cells, i.e., universal donor cells, to increase their survival or viability and/or evade immune response following engraftment into a subject. In some embodiments, these strategies enable universal donor cells to survive and/or evade immune response at higher success rates than an unmodified cell. In some embodiments, genetically modified cells comprise the introduction of at least one genetic modification within or near at least one gene that encodes a survival factor, wherein the genetic modification comprises an insertion of a polynucleotide encoding a tolerogenic factor. The universal donor cells may further comprise at least one genetic modification within or near a gene that encodes one or more MHC-I or MHC-II human leukocyte antigens or a component or a transcriptional regulator of a MHC-I or MHC-II complex, wherein said genetic modification comprises an insertion of a polynucleotide encoding a second tolerogenic factor.

In some embodiments, genetically modified cells comprise the introduction of at least one genetic modification within or near at least one gene that decreases the expression of one or more MHC-I and MHC-II human leukocyte antigens relative to an unmodified cell; at least one genetic modification that increases the expression of at least one polynucleotide that encodes a tolerogenic factor relative to an unmodified cell; and at least one genetic modification that alters the expression of at least one gene that encodes a survival factor relative to an unmodified cell. In other embodiments, genetically modified cells comprise at least one deletion or insertion-deletion mutation within or near at least one gene that alters the expression of one or more MHC-I and MHC-II human leukocyte antigens relative to an unmodified cell; and at least one insertion of a polynucleotide that encodes at least one tolerogenic factor at a site that partially overlaps, completely overlaps, or is contained within, the site of a deletion of a gene that alters the expression of one or more MHC-I and MHC-II HLAs. In yet other embodiments, genetically modified cells comprise at least one genetic modification that alters the expression of at least one gene that encodes a survival factor relative to an unmodified cell.

The genes that encode the major histocompatibility complex (MHC) are located on human Chr. 6p21. The resultant proteins coded by the MHC genes are a series of surface proteins that are essential in donor compatibility during cellular transplantation. MHC genes are divided into MHC class I (MHC-I) and MHC class II (MHC-II). MHC-I genes (HLA-A, HLA-B, and HLA-C) are expressed in almost all tissue cell types, presenting "non-self" antigen-processed peptides to CD8+ T cells, thereby promoting their activation to cytolytic CD8+ T cells. Transplanted or engrafted cells expressing "non-self" MHC-I molecules will cause a robust cellular immune response directed at these cells and ultimately resulting in their demise by activated cytolytic CD8+ T cells. MHC-I proteins are intimately associated with B2M in the endoplasmic reticulum, which is essential for forming functional MHC-I molecules on the cell surface. In addition, there are three non-classical MHC-Ib molecules (HLA-E, HLA-F, and HLA-G), which have immune regulatory functions. MHC-II biomolecule include HLA-DP, HLA-DM, HLA-DOA, HLA-DOB, HLA-DQ, and HLA-DR. Due to their primary function in the immune response, MHC-I and MHC-II biomolecules contribute to immune rejection following cellular engraftment of non-host cells, e.g., cellular engraftment for purposes of regenerative medicine.

MHC-I cell surface molecules are composed of MHC-encoded heavy chains (HLA-A, HLA-B, or HLA-C) and the invariant subunit B2M. Thus, a reduction in the concentration of B2M within a cell allows for an effective method of reducing the cell surface expression of MHC-I cell surface molecules.

In some embodiments, a cell comprises a genomic modification of one or more MHC-I or MHC-II genes. In some embodiments, a cell comprises a genomic modification of one or more polynucleotide sequences that regulates the expression of MHC-I and/or MHC-II. In some embodiments, a genetic modification of the disclosure is performed using any gene editing method including but not limited to those methods described herein.

In some embodiments, decreasing the expression of one or more MHC-I and MHC-II human leukocyte antigens relative to an unmodified cell is accomplished by targeting, e.g., for genetic deletion and/or insertion of at least one base pair, in a MHC-I and/or MHC-II gene directly. In some embodiments, decreasing the expression of one or more MHC-I and MHC-II human leukocyte antigens relative to an unmodified cell is accomplished by targeting, e.g., for genetic deletion, a CIITA gene. In some embodiments, decreasing the expression of one or more MHC-I and MHC-II human leukocyte antigens relative to an unmodified cell is accomplished by targeting, e.g., for genetic deletion, at least one transcriptional regulator of MHC-I or MHC-II. In some embodiments, a transcriptional regulator of MHC-I or MHC-II is a NLRC5, or CIITA gene. In some embodiments, a transcriptional regulator of MHC-I or MHC-II is a RFX5, RFXAP, RFXANK, NFY-A, NFY-B, NFY-C, IRF-1, and/or TAP1 gene.

In some embodiments, the genome of a cell has been modified to delete the entirety or a portion of an HLA-A, HLA-B, and/or HLA-C gene. In some embodiments, the genome of a cell has been modified to delete the entirety or a portion of a promoter region of an HLA-A, HLA-B, and/or HLA-C gene. In some embodiments, the genome of a cell has been modified to delete the entirety or a portion of a gene that encodes a transcriptional regulator of MHC-I or MHC- II. In some embodiments, the genome of a cell has been modified to delete the entirety or a portion of a promoter region of a gene that encodes a transcriptional regulator of MHC-I or MHC-II.

In some embodiments, the genome of a cell has been modified to disrupt or decrease the expression of beta-2-microglobulin (B2M), also known as β2 microglobulin, B2 microglubulin, or IMD43. B2M is a non-polymorphic gene that encodes a common protein subunit required for surface expression of all polymorphic MHC class I heavy chains. HLA-I proteins are intimately associated with B2M in the endoplasmic reticulum, which is essential for forming functional, cell-surface expressed HLA-I molecules. In some embodiments, the gRNA targets a site within the B2M gene comprising a 5'-GCTACTCTCTCTTTCTGGCC-3' sequence (SEQ ID NO: 1). In some embodiments, the gRNA targets a site within the B2M gene comprising a 5'-GGCCGAGATGTCTCGCTCCG-3' sequence (SEQ ID NO: 2). In some embodiments, the gRNA targets a site within the B2M gene comprising a 5'-CGCGAGCACAGCTAAGGCCA-3' sequence (SEQ ID NO: 3). In alternate embodiments, the gRNA targets a site within the B2M gene comprising any of the following sequences: 5'-TATAAGTGGAGGCGTCGCGC-3' (SEQ ID NO: 4), 5'-GAGTAGCGCGAGCACAGCTA-3' (SEQ ID NO: 5), 5'-ACTGGACGCGTCGCGCTGGC-3' (SEQ ID NO: 6), 5'-AAGTGGAGGCGTCGCGCTGG-3' (SEQ ID NO: 7), 5-GGCCACGGAGCGAGACATCT-3' (SEQ ID NO: 8), 5'-GCCCGAATGCTGTCAGCTTC-3' (SEQ ID NO: 9). 5'-CTCGCGCTACTCTCTCTTTC-3' (SEQ ID NO: 10), 5'-TCCTGAAGCTGACAGCATTC-3' (SEQ ID NO: 11), 5'-TTCCTGAAGCTGACAGCATT-3' (SEQ ID NO: 12), or 5'-ACTCTCTCTTTCTGGCCTGG-3' (SEQ ID NO: 13). In some embodiments, the gRNA comprises an RNA version of the polynucleotide sequence of SEQ ID NO: 2. In other embodiments, the gRNA comprises an RNA version of any of SEQ ID NO: 1 or 3-13. The gRNA/CRISPR nuclease complex targets and cleaves a target site in the B2M locus. Repair of a double-stranded break by NHEJ can result in a deletion of at least on nucleotide and/or an insertion of at least one nucleotide, thereby disrupting or eliminating expression of B2M. Alternatively, the B2M locus can be targeted by at least two CRISPR systems each comprising a different gRNA, such that cleavage at two sites in the B2M locus leads to a deletion of the sequence between the two cuts, thereby eliminating expression of B2M.

In some embodiments, genetically modified cells comprise at least one genetic modification that disrupts the expression of at least one gene that encodes a survival factor, such as TXNIP, relative to an unmodified cell. In some embodiments, the genome of a cell has been modified to decrease the expression of thioredoxin interacting protein (TXNIP), which is also known as EST01027, HHCPA78, THIF, VDUP1, or ARRDC6. TXNIP is metabolic gene involved in redox regulation that can also function as a tumor suppressor. Downregulation or knockout of TXNIP can protect cells from metabolic stress. In some embodiments, the gRNA targets a site within the TXNIP gene comprising a 5'-GAAGCGTGTCTTCATAGCGC-3' sequence (SEQ ID NO: 32). In some embodiments, the gRNA targets a site within the TXNIP gene comprising a 5'-TTACTCGTGTCAAAGCCGTT-3' sequence (SEQ ID NO: 33). In some embodiments, the gRNA targets a site within the TXNIP gene comprising a 5'-TGTCAAAGCCGTTAGGATCC-3' sequence (SEQ ID NO: 34). In some embodiments, the gRNA targets a site within the TXNIP gene comprising a 5'-GCCGTTAGGATCCTGGCTTG-3' sequence (SEQ ID NO: 35). In some embodiments, the gRNA targets a site within the TXNIP gene comprising a 5'-GCGGAGTGGCTAAAGTGCTT-3' sequence (SEQ ID NO: 36). In some embodiments, the gRNA targets a site within the TXNIP gene comprising a 5'-TCCGCAAGCCAGGATCCTAA-3' sequence (SEQ ID NO: 37). In some embodiments, the gRNA targets a site within the TXNIP gene comprising a 5'-GTTCGGCTTTGAGCTTCCTC-3' sequence (SEQ ID NO: 38). In some embodiments, the gRNA targets site within the TXNIP gene comprising a 5'-GAGATGGTGATCATGAGACC-3' sequence (SEQ ID NO: 39). In some embodiments, the gRNA targets a site within the TXNIP gene comprising a 5'-TTGTACTCATATTTGTTTCC-3' sequence (SEQ ID NO: 40). In some embodiments, the gRNA targets a site within the TXNIP gene comprising a 5'-AACAAATATGAGTACAAGTT-3' sequence (SEQ ID NO: 41). In some embodiments, the gRNA comprises an RNA version of the polynucleotide sequence of SEQ IN NO: 37. In other embodiments, the gRNA comprises an RNA version of any one of SEQ ID NO: 32-36 or 38-41. The gRNA/CRISPR nuclease complex targets and cleaves a target site in the TXNIP gene locus. Repair of a double-stranded break by NHEJ can result in a deletion of at least one nucleotide and/or an insertion of at least one nucleotide, thereby disrupting or eliminating expression of TXNIP. Alternatively, insertion of a polynucleotide encoding an exogenous gene into the TXNIP gene locus can disrupt or eliminate expression of TXNIP.

In some embodiments, the genome of a cell has been modified to disrupt the expression of Class II transactivator (CIITA), which is also known as C2TA, CIITAIV, MHC2TA, NLRA, or class II major histocompatibility complex transactivator. CIITA is a master regulator of major histocompatibility complex (MHC) gene expression. CIITA is a member of the nucleotide binding domain (NBD) leucine-rich repeat (LRR) family of proteins and regulates the transcription of MHC-II by associating with the MHC enhanceosome. The expression of CIITA is induced in B cells and dendritic cells as a function of developmental stage and is inducible by IFN-γ in most cell types. In some embodiments, the gRNA targets a site in the CIITA gene comprising 5'-GGTCCATCTGGTCATAGAAG-3' (SEQ ID NO: 25). In some embodiments, the gRNA targets a site in the CIITA gene comprising 5'-GCTCCAGGTAGCCACCTTCT-3' (SEQ ID NO: 48). In some embodiments, the gRNA targets a site in the CIITA gene comprising 5'-TAGGGGCCCCAACTCCATGG-3' (SEQ ID NO: 49). In some embodiments, the gRNA targets a site in the CIITA gene comprising 5'-GGCTTATGCCAATATCGGTG-3' (SEQ ID NO: 50). In some embodiments, the gRNA targets a site in the CIITA gene comprising 5'-AGGTGATGAAGAGACCAGGG-3' (SEQ ID NO: 51). In some embodiments, the gRNA comprises an RNA version of the sequence of SEQ ID NO: 25. The gRNA/CRISPR nuclease complex targets and cleaves a target site in the CIITA gene locus. Repair of a double-stranded break by NHEJ can result in a deletion of at least on nucleotide and/or an insertion of at least one nucleotide, thereby disrupting or eliminating expression of CIITA. Alternatively, insertion of a polynucleotide encoding an exogenous gene into the CIITA gene locus can disrupt or eliminate expression of CIITA.

In some embodiments, the genome of the cell has been modified to disrupt the expression of TGF-β2, also known as TGFB2, Transforming Growth Factor Beta 2, Glioblastoma-Derived T-Cell Suppressor Factor, Transforming Growth Factor Beta-2 Proprotein Prepro-Transforming Growth Factor Beta-2, Cetermin, G-TSF, Transforming Growth Factor Beta-2, BSC-1 Cell Growth Inhibitor 3, TGF-Beta2, Polyergin, LDS4. The gene encodes a secreted ligand of the TGF-β2 superfamily of proteins. TGF-β2 is a key activator of fibroblasts, the central effector of fibrotic response and also promotes fibrogenic phenotype in immune and vascular cells. Disruption of TGF-β2 expression may improve long term survival of engrafted universal donor cells. In some embodiments, the genome of the cell has been modified to disrupt the TGF-β2 gene. A gRNA targets a site in the TGF-β2 gene comprising 5'-GTTCATGCGCAAGAGGATCG-3' (SEQ ID NO: 57). The gRNA/CRISPR nuclease complex targets and cleaves a target site in the TGF-β2 gene locus. Repair of a double-stranded break by NHEJ can result in a deletion of at least on nucleotide and/or an insertion of at least one nucleotide, thereby disrupting or eliminating expression of TGF-β2. Alternatively, insertion of a polynucleotide encoding an exogenous gene into the TGF-β2 gene locus can disrupt or eliminate expression of TGF-β2.

In some embodiments, the genome of a cell has been modified to decrease the expression of the NLR family, CARD domain containing 5 (NLRC5). NLRC5 is a critical regulator of MHC-I-mediated immune responses and, similar to CIITA, NLRC5 is highly inducible by IFN-γ and can translocate into the nucleus. NLRC5 activates the promoters of MHC-I genes and induces the transcription of MHC-I as well as related genes involved in MHC-I antigen presentation.

In some embodiments, a polynucleotide encoding one or more tolerogenic factors can be inserted into cells, e.g., genetically modified or genetically unmodified cells, to create immune-privileged universal donor cells. Exemplary tolerogenic factors include, without limitation, one or more of TNFAIP3, CD39, PD-L-1, HLA-E, CD73, HLA-C, HLA-F, HLA-G, CTLA-4-Ig, CD47, Cl-inhibitor, and IL-35. In some embodiments, the tolerogenic factor is TNFAIP3 or A20, also known as OTUD7C, TNFA1P2, AISBL, or TNF alpha induced protein 3. TNFAIP3 or A20 is a key regulator of inflammation and immunity and is known to inhibit NF-kappa B activation as well as TNF-mediated apoptosis. In some embodiments the tolerogenic factor is CD39, which is also known as ENTPD1 (ectonucleoside triphosphate diphosphohydrolase-1), NTPDase1, ATPDase, or SPG64. While CD39 is a tolerogenic factor, it may also provide benefit through increasing angiogenesis, anti-inflammatory activity, and/or other means. In some embodiments, the tolerogenic factor is PD-L-1 (programmed death ligand 1) also known as cluster of differentiation 274 (CD274), B7 homolog (B7-H, B7H1), PDCD1L1, PDCD1LG1, or PDL1. PD-L-1 appears to play a major role in suppressing the adaptive arm of immune system and is considered to be a co-inhibitory factor of the immune response. In some embodiments, the tolerogenic factor is HLA-E, also known as EA1.2, EA2.1, HLA-6.2, MHC, QA1, or major histocompatibility complex, class I, E. HLA-E is an important modulator of natural killer (NK) and cytotoxic T lymphocyte (CTL) activation and inhibitory function. In some embodiments, the tolerogenic factor is CD73, also known as 5'-nucleotidase ecto (NT5E), 5'-nucleotidase (5'-NT), ecto-5'-nucleotidase, ENT, EN, NT5, NTE, or E5NT. CD73 is a plasma membrane protein that catalyzes the conversion of AMP to adenosine. CD73-derived adenosine promotes aberrant differentiation of dendritic cells (DCs) by activating the A2b receptor on DCs which promotes a tolerogenic phenotype characterized by increased production of IL-6, IL-10, VEGF, and IL-8 and expression of immunosuppressive proteins like IDO, TGF-β, arginase 2 and COX2. In some embodiments, the genetic modification, e.g., insertion of at least one polynucleotide encoding at least one tolerogenic factor enables a universal donor cell to inhibit or evade immune rejection with rates at least 1.05, at least 1.1, at least 1.25, at least 1.5, at least 2, at least 3, at least 4, at least 5, at least 10, at least 20, or at least 50 times higher than an unmodified cell following engraftment. In some embodiments, an insertion of a polynucleotide that encodes TNFAIP3, CD39, PD-L-1, HLA-E, CD73, HLA-G, CTLA-4, and/or CD47 enables a universal donor cell to inhibit or evade immune rejection after transplantation or engraftment into a host subject.

In some embodiments, a polynucleotide encoding one or more survival factors, such as MANF, can be inserted into genetically modified or genetically unmodified cells to create universal donor cells having increased survival. In some embodiments, the survival factor is MANF, which is also known as arginine-rich, mutated in early-stage tumors (ARMET), arginine-rich protein (ARP), or mesencephalic astrocyte derived neurotrophic factor. MANF is an endoplasmic reticulum (ER) stress-inducible neurotrophic factor that promotes proliferation and survival of pancreatic beta cells, as well as survival of dopaminergic neurons. In some embodiments, insertion of a polynucleotide encoding one or more survival factors, such as MANF, enables a universal donor cell to survive after transplantation or engraftment into a host subject with rates at least 1.05, at least 1.1, at least 1.25, at least 1.5, at least 2, at least 3, at least 4, at least 5, at least 10, at least 20, or at least 50 times higher than an unmodified cell following transplantation or engraftment.

The polynucleotide encoding the tolerogenic factor and/or survival factor generally comprises left and right homology arms that flank the nucleotide sequence encoding the tolerogenic factor. The homology arms have substantial sequence homology to genomic DNA at or near the targeted insertion site. For example, the left homology arm can be a nucleotide sequence homologous with a region located to the left or upstream of the target site or cut site, and the right homology arm can be a nucleotide sequence homologous with a region located to the right or downstream of the target site or cut site. The proximal end of each homology arm can be homologous to genomic DNA sequence abutting the cut site. Alternatively, the proximal end of each homology arm can be homologous to genomic DNA sequence located up to about 10, 20, 30, 40, 50, 60, or 70 nucleobases away from the cut site. As such, the polynucleotide encoding the tolerogenic factor can be inserted into or replace the targeted gene locus within about 10, 20, 30, 40, 50, 60, or 70 base pairs of the cut site, and additional genomic DNA bordering the cut site (and having no homology to a homolog arm) can be deleted. The homology arms can range in length from about 50 nucleotides to several of thousands of nucleotides. In some embodiments, the homology arms can range in length from about 500 nucleobases to about 1000 nucleobases. In some embodiments, the homology arms are about 700, about 800, or about 900 nucleobases in length. In some embodiments, the homology arms are about 800 nucleobases in length. The substantial sequence homology between the homology arms and the genomic DNA can be at least about 80%, at least about 85%, at least about 90%, at least about 95%, or at least about 99%. In some embodiments, the homology arms are identical to the genomic DNA.

In some embodiments, the homology arms are used with B2M guides (e.g., gRNAs comprising RNA version of SEQ ID NO: 1-13). In some embodiments, the homology arms are designed to be used with any B2M guide that would eliminate the start site of the B2M gene. In some embodiments, the B2M homology arms can comprise or consist essentially of a nucleotide sequence of SEQ ID NO: 15 or 22, or a nucleotide sequence having at least 85%, 90%, 95%, or 99% sequence identity with that of SEQ ID NO: 15 or 22. In some embodiments, the left B2M homology arm can comprise or consist essentially of a nucleotide sequence of SEQ ID NO: 15, or a nucleotide sequence having at least 85%, 90%, 95%, or 99% sequence identity with that of SEQ ID NO: 15. In some embodiments, the right B2M homology arm can comprise or consist essentially of a nucleotide sequence of SEQ ID NO: 22, or a nucleotide sequence having at least 85%, 90%, 95%, or 99% sequence identity with that of SEQ ID NO: 22.

In some embodiments, the homology arms are used with TXNIP guides (e.g., gRNAs comprising RNA version of SEQ ID NO: 32-41). In some embodiments, the homology arms are designed to be used with any TXNIP guide that targets exon 1 of TXNIP (e.g., gRNAs comprising RNA version of SEQ ID NO: 32-41). In some embodiments, the TXNIP homology arms can comprise or consist essentially of a nucleotide sequence of SEQ ID NO: 26 or 28, or a nucleotide sequence having at least 85%, 90%, 95%, or 99% sequence identity with that of SEQ ID NO: 26 or 28. In some embodiments, the left TXNIP homology arm can comprise or consist essentially of a nucleotide sequence of SEQ ID NO: 26, or a nucleotide sequence having at least 85%, 90%, 95%, or 99% sequence identity with that of SEQ ID NO: 26. In some embodiments, the right TXNIP homology arm can comprise or consist essentially of a nucleotide sequence of SEQ ID NO: 28, or a nucleotide sequence having at least 85%, 90%, 95%, or 99% sequence identity with that of SEQ ID NO: 28.

In some embodiments, the homology arms are used with CIITA guides (e.g., gRNAs comprising RNA version of SEQ ID NO: 25 or 48-51). In some embodiments, the CIITA homology arms can comprise or consist essentially of a nucleotide sequence of SEQ ID NO: 42 or 44, or a nucleotide sequence having at least 85%, 90%, 95%, or 99% sequence identity with that of SEQ ID NO: 42 or 44. In some embodiments, the left CIITA homology arm can comprise or consist essentially of a nucleotide sequence of SEQ ID NO: 42, or a nucleotide sequence having at least 85%, 90%, 95%, or 99% sequence identity with that of SEQ ID NO: 42. In some embodiments, the right CIITA homology arm can comprise or consist essentially of a nucleotide sequence of SEQ ID NO: 44, or a nucleotide sequence having at least 85%, 90%, 95%, or 99% sequence identity with that of SEQ ID NO: 44.

In some embodiments, the homology arms are used with TGF-β2 guides (e.g., gRNAs targeting a target sequence comprising SEQ ID NO: 57).

The at least one polynucleotide encoding at least one tolerogenic factor and/or survival factor can comprise sequence encoding a one or more ribosome skips, such that, upon expression, a single transcript is produced but due to a ribosome skip during translation, two or more separate proteins are produced. In some embodiments, the ribosome skip can be a short peptide (~20 aa) that prevents the ribosome from creating the peptide bond between a glycine and a proline at the C terminal end of the growing polypeptide chain. The ribosome pauses after the glycine, resulting in release of the nascent polypeptide chain. Translation resumes, with the proline becoming the first amino acid of a second polypeptide chain. This mechanism results in apparent co-translational cleavage of the polypeptide. A highly conserved sequence at the C-terminus of the ribosome skip peptide contributes to steric hindrance and ribosome skipping. In some embodiment, the ribosome skip peptide is a 2A sequence family member. Suitable 2A sequence family members include F2A, T2A, E2A, and P2A, wherein F2A is derived from foot-and-mouth disease virus 2A, T2A is derived from thosea asigna virus 2A, E2A is derived from equine rhinitis A virus, and P2A derived from porcine teschovirus-1 2A. In some embodiments, the ribosome skip peptide is P2A. In some embodiments, sequence encoding the ribosome skip P2A comprises or consists of a nucleotide sequence of SEQ ID NO: 18. In other embodiments, the ribosome skip can be an internal ribosome entry sequence (IRES), which is an RNA element that allows for translation initiation in a cap-independent manner. The IRES, therefore, allows for the production of two separate proteins from the single transcription unit. IRES elements are well known in the art, e.g., can be derived from viral genome (e.g., picornavirus, aphthovirus, pestivirus IRES) or from cellular mRNAs (e.g., various growth factors, transcription factors, oncogenes, and the like).

The at least one polynucleotide encoding at least one tolerogenic factor and/or survival factor can be operably linked to an exogenous promoter. The exogenous promoter can be a constitutive, inducible, temporal-, tissue-, or cell type-specific promoter. In some embodiments, the exogenous promoter is a CMV, EFla, PGK, CAG/CAGGS, or UBC promoter. In general, a CAG or CAGGS promoter comprises a CMV enhancer, a chicken 3-actin promoter, and a chimeric intron. In some embodiments, a CAG or CAGGS promoter comprises or consists essentially of a nucleotide sequence of SEQ ID NO: 16 or nucleotide sequence having at least 85%, 90%, 95%, or 99% sequence identity with that of SEQ ID NO: 16.

In some embodiments, the at least one polynucleotide encoding at least one tolerogenic factor and/or survival factor can be inserted into a safe harbor locus, e.g., the AAVS 1 locus. In some embodiments, the at least one polynucleotide encoding at least one tolerogenic factor and/or survival factor is inserted into a site or region of genomic DNA that partially overlaps, completely overlaps, or is contained within (i.e., is within or near) a MHC-I gene, MHC-II gene, a transcriptional regulator of MHC-I or MHC-II, or a survival factor gene.

In certain embodiments the current disclosure envisages universal donor cells with one or more insertions of exogenous polynucleotide corresponding to any of genes listed as knock-ins in Table 1 and/or disrupted expression of one or more of the genes listed as knock-outs in Table 1. The engineered universal donor cells can comprise an insertion of one polynucleotide, insertion of any two polynucleotides, insertion of any three polynucleotides, insertion of any four polynucleotides, insertion of any five polynucleotides, or insertion of all six polynucleotides corresponding to the genes listed in Table 1 in any target genomic location (e.g., a safe harbor location) and/or the engineered universal donor cells can comprise disrupted expression (e.g., reduced or eliminated expression) of one, two, three, or four of the target genes listed in Table 1. The cells can comprise any possible combination of listed gene knock-ins and gene knock-outs. In some embodiments, two or more polynucleotides to be inserted can be linked via one or more sequences encoding a ribosome skip such as a 2A peptide such that two or more separate proteins can be expressed from a single RNA transcript. In some embodiments, a polynucleotide or polynucleotides to be inserted into the genome of the cell are operably linked to an exogenous promoter.

TABLE 1

| List of possible gene knock-ins and gene knock-outs | |
|---|---|
| Gene knock-in | Gene knock-out |
| PD-L-1 | B2M |
| TNFAIP3 (A20) | TXNIP |
| MANF | CIITA |
| CD39 | TGF-β2 |
| HLA-E | |
| CD73 | |

In some embodiments, a polynucleotide encoding PD-L-1 is inserted at a site within or near a B2M gene locus, within or near a TXNIP gene locus, within or near a CIITA gene locus, or within or near the TGF-β2 gene locus. In some embodiments, a polynucleotide encoding PD-L-1 is inserted at a site within or near a B2M gene locus, within or near a TXNIP gene locus, or within or near a CIITA gene locus. In some embodiments, a polynucleotide encoding PD-L-1 is inserted at a site within or near a B2M gene locus. In some embodiments, a polynucleotide encoding PD-L-1 is inserted at a site within or near a B2M gene locus concurrent with or following a deletion of all or part of a B2M gene or promoter. In some embodiments, a polynucleotide encoding PD-L-1 is inserted at a site within or near a TXNIP gene locus concurrent with or following a deletion of all or part of a TXNIP gene or promoter. In some embodiments, a polynucleotide encoding PD-L-1 is inserted at a site within or near a CIITA gene locus concurrent with or following a deletion of all or part of a CIITA gene or promoter. In other embodiments, a polynucleotide encoding PD-L-1 is inserted at a site within or near a TGF-β2 gene locus concurrent with or following a deletion of all or part of a TGF-β2 gene or promoter. The polynucleotide encoding PD-L-1 is operably linked to an exogenous promoter. The exogenous promoter can be a CAG or CAGGS promoter. In some embodiments, the polynucleotide encoding PD-L-1 comprises a nucleotide sequence of SEQ ID NO: 20, or nucleotide sequence having at least 85%, 90%, 95%, or 99% sequence identity with that of SEQ ID NO: 20.

In some embodiments, a polynucleotide encoding TNFAIP3 is inserted at a site within or near a B2M gene locus, within or near a TXNIP gene locus, within or near a CIITA gene locus, or within or near the TGF-β2 locus. In some embodiments, a polynucleotide encoding TNFAIP3 is inserted at a site within or near a B2M gene locus, within or near a TXNIP gene locus, or within or near a CIITA gene locus. In some embodiments, a polynucleotide encoding TNFAIP3 is inserted at a site within or near a B2M gene locus. In some embodiments, a polynucleotide encoding TNFAIP3 is inserted at a site within or near a B2M gene locus concurrent with or following a deletion of all or part of a B2M gene or promoter. In some embodiments, a polynucleotide encoding TNFAIP3 is inserted at a site within or near a TXNIP gene locus concurrent with or following a deletion of all or part of a TXNIP gene or promoter. In some embodiments, a polynucleotide encoding TNFAIP3 is inserted at a site within or near a CIITA gene locus concurrent with or following a deletion of all or part of a CIITA gene or promoter. In other embodiments, a polynucleotide encoding TNFAIP3 is inserted at a site within or near a TGF-β2 gene locus concurrent with or following a deletion of all or part of a TGF-β2 gene or promoter. The polynucleotide encoding TNFAIP3 is operably linked to an exogenous promoter. The exogenous promoter can be a CAG or CAGGS promoter. In some embodiments, the polynucleotide encoding TNFAIP3 comprises a nucleotide sequence of SEQ ID NO: 19, or nucleotide sequence having at least 85%, 90%, 95%, or 99% sequence identity with that of SEQ ID NO: 19.

In some embodiments, a polynucleotide encoding MANF is inserted at a site within or near a B2M gene locus, within or near a TXNIP gene locus, or within or near a CIITA gene locus, or within or near the TGF-β2 locus. In some embodiments, a polynucleotide encoding MANF is inserted at a site within or near a B2M gene locus, within or near a TXNIP gene locus, or within or near a CIITA gene locus. In some embodiments, a polynucleotide encoding MANF is inserted at a site within or near a B2M gene locus. In some embodiments, a polynucleotide encoding MANF is inserted at a site within or near a B2M gene locus concurrent with or following a deletion of all or part of a B2M gene or promoter. In other embodiments, a polynucleotide encoding MANF is inserted at a site within or near a TXNIP gene locus concurrent with or following a deletion of all or part of a TXNIP gene or promoter. In some embodiments, a polynucleotide encoding MANF is inserted at a site within or near a CIITA gene locus concurrent with or following a deletion of all or part of a CIITA gene or promoter. In other embodiments, a polynucleotide encoding MANF is inserted at a site within or near a TGF-β2 gene locus concurrent with or following a deletion of all or part of a TGF-β2 gene or promoter. The polynucleotide encoding MANF is operably linked to an exogenous promoter. The exogenous promoter can be a CAG or CAGGS promoter. In some embodiments, the polynucleotide encoding MANF comprises a nucleotide sequence of SEQ ID NO: 17, or nucleotide sequence having at least 85%, 90%, 95%, or 99% sequence identity with that of SEQ ID NO: 17.

In some embodiments, a polynucleotide encoding CD39 is inserted at a site within or near a B2M gene locus, within or near a TXNIP gene locus, within or near a CIITA gene locus, or within or near the TGF-β2 locus. In some embodiments, a polynucleotide encoding CD39 is inserted at a site within or near a B2M gene locus, within or near a TXNIP gene locus, or within or near a CIITA gene locus. In some embodiments, a polynucleotide encoding CD39 is inserted at a site within or near a CIITA gene locus or within or near a B2M gene locus. In some embodiments, a polynucleotide encoding CD39 is inserted at a site within or near a B2M gene locus concurrent with or following a deletion of all or part of a B2M gene or promoter. In other embodiments, a polynucleotide encoding CD39 is inserted at a site within or near a TXNIP gene locus concurrent with or following a deletion of all or part of a TXNIP gene or promoter. In some embodiments, a polynucleotide encoding CD39 is inserted at a site within or near a CIITA gene locus concurrent with, or following a deletion of a CIITA gene or promoter. In other embodiments, a polynucleotide encoding CD39 is inserted at a site within or near a TGF-β2 gene locus concurrent with or following a deletion of all or part of a TGF-β2 gene or promoter. The polynucleotide encoding CD39 is operably linked to an exogenous promoter. The exogenous promoter can be a CAG or CAGGS promoter. In some embodiments, the polynucleotide encoding CD39 comprises a nucleotide sequence of SEQ ID NO: 27, or nucleotide sequence having at least 85%, 90%, 95%, or 99% sequence identity with that of SEQ ID NO: 27.

In some embodiments, a polynucleotide encoding HLA-E is inserted at a site within or near a B2M gene locus, within or near a TXNIP gene locus, within or near a CIITA gene locus, or within or near the TGF-β2 locus. In some embodiments, a polynucleotide encoding HLA-E is inserted at a site within or near a B2M gene locus, within or near a TXNIP gene locus, or within or near a CIITA gene locus. In some embodiments, a polynucleotide encoding HLA-E is inserted at a site within or near a TXNIP gene locus. In some embodiments, a polynucleotide encoding HLA-E is inserted at a site within or near a B2M gene locus concurrent with or following a deletion of all or part of a B2M gene or promoter. In other embodiments, a polynucleotide encoding HLA-E is inserted at a site within or near a TXNIP gene locus concurrent with or following a deletion of all or part of a TXNIP gene or promoter. In some embodiments, a polynucleotide encoding HLA-E is inserted at a site within or near a CIITA gene locus concurrent with, or following a deletion of a CIITA gene or promoter. In other embodiments, a polynucleotide encoding HLA-E is inserted at a site within or near a TGF-β2 gene locus concurrent with or following a deletion of all or part of a TGF-β2 gene or promoter. The polynucleotide encoding HLA-E comprises a sequence encoding a HLA-E trimer, the HLA-E trimer comprising a B2M signal peptide fused to an HLA-G presentation peptide fused to a B2M membrane protein fused to HLA-E without its signal peptide. The polynucleotide encoding HLA-E is operably linked to an exogenous promoter. The exogenous promoter can be a CMV promoter. In some embodiments, the polynucleotide encoding HLA-E comprises a nucleotide sequence of SEQ ID NO: 43, or nucleotide sequence having at least 85%, 90%, 95%, or 99% sequence identity with that of SEQ ID NO: 43.

In some embodiments, a polynucleotide encoding CD73 is inserted at a site within or near a B2M gene locus, within or near a TXNIP gene locus, within or near a CIITA gene locus, or within or near the TGF-β2 locus. In some embodiments, a polynucleotide encoding CD73 is inserted at a site within or near a B2M gene locus, within or near a TXNIP gene locus, or within or near a CIITA gene locus. In some embodiments, a polynucleotide encoding CD73 is inserted at a site within or near a B2M gene locus or within or near a CIITA gene locus. In some embodiments, a polynucleotide encoding CD73 is inserted at a site within or near a B2M gene locus concurrent with or following a deletion of a B2M gene or promoter. In some embodiments, a polynucleotide encoding CD73 is inserted at a site within or near a TXNIP gene locus concurrent with or following a deletion of a TXNIP gene or promoter. In some embodiments, a polynucleotide encoding CD73 is inserted at a site within or near a CIITA gene locus concurrent with or following a deletion of a CIITA gene or promoter. In other embodiments, a polynucleotide encoding CD73 is inserted at a site within or near a TGF-β2 gene locus concurrent with or following a deletion of all or part of a TGF-β2 gene or promoter. The polynucleotide encoding CD73 is operably linked to an exogenous promoter. The exogenous promoter can be a CAG or CAGGS promoter. In some embodiments, the polynucleotide encoding CD73 comprises a nucleotide sequence of SEQ ID NO: 46, or nucleotide sequence having at least 85%, 90%, 95%, or 99% sequence identity with that of SEQ ID NO: 46.

In some embodiments, a polynucleotide encoding MANF, TNFAIP3, and PD-L-1 is inserted at a site within or near a B2M gene locus, within or near a TXNIP gene locus, within or near a CIITA gene locus, or within or near the TGF-β2 locus. In some embodiments, a polynucleotide encoding MANF, TNFAIP3, and PD-L-1 is inserted at a site within or near a B2M gene locus, within or near a TXNIP gene locus, or within or near a CIITA gene locus. In some embodiments, a polynucleotide encoding MANF, TNFAIP3, and PD-L-1 is inserted at a site within or near a B2M gene locus. In some embodiments, a polynucleotide encoding MANF, TNFAIP3, and PD-L-1 is inserted at a site within or near a B2M gene locus concurrent with or following a deletion of all or part of a B2M gene or promoter. In some embodiments, a polynucleotide encoding MANF, TNFAIP3, and PD-L-1 is inserted at a site within or near a TXNIP gene locus concurrent with or following a deletion of all or part of a TXNIP gene or promoter. In some embodiments, a polynucleotide encoding MANF, TNFAIP3, and PD-L-1 is inserted at a site within or near a CIITA gene locus concurrent with or following a deletion of all or part of a CIITA gene or promoter. In other embodiments, a polynucleotide encoding MANF, TNFAIP3, and PD-L-1 is inserted at a site within or near a TGF-β2 gene locus concurrent with or following a deletion of all or part of a TGF-β2 gene or promoter. The polynucleotide encoding MANF, TNFAIP3, and PD-L-1 comprises sequence encoding MANF that is linked to sequence encoding a first ribosome skip that is linked to sequence encoding TNFAIP3 that is linked to sequence encoding a second ribosome skip that is linked to sequence encoding PD-L-1. The first and second ribosome skips can be 2A sequence family members, e.g., both can be P2A. In some embodiments, the polynucleotide comprises a MANF-P2A-TNFAIP3-P2A-PD-L-1 coding sequence. In some embodiments, the polynucleotide encoding MANF-P2A-TNFAIP3-P2A-PD-L-1 comprises or consists of a nucleotide sequence of SEQ ID NO: 52 or a nucleotide sequence having at least 85%, 90%, 95%, or 99% sequence identity with that of SEQ ID NO: 52. In some embodiments, the polynucleotide encoding MANF-P2A-TNFAIP3-P2A-PD-L-1 is operably linked to an exogenous promoter. The exogenous promoter can be a CAG or CAGGS promoter. In some embodiments, a donor vector encoding MANF-P2A-TNFAIP3-P2A-PD-L-1 and comprising B2M homology arms has a nucleotide sequence of SEQ ID NO: 24. In some embodiments, a donor vector encodes MANF-P2A-TNFAIP3-P2A-PD-L-1 and comprises TXNIP homology arms. In some embodiments, a donor vector encodes MANF-P2A-TNFAIP3-P2A-PD-L-1 and comprises CTIIA homology arms. In some embodiments, a donor vector encodes MANF-P2A-TNFAIP3-P2A-PD-L-1 and comprises TGF-β2 homology arms.

In some embodiments, a polynucleotide encoding TNFAIP3 and PD-L-1 is inserted at a site within or near a B2M gene locus, within or near a TXNIP gene locus, within or near a CIITA gene locus, or within or near the TGF-β2 locus. In some embodiments, a polynucleotide encoding TNFAIP3 and PD-L-1 is inserted at a site within or near a B2M gene locus, within or near a TXNIP gene locus, or within or near a CIITA gene locus. In some embodiments, a polynucleotide encoding TNFAIP3 and PD-L-1 is inserted at a site within or near a B2M gene locus. In some embodiments, a polynucleotide encoding TNFAIP3 and PD-L-1 is inserted at a site within or near a B2M gene locus concurrent with or following a deletion of all or part of a B2M gene or promoter. In some embodiments, a polynucleotide encoding TNFAIP3 and PD-L-1 is inserted at a site within or near a TXNIP gene locus concurrent with or following a deletion of all or part of a TXNIP gene or promoter. In some embodiments, a polynucleotide encoding TNFAIP3 and PD-L-1 is inserted at a site within or near a CIITA gene locus concurrent with or following a deletion of all or part of a CIITA gene or promoter. In other embodiments, a polynucleotide encoding TNFAIP3 and PD-L-1 is inserted at a site within or near a TGF-β2 gene locus concurrent with or following a deletion of all or part of a TGF-β2 gene or promoter. The polynucleotide encoding TNFAIP3 and PD- L-1 comprises sequence encoding TNFAIP3 that is linked to sequence encoding a ribosome skip that is linked to sequence encoding PD-L-1. The ribosome skip can be a 2A sequence family member, such as P2A. In some embodiments, the polynucleotide comprises TNFAIP3-P2A-PD-L-1 coding sequence. In some embodiments, the polynucleotide encoding TNFAIP3-P2A-PD-L-1 comprises or consists of a nucleotide sequence of SEQ ID NO: 54 or a nucleotide sequence having at least 85%, 90%, 95%, or 99% sequence identity with that of SEQ ID NO: 54. In some embodiments, the polynucleotide encoding TNFAIP3-P2A-PD-L-1 is operably linked to an exogenous promoter. The exogenous promoter can be a CAG or CAGGS promoter. In some embodiments, a donor plasmid encoding TNFAIP3-P2A-PD-L-1 and comprising B2M homology arms has a nucleotide sequence of SEQ ID NO: 31. In some embodiments, a donor plasmid encodes TNFAIP3-P2A-PD-L-1 and comprises TXNIP homology arms. In some embodiments, a donor plasmid encodes TNFAIP3-P2A-PD-L-1 and comprises CIITA homology arms. In some embodiments, a donor vector encodes TNFAIP3-P2A-PD-L-1 and comprises TGF-β2 homology arms.

In some embodiments, a polynucleotide encoding MANF and HLA-E is inserted at a site within or near a B2M gene locus, within or near a TXNIP gene locus, or within or near a CIITA gene locus, or within or near the TGF-β2 locus. In some embodiments, a polynucleotide encoding MANF and HLA-E is inserted at a site within or near a B2M gene locus, or within or near a TXNIP gene locus. In some embodiments, a polynucleotide encoding MANF and HLA-E is inserted at a site within or near a TXNIP gene locus. In some embodiments, a polynucleotide encoding MANF and HLA-E is inserted at a site within or near a B2M gene locus concurrent with, or following a deletion of all or part of a B2M gene or promoter. In some embodiments, a polynucleotide encoding MANF and HLA-E is inserted at a site within or near a TXNIP gene locus concurrent with, or following a deletion of all or part of a TXNIP gene or promoter. In some embodiments, a polynucleotide encoding MANF and HLA-E is inserted at a site within or near a CIITA gene locus concurrent with, or following a deletion of all or part of a CIITA gene or promoter. In other embodiments, a polynucleotide encoding HLA-E is inserted at a site within or near a TGF-β2 gene locus concurrent with or following a deletion of all or part of a TGF-β2 gene or promoter. The polynucleotide encoding MANF and HLA-E comprises sequence encoding MANF that is linked to sequence encoding a ribosome skip that is linked to sequence encoding HLA-E. The ribosome skip can be a 2A sequence family member, such as P2A. The sequence encoding HLA-E comprises sequence encoding a HLA-E trimer, the HLA-E trimer comprising a B2M signal peptide fused to an HLA-G presentation peptide fused to a B2M membrane protein fused to HLA-E without its signal peptide. In some embodiments the polynucleotide comprises MANF-P2A-HLA-E coding sequence. In some embodiments, the polynucleotide encoding MANF-P2A-HLA-E comprises or consists of a nucleotide sequence of SEQ ID NO: 55 or a nucleotide sequence having at least 85%, 90%, 95%, or 99% sequence identity with that of SEQ ID NO: 55. In some embodiments, the polynucleotide encoding MANF-P2A-HLA-E is operably linked to an exogenous promoter. The exogenous promoter can be a CAG or CAGGS promoter. In some embodiments, a donor plasmid MANF-P2A-HLA-E and comprising TXNIP homology arms has a nucleotide sequence of SEQ ID NO: 45. In some embodiments, a donor plasmid encodes MANF-P2A-HLA-E and comprises B2M homology arms. In some embodiments, a donor plasmid encodes MANF-P2A-HLA-E and comprises CIITA homology arms. In some embodiments, a donor plasmid encodes MANF-P2A-HLA-E and comprises TGF-β2 homology arms.

In some embodiments, a polynucleotide encoding CD39 and PD-L-1 is inserted at a site within or near a B2M gene locus, within or near a TXNIP gene locus, within or near a CIITA gene locus, or within or near the TGF-β2 locus. In some embodiments, a polynucleotide encoding CD39 and PD-L-1 is inserted at a site within or near a B2M gene locus, within or near a TXNIP gene locus, or within or near a CIITA gene locus. In some embodiments, a polynucleotide encoding CD39 and PD-L-1 is inserted at a site within or near a B2M gene locus. In some embodiments, a polynucleotide encoding CD39 and PD-L-1 is inserted at a site within or near a B2M gene locus concurrent with or following a deletion of all or part of a B2M gene or promoter. In some embodiments, a polynucleotide encoding CD39 and PD-L-1 is inserted at a site within or near a TXNIP gene locus concurrent with or following a deletion of all or part of a TXNIP gene or promoter. In some embodiments, a polynucleotide encoding CD39 and PD-L-1 is inserted at a site within or near a CIITA gene locus concurrent with or following a deletion of all or part of a CIITA gene or promoter. In other embodiments, a polynucleotide encoding CD39 and PD-L-1 is inserted at a site within or near a TGF-β2 gene locus concurrent with or following a deletion of all or part of a TGF-β2 gene or promoter. The polynucleotide encoding CD39 and PD-L-1 comprises sequence encoding CD39 that is linked to sequence encoding a ribosome skip that is linked to sequence encoding PD-L-1. The ribosome skip can be a 2A sequence family member, such as P2A. In some embodiments the polynucleotide comprises CD39-P2A-PD-L-1 coding sequence. In some embodiments, the polynucleotide encoding CD39-P2A-PD-L-1 comprises or consists of a nucleotide sequence of SEQ ID NO: 53 or a nucleotide sequence having at least 85%, 90%, 95%, or 99% sequence identity with that of SEQ ID NO: 53. In some embodiments, the polynucleotide encoding CD39-P2A-PD-L-1 is operably linked to an exogenous promoter. The exogenous promoter can be a CAG or CAGGS promoter. In some embodiments, a donor plasmid encoding CD39-P2A-PD-L-1 and comprising B2M homology arms has a nucleotide sequence of SEQ ID NO: 30. In some embodiments, a donor plasmid encodes CD39-P2A-PD-L-1 and comprises TXNIP homology arms. In some embodiments, a donor plasmid encodes CD39-P2A-PD-L-1 and comprises CIITA homology arms. In some embodiments, a donor plasmid encodes CD39-P2A-PD-L-1 and comprises TGF-β2 homology arms In some embodiments, a polynucleotide encoding CD39, CD73, and PD-L-1 is inserted at a site within or near a B2M gene locus, within or near a TXNIP gene locus, within or near a CIITA gene locus, or within or near the TGF-β2 locus. In some embodiments, a polynucleotide encoding CD39, CD73, and PD-L-1 is inserted at a site within or near a B2M gene locus, within or near a TXNIP gene locus, or within or near a CIITA gene locus. In some embodiments, a polynucleotide encoding CD39, CD73, and PD-L-1 is inserted at a site within or near a B2M gene locus. In some embodiments, a polynucleotide encoding CD39, CD73, and PD-L-1 is inserted at a site within or near a B2M gene locus concurrent with or following a deletion of all or part of a B2M gene or promoter. In some embodiments, a polynucleotide encoding CD39, CD73, and PD-L-1 is inserted at a site within or near a TXNIP gene locus concurrent with or following a deletion of all or part of a TXNIP gene or promoter. In some embodiments, a polynucleotide encoding CD39, CD73, and PD-L-1 is inserted at a site within or near a CIITA gene locus concurrent with or following a deletion of all or part of a CIITA gene or promoter. In other embodiments, a polynucleotide encoding CD39, CD73, and PD-L-1 is inserted at a site within or near a TGF-β2 gene locus concurrent with or following a deletion of all or part of a TGF-β2 gene or promoter. The polynucleotide encoding CD39, CD73, and PD-L-1 comprises sequence encoding CD39 that is linked to sequence encoding a ribosome skip that is linked to sequence encoding CD73 that is linked to sequence encoding a ribosome skip that is linked to sequence encoding PD-L-1. The ribosome skip can be a 2A sequence family member, such as P2A. In some embodiments the polynucleotide comprises CD39-P2A-CD73-P2A-PD-L-1 coding sequence. In some embodiments, the polynucleotide encoding CD39-P2A-CD73-P2A-PD-L-1 comprises or consists of a nucleotide sequence of SEQ ID NO: 56 or a nucleotide sequence having at least 85%, 90%, 95%, or 99% sequence identity with that of SEQ ID NO: 56. In some embodiments, the polynucleotide encoding CD39-P2A-CD73-P2A-PD-L-1 is operably linked to an exogenous promoter. The exogenous promoter can be a CAG or CAGGS promoter. In some embodiments, a donor plasmid encoding CD39-P2A-CD73-P2A-PD-L-1 and comprising B2M homology arms has a nucleotide sequence of SEQ ID NO: 47. In some embodiments, a donor plasmid encodes CD39-P2A-CD73-P2A-PD-L-1 and comprises TXNIP homology arms. In some embodiments, a donor plasmid encodes CD39-P2A-CD73-P2A-PD-L-1 and comprises CIITA homology arms. In some embodiments, a donor plasmid encodes CD39-P2A-CD73-P2A-PD-L-1 and comprises TGF-β2 homology arms.

In some embodiments, a polynucleotide encoding CD39 and CD73 is inserted at a site within or near a B2M gene locus, within or near a TXNIP gene locus, within or near a CIITA gene locus, or within or near the TGF-β2 locus. In some embodiments, a polynucleotide encoding CD39 and CD73 is inserted at a site within or near a B2M gene locus, within or near a TXNIP gene locus, or within or near a CIITA gene locus. In some embodiments, a polynucleotide encoding CD39 and CD73 is inserted at a site within or near a B2M gene locus. In some embodiments, a polynucleotide encoding CD39 and CD73 is inserted at a site within or near a B2M gene locus concurrent with or following a deletion of all or part of a B2M gene or promoter. In some embodiments, a polynucleotide encoding CD39 and CD73 is inserted at a site within or near a TXNIP gene locus concurrent with or following a deletion of all or part of a TXNIP gene or promoter. In some embodiments, a polynucleotide encoding CD39 and CD73 is inserted at a site within or near a CIITA gene locus concurrent with or following a deletion of all or part of a CIITA gene or promoter. In other embodiments, a polynucleotide encoding CD39 and CD73 is inserted at a site within or near a TGF-β2 gene locus concurrent with or following a deletion of all or part of a TGF-β2 gene or promoter. The polynucleotide encoding CD39 and CD73 comprises sequence encoding CD39 that is linked to sequence encoding a ribosome skip that is linked to sequence encoding CD73. The ribosome skip can be a 2A sequence family member, such as P2A. In some embodiments the polynucleotide comprises CD39-P2A-CD73 coding sequence. In some embodiments, the polynucleotide encoding CD39-P2A-CD73 comprises or consists of a nucleotide sequence of SEQ ID NO: 58 or a nucleotide sequence having at least 85%, 90%, 95%, or 99% sequence identity with that of SEQ ID NO: 58. In some embodiments, the polynucleotide encoding CD39-P2A-CD73 is operably linked to an exogenous promoter. The exogenous promoter can be a CAG or CAGGS promoter. In some embodiments, a donor plasmid encodes CD39-P2A-CD73 and comprises B2M homology arms. In some embodiments, a donor plasmid encodes CD39-P2A-CD73-P2A-PD-L-1 and comprises TXNIP homology arms. In some embodiments, a donor plasmid encodes CD39-P2A-CD73-P2A-PD-L-1 and comprises CIITA homology arms. In some embodiments, a donor plasmid encodes CD39-P2A-CD73-P2A-PD-L-1 and comprises TGF-β2 homology arms.

In some embodiments, the at least one polynucleotide encoding at least one tolerogenic factor and/or survival factor can be delivered to the cells as part of a vector. For example, the vector may be a plasmid vector. In various embodiments, the amount of plasmid vector delivered to the cells may range from about 0.5 μg to about 10 μg (per about 106 cells). In some embodiments, the amount of plasmid may range from about 1 μg to about 8 μg, from about 2 μg to about 6 μg, or from about 3 μg to about 5 μg. In specific embodiments, the amount of plasmid delivered to the cells may be about 4 μg.

In certain embodiments, cells having no MHC-II expression and moderate expression of MHC-I are genetically modified to have no surface expression of MHC-I or MHC-II. In another embodiment, cells with no surface expression of MHC-I/II are further edited to have expression of PD-L-1, e.g., insertion of a polynucleotide encoding PD-L-1, have expression of MANF, e.g., insertion of a polynucleotide encoding MANF, have expression of CD39, e.g., insertion of a polynucleotide encoding CD39, have expression of CD73, e.g., insertion of a polynucleotide encoding CD73, have expression of HLA-E, e.g., insertion of a polynucleotide encoding HLA-E, have expression of TNFAIP3, e.g., insertion of a polynucleotide encoding TNFAIP, and/or any combination(s) thereof. In another embodiment, cells with no surface expression of MHC-I/II are further edited to have expression of PD-L-1, e.g., insertion of a polynucleotide encoding PD-L-1. In yet another embodiment, cells with no surface expression of MHC-I/II are further edited to have expression of PD-L-1, e.g., insertion of a polynucleotide encoding PD-L-1, and are also genetically modified to increase or decrease the expression of at least one gene that encodes a survival factor relative to an unmodified cell.

In some embodiments, the cells further comprise increased or decreased expression, e.g., by a genetic modification, of one or more additional genes that are not necessarily implicated in either immune evasion or cell survival post-engraftment or post-transplantation. In some embodiments, the cells further comprise increased expression of one or more safety switch proteins relative to an unmodified cell. In some embodiments, the cells comprise increased expression of one or more additional genes that encode a safety switch protein. In some embodiments, a safety switch is also a suicide gene. In some embodiments, a safety switch is herpes simplex virus-1 thymidine kinase (HSV-tk) or inducible caspase-9. In some embodiments, a polynucleotide that encodes at least one safety switch is inserted into a genome, e.g., into a safe harbor locus. In some other embodiments, the one or more additional genes that are genetically modified encode one or more of safety switch proteins; targeting modalities; receptors; signaling molecules; transcription factors; pharmaceutically active proteins or peptides; drug target candidates; and proteins promoting engraftment, trafficking, homing, viability, self-renewal, persistence, and/or survival thereof integrated with the construct.

One aspect of the present invention provides a method of generating genome-engineered universal donor cells, wherein a universal donor cell comprises at least one targeted genomic modification at one or more selected sites in genome, the method comprising genetically engineering a cell type as described herein by introducing into said cells one or more construct to allow targeted modification at selected site; introducing into said cells one or more double strand breaks at the selected sites using one or more endonuclease capable of selected site recognition; and culturing the edited cells to allow endogenous DNA repair to generate targeted insertions or deletions at the selected sites; thereby obtaining genome-modified universal donor cells. Targeted gene knockdowns or knockouts can be performed prior to, simultaneously with, or after targeted polynucleotide insertions. The genome-modified universal donor cells can undergo successive rounds of genome modification such that multiple sites are targeted and modified. The genome-modified cells are cultured, characterized, selected, and expanded using techniques well known in the art. The universal donor cells generated by this method will comprise at least one functional targeted genomic modification, and wherein the genome-modified cells, if they are stem cells, are then capable of being differentiated into progenitor cells or fully differentiated cells.

In some other embodiments, the genome-engineered universal donor cells comprise introduced or increased expression in at least one of HLA-E, HLA-G, CD47, PD-L-1, TNFAIP3, MANF, CD73, and/or CD39. In some embodiments, the genome-engineered universal donor cells comprise introduced or increased expression of HLA-E, PD-L-1, TNFAIP3, and/or MANE. In some embodiments, the genome-engineered universal donor cells comprise introduced or increased expression of HLA-E, PD-L-1, TNFAIP3, MANF, and/or CD39. In some embodiments, the genome-engineered universal donor cells comprise introduced or increased expression of PD-L-1 and CD39 and/or introduced or increased expression of PD-L-1, CD73, and CD39. In some embodiments, the genome-engineered universal donor cells are HLA class I and/or class II deficient. In some embodiments, the genome-engineered universal donor cells comprise B2M null or low. In some embodiments, the genome-engineered universal donor cells comprise B2M null or low and TXNIP null or low. In some embodiments, the genome-engineered universal donor cells comprise B2M null or low, TXNIP null or low, and CIITA null or low. In some embodiments, the genome-engineered universal donor cells comprise B2M null or low, TXNIP null or low, CIITA null or low, and TGF-β2 null or low.

In some embodiments, the genome-engineered universal donor cells comprise integrated or non-integrated exogenous polynucleotide encoding one or more of HLA-E, HLA-G, CD47, PD-L-1, TNFAIP3, MANF, CD73, and/or CD39. In some embodiments, the genome-engineered universal donor cells comprise integrated or non-integrated exogenous polynucleotide encoding one or more of HLA-E, PD-L-1, TNFAIP3, MANF, CD73, and/or CD39. In some embodiments, said introduced expression is an increased expression from either non-expressed or lowly expressed genes comprised in said cells. In some embodiments, the non-integrated exogenous polynucleotides are introduced using Sendai virus, AAV, episomal, or plasmid. In some embodiments, the universal donor cells are B2M null and TXNIP null with introduced expression of TNFAIP3, PD-L-1, MANF, and HLA-E. In some embodiments, the universal donor cells are CIITA null. In some embodiments the universal donor cells are TGF-β2 null. In some embodiments, the universal donor cells are (i) B2M null with a polynucleotide encoding TNFAIP3 and PD-L-1 inserted within or near the B2M gene locus, and (ii) TXNIP null with polynucleotide encoding MANF and HLA-E inserted within or near the TXNIP gene locus. In some embodiments, the universal donor cells are (i) B2M null with a polynucleotide encoding TNFAIP3 and PD-L-1 inserted within or near the B2M gene locus, (ii) TXNIP null with polynucleotide encoding MANF and HLA-E inserted within or near the TXNIP gene locus, and (iii) CIITA null with polynucleotide encoding CD39 inserted into or near the CIITA gene locus. In some embodiments, the universal donor cells are (i) B2M null with a polynucleotide encoding TNFAIP3 and PD-L-1 inserted within or near the B2M gene locus, (ii) TXNIP null with polynucleotide encoding MANF and HLA-E inserted within or near the TXNIP gene locus, and (iii) CIITA null with polynucleotide encoding CD39 inserted into or near the CIITA gene locus, and (iv) TGF-β2 null. In some embodiments, the universal donor cells are (i) B2M null with a first polynucleotide encoding TNFAIP3 and PD-L-1 inserted within or near a first site in the B2M gene locus and a second polynucleotide encoding CD39 and PD-L-1 inserted within or near a second site in the B2M gene locus, and (ii) TXNIP null with polynucleotide encoding MANF and HLA-E inserted within or near the TXNIP gene locus. In some embodiments, the universal donor cells are (i) B2M null with a first polynucleotide encoding TNFAIP3 and PD-L-1 inserted within or near a first site in the B2M gene locus and a second polynucleotide encoding CD39 and PD-L-1 inserted within or near a second site in the B2M gene locus, (ii) TXNIP null with polynucleotide encoding MANF and HLA-E inserted within or near the TXNIP gene locus, and (iii) TGF-β2 null. In a further embodiment, the universal donor cells are B2M null with a polynucleotide encoding MANF, TNFAIP3, and PD-L-1 inserted within or near the B2M gene locus. In some embodiments, the universal donor cells are (i) B2M null with a polynucleotide encoding PD-L-1 inserted within or near the B2M gene locus, (ii) TXNIP null with polynucleotide encoding HLA-E inserted within or near the TXNIP gene locus and, (iii) CIITA null with polynucleotide encoding CD39 inserted within or near the CIITA gene locus and, (iv) TGF-β2 null. In still other embodiments, the universal donor cells are B2M null with a polynucleotide encoding MANF, TNFAIP3, and PD-L-1 inserted within or near the B2M gene locus, and optionally CIITA null with polynucleotide encoding CD39 inserted within or near the CIITA gene locus. In still other embodiments, the universal donor cells are B2M null with a first polynucleotide encoding MANF, TNFAIP3, and PD-L-1 inserted within or near a first site in the B2M gene locus and a second polynucleotide encoding CD39 and PD-L-1 inserted within or near a second site in the B2M gene locus and optionally TGF-β2 null. In other embodiments, the universal donor cells are (i) B2M null with a polynucleotide encoding MANF, TNFAIP3, and PD-L-1 inserted within or near the B2M gene locus, (ii) CIITA null with a polynucleotide encoding CD39 inserted within or near the CIITA gene locus, and (iii) TGF-β2 null. In further embodiments, the universal donor cells are (i) B2M null with a polynucleotide encoding PD-L-1 inserted within or near the B2M gene locus, (ii) TXNIP null with polynucleotide encoding HLA-E inserted within or near the TXNIP gene locus, (iii) CIITA null with a polynucleotide encoding CD39 inserted within or near the CIITA gene locus and, and (iv) TGF-β2 null. In still other embodiments, the universal donor cells are (i) B2M null with a first polynucleotide encoding PD-L-1 inserted within or near a first site in the B2M gene locus and a second polynucleotide encoding CD39 inserted within or near a second site in the B2M gene locus and (ii) TXNIP null with polynucleotide encoding HLA-E inserted within or near the TXNIP gene locus. In some embodiments, the universal donor cells are B2M null with a polynucleotide encoding CD39 and PD-L-1 inserted within or near the B2M gene locus. In some embodiments, the universal donor cells are B2M null with a polynucleotide encoding CD39, CD73, and PD-L-1 inserted within or near the B2M gene locus and further optionally TGF-β2 null.

In certain embodiments, said universal donor cells further comprise increased or decreased expression of at least one safety switch protein. Methods of generating any of the genetically modified cells described herein are contemplated to be performed using at least any of the gene editing methods described herein.

III. Genome Editing Methods

Genome editing generally refers to the process of modifying the nucleotide sequence of a genome, preferably in a precise or pre-determined manner. In some embodiments, genome editing methods as described herein, e.g., the CRISPR-endonuclease system, may be used to genetically modify a cell as described herein, e.g., to create a universal donor cell. In some embodiments, genome editing methods as described herein, e.g., the CRISPR-endonuclease system, may be used to genetically modify a cell as described herein, e.g., to introduce at least one genetic modification within or near at least one gene that decreases the expression of one or more MIC-I and/or MHC-II human leukocyte antigens or other components of the MIC-I or MHC-II complex relative to an unmodified cell; to introduce at least one genetic modification that increases the expression of at least one polynucleotide that encodes a tolerogenic factor relative to an unmodified cell; and/or to introduce at least one genetic modification that increases or decreases the expression of at least one gene that encodes a survival factor relative to an unmodified cell.

Examples of methods of genome editing described herein include methods of using site-directed nucleases to cut deoxyribonucleic acid (DNA) at precise target locations in the genome, thereby creating single-strand or double-strand DNA breaks at particular locations within the genome. Such breaks can be and regularly are repaired by natural, endogenous cellular processes, such as homology-directed repair (HDR) and non-homologous end joining (NHEJ), as described in Cox et al., "Therapeutic genome editing: prospects and challenges,", Nature Medicine, 2015, 21(2), 121-31. These two main DNA repair processes consist of a family of alternative pathways. NHEJ directly joins the DNA ends resulting from a double-strand break, sometimes with the loss or addition of nucleotide sequence, which may disrupt or enhance gene expression. HDR utilizes a homologous sequence, or donor sequence, as a template for inserting a defined DNA sequence at the break point. The homologous sequence can be in the endogenous genome, such as a sister chromatid. Alternatively, the donor sequence can be an exogenous polynucleotide, such as a plasmid, a single-strand oligonucleotide, a double-stranded oligonucleotide, a duplex oligonucleotide or a virus, that has regions (e.g., left and right homology arms) of high homology with the nuclease-cleaved locus, but which can also contain additional sequence or sequence changes including deletions that can be incorporated into the cleaved target locus. A third repair mechanism can be microhomology-mediated end joining (MMEJ), also referred to as "Alternative NHEJ," in which the genetic outcome is similar to NHEJ in that small deletions and insertions can occur at the cleavage site. MMEJ can make use of homologous sequences of a few base pairs flanking the DNA break site to drive a more favored DNA end joining repair outcome, and recent reports have further elucidated the molecular mechanism of this process; see, e.g., Cho and Greenberg, Nature, 2015, 518, 174-76; Kent et al., Nature Structural and Molecular Biology, 2015, 22(3):230-7; Mateos-Gomez et al., Nature, 2015, 518, 254-57; Ceccaldi et al., Nature, 2015, 528, 258-62. In some instances, it may be possible to predict likely repair outcomes based on analysis of potential microhomologies at the site of the DNA break.

Each of these genome editing mechanisms can be used to create desired genetic modifications. A step in the genome editing process can be to create one or two DNA breaks, the latter as double-strand breaks or as two single-stranded breaks, in the target locus as near the site of intended mutation. This can be achieved via the use of endonucleases, as described and illustrated herein.

In general, the genome editing methods described herein can be in vitro or ex vivo methods. In some embodiments, the genome editing methods disclosed herein are not methods for treatment of the human or animal body by therapy and/or are not processes for modifying the germ line genetic identity of human beings.

CRISPR Endonuclease System

The CRISPR-endonuclease system is a naturally occurring defense mechanism in prokaryotes that has been repurposed as a RNA-guided DNA-targeting platform used for gene editing. CRISPR systems include Types I, II, III, IV, V, and VI systems. In some aspects, the CRISPR system is a Type II CRISPR/Cas9 system. In other aspects, the CRISPR system is a Type V CRISPR/Cpf system. CRISPR systems rely on a DNA endonuclease, e.g., Cas9, and two noncoding RNAs—crisprRNA (crRNA) and trans-activating RNA (tracrRNA)—to target the cleavage of DNA.

The crRNA drives sequence recognition and specificity of the CRISPR-endonuclease complex through Watson-Crick base pairing, typically with a ~20 nucleotide (nt) sequence in the target DNA. Changing the sequence of the 5' 20 nt in the crRNA allows targeting of the CRISPR-endonuclease complex to specific loci. The CRISPR-endonuclease complex only binds DNA sequences that contain a sequence match to the first 20 nt of the single-guide RNA (sgRNA) if the target sequence is followed by a specific short DNA motif (with the sequence NGG) referred to as a protospacer adjacent motif (PAM).

TracrRNA hybridizes with the 3' end of crRNA to form an RNA-duplex structure that is bound by the endonuclease to form the catalytically active CRISPR-endonuclease complex, which can then cleave the target DNA.

Once the CRISPR-endonuclease complex is bound to DNA at a target site, two independent nuclease domains within the endonuclease each cleave one of the DNA strands three bases upstream of the PAM site, leaving a double-strand break (DSB) where both strands of the DNA terminate in a base pair (a blunt end).

In some embodiments, the endonuclease is a Cas9 (CRISPR associated protein 9). In some embodiments, the Cas9 endonuclease is from *Streptococcus pyogenes*, although other Cas9 homologs may be used, e.g., *S. aureus* Cas9, *N. meningitidis* Cas9, *S. thermophilus* CRISPR 1 Cas9, *S. thermophilus* CRISPR 3 Cas9, or *T. denticola* Cas9. In other instances, the CRISPR endonuclease is Cpf1, e.g.,

*L. bacterium* ND2006 Cpf1 or *Acidaminococcus* sp. BV3L6 Cpf1. In some embodiments, the endonuclease is Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease. In some embodiments, wild-type variants may be used. In some embodiments, modified versions (e.g., a homolog thereof, a recombination of the naturally occurring molecule thereof, codon-optimized thereof, or modified versions thereof) of the preceding endonucleases may be used.

The CRISPR nuclease can be linked to at least one nuclear localization signal (NLS). The at least one NLS can be located at or within 50 amino acids of the amino-terminus of the CRISPR nuclease and/or at least one NLS can be located at or within 50 amino acids of the carboxy-terminus of the CRISPR nuclease.

Exemplary CRISPR/Cas polypeptides include the Cas9 polypeptides as published in Fonfara et al., "Phylogeny of Cas9 determines functional exchangeability of dual-RNA and Cas9 among orthologous type II CRISPR-Cas systems," Nucleic Acids Research, 2014, 42: 2577-2590. The CRISPR/Cas gene naming system has undergone extensive rewriting since the Cas genes were discovered. Fonfara et al. also provides PAM sequences for the Cas9 polypeptides from various species.

Zinc Finger Nucleases

Zinc finger nucleases (ZFNs) are modular proteins comprised of an engineered zinc finger DNA binding domain linked to the catalytic domain of the type II endonuclease FokI. Because FokI functions only as a dimer, a pair of ZFNs must be engineered to bind to cognate target "half-site" sequences on opposite DNA strands and with precise spacing between them to enable the catalytically active FokI dimer to form. Upon dimerization of the FokI domain, which itself has no sequence specificity per se, a DNA double-strand break is generated between the ZFN half-sites as the initiating step in genome editing.

The DNA binding domain of each ZFN is typically comprised of 3-6 zinc fingers of the abundant Cys2-His2 architecture, with each finger primarily recognizing a triplet of nucleotides on one strand of the target DNA sequence, although cross-strand interaction with a fourth nucleotide also can be important. Alteration of the amino acids of a finger in positions that make key contacts with the DNA alters the sequence specificity of a given finger. Thus, a four-finger zinc finger protein will selectively recognize a 12 bp target sequence, where the target sequence is a composite of the triplet preferences contributed by each finger, although triplet preference can be influenced to varying degrees by neighboring fingers. An important aspect of ZFNs is that they can be readily re-targeted to almost any genomic address simply by modifying individual fingers. In most applications of ZFNs, proteins of 4-6 fingers are used, recognizing 12-18 bp respectively. Hence, a pair of ZFNs will typically recognize a combined target sequence of 24-36 bp, not including the typical 5-7 bp spacer between half-sites. The binding sites can be separated further with larger spacers, including 15-17 bp. A target sequence of this length is likely to be unique in the human genome, assuming repetitive sequences or gene homologs are excluded during the design process. Nevertheless, the ZFN protein-DNA interactions are not absolute in their specificity so off-target binding and cleavage events do occur, either as a heterodimer between the two ZFNs, or as a homodimer of one or the other of the ZFNs. The latter possibility has been effectively eliminated by engineering the dimerization interface of the FokI domain to create "plus" and "minus" variants, also known as obligate heterodimer variants, which can only dimerize with each other, and not with themselves. Forcing the obligate heterodimer prevents formation of the homodimer. This has greatly enhanced specificity of ZFNs, as well as any other nuclease that adopts these FokI variants.

A variety of ZFN-based systems have been described in the art, modifications thereof are regularly reported, and numerous references describe rules and parameters that are used to guide the design of ZFNs; see, e.g., Segal et al., Proc Natl Acad Sci, 1999 96(6):2758-63; Dreier B et al., J Mol Biol., 2000, 303(4):489-502; Liu Q et al., J Biol Chem., 2002, 277(6):3850-6; Dreier et al., J Biol Chem., 2005, 280(42):35588-97; and Dreier et al., J Biol Chem. 2001, 276(31):29466-78.

Transcription Activator-Like Effector Nucleases (TALENs)

TALENs represent another format of modular nucleases whereby, as with ZFNs, an engineered DNA binding domain is linked to the FokI nuclease domain, and a pair of TALENs operate in tandem to achieve targeted DNA cleavage. The major difference from ZFNs is the nature of the DNA binding domain and the associated target DNA sequence recognition properties. The TALEN DNA binding domain derives from TALE proteins, which were originally described in the plant bacterial pathogen *Xanthomonas* sp. TALEs are comprised of tandem arrays of 33-35 amino acid repeats, with each repeat recognizing a single base pair in the target DNA sequence that is typically up to 20 bp in length, giving a total target sequence length of up to 40 bp. Nucleotide specificity of each repeat is determined by the repeat variable diresidue (RVD), which includes just two amino acids at positions 12 and 13. The bases guanine, adenine, cytosine and thymine are predominantly recognized by the four RVDs: Asn-Asn, Asn-Ile, His-Asp and Asn-Gly, respectively. This constitutes a much simpler recognition code than for zinc fingers, and thus represents an advantage over the latter for nuclease design. Nevertheless, as with ZFNs, the protein-DNA interactions of TALENs are not absolute in their specificity, and TALENs have also benefitted from the use of obligate heterodimer variants of the FokI domain to reduce off-target activity.

Additional variants of the FokI domain have been created that are deactivated in their catalytic function. If one half of either a TALEN or a ZFN pair contains an inactive FokI domain, then only single-strand DNA cleavage (nicking) will occur at the target site, rather than a DSB. The outcome is comparable to the use of CRISPR/Cas9 or CRISPR/Cpf1 "nickase" mutants in which one of the Cas9 cleavage domains has been deactivated. DNA nicks can be used to drive genome editing by HDR, but at lower efficiency than with a DSB. The main benefit is that off-target nicks are quickly and accurately repaired, unlike the DSB, which is prone to NHEJ-mediated mis-repair.

A variety of TALEN-based systems have been described in the art, and modifications thereof are regularly reported; see, e.g., Boch, Science, 2009 326(5959):1509-12; Mak et al., Science, 2012, 335(6069):716-9; and Moscou et al., Science, 2009, 326(5959):1501. The use of TALENs based on the "Golden Gate" platform, or cloning scheme, has been described by multiple groups; see, e.g., Cermak et al., Nucleic Acids Res., 2011, 39(12):e82; Li et al., Nucleic Acids Res., 2011, 39(14):6315-25; Weber et al., PLoS One., 2011, 6(2):e16765; Wang et al., J Genet Genomics, 2014, 41(6):339-47.; and Cermak T et al., Methods Mol Biol., 2015 1239:133-59.

Homing Endonucleases

Homing endonucleases (HEs) are sequence-specific endonucleases that have long recognition sequences (14-44 base pairs) and cleave DNA with high specificity—often at sites unique in the genome. There are at least six known families of HEs as classified by their structure, including GIY-YIG, His-Cis box, H-N-H, PD-(D/E)xK, and Vsr-like that are derived from a broad range of hosts, including eukarya, protists, bacteria, archaea, cyanobacteria and phage. As with ZFNs and TALENs, HEs can be used to create a DSB at a target locus as the initial step in genome editing. In addition, some natural and engineered HEs cut only a single strand of DNA, thereby functioning as site-specific nickases. The large target sequence of HEs and the specificity that they offer have made them attractive candidates to create site-specific DSBs.

A variety of HE-based systems have been described in the art, and modifications thereof are regularly reported; see, e.g., the reviews by Steentoft et al., Glycobiology, 2014, 24(8):663-80; Belfort and Bonocora, Methods Mol Biol., 2014, 1123:1-26; and Hafez and Hausner, Genome, 2012, 55(8):553-69.

MegaTAL/Tev-mTALEN/MegaTev

As further examples of hybrid nucleases, the MegaTAL platform and Tev-mTALEN platform use a fusion of TALE DNA binding domains and catalytically active HEs, taking advantage of both the tunable DNA binding and specificity of the TALE, as well as the cleavage sequence specificity of the HE; see, e.g., Boissel et al., Nucleic Acids Res., 2014, 42: 2591-2601; Kleinstiver et al., G3, 2014, 4:1155-65; and Boissel and Scharenberg, Methods Mol. Biol., 2015, 1239: 171-96.

In a further variation, the MegaTev architecture is the fusion of a meganuclease (Mega) with the nuclease domain derived from the GIY-YIG homing endonuclease I-TevI (Tev). The two active sites are positioned ~30 bp apart on a DNA substrate and generate two DSBs with non-compatible cohesive ends; see, e.g., Wolfs et al., Nucleic Acids Res., 2014, 42, 8816-29. It is anticipated that other combinations of existing nuclease-based approaches will evolve and be useful in achieving the targeted genome modifications described herein.

dCas9-FokI or dCpf1-Fok1 and Other Nucleases

Combining the structural and functional properties of the nuclease platforms described above offers a further approach to genome editing that can potentially overcome some of the inherent deficiencies. As an example, the CRISPR genome editing system typically uses a single Cas9 endonuclease to create a DSB. The specificity of targeting is driven by a 20 or 24 nucleotide sequence in the guide RNA that undergoes Watson-Crick base-pairing with the target DNA (plus an additional 2 bases in the adjacent NAG or NGG PAM sequence in the case of Cas9 from *S. pyogenes*). Such a sequence is long enough to be unique in the human genome, however, the specificity of the RNA/DNA interaction is not absolute, with significant promiscuity sometimes tolerated, particularly in the 5' half of the target sequence, effectively reducing the number of bases that drive specificity. One solution to this has been to completely deactivate the Cas9 or Cpf1 catalytic function—retaining only the RNA-guided DNA binding function—and instead fusing a FokI domain to the deactivated Cas9; see, e.g., Tsai et al., Nature Biotech, 2014, 32: 569-76; and Guilinger et al., Nature Biotech., 2014, 32: 577-82. Because FokI must dimerize to become catalytically active, two guide RNAs are required to tether two FokI fusions in close proximity to form the dimer and cleave DNA. This essentially doubles the number of bases in the combined target sites, thereby increasing the stringency of targeting by CRISPR-based systems.

As further example, fusion of the TALE DNA binding domain to a catalytically active HE, such as I-TevI, takes advantage of both the tunable DNA binding and specificity of the TALE, as well as the cleavage sequence specificity of I-TevI, with the expectation that off-target cleavage can be further reduced.

Base Editing

In some embodiments, a gene is edited in a cell using base editing. Base Editing is a technique enabling the conversion of one nucleotide into another without double-stranded breaks in the DNA. Base editing allows for conversion of a C to T, G to A, or vice versa. An example editor for cytosine includes rAPOBEC1 which is fused to a catalytically inactive form of Cas9. The Cas9 helps to bind a site of interest and the rAPOBEC1 cytidine deaminase induces the point mutation. Conversion of adenine requires a mutant transfer RNA adenosine deaminase (TadA), a Cas9 nickase, and a sgRNA, as described herein. The construct is able to introduce the site-specific mutation without introducing a strand break. In some embodiments, Base Editing is used to introduce one or more mutations in a cell described herein.

RNA-Guided Endonucleases

The RNA-guided endonuclease systems as used herein can comprise an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to a wild-type exemplary endonuclease, e.g., Cas9 from *S. pyogenes*, US2014/0068797 Sequence ID No. 8 or Sapranauskas et al., Nucleic Acids Res, 39(21): 9275-9282 (2011). The endonuclease can comprise at least 70, 75, 80, 85, 90, 95, 97, 99, or 100% identity to a wild-type endonuclease (e.g., Cas9 from *S. pyogenes*, supra) over 10 contiguous amino acids. The endonuclease can comprise at most: 70, 75, 80, 85, 90, 95, 97, 99, or 100% identity to a wild-type endonuclease (e.g., Cas9 from *S. pyogenes*, supra) over 10 contiguous amino acids. The endonuclease can comprise at least: 70, 75, 80, 85, 90, 95, 97, 99, or 100% identity to a wild-type endonuclease (e.g., Cas9 from *S. pyogenes*, supra) over 10 contiguous amino acids in a HNH nuclease domain of the endonuclease. The endonuclease can comprise at most: 70, 75, 80, 85, 90, 95, 97, 99, or 100% identity to a wild-type endonuclease (e.g., Cas9 from *S. pyogenes*, supra) over 10 contiguous amino acids in a HNH nuclease domain of the endonuclease. The endonuclease can comprise at least: 70, 75, 80, 85, 90, 95, 97, 99, or 100% identity to a wild-type endonuclease (e.g., Cas9 from *S. pyogenes*, supra) over 10 contiguous amino acids in a RuvC nuclease domain of the endonuclease. The endonuclease can comprise at most: 70, 75, 80, 85, 90, 95, 97, 99, or 100% identity to a wild-type endonuclease (e.g., Cas9 from *S. pyogenes*, supra) over 10 contiguous amino acids in a RuvC nuclease domain of the endonuclease.

The endonuclease can comprise a modified form of a wild-type exemplary endonuclease. The modified form of the wild-type exemplary endonuclease can comprise a mutation that reduces the nucleic acid-cleaving activity of the endonuclease. The modified form of the wild-type exemplary endonuclease can have less than 90%, less than 80%, less than 70%, less than 60%, less than 50%, less than 40%, less than 30%, less than 20%, less than 10%, less than 5%, or less than 1% of the nucleic acid-cleaving activity of the wild-type exemplary endonuclease (e.g., Cas9 from *S. pyogenes*, supra). The modified form of the endonuclease can have no substantial nucleic acid-cleaving activity. When an endonuclease is a modified form that has no substantial nucleic acid-cleaving activity, it is referred to herein as "enzymatically inactive."

Mutations contemplated can include substitutions, additions, and deletions, or any combination thereof. The mutation converts the mutated amino acid to alanine. The mutation converts the mutated amino acid to another amino acid (e.g., glycine, serine, threonine, cysteine, valine, leucine, isoleucine, methionine, proline, phenylalanine, tyrosine, tryptophan, aspartic acid, glutamic acid, asparagine, glutamine, histidine, lysine, or arginine). The mutation converts the mutated amino acid to a non-natural amino acid (e.g., selenomethionine). The mutation converts the mutated amino acid to amino acid mimics (e.g., phosphomimics). The mutation can be a conservative mutation. For example, the mutation converts the mutated amino acid to amino acids that resemble the size, shape, charge, polarity, conformation, and/or rotamers of the mutated amino acids (e.g., cysteine/serine mutation, lysine/asparagine mutation, histidine/phenylalanine mutation). The mutation can cause a shift in reading frame and/or the creation of a premature stop codon. Mutations can cause changes to regulatory regions of genes or loci that affect expression of one or more genes.

Guide RNAs

The present disclosure provides a guide RNAs (gRNAs) that can direct the activities of an associated endonuclease to a specific target site within a polynucleotide. A guide RNA can comprise at least a spacer sequence that hybridizes to a target nucleic acid sequence of interest, and a CRISPR repeat sequence. In CRISPR Type II systems, the gRNA also comprises a second RNA called the tracrRNA sequence. In the CRISPR Type II guide RNA (gRNA), the CRISPR repeat sequence and tracrRNA sequence hybridize to each other to form a duplex. In CRISPR Type V systems, the gRNA comprises a crRNA that forms a duplex. In some embodiments, a gRNA can bind an endonuclease, such that the gRNA and endonuclease form a complex. The gRNA can provide target specificity to the complex by virtue of its association with the endonuclease. The genome-targeting nucleic acid thus can direct the activity of the endonuclease.

Exemplary guide RNAs include a spacer sequences that comprises 15-200 nucleotides wherein the gRNA targets a genome location based on the GRCh38 human genome assembly. As is understood by the person of ordinary skill in the art, each gRNA can be designed to include a spacer sequence complementary to its genomic target site or region. See Jinek et al., Science, 2012, 337, 816-821 and Deltcheva et al., Nature, 2011, 471, 602-607.

The gRNA can be a double-molecule guide RNA. The gRNA can be a single-molecule guide RNA.

A double-molecule guide RNA can comprise two strands of RNA. The first strand comprises in the 5' to 3' direction, an optional spacer extension sequence, a spacer sequence and a minimum CRISPR repeat sequence. The second strand can comprise a minimum tracrRNA sequence (complementary to the minimum CRISPR repeat sequence), a 3' tracrRNA sequence and an optional tracrRNA extension sequence.

A single-molecule guide RNA (sgRNA) can comprise, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension can comprise elements that contribute additional functionality (e.g., stability) to the guide RNA. The single-molecule guide linker can link the minimum CRISPR repeat and the minimum tracrRNA sequence to form a hairpin structure. The optional tracrRNA extension can comprise one or more hairpins.

In some embodiments, a sgRNA comprises a 20 nucleotide spacer sequence at the 5' end of the sgRNA sequence. In some embodiments, a sgRNA comprises a less than a 20 nucleotide spacer sequence at the 5' end of the sgRNA sequence. In some embodiments, a sgRNA comprises a more than 20 nucleotide spacer sequence at the 5' end of the sgRNA sequence. In some embodiments, a sgRNA comprises a variable length spacer sequence with 17-30 nucleotides at the 5' end of the sgRNA sequence. In some embodiments, a sgRNA comprises a spacer extension sequence with a length of more than 1, 5, 10, 15, 20, 25, 30, 35, 40, 45, 50, 60, 70, 80, 90, 100, 120, 140, 160, 180, or 200 nucleotides. In some embodiments, a sgRNA comprises a spacer extension sequence with a length of less than 3, 5, 10, 15, 20, 25, 30, 35, 40, 45, 50, 60, 70, 80, 90, or 100 nucleotides.

In some embodiments, a sgRNA comprises a spacer extension sequence that comprises another moiety (e.g., a stability control sequence, an endoribonuclease binding sequence, or a ribozyme). The moiety can decrease or increase the stability of a nucleic acid targeting nucleic acid. The moiety can be a transcriptional terminator segment (i.e., a transcription termination sequence). The moiety can function in a eukaryotic cell. The moiety can function in a prokaryotic cell. The moiety can function in both eukaryotic and prokaryotic cells. Non-limiting examples of suitable moieties include: a 5' cap (e.g., a 7-methylguanylate cap (m7 G)), a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like).

In some embodiments, a sgRNA comprises a spacer sequence that hybridizes to a sequence in a target polynucleotide. The spacer of a gRNA can interact with a target polynucleotide in a sequence-specific manner via hybridization (i.e., base pairing). The nucleotide sequence of the spacer can vary depending on the sequence of the target nucleic acid of interest.

In a CRISPR-endonuclease system, a spacer sequence can be designed to hybridize to a target polynucleotide that is located 5' of a PAM of the endonuclease used in the system. The spacer may perfectly match the target sequence or may have mismatches. Each endonuclease, e.g., Cas9 nuclease, has a particular PAM sequence that it recognizes in a target DNA. For example, *S. pyogenes* Cas9 recognizes a PAM that comprises the sequence 5'-NRG-3', where R comprises either A or G, where N is any nucleotide and N is immediately 3' of the target nucleic acid sequence targeted by the spacer sequence.

A target polynucleotide sequence can comprise 20 nucleotides. The target polynucleotide can comprise less than 20 nucleotides. The target polynucleotide can comprise more than 20 nucleotides. The target polynucleotide can comprise at least: 5, 10, 15, 16, 17, 18, 19, 20, 21, 22, 23, 24, 25, 30 or more nucleotides. The target polynucleotide can comprise at most: 5, 10, 15, 16, 17, 18, 19, 20, 21, 22, 23, 24, 25, 30 or more nucleotides. The target polynucleotide sequence can comprise 20 bases immediately 5' of the first nucleotide of the PAM.

A spacer sequence that hybridizes to a target polynucleotide can have a length of at least about 6 nucleotides (nt). The spacer sequence can be at least about 6 nt, at least about 10 nt, at least about 15 nt, at least about 18 nt, at least about 19 nt, at least about 20 nt, at least about 25 nt, at least about 30 nt, at least about 35 nt or at least about 40 nt, from about 6 nt to about 80 nt, from about 6 nt to about 50 nt, from about 6 nt to about 45 nt, from about 6 nt to about 40 nt, from about 6 nt to about 35 nt, from about 6 nt to about 30 nt, from about 6 nt to about 25 nt, from about 6 nt to about 20 nt, from about 6 nt to about 19 nt, from about 10 nt to about 50 nt, from about 10 nt to about 45 nt, from about 10 nt to about 40 nt, from about 10 nt to about 35 nt, from about 10 nt to about 30 nt, from about 10 nt to about 25 nt, from about 10 nt to about 20 nt, from about 10 nt to about 19 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some examples, the spacer sequence can comprise 20 nucleotides. In some examples, the spacer can comprise 19 nucleotides. In some examples, the spacer can comprise 18 nucleotides. In some examples, the spacer can comprise 22 nucleotides.

In some examples, the percent complementarity between the spacer sequence and the target nucleic acid is at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. In some examples, the percent complementarity between the spacer sequence and the target nucleic acid is at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%. In some examples, the percent complementarity between the spacer sequence and the target nucleic acid is 100% over the six contiguous 5'-most nucleotides of the target sequence of the complementary strand of the target nucleic acid. The percent complementarity between the spacer sequence and the target nucleic acid can be at least 60% over about 20 contiguous nucleotides. The length of the spacer sequence and the target nucleic acid can differ by 1 to 6 nucleotides, which may be thought of as a bulge or bulges.

A tracrRNA sequence can comprise nucleotides that hybridize to a minimum CRISPR repeat sequence in a cell. A minimum tracrRNA sequence and a minimum CRISPR repeat sequence may form a duplex, i.e. a base-paired double-stranded structure. Together, the minimum tracrRNA sequence and the minimum CRISPR repeat can bind to an RNA-guided endonuclease. At least a part of the minimum tracrRNA sequence can hybridize to the minimum CRISPR repeat sequence. The minimum tracrRNA sequence can be at least about 30%, about 40%, about 50%, about 60%, about 65%, about 70%, about 75%, about 80%, about 85%, about 90%, about 95%, or 100% complementary to the minimum CRISPR repeat sequence.

The minimum tracrRNA sequence can have a length from about 7 nucleotides to about 100 nucleotides. For example, the minimum tracrRNA sequence can be from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt long. The minimum tracrRNA sequence can be approximately 9 nucleotides in length. The minimum tracrRNA sequence can be approximately 12 nucleotides. The minimum tracrRNA can consist of tracrRNA nt 23-48 described in Jinek et al., supra.

The minimum tracrRNA sequence can be at least about 60% identical to a reference minimum tracrRNA (e.g., wild type, tracrRNA from *S. pyogenes*) sequence over a stretch of at least 6, 7, or 8 contiguous nucleotides. For example, the minimum tracrRNA sequence can be at least about 65% identical, about 70% identical, about 75% identical, about 80% identical, about 85% identical, about 90% identical, about 95% identical, about 98% identical, about 99% identical or 100% identical to a reference minimum tracrRNA sequence over a stretch of at least 6, 7, or 8 contiguous nucleotides.

The duplex between the minimum CRISPR RNA and the minimum tracrRNA can comprise a double helix. The duplex between the minimum CRISPR RNA and the minimum tracrRNA can comprise at least about 1, 2, 3, 4, 5, 6, 7, 8, 9, or 10 or more nucleotides. The duplex between the minimum CRISPR RNA and the minimum tracrRNA can comprise at most about 1, 2, 3, 4, 5, 6, 7, 8, 9, or 10 or more nucleotides.

The duplex can comprise a mismatch (i.e., the two strands of the duplex are not 100% complementary). The duplex can comprise at least about 1, 2, 3, 4, or 5 or mismatches. The duplex can comprise at most about 1, 2, 3, 4, or 5 or mismatches. The duplex can comprise no more than 2 mismatches.

In some embodiments, a tracrRNA may be a 3' tracrRNA. In some embodiments, a 3' tracrRNA sequence can comprise a sequence with at least about 30%, about 40%, about 50%, about 60%, about 65%, about 70%, about 75%, about 80%, about 85%, about 90%, about 95%, or 100% sequence identity to a reference tracrRNA sequence (e.g., a tracrRNA from *S. pyogenes*).

In some embodiments, a gRNA may comprise a tracrRNA extension sequence. A tracrRNA extension sequence can have a length from about 1 nucleotide to about 400 nucleotides. The tracrRNA extension sequence can have a length of more than 1, 5, 10, 15, 20, 25, 30, 35, 40, 45, 50, 60, 70, 80, 90, 100, 120, 140, 160, 180, or 200 nucleotides. The tracrRNA extension sequence can have a length from about 20 to about 5000 or more nucleotides. The tracrRNA extension sequence can have a length of less than 5, 10, 15, 20, 25, 30, 35, 40, 45, 50, 60, 70, 80, 90, or 100 nucleotides. The tracrRNA extension sequence can comprise less than 10 nucleotides in length. The tracrRNA extension sequence can be 10-30 nucleotides in length. The tracrRNA extension sequence can be 30-70 nucleotides in length.

The tracrRNA extension sequence can comprise a functional moiety (e.g., a stability control sequence, ribozyme, endoribonuclease binding sequence). The functional moiety can comprise a transcriptional terminator segment (i.e., a transcription termination sequence). The functional moiety can have a total length from about 10 nucleotides (nt) to about 100 nucleotides, from about 10 nt to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, from about 15 nt to about 80 nt, from about 15 nt to about 50 nt, from about 15 nt to about 40 nt, from about 15 nt to about 30 nt, or from about 15 nt to about 25 nt.

In some embodiments, a sgRNA may comprise a linker sequence with a length from about 3 nucleotides to about 100 nucleotides. In Jinek et al., supra, for example, a simple 4 nucleotide "tetraloop" (-GAAA-) was used (Jinek et al., Science, 2012, 337(6096):816-821). An illustrative linker has a length from about 3 nucleotides (nt) to about 90 nt, from about 3 nt to about 80 nt, from about 3 nt to about 70 nt, from about 3 nt to about 60 nt, from about 3 nt to about 50 nt, from about 3 nt to about 40 nt, from about 3 nt to about 30 nt, from about 3 nt to about 20 nt, from about 3 nt to about 10 nt. For example, the linker can have a length from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. The linker of a single-molecule guide nucleic acid can be between 4 and 40 nucleotides. The linker can be at least about 100, 500, 1000, 1500, 2000, 2500, 3000, 3500, 4000, 4500, 5000, 5500, 6000, 6500, or 7000 or more nucleotides. The linker can be at most about 100, 500, 1000, 1500, 2000, 2500, 3000, 3500, 4000, 4500, 5000, 5500, 6000, 6500, or 7000 or more nucleotides.

Linkers can comprise any of a variety of sequences, although in some examples the linker will not comprise sequences that have extensive regions of homology with other portions of the guide RNA, which might cause intramolecular binding that could interfere with other functional regions of the guide. In Jinek et al., supra, a simple 4 nucleotide sequence -GAAA- was used (Jinek et al., Science, 2012, 337(6096):816-821), but numerous other sequences, including longer sequences can likewise be used.

The linker sequence can comprise a functional moiety. For example, the linker sequence can comprise one or more features, including an aptamer, a ribozyme, a protein-interacting hairpin, a protein binding site, a CRISPR array, an intron, or an exon. The linker sequence can comprise at least about 1, 2, 3, 4, or 5 or more functional moieties. In some examples, the linker sequence can comprise at most about 1, 2, 3, 4, or 5 or more functional moieties.

In some embodiments, a sgRNA does not comprise a uracil, e.g., at the 3'end of the sgRNA sequence. In some embodiments, a sgRNA does comprise one or more uracils, e.g., at the 3'end of the sgRNA sequence. In some embodiments, a sgRNA comprises 1, 2, 3, 4, 5, 6, 7, 8, 9, or 10 uracils (U) at the 3' end of the sgRNA sequence.

A sgRNA may be chemically modified. In some embodiments, a chemically modified gRNA is a gRNA that comprises at least one nucleotide with a chemical modification, e.g., a 2'-O-methyl sugar modification. In some embodiments, a chemically modified gRNA comprises a modified nucleic acid backbone. In some embodiments, a chemically modified gRNA comprises a 2'-O-methyl-phosphorothioate residue. In some embodiments, chemical modifications enhance stability, reduce the likelihood or degree of innate immune response, and/or enhance other attributes, as described in the art.

In some embodiments, a modified gRNA may comprise modified backbones, for example, phosphorothioates, phosphotriesters, morpholinos, methyl phosphonates, short chain alkyl or cycloalkyl intersugar linkages or short chain heteroatomic or heterocyclic intersugar linkages.

Morpholino-based compounds are described in Braasch and David Corey, Biochemistry, 2002, 41(14): 4503-4510; Genesis, 2001, Volume 30, Issue 3; Heasman, Dev. Biol., 2002, 243: 209-214; Nasevicius et al., Nat. Genet., 2000, 26:216-220; Lacerra et al., Proc. Natl. Acad. Sci., 2000, 97: 9591-9596.; and U.S. Pat. No. 5,034,506, issued Jul. 23, 1991.

Cyclohexenyl nucleic acid oligonucleotide mimetics are described in Wang et al., J. Am. Chem. Soc., 2000, 122: 8595-8602.

In some embodiments, a modified gRNA may comprise one or more substituted sugar moieties, e.g., one of the following at the 2' position: OH, SH, SCH3, F, OCN, OCH3, OCH3 O(CH2)n CH3, O(CH2)n NH2, or O(CH2)n CH3, where n is from 1 to about 10; C1 to C10 lower alkyl, alkoxyalkoxy, substituted lower alkyl, alkaryl or aralkyl; C1; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; 2'-O-(2-methoxyethyl); 2'-methoxy (2'-O—CH3); 2'-propoxy (2'-OCH2 CH2CH3); and 2'-fluoro (2'-F). Similar modifications may also be made at other positions on the gRNA, particularly the 3' position of the sugar on the 3' terminal nucleotide and the 5' position of 5' terminal nucleotide. In some examples, both a sugar and an internucleoside linkage, i.e., the backbone, of the nucleotide units can be replaced with novel groups.

Guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C), and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine, and 2,6-diaminopurine. Kornberg, A., DNA Replication, W. H. Freeman & Co., San Francisco, pp. 75-77, 1980; Gebeyehu et al., Nucl. Acids Res. 1997, 15:4513. A "universal" base known in the art, e.g., inosine, can also be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are aspects of base substitutions.

Modified nucleobases can comprise other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine, and 3-deazaguanine and 3-deazaadenine. Complexes of a Genome-targeting Nucleic Acid and an Endonuclease A gRNA interacts with an endonuclease (e.g., a RNA-guided nuclease such as Cas9), thereby forming a complex. The gRNA guides the endonuclease to a target polynucleotide.

The endonuclease and gRNA can each be administered separately to a cell or a subject. In some embodiments, the endonuclease can be pre-complexed with one or more guide RNAs, or one or more crRNA together with a tracrRNA. The pre-complexed material can then be administered to a cell or a subject. Such pre-complexed material is known as a ribonucleoprotein particle (RNP). The endonuclease in the RNP can be, for example, a Cas9 endonuclease or a Cpf1 endonuclease. The endonuclease can be flanked at the N-terminus, the C-terminus, or both the N-terminus and C-terminus by one or more nuclear localization signals (NLSs). For example, a Cas9 endonuclease can be flanked by two NLSs, one NLS located at the N-terminus and the second NLS located at the C-terminus. The NLS can be any NLS known in the art, such as a SV40 NLS. The molar ratio of genome-targeting nucleic acid to endonuclease in the RNP can range from about 1:1 to about 10:1. For example, the molar ratio of sgRNA to Cas9 endonuclease in the RNP can be 3:1.

Nucleic Acids Encoding System Components

The present disclosure provides a nucleic acid comprising a nucleotide sequence encoding a genome-targeting nucleic acid of the disclosure, an endonuclease of the disclosure, and/or any nucleic acid or proteinaceous molecule necessary to carry out the aspects of the methods of the disclosure. The encoding nucleic acids can be RNA, DNA, or a combination thereof.

The nucleic acid encoding a genome-targeting nucleic acid of the disclosure, an endonuclease of the disclosure, and/or any nucleic acid or proteinaceous molecule necessary to carry out the aspects of the methods of the disclosure can comprise a vector (e.g., a recombinant expression vector).

The term "vector" refers to a nucleic acid molecule capable of transporting another nucleic acid to which it has been linked. One type of vector is a "plasmid", which refers to a circular double-stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

In some examples, vectors can be capable of directing the expression of nucleic acids to which they are operatively linked. Such vectors are referred to herein as "recombinant expression vectors", or more simply "expression vectors", which serve equivalent functions.

The term "operably linked" means that the nucleotide sequence of interest is linked to regulatory sequence(s) in a manner that allows for expression of the nucleotide sequence. The term "regulatory sequence" is intended to include, for example, promoters, enhancers and other expression control elements (e.g., polyadenylation signals). Such regulatory sequences are well known in the art and are described, for example, in Goeddel; Gene Expression Technology: Methods in Enzymology, 1990, 185, Academic Press, San Diego, Calif. Regulatory sequences include those that direct constitutive expression of a nucleotide sequence in many types of host cells, and those that direct expression of the nucleotide sequence only in certain host cells (e.g., tissue-specific regulatory sequences). It will be appreciated by those skilled in the art that the design of the expression vector can depend on such factors as the choice of the target cell, the level of expression desired, and the like.

Expression vectors contemplated include, but are not limited to, viral vectors based on vaccinia virus, poliovirus, adenovirus, adeno-associated virus, SV40, herpes simplex virus, human immunodeficiency virus, retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus) and other recombinant vectors. Other vectors contemplated for eukaryotic target cells include, but are not limited to, the vectors pXT1, pSG5, pSVK3, pBPV, pMSG, and pSVLSV40 (Pharmacia). Other vectors can be used so long as they are compatible with the host cell.

In some examples, a vector can comprise one or more transcription and/or translation control elements. Depending on the host/vector system utilized, any of a number of suitable transcription and translation control elements, including constitutive and inducible promoters, transcription enhancer elements, transcription terminators, etc. can be used in the expression vector. The vector can be a self-inactivating vector that either inactivates the viral sequences or the components of the CRISPR machinery or other elements.

Non-limiting examples of suitable eukaryotic promoters (i.e., promoters functional in a eukaryotic cell) include those from cytomegalovirus (CMV) immediate early, herpes simplex virus (HSV) thymidine kinase, early and late SV40, long terminal repeats (LTRs) from retrovirus, human elongation factor-1 $\alpha$ promoter (EF1$\alpha$), chicken beta-actin promoter (CBA), ubiquitin C promoter (UBC), a hybrid construct comprising the cytomegalovirus enhancer fused to the chicken beta-actin promoter, a hybrid construct comprising the cytomegalovirus enhancer fused to the promoter, the first exon, and the first intron of chicken beta-actin gene (CAG or CAGGS), murine stem cell virus promoter (MSCV), phosphoglycerate kinase-1 locus promoter (PGK), and mouse metallothionein-I promoter.

A promoter can be an inducible promoter (e.g., a heat shock promoter, tetracycline-regulated promoter, steroid-regulated promoter, metal-regulated promoter, estrogen receptor-regulated promoter, etc.). The promoter can be a constitutive promoter (e.g., CMV promoter, UBC promoter, CAG or CAGGS promoter). In some cases, the promoter can be a spatially restricted and/or temporally restricted promoter (e.g., a tissue specific promoter, a cell type specific promoter, etc.).

Introduction of the complexes, polypeptides, and nucleic acids of the disclosure into cells can occur by viral or bacteriophage infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

IV. Cell Types

Cells as described herein, e.g., universal donor cells (and corresponding unmodified cells) may belong to any possible class of cell type. In some embodiments, a cell, e.g., universal donor cell (and corresponding unmodified cell) may be a mammalian cell. In some embodiments, a cell, e.g., universal donor cell (and corresponding unmodified cell) may be a human cell. In some embodiments, a cell, e.g., universal donor cell (and corresponding unmodified cell) may be a stem cell. In some embodiments, a cell, e.g., universal donor cell (and corresponding unmodified cell) may be a pluripotent stem cell (PSC). In some embodiments, a cell, e.g., a universal donor cell (and corresponding unmodified cell) may be an embryonic stem cell (ESC), an adult stem cell (ASC), an induced pluripotent stem cell (iPSC), or a hematopoietic stem or progenitor cell (HSPC) (also called a hematopoietic stem cell (HSC)). In some embodiments, a cell, e.g., universal donor cell (and corresponding unmodified cell) may be a differentiated cell. In some embodiments, a cell, e.g., universal donor cell (and corresponding unmodified cell) may be a somatic cell, e.g., an immune system cell, a pancreatic cell or a contractile cell, e.g., a skeletal muscle cell.

The cells, e.g., universal donor stem cells, described herein may be differentiated into relevant cell types to assess HLA expression, as well as the evaluation of immunogenicity of the universal stem cell lines. In general, differentiation comprises maintaining the cells of interest for a period time and under conditions sufficient for the cells to differentiate into the differentiated cells of interest. For example, the universal stem cells disclosed herein may be differentiated into mesenchymal progenitor cells (MPCs), hypoimmunogenic cardiomyocytes, muscle progenitor cells, blast cells, endothelial cells (ECs), macrophages, hepatocytes, beta cells (e.g., pancreatic beta cells), pancreatic endoderm progenitors, pancreatic endocrine progenitors, pancreatic endocrine cells, hematopoietic progenitor cells, or neural progenitor cells (NPCs). In some embodiments, the universal donor cell may be differentiated into definitive endoderm cells, primitive gut tube cells, posterior foregut cells, pancreatic endoderm cells (PEC), pancreatic endocrine cells, immature beta cells, or maturing beta cells.

Stem cells are capable of both proliferation and giving rise to more progenitor cells, these in turn having the ability to generate a large number of mother cells that can in turn give rise to differentiated or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one aspect, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell that itself is derived from a multipotent cell, and so on. While each of these multipotent cells may be considered stem cells, the range of cell types that each can give rise to may vary considerably. Some differentiated cells also have the capacity to give rise to cells of greater developmental potential. Such capacity may be natural or may be induced artificially upon treatment with various factors.

For instance, the human embryonic stem cells (hESCs) can be differentiated artificially into insulin producing cells via a seven-stage process requiring the addition of specific growth factors and small molecules. These seven stages include 1) definitive endoderm, 2) primitive gut tube, 3) posterior foregut, 4) pancreatic endoderm, 5) pancreatic endoderm precursors, 6) immature beta cells, and 7) maturing beta cells. For example, human pluripotent stem cells can be differentiated into pancreatic lineages as described in Schulz et al. (2012) PLoS ONE 7(5): e37004, Rezania et al. (2014) Nat. Biotechnol. 32(11): 1121-1133, and/or US20200208116. In many biological instances, stem cells can also be "multipotent" because they can produce progeny of more than one distinct cell type, but this is not required for "stem-ness."

A "differentiated cell" is a cell that has progressed further down the developmental pathway than the cell to which it is being compared. Thus, stem cells can differentiate into lineage-restricted precursor cells (such as a myocyte progenitor cell), which in turn can differentiate into other types of precursor cells further down the pathway (such as a myocyte precursor), and then to an end-stage differentiated cell, such as a myocyte, which plays a characteristic role in a certain tissue type, and may or may not retain the capacity to proliferate further. In some embodiments, the differentiated cell may be a pancreatic beta cell.

Embryonic Stem Cells

The cells described herein may be embryonic stem cells (ESCs). ESCs are derived from blastocytes of mammalian embryos and are able differentiate into any cell type and propagate rapidly. ESCs are also believed to have a normal karyotype, maintaining high telomerase activity, and exhibiting remarkable long-term proliferative potential, making these cells excellent candidates for use as universal donor cells.

Adult Stem Cells

The cells described herein may be adult stem cells (ASCs). ASCs are undifferentiated cells that may be found in mammals, e.g., humans. ASCs are defined by their ability to self-renew, e.g., be passaged through several rounds of cell replication while maintaining their undifferentiated state, and ability to differentiate into several distinct cell types, e.g., glial cells. Adult stem cells are a broad class of stem cells that may encompass hematopoietic stem cells, mammary stem cells, intestinal stem cells, mesenchymal stem cells, endothelial stem cells, neural stem cells, olfactory adult stem cells, neural crest stem cells, and testicular cells.

Induced Pluripotent Stem Cells

The cells described herein may be induced pluripotent stem cells (iPSCs). An iPSC may be generated directly from an adult human cell by introducing genes that encode critical transcription factors involved in pluripotency, e.g., OCT4, SOX2, cMYC, and KLF4. An iPSC may be derived from the same subject to which subsequent progenitor cells are to be administered. That is, a somatic cell can be obtained from a subject, reprogrammed to an induced pluripotent stem cell, and then re-differentiated into a progenitor cell to be administered to the subject (e.g., autologous cells). However, in the case of autologous cells, a risk of immune response and poor viability post-engraftment remain. In some embodiments, the iPSCs are derived from a commercial source. In some embodiments, iPSCs are gene-edited before differentiation into lineage-restricted progenitor cells or fully differentiated somatic cells.

Human Hematopoietic Stem and Progenitor Cells

The cells described herein may be human hematopoietic stem and progenitor cells (hHSPCs). This stem cell lineage gives rise to all blood cell types, including erythroid (erythrocytes or red blood cells (RBCs)), myeloid (monocytes and macrophages, neutrophils, basophils, eosinophils, megakaryocytes/platelets, and dendritic cells), and lymphoid (T-cells, B-cells, NK-cells). Blood cells are produced by the proliferation and differentiation of a very small population of pluripotent hematopoietic stem cells (HSCs) that also have the ability to replenish themselves by self-renewal. During differentiation, the progeny of HSCs progress through various intermediate maturational stages, generating multi-potential and lineage-committed progenitor cells prior to reaching maturity. Bone marrow (BM) is the major site of hematopoiesis in humans and, under normal conditions, only small numbers of hematopoietic stem and progenitor cells (HSPCs) can be found in the peripheral blood (PB). Treatment with cytokines, some myelosuppressive drugs used in cancer treatment, and compounds that disrupt the interaction between hematopoietic and BM stromal cells can rapidly mobilize large numbers of stem and progenitors into the circulation.

Differentiation of Cells into Other Cell Types

Another step of the methods of the present disclosure may comprise differentiating cells into differentiated cells. The differentiating step may be performed according to any method known in the art. For example, human iPSCs are differentiated into definitive endoderm using various treatments, including activin and B27 supplement (Life Technologies). The definitive endoderm is further differentiated into hepatocyte, the treatment includes: FGF4, HGF, BMP2, BMP4, Oncostatin M, Dexamethasone, etc. (Duan et al, Stem Cells, 2010; 28:674-686; Ma et al, Stem Cells Translational Medicine, 2013; 2:409-419). In another embodiment, the differentiating step may be performed according to Sawitza et al, Sci Rep. 2015; 5:13320. A differentiated cell may be any somatic cell of a mammal, e.g., a human. In some embodiments, a somatic cell may be an exocrine secretory epithelial cells (e.g., salivary gland mucous cell, prostate gland cell), a hormone-secreting cell (e.g., anterior pituitary cell, gut tract cell, pancreatic islet), a keratinizing epithelial cell (e.g., epidermal keratinocyte), a wet stratified barrier epithelial cell, a sensory transducer cell (e.g., a photoreceptor), an autonomic neuron cells, a sense organ and peripheral neuron supporting cell (e.g., Schwann cell), a central nervous system neuron, a glial cell (e.g., astrocyte, oligodendrocyte), a lens cell, an adipocyte, a kidney cell, a barrier function cell (e.g., a duct cell), an extracellular matrix cell, a contractile cell (e.g., skeletal muscle cell, heart muscle cell, smooth muscle cell), a blood cell (e.g., erythrocyte), an immune system cell (e.g., megakaryocyte, microglial cell, neutrophil, Mast cell, a T cell, a B cell, a Natural Killer cell), a germ cell (e.g., spermatid), a nurse cell, or an interstitial cell.

In general, populations of the universal donor cells disclosed herein maintain expression of the inserted one or more nucleotide sequences over time. For example, at least about 50%, at least about 55%, at least about 60%, at least about 65%, at least about 70%, at least about 75%, at least about 80%, at least about 85%, at least about 90%, at least about 95%, or at least about 99% of the universal donor cells express the inserted one or more tolerogenic factors and/or survival factors. Moreover, populations of lineage-restricted or fully differentiated cells derived from the universal donor cells disclosed herein maintain expression of the inserted one or more nucleotide sequences over time. For example, at least about 50%, at least about 55%, at least about 60%, at least about 65%, at least about 70%, at least about 75%, at least about 80%, at least about 85%, at least about 90%, at least about 95%, or at least about 99% of the lineage-restricted or fully differentiated cells express the one or more tolerogenic factors and/or survival factors.

V. Formulations and Administrations

Formulation and Delivery for Gene Editing

Guide RNAs, polynucleotides, e.g., polynucleotides that encode a tolerogenic factor and/or survival factor, or polynucleotides that encode an endonuclease, and endonucleases as described herein may be formulated and delivered to cells in any manner known in the art.

Guide RNAs and/or polynucleotides may be formulated with pharmaceutically acceptable excipients such as carriers, solvents, stabilizers, adjuvants, diluents, etc., depending upon the particular mode of administration and dosage form. Guide RNAs and/or polynucleotides compositions can be formulated to achieve a physiologically compatible pH, and range from a pH of about 3 to a pH of about 11, about pH 3 to about pH 7, depending on the formulation and route of administration. In some cases, the pH can be adjusted to a range from about pH 5.0 to about pH 8. In some cases, the compositions can comprise a therapeutically effective amount of at least one compound as described herein, together with one or more pharmaceutically acceptable excipients. Optionally, the compositions can comprise a combination of the compounds described herein, or can include a second active ingredient useful in the treatment or prevention of bacterial growth (for example and without limitation, anti-bacterial or anti-microbial agents), or can include a combination of reagents of the present disclosure.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients can include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol), wetting or emulsifying agents, pH buffering substances, and the like.

Guide RNA polynucleotides (RNA or DNA) and/or endonuclease polynucleotide(s) (RNA or DNA) can be delivered by viral or non-viral delivery vehicles known in the art. Alternatively, endonuclease polypeptide(s) can be delivered by viral or non-viral delivery vehicles known in the art, such as electroporation or lipid nanoparticles. In further alternative aspects, the DNA endonuclease can be delivered as one or more polypeptides, either alone or pre-complexed with one or more guide RNAs, or one or more crRNA together with a tracrRNA.

Polynucleotides can be delivered by non-viral delivery vehicles including, but not limited to, nanoparticles, liposomes, ribonucleoproteins, positively charged peptides, small molecule RNA-conjugates, aptamer-RNA chimeras, and RNA-fusion protein complexes. Some exemplary non-viral delivery vehicles are described in Peer and Lieberman, Gene Therapy, 2011, 18: 1127-1133 (which focuses on non-viral delivery vehicles for siRNA that are also useful for delivery of other polynucleotides).

For polynucleotides of the disclosure, the formulation may be selected from any of those taught, for example, in International Application PCT/US2012/069610.

Polynucleotides, such as guide RNA, sgRNA, and mRNA encoding an endonuclease, may be delivered to a cell or a subject by a lipid nanoparticle (LNP).

A LNP refers to any particle having a diameter of less than 1000 nm, 500 nm, 250 nm, 200 nm, 150 nm, 100 nm, 75 nm, 50 nm, or 25 nm. Alternatively, a nanoparticle may range in size from 1-1000 nm, 1-500 nm, 1-250 nm, 25-200 nm, 25-100 nm, 35-75 nm, or 25-60 nm.

LNPs may be made from cationic, anionic, or neutral lipids. Neutral lipids, such as the fusogenic phospholipid DOPE or the membrane component cholesterol, may be included in LNPs as 'helper lipids' to enhance transfection activity and nanoparticle stability. Limitations of cationic lipids include low efficacy owing to poor stability and rapid clearance, as well as the generation of inflammatory or anti-inflammatory responses.

LNPs may also be comprised of hydrophobic lipids, hydrophilic lipids, or both hydrophobic and hydrophilic lipids.

Any lipid or combination of lipids that are known in the art can be used to produce a LNP. Examples of lipids used to produce LNPs are: DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). Examples of cationic lipids are: 98N12-5, C12-200, DLin-KC2-DMA (KC2), DLin-MC3-DMA (MC3), XTC, MD1, and 7C1. Examples of neutral lipids are: DPSC, DPPC, POPC, DOPE, and SM. Examples of PEG-modified lipids are: PEG-DMG, PEG-CerC14, and PEG-CerC20.

The lipids can be combined in any number of molar ratios to produce a LNP. In addition, the polynucleotide(s) can be combined with lipid(s) in a wide range of molar ratios to produce a LNP.

A recombinant adeno-associated virus (AAV) vector can be used for delivery. Techniques to produce rAAV particles, in which an AAV genome to be packaged that includes the polynucleotide to be delivered, rep and cap genes, and helper virus functions are provided to a cell are standard in the art. Production of rAAV typically requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived from and may be from a different AAV serotype than the rAAV genome ITRs, including, but not limited to, AAV serotypes described herein. Production of pseudotyped rAAV is disclosed in, for example, international patent application publication number WO 01/83692.

Formulation and Administration of Cells, e.g., Universal Donor Cells

Genetically modified cells, e.g., universal donor cells, as described herein may be formulated and administered to a subject by any manner known in the art.

The terms "administering," "introducing", "implanting", "engrafting" and "transplanting" are used interchangeably in the context of the placement of cells, e.g., progenitor cells, into a subject, by a method or route that results in at least partial localization of the introduced cells at a desired site. The cells e.g., progenitor cells, or their differentiated progeny can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the lifetime of the subject, i.e., long-term engraftment.

A genetically modified cell, e.g., universal donor cell, as described herein may be viable after administration to a subject for a period that is longer than that of an unmodified cell.

In some embodiments, a composition comprising cells as described herein may be administered by a suitable route, which may include intravenous administration, e.g., as a bolus or by continuous infusion over a period of time. In some embodiments, intravenous administration may be performed by intramuscular, intraperitoneal, intracerebrospinal, subcutaneous, intra-articular, intrasynovial, or intrathecal routes. In some embodiments, a composition may be in solid form, aqueous form, or a liquid form. In some embodiments, an aqueous or liquid form may be nebulized or lyophilized. In some embodiments, a nebulized or lyophilized form may be reconstituted with an aqueous or liquid solution.

A cell composition can also be emulsified or presented as a liposome composition, provided that the emulsification procedure does not adversely affect cell viability. The cells and any other active ingredient can be mixed with excipients that are pharmaceutically acceptable and compatible with the active ingredient, and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, mandelic and the like. Salts formed with the free carboxyl groups can also be derived from inorganic bases, such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions that is effective in the treatment of a particular disorder or condition can depend on the nature of the disorder or condition and can be determined by standard clinical techniques.

In some embodiments, a composition comprising cells may be administered to a subject, e.g., a human subject, who has, is suspected of having, or is at risk for a disease or disorder. In some embodiments, a composition may be administered to a subject who does not have, is not suspected of having or is not at risk for a disease or disorder. In some embodiments, a subject is a healthy human. In some embodiments, a subject e.g., a human subject, who has, is suspected of having, or is at risk for a genetically inheritable disease or disorder. In some embodiments, the subject is suffering or is at risk of developing symptoms indicative of a disease or disorder. In some embodiments, the disease is diabetes, e.g., type I diabetes or type II diabetes. In some embodiments, the disorder is a pancreactomy.

VI. Specific Compositions and Methods of the Disclosure

Accordingly, the present disclosure relates, in particular, to the following non-limiting compositions and methods.

In a first composition, Composition 1, the present disclosure provides a composition comprising a genetically modified cell comprising: (a) a disrupted B2M gene and a first insertion of a first polynucleotide encoding mesencephalic astrocyte derived neurotrophic factor (MANF) into the disrupted B2M gene; (b) a disrupted TXNIP gene and a second insertion of a second polynucleotide encoding tumor necrosis factor alpha induced protein 3 (TNFAIP3) into the disrupted TXNIP gene; wherein the cell expresses MANF and TNFAIP3 and has disrupted expression of B2M and TXNIP.

In another composition, Composition 2, the present disclosure provides a composition according to composition 1, wherein the first insertion further comprises a third polynucleotide encoding HLA class I histocompatibility antigen, alpha chain E (HLA-E).

In another composition, Composition 3, the present disclosure provides a composition according to composition 1 or 2, wherein the nucleotide sequence encoding HLA-E comprises a sequence encoding a HLA-E trimer, the HLA-E trimer comprising a B2M signal peptide fused to an HLA-G presentation peptide fused to a B2M membrane protein fused to HLA-E without its signal peptide.

In another composition, Composition 4, the present disclosure provides a composition according to any one of compositions 1 to 3, wherein the first polynucleotide encoding MANF is linked to the third polynucleotide HLA-E by a polynucleotide encoding a P2A peptide such that the first insertion comprises a MANF-P2A-HLA-E construct.

In another composition, Composition 5, the present disclosure provides a composition according to composition 4, wherein the MANF-P2A-HLA-E construct comprises a polynucleotide sequence consisting essentially of SEQ ID NO: 55.

In another composition, Composition 6, the present disclosure provides a composition according to composition 4 or 5, wherein the MANF-P2A-HLA-E construct is operably linked to an exogenous promoter.

In another composition, Composition 7, the present disclosure provides a composition according to any one of compositions 1 to 6, wherein the second insertion further comprises a fourth polynucleotide encoding programmed death-ligand 1 (PD-L-1).

In another composition, Composition 8, the present disclosure provides a composition according to any one of compositions 1 to 7 wherein the second nucleotide sequence encoding TNFAIP3 is linked to the fourth nucleotide sequence encoding PD-L-1 by a nucleotide sequence encoding a P2A peptide such that the second insertion comprises a TNFAIP3-P2A-PD-L-1 construct.

In another composition, Composition 9, the present disclosure provides a composition according to composition 8, wherein the TNFAIP3-P2A-PD-L-1 construct comprises a nucleotide sequence consisting essentially of SEQ ID NO: 54.

In another composition, Composition 10, the present disclosure provides a composition according to composition 8 or 9, wherein the TNFAIP3-P2A-PD-L-1 construct is operably linked to an exogenous promoter.

In another composition, Composition 11, the present disclosure provides a composition according to any one of compositions 1 to 10, wherein the disrupted expression of B2M and TXNIP comprises reduced or eliminated expression of B2M and/or TXNIP.

In another composition, Composition 12, the present disclosure provides a composition according to any one of compositions 1 to 11, wherein the universal donor cell has increased immune evasion and/or post-transplantation survival compared to a comparable cell without the polynucleotide insertion and gene disruption.

In another composition, Composition 13, the present disclosure provides a composition according to any one of compositions 1 to 12, wherein the cell is a stem cell.

In another composition, Composition 14, the present disclosure provides a composition according to composition 13, wherein the stem cell is an embryonic stem cell, an adult stem cell, an induced pluripotent stem cell, or a hematopoietic stem cell.

In another composition, Composition 15, the present disclosure provides a composition according to any one of compositions 1 to 12, wherein the cell is a differentiated cell or a somatic cell.

In another composition, Composition 16, the present disclosure provides a composition according to composition 15, wherein the cell is differentiated into lineage-restricted progenitor cells or fully differentiated somatic cells.

In another composition, Composition 17, the present disclosure provides a composition according to composition 16, wherein the lineage-restricted progenitor cells are definitive endoderm cells, primitive gut tube cells, posterior foregut cells, pancreatic endoderm progenitors, pancreatic endocrine progenitors, or immature beta cells, and the fully differentiated somatic cells are beta cells.

In another composition, Composition 18, the present disclosure provides a composition comprising a plurality of genetically modified cells according to any one of Compositions 1 to 17.

In another composition, Composition 19, the present disclosure provides a composition comprising population of lineage-restricted progenitor cells or fully differentiated somatic cells derived from the plurality of genetically modified cells of composition 18.

In another composition, Composition 20, the present disclosure provides a composition according to composition 19, wherein the population comprises definitive endoderm cells, primitive gut tube cells, posterior foregut cells, pancreatic endoderm cells, pancreatic endocrine precursor cells, immature beta cells, and/or pancreatic beta cells.

In another composition, Composition 21, the present disclosure provides a composition comprising the plurality of cells of composition 18 or the population of cells of composition 19 and at least one pharmaceutically acceptable excipient.

In a first method, Method 22, the present disclosure provides a method for treating a pancreatic disease or disorder in a subject in need thereof, Method 22, the method comprising: (a) obtaining or having obtained the population of lineage restricted progenitor cells or fully differentiated somatic cells of claim 19, wherein the lineage restricted progenitor cells or fully differentiated somatic cells comprise pancreatic endoderm cells, pancreatic endocrine precursor cells, immature beta cells, and/or pancreatic beta cells; and (b) administering the pancreatic endoderm cells, pancreatic endocrine cells, immature beta cells, and/or beta cells to the subject.

In another method, Method 23, the present disclosure provides a method for treating a pancreatic disease or disorder in a subject in need thereof, Method 23, the method comprising (a) obtaining or having obtained the plurality of genetically modified cells of claim 18, wherein the plurality of genetically modified cells comprises stem cells; (b) differentiating the genetically modified cells into pancreatic endoderm cells, pancreatic endocrine precursor cells, immature beta cells, and/or pancreatic beta cells; and (c) administering the pancreatic endoderm cells, pancreatic endocrine precursor cells, immature beta cells, and/or pancreatic beta cells to the subject.

In another method, Method 24, the present disclosure provides a method as provided in Method 22 or 23, wherein the pancreatic disease or disorder is Type I diabetes, Type II diabetes or a pancreactomy.

In another composition, Composition 25, the present disclosure provides a composition comprising a genetically modified cell comprising (a) a first exogenous polynucleotide insertion encoding mesencephalic astrocyte derived neurotrophic factor (MANF), a second exogenous polynucleotide insertion encoding tumor necrosis factor alpha induced protein 3 (TNFAIP3), a third exogenous polynucleotide insertion encoding cluster of differentiation 39 (CD39), and/or a fourth exogenous polynucleotide insertion encoding cluster of differentiation 73 (CD73), wherein the genetically modified cell expresses CD39, MANF, TNFAIP3, and/or CD73; and/or (b) a disrupted gene encoding a transforming growth factor beta (TGFβ) protein, a beta-2-microglobulin (B2M) protein, a thioredoxin interacting protein (TXNIP) protein, and/or a class II transactivator (CIITA) protein wherein the genetically modified cell has disrupted expression of the TGFβ protein, the B2M protein, the TXNIP protein, and/or the CIITA protein.

In another composition, Composition 26, the present disclosure provides a composition according to composition 25, wherein the genetically modified cell comprises the first exogenous polynucleotide encoding MANF and expresses MANE.

In another composition, Composition 27, the present disclosure provides a composition according to composition 25 or 26, wherein the first exogenous polynucleotide is operably connected to an exogenous promoter.

In another composition, Composition 28, the present disclosure provides a composition according to any one of compositions 25 to 27, wherein the first exogenous polynucleotide comprises a nucleotide sequence consisting essentially of SEQ ID NO: 17

In another composition, Composition 29, the present disclosure provides a composition according to any one of compositions 25 to 28, wherein the genetically modified cell comprises the second exogenous polynucleotide encoding TNFAIP3 and expresses TNFAIP3.

In another composition, Composition 30, the present disclosure provides a composition according to any one of compositions 25 to 29, wherein the second exogenous polynucleotide is operably linked to an exogenous promoter.

In another composition, Composition 31, the present disclosure provides a composition according to any one of compositions 25 to 30, wherein the second exogenous polynucleotide comprises a nucleotide sequence consisting essentially of SEQ ID NO: 19.

In another composition, Composition 32, the present disclosure provides a composition according to any one of compositions 25 to 31, wherein the genetically modified cell comprises the third exogenous polynucleotide encoding CD39 and expresses CD39.

In another composition, Composition 33, the present disclosure provides a composition according to any one of compositions 25 to 32, wherein the third exogenous polynucleotide is operably linked to an exogenous promoter.

In another composition, Composition 34, the present disclosure provides a composition according to any one of compositions 25 to 33, wherein the third exogenous polynucleotide comprises a nucleotide sequence consisting essentially of SEQ ID NO: 27.

In another composition, Composition 35, the present disclosure provides a composition according to any one of compositions 25 to 34, wherein the genetically modified cell comprises the fourth exogenous polynucleotide encoding CD73 and expresses CD73.

In another composition, Composition 36, the present disclosure provides a composition according to any one of compositions 25 to 35, wherein the fourth exogenous polynucleotide encoding CD73 is operably linked to an exogenous promoter.

In another composition, Composition 37, the present disclosure provides a composition according to any one of compositions 25 to 36, wherein the fourth exogenous polynucleotide encoding CD73 comprises a nucleotide sequence consisting essentially of SEQ ID NO: 46.

In another composition, Composition 38, the present disclosure provides a composition according to any one of compositions 25 to 37, wherein the genetically modified cell comprises the third exogenous polynucleotide encoding CD39 and the fourth exogenous polynucleotide encoding CD73 and expresses CD39 and CD73, wherein the third exogenous polynucleotide encoding CD39 is linked to the fourth exogenous polynucleotide encoding CD73 by a polynucleotide encoding a P2A peptide, such that the third exogenous polynucleotide encoding CD39, the polynucleotide encoding the P2A peptide and the fourth exogenous polynucleotide encoding CD73 form a CD39-P2A-CD73 construct.

In another composition, Composition 39, the present disclosure provides a composition according to composition 38, wherein the CD39-P2A-CD73 construct is operably linked to an exogenous promoter.

In another composition, Composition 40, the present disclosure provides a composition according to composition 38 or 39, wherein the CD39-P2A-CD73 construct comprises a nucleotide sequence consisting essentially of SEQ ID NO: 58.

In another composition, Composition 41, the present disclosure provides a composition according to any one of compositions 25 to 40, further comprising a fifth exogenous polynucleotide encoding HLA class I histocompatibility antigen, alpha chain E (HLA-E), wherein the genetically modified cell expresses HLA-E.

In another composition, Composition 42, the present disclosure provides a composition according to composition 41, wherein the fifth exogenous polynucleotide encoding HLA-E comprises a polynucleotide encoding a HLA-E trimer, the HLA-E trimer comprising a B2M signal peptide fused to an HLA-G presentation peptide fused to a B2M membrane protein fused to HLA-E without its signal peptide.

In another composition, Composition 43, the present disclosure provides a composition according to composition 41 or 42, wherein the fifth exogenous polynucleotide encoding HLA-E is operably linked to an exogenous promoter.

In another composition, Composition 44, the present disclosure provides a composition according to any one of compositions 41 to 43, wherein the fifth exogenous polynucleotide encoding HLA-E comprises a nucleotide sequence consisting essentially of SEQ ID NO: 43.

In another composition, Composition 45, the present disclosure provides a composition according to any one of compositions 41 to 44, comprising the first exogenous polynucleotide encoding MANF and the fifth exogenous polynucleotide encoding HLA-E, wherein the first exogenous polynucleotide encoding MANF is linked to the fifth exogenous polynucleotide encoding HLA-E by a polynucleotide encoding a P2A peptide such that the first exogenous polynucleotide, the polynucleotide encoding the P2A peptide and the fifth exogenous polynucleotide form a MANF-P2A-HLA-E construct.

In another composition, Composition 46, the present disclosure provides a composition according to composition 45, wherein the MANF-P2A-HLA-E construct is operably linked to an exogenous promoter.

In another composition, Composition 47, the present disclosure provides a composition according to composition 45 or 46, wherein the MANF-P2A-HLA-E construct comprises a polynucleotide sequence consisting essentially of SEQ ID NO: 55.

In another composition, Composition 48, the present disclosure provides a composition according to any one of compositions 25 to 47, further comprising a sixth exogenous polynucleotide encoding programmed death-ligand 1 (PD-L-1), wherein the genetically modified cell expresses PD-L-1.

In another composition, Composition 49, the present disclosure provides a composition according to composition 48, wherein the sixth exogenous polynucleotide encoding PD-L-1 is operably linked to an exogenous promoter.

In another composition, Composition 50, the present disclosure provides a composition according to composition 48 or 49, wherein the sixth exogenous polynucleotide comprises a nucleotide sequence consisting essentially of SEQ ID NO: 20.

In another composition, Composition 51, the present disclosure provides a composition according to any one of compositions 48 to 50, comprising the second exogenous polynucleotide encoding TNFAIP3 and the sixth exogenous polynucleotide encoding PD-L-1, wherein the second exogenous polynucleotide encoding TNFAIP3 is linked to the sixth exogenous polynucleotide sequence encoding PD-L-1 by a polynucleotide encoding a P2A peptide such that the second exogenous polynucleotide, the polynucleotide encoding the P2A peptide and the sixth exogenous polynucleotide form a TNFAIP3-P2A-PD-L-1 construct.

In another composition, Composition 52, the present disclosure provides a composition according to composition 51, wherein the TNFAIP3-P2A-PD-L-1 construct is operably linked to an exogenous promoter.

In another composition, Composition 53, the present disclosure provides a composition according to composition 51 or 52, wherein the TNFAIP3-P2A-PD-L-1 construct comprises a nucleotide sequence consisting essentially of SEQ ID NO: 54.

In another composition, Composition 54, the present disclosure provides a composition according to any one of compositions 48 to 53, comprising the third exogenous polynucleotide encoding CD39 and the sixth exogenous polynucleotide encoding PD-L-1, wherein the third exogenous polynucleotide encoding CD39 is linked to the sixth exogenous polynucleotide encoding PD-L-1 by a polynucleotide encoding a P2A peptide such that the third exogenous polynucleotide, the polynucleotide encoding the P2A peptide and the sixth exogenous polynucleotide form a CD39-P2A-PD-L-1 construct.

In another composition, Composition 55, the present disclosure provides a composition according to composition 54, wherein the CD39-P2A-PD-L-1 construct is operably linked to an exogenous promoter.

In another composition, Composition 56, the present disclosure provides a composition according to composition 54 or 55, wherein the CD39-P2A-PD-L-1 construct comprises a nucleotide sequence consisting essentially of SEQ ID NO: 53.

In another composition, Composition 57, the present disclosure provides a composition according to any one of compositions 48 to 56 comprising the first exogenous polynucleotide encoding MANF, the second exogenous polynucleotide encoding TNFAIP3, and the sixth exogenous polynucleotide encoding PD-L-1, wherein the first exogenous polynucleotide is linked to the second exogenous polynucleotide by a first polynucleotide encoding a P2A peptide and the second exogenous polynucleotide is linked to the sixth exogenous polynucleotide by a second polynucleotide encoding a P2A peptide, such that the first exogenous polynucleotide encoding MANF, the first polynucleotide encoding a P2A peptide, the second exogenous polynucleotide encoding TNFAIP3, the second polynucleotide encoding a P2A peptide, and the sixth exogenous polynucleotide encoding PD-L-1 form a MANF-P2A-TNFAIP3-P2A-PD-L-1 construct.

In another composition, Composition 58, the present disclosure provides a composition according to composition 57, wherein the MANF-P2A-TNFAIP3-P2A-PD-L-1 is operably linked to an exogenous promoter.

In another composition, Composition 59, the present disclosure provides a composition according to composition 57 or 58, wherein the MANF-P2A-TNFAIP3-P2A-PD-L-1 construct comprises a nucleotide sequence consisting essentially of SEQ ID NO: 52.

In another composition, Composition 60, the present disclosure provides a composition according to any one of compositions 48 to 59, comprising the third exogenous polynucleotide encoding CD39, the fourth exogenous polynucleotide encoding CD73, and the sixth exogenous polynucleotide encoding PD-L-1, wherein the third exogenous polynucleotide encoding CD39 is linked to the fourth exogenous polynucleotide encoding CD73 by a first polynucleotide encoding a P2A peptide and the fourth exogenous polynucleotide is linked to the sixth exogenous polynucleotide by a second polynucleotide encoding a P2A peptide, such that the third exogenous polynucleotide encoding CD39, the first polynucleotide encoding a P2A peptide, the fourth exogenous polynucleotide encoding CD73, the second polynucleotide encoding a P2A peptide and the sixth exogenous polynucleotide encoding PD-L-1 form a CD39-P2A-CD73-P2A-PD-L-1 construct.

In another composition, Composition 61, the present disclosure provides a composition according to composition 60, wherein the CD39-P2A-CD73-P2A-PD-L-1 construct is operably linked to an exogenous promoter.

In another composition, Composition 62, the present disclosure provides a composition according to composition 60 or 61, wherein the CD39-P2A-CD73-P2A-PD-L-1 construct comprises a nucleotide sequence consisting essentially of SEQ ID NO: 56.

In another composition, Composition 63, the present disclosure provides a composition according to any one of compositions 25 to 62, wherein the genetically modified cell comprises the disrupted B2M gene, the disrupted TXNIP gene, the disrupted CIITA gene, and/or the disrupted TGFβ gene, and the cell has disrupted expression of the B2M protein, the TXNIP protein, the CIITA protein and/or the TGFβ protein.

In another composition, Composition 64, the present disclosure provides a composition according to any one of compositions 25 to 63, wherein the first exogenous polynucleotide encoding MANF, the second exogenous polynucleotide encoding TNFAIP3, the third exogenous polynucleotide encoding CD39 and/or the fourth exogenous polynucleotide encoding CD73 are each independently inserted within or near the B2M gene, the TXNIP gene, the CIITA gene, and/or the TGFβ gene, thereby disrupting expression of the B2M protein, the TXNIP protein, the CIITA protein, and/or the TGFβ protein.

In another composition, Composition 65, the present disclosure provides a composition according to any one of compositions 25 to 64, further comprising a fifth exogenous polynucleotide encoding HLA class I histocompatibility antigen, alpha chain E (HLA-E), wherein the fifth exogenous polynucleotide encoding HLA-E is inserted within or near the B2M gene, the TXNIP gene, the CIITA gene, and/or the TGFβ gene, thereby disrupting expression of the B2M protein, the TXNIP protein, the CIITA protein, and/or the TGFβ protein and wherein the universal donor cell further expresses HLA-E.

In another composition, Composition 66, the present disclosure provides a composition according to any one of compositions 25 to 65, further comprising a sixth exogenous polynucleotide encoding programmed death-ligand 1 (PD-L-1), wherein the sixth exogenous polynucleotide encoding PD-L-1 is inserted within or near the B2M gene, the TXNIP gene, the CIITA gene, and/or the TGFβ gene, thereby disrupting expression of the B2M protein, the TXNIP protein, the CIITA protein, and/or the TGFβ protein, and wherein the universal donor cell expresses PD-L-1.

In another composition, Composition 67, the present disclosure provides a composition according to any one of compositions 64 to 66, wherein the first exogenous polynucleotide encoding MANF is inserted within or near the B2M gene, the TXNIP gene, or the CIITA gene, and/or the TGFβ gene.

In another composition, Composition 68, the present disclosure provides a composition according to any one of compositions 64 to 67, wherein the first exogenous polynucleotide encoding MANF is inserted within or near the B2M gene and/or the TXNIP gene, thereby disrupting expression of the B2M protein and/or the TXNIP protein.

In another composition, Composition 69, the present disclosure provides a composition according to compositions 64 to 68, wherein the second exogenous polynucleotide encoding TNFAIP3 is inserted within or near the B2M gene, the TXNIP gene, or the CIITA gene, and/or the TGFβ gene.

In another composition, Composition 70, the present disclosure provides a composition according to compositions 64 to 69, wherein the second exogenous polynucleotide encoding TNFAIP3 is inserted within or near the B2M gene, thereby disrupting expression of the B2M protein.

In another composition, Composition 71, the present disclosure provides a composition according to any one of compositions 64 to 70, wherein the third exogenous polynucleotide encoding CD39 is inserted within or near the B2M gene, the TXNIP gene, the CIITA gene, and/or the TGFβ gene.

In another composition, Composition 72, the present disclosure provides a composition according to any one of compositions 64 to 71, wherein the third exogenous polynucleotide encoding CD39 is inserted within or near the CIITA gene and/or the B2M gene, thereby disrupting expression of the CIITA protein and/or the B2M protein.

In another composition, Composition 73, the present disclosure provides a composition according to any one of compositions 64 to 72, wherein the fourth exogenous polynucleotide encoding CD73 is inserted within or near the B2M gene, the TXNIP gene, the CIITA gene, and/or the TGFβ gene.

In another composition, Composition 74, the present disclosure provides a composition according to any one of compositions 64 to 73, wherein the fourth exogenous polynucleotide encoding CD73 is inserted within or near the B2M gene, thereby disrupting expression of the B2M protein.

In another composition, Composition 75, the present disclosure provides a composition according to any one of compositions 64 to 74, comprising the MANF-P2A-HLA-E construct wherein the MANF-P2A-HLA-E construct is inserted within or near the B2M gene, the TXNIP gene, the CIITA gene, or the TGFβ gene, thereby disrupting expression of the B2M protein, the TXNIP protein, the CIITA protein, and/or the TGFβ protein.

In another composition, Composition 76, the present disclosure provides a composition according to any one of compositions 64 to 75, Wherein the MANF-P2A-HLA-E construct is inserted within or near the TXNIP gene, thereby disrupting expression of the TXNIP protein.

In another composition, Composition 77, the present disclosure provides a composition according to any one of compositions 64 to 76, comprising the TNFAIP3-P2A-PD-L-1 construct, wherein the TNFAIP3-P2A-PD-L-1 construct is inserted within or near the B2M gene, the TXNIP gene, the CIITA gene, and/or the TGFβ gene, thereby disrupting expression of the B2M protein, the TXNIP protein, the CIITA protein, and/or the TGFβ protein.

In another composition, Composition 78, the present disclosure provides a composition according to any one of compositions 64 to 77, Wherein the TNFAIP3-P2A-PD-L-1 construct is inserted within or near the B2M gene, thereby disrupting expression of the B2M protein.

In another composition, Composition 79, the present disclosure provides a composition according to any one of compositions 64 to 78, comprising the CD39-P2A-PD-L-1 construct, wherein the CD39-P2A-PD-L-1 construct is inserted within or near the B2M gene, the TXNIP gene, the CIITA gene, and/or the TGFβ gene, thereby disrupting expression of the B2M protein, the TXNIP protein, the CIITA protein, and/or the TGFβ protein.

In another composition, Composition 80, the present disclosure provides a composition according to any one of compositions 64 to 79, Wherein the CD39-P2A-PD-L-1 construct is inserted within or near the B2M gene, thereby disrupting expression of the B2M protein.

In another composition, Composition 81, the present disclosure provides a composition according to any one of compositions 64 to 80, comprising the MANF-P2A-TNFAIP3-P2A-PD-L-1 construct, wherein the MANF-P2A-TNFAIP3-P2A-PD-L-1 construct is inserted within or near the B2M gene, the TXNIP gene, the CIITA gene, and/or the TGFβ gene, thereby disrupting expression the B2M protein, the TXNIP protein, the CIITA protein, and/or the TGFβ protein.

In another composition, Composition 82, the present disclosure provides a composition according to any one of compositions 64 to 81, Wherein the MANF-P2A-TNFAIP3-P2A-PD-L-1 construct is inserted within or near the B2M gene, thereby disrupting expression of the B2M protein.

In another composition, Composition 83, the present disclosure provides a composition according to any one of compositions 64 to 82, comprising the CD39-P2A-CD73 construct, wherein the CD39-P2A-CD73 construct is inserted within or near the B2M gene, the TXNIP gene, the CIITA gene, and/or the TGFβ gene, thereby disrupting expression of the B2M protein, the TXNIP protein, the CIITA protein, and/or the TGFβ protein.

In another composition, Composition 84, the present disclosure provides a composition according to any one of compositions 64 to 83, Wherein the CD39-P2A-CD73 construct is inserted within or near the B2M gene, thereby disrupting expression of the B2M protein.

In another composition, Composition 85, the present disclosure provides a composition according to any one of compositions 64 to 84, comprising the CD39-P2A-CD73-P2A-PD-L-1 construct, wherein the CD39-P2A-CD73-P2A-PD-L-1 construct is inserted within or near the B2M gene, the TXNIP gene, the CIITA gene, and/or the TGFβ gene, thereby disrupting expression of the B2M protein, the TXNIP protein, the CIITA protein, and/or the TGFβ protein.

In another composition, Composition 86, the present disclosure provides a composition according to any one of compositions 64 to 85, wherein the CD39-P2A-CD73-P2A-PD-L-1 construct is inserted within or near the B2M gene, thereby disrupting expression of the B2M protein.

In another composition, Composition 87, the present disclosure provides a composition according to any one of compositions 25 to 86, wherein the disrupted expression of the B2M protein, the TXNIP protein, the CIITA protein, and/or the TGFβ protein comprises reduced or eliminated expression of the B2M protein, the TXNIP protein, the CIITA protein, and/or the TGFβ protein.

In another composition, Composition 88, the present disclosure provides a composition according to any one of compositions 25 to 87, wherein the TGFβ protein is TGFβ-2.

In another composition, Composition 89, the present disclosure provides a composition according to any one of compositions 25 to 88, wherein the cell is a stem cell.

In another composition, Composition 90, the present disclosure provides a composition according to composition 89, wherein the stem cell is an embryonic stem cell, an adult stem cell, an induced pluripotent stem cell, or a hematopoietic stem cell.

In another composition, Composition 91, the present disclosure provides a composition according to any one of compositions 25 to 88, wherein the cell is a differentiated cell or a somatic cell.

In another composition, Composition 92, the present disclosure provides a composition according to composition 91, wherein the cell is a lineage-restricted progenitor cell or a fully differentiated somatic cell.

In another composition, Composition 93, the present disclosure provides a composition according to composition 92, wherein the lineage-restricted progenitor cell is a definitive endoderm cell, primitive gut tube cell, posterior foregut cell, pancreatic endoderm progenitor cell, pancreatic endocrine progenitor cell, pancreatic endocrine cell, or immature beta cell, and the fully differentiated somatic cell is a pancreatic beta cell.

In another composition, Composition 94, the present disclosure provides a composition comprising a plurality of genetically modified cells according to any one of claims 1 to 93.

In another composition, Composition 95, the present disclosure provides a composition according to composition 94, wherein at least about 50% of the cells express MANF, HLA-E, TNFAIP3, PD-L-1, CD39 and/or CD73.

In another composition, Composition 96, the present disclosure provides a composition comprising a population of lineage-restricted progenitor cells or fully differentiated somatic cells derived from the plurality of genetically modified cells of compositions 94 or 95.

In another composition, Composition 97, the present disclosure provides a composition according to composition 96, wherein the lineage-restricted progenitor cells are definitive endoderm cells, primitive gut tube cells, posterior foregut cells, pancreatic endoderm progenitors, pancreatic endocrine progenitors, or immature beta cells and the fully differentiated somatic cells are pancreatic beta cells.

In another composition, Composition 98, the present disclosure provides a composition according to composition 96 or 97, wherein at least about 50% of the cells express MANF, HLA-E, TNFAIP3, PD-L-1, CD39 and/or CD73.

In another composition, Composition 99, the present disclosure provides a composition comprising the plurality of cells of composition 94 or 95 or the population of cells of any one of compositions 96 to 98.

In another composition, Composition 100, the present disclosure provides a composition according to composition 99, further comprising at least one pharmaceutically acceptable excipient.

In another composition, Composition 101, the present disclosure provides a composition according to composition 99 or 100 for use in treating a pancreatic disease or disorder.

In another composition, Composition 102, the present disclosure provides a composition according to composition claim 101, wherein the pancreatic disease or disorder is Type I diabetes, Type II diabetes or a pancreactomy.

In another composition, Composition 103, the present disclosure provides a composition according to composition 101 or 102, wherein a human comprises the pancreatic disease or disorder.

In another method, Method 104, the present disclosure provides a method for treating a subject in need thereof, the method comprising: (a) obtaining or having obtained the plurality of genetically modified cells claim 94 or 95 following differentiation into pancreatic endoderm cells, pancreatic endocrine cells, immature beta cells, and/or pancreatic beta cells; and (b) administering the pancreatic endoderm cells, pancreatic endocrine cells, immature beta cells, and/or pancreatic beta cells to the subject.

In another method, Method 105, the present disclosure provides a method for treating a subject in need thereof, the method comprising: (a) obtaining or having obtained the population of lineage restricted progenitor cells or fully differentiated somatic cells of any one of claims 96 to 98, wherein the lineage restricted progenitor cells or fully differentiated somatic cells comprise pancreatic endoderm cells, pancreatic endocrine precursor cells, immature beta cells, and/or pancreatic beta cells; and (b) administering the pancreatic endoderm cells, pancreatic endocrine cells, immature beta cells, and/or beta cells to the subject.

In another method, Method 106, the present disclosure provides a method for treating a subject in need thereof, the method comprising: (a) obtaining or having obtained the plurality of genetically modified cells of claim 94 or 95, wherein the plurality of genetically modified cells comprises stem cells; (b) differentiating the genetically modified cells into pancreatic endoderm cells, pancreatic endocrine precursor cells, immature beta cells, and/or pancreatic beta cells; and (c) administering the pancreatic endoderm cells, pancreatic endocrine precursor cells, immature beta cells, and/or pancreatic beta cells to the subject.

In another method, Method 107, the present disclosure provides a method as provided in any one of Methods 104 to 106, wherein administering comprises implanting a device comprising the pancreatic endoderm cells, pancreatic endocrine cells, immature beta cells, or mature beta cells into the subject.

In another method, Method 108, the present disclosure provides a method as provided in any one of Methods 104 to 107, wherein the subject has, is suspected of having, or is at risk for a pancreatic disease or disorder.

In another method, Method 109, the present disclosure provides a method as provided in Method 108, wherein the pancreatic disease or disorder is Type I diabetes, Type II diabetes or a pancreactomy.

In another method, Method 110, the present disclosure provides a method as provided in any one of Methods 104 to 109, wherein the subject is human.

In another composition, Composition 111, the present disclosure provides a composition comprising a genetically modified cell comprising: (a) a first polynucleotide encoding mesencephalic astrocyte derived neurotrophic factor (MANF) inserted within or near a gene encoding thioredoxin interacting protein (TXNIP) and (b) a second polynucleotide encoding tumor necrosis factor alpha induced protein 3 (TNFAIP3) inserted within or near a gene encoding beta-2-microglobulin (B2M), wherein the genetically modified cell expresses MANF and TNFAIP3 and has disrupted expression of TXNIP and B2M.

In another composition, Composition 112, the present disclosure provides a composition according to composition 111, wherein the disrupted expression of B2M and TXNIP comprises reduced or eliminated expression of B2M and/or TXNIP.

In another composition, Composition 113, the present disclosure provides a composition according to compositions 111 or 112, further comprising a third polynucleotide encoding HLA class I histocompatibility antigen, alpha chain E (HLA-E) inserted within or near the TXNIP gene.

In another composition, Composition 114, the present disclosure provides a composition according to composition 113, wherein the third polynucleotide encoding HLA-E comprises a polynucleotide encoding a HLA-E trimer, the HLA-E trimer comprising a B2M signal peptide fused to an HLA-G presentation peptide fused to a B2M membrane protein fused to HLA-E without its signal peptide.

In another composition, Composition 115, the present disclosure provides a composition according to composition 113 or 114, wherein the first polynucleotide encoding MANF and the third polynucleotide encoding HLA-E are operably linked to an exogenous promoter.

In another composition, Composition 116, the present disclosure provides a composition according to any one of compositions 113 to 115, wherein the first polynucleotide encoding MANF is linked to the third polynucleotide encoding HLA-E by a polynucleotide encoding a P2A peptide such that the first polynucleotide, the polynucleotide encoding the P2A peptide and the third polynucleotide form a MANF-P2A-HLA-E construct.

In another composition, Composition 117, the present disclosure provides a composition according to composition 116, wherein the MANF-P2A-HLA-E construct comprises a polynucleotide sequence consisting essentially of SEQ ID NO: 55.

In another composition, Composition 118, the present disclosure provides a composition according to any one of compositions 111 to 117, further comprising a fourth polynucleotide encoding programmed death-ligand 1 (PD-L-1) inserted within or near the B2M gene.

In another composition, Composition 119, the present disclosure provides a composition according to composition 118, wherein the second polynucleotide encoding TNFAIP3 and the fourth polynucleotide encoding PD-L-1 are operably linked to an exogenous promoter.

In another composition, Composition 120, the present disclosure provides a composition according to compositions 118 or 119, wherein the second polynucleotide encoding TNFAIP3 is linked to the fourth polynucleotide sequence encoding PD-L-1 by a polynucleotide encoding a P2A peptide such that the second polynucleotide, the polynucleotide encoding the P2A peptide and the fourth polynucleotide form a TNFAIP3-P2A-PD-L-1 construct.

In another composition, Composition 121, the present disclosure provides a composition according to composition 120, wherein the TNFAIP3-P2A-PD-L-1 construct comprises a nucleotide sequence consisting essentially of SEQ ID NO: 54.

In another composition, Composition 122, the present disclosure provides a composition according to any one of compositions 111 to 121, wherein the cell is a stem cell.

In another composition, Composition 123, the present disclosure provides a composition according to composition 112, wherein the stem cell is an embryonic stem cell, an adult stem cell, an induced pluripotent stem cell, or a hematopoietic stem cell.

In another composition, Composition 124, the present disclosure provides a composition according to any one of compositions 111 to 121, wherein the cell is a differentiated cell or a somatic cell.

In another composition, Composition 125, the present disclosure provides a composition according to composition 124, wherein the cell is a lineage-restricted progenitor cell or a fully differentiated somatic cell.

In another composition, Composition 126, the present disclosure provides a composition according to composition 125, wherein the lineage-restricted progenitor cell is a definitive endoderm cell, primitive gut tube cell, posterior foregut cell, pancreatic endoderm progenitor cell, pancreatic endocrine progenitor cell, pancreatic endocrine cell, or immature beta cell, and the fully differentiated somatic cell is a pancreatic beta cell.

In another composition, Composition 127, the present disclosure provides a composition comprising a plurality of genetically modified cells according to any one of claims 111 to 126.

In another composition, Composition 128, the present disclosure provides a composition according to composition 127, wherein at least about 50% of the cells express MANF, HLA-E, TNFAIP3, and/or PD-L-1.

In another composition, Composition 129, the present disclosure provides a composition comprising a population of lineage-restricted progenitor cells or fully differentiated somatic cells derived from the plurality of genetically modified cells of compositions 127 or 128.

In another composition, Composition 130, the present disclosure provides a composition according to composition 129, wherein the lineage-restricted progenitor cells are definitive endoderm cells, primitive gut tube cells, posterior foregut cells, pancreatic endoderm progenitors, pancreatic endocrine progenitors, or immature beta cells and the fully differentiated somatic cells are pancreatic beta cells.

In another composition, Composition 131, the present disclosure provides a composition according to composition 129 or 130, wherein at least about 50% of the cells express MANF, HLA-E, TNFAIP3, and/or PD-L-1.

In another composition, Composition 132, the present disclosure provides a composition comprising the plurality of cells of compositions 17 or 18 or the population of cells of any one of compositions 130 or 131.

In another composition, Composition 133, the present disclosure provides a composition according to composition 132 further comprising at least one pharmaceutically acceptable excipient.

In another composition, Composition 134, the present disclosure provides a composition according to composition 132 or 133 for use in treating a pancreatic disease or disorder.

In another composition, Composition 135, the present disclosure provides a composition according to composition 134, wherein a human comprises the pancreatic disease or disorder.

In another composition, Composition 136, the present disclosure provides a composition according to composition 134 or 135, wherein the pancreatic disease or disorder is Type I diabetes, Type II diabetes or a pancreactomy.

In another method, Method 137, the present disclosure provides a method for treating a subject in need thereof, the method comprising: (a) obtaining or having obtained the plurality of genetically modified cells of any one of claims 111 to 139 following differentiation into pancreatic endoderm cells, pancreatic endocrine cells, immature beta cells, and/or pancreatic beta cells; and (b) administering the pancreatic endoderm cells, pancreatic endocrine cells, immature beta cells, and/or pancreatic beta cells to the subject.

In another method, Method 138, the present disclosure provides a method for treating a subject in need thereof, the method comprising: (a) obtaining or having obtained the population of lineage restricted progenitor cells or fully differentiated somatic cells of claim 129, wherein the lineage restricted progenitor cells or fully differentiated somatic cells comprise pancreatic endoderm cells, pancreatic endocrine precursor cells, immature beta cells, and/or pancreatic beta cells; and (b) administering the pancreatic endoderm cells, pancreatic endocrine cells, immature beta cells, and/or beta cells to the subject.

In another method, Method 139, the present disclosure provides a method for treating a subject in need thereof, the method comprising: (a) obtaining or having obtained the plurality of genetically modified cells of claim 127 or claim 128, wherein the plurality of genetically modified cells comprises stem cells; (b) differentiating the genetically modified cells into pancreatic endoderm cells, pancreatic endocrine precursor cells, immature beta cells, and/or pancreatic beta cells; and (c) administering the pancreatic endoderm cells, pancreatic endocrine precursor cells, immature beta cells, and/or pancreatic beta cells to the subject.

In another method, Method 140, the present disclosure provides a method as provided in any one of Methods 137 to 139, wherein administering comprises implanting a device comprising the pancreatic endoderm cells, pancreatic endocrine cells, immature beta cells, or mature beta cells into the subject.

In another method, Method 141, the present disclosure provides a method as provided in any one of Methods 137 to 140, wherein the subject has, is suspected of having, or is at risk for a pancreatic disease or disorder.

In another method, Method 142, the present disclosure provides a method as provided in Method 141, wherein the pancreatic disease or disorder is Type I diabetes, Type II diabetes or a pancreactomy.

In another method, Method 143, the present disclosure provides a method as provided in any one of Methods 137 to 142, wherein the subject is human.

In another method, Method 144, the present disclosure provides an in vitro method for generating a universal donor cell, the method comprising delivering to a stem cell: (a) a first RNA-guided nuclease and a first guide RNA (gRNA) targeting a target site in a beta-2 microglobulin (B2M) gene locus; (b) a first vector comprising a nucleic acid, the nucleic acid comprising: (i) a nucleotide sequence encoding tumor necrosis factor alpha induced protein 3 (TNFAIP3) and a nucleotide sequence encoding programmed death-ligand 1 (PD-L-1); (ii) a nucleotide sequence having sequence homology with a genomic region located left of the target site in the B2M gene locus; and (iii) a nucleotide sequence having sequence homology with a genomic region located right of the target site in the B2M gene locus, wherein (i) is flanked by (ii) and (iii); wherein the B2M gene locus is cleaved at the target site and the nucleic acid comprising the nucleotide sequences encoding TNFAIP3 and PD-L-1 is inserted into the B2M gene locus, thereby disrupting the B2M gene; and (c) a second RNA-guided nuclease and a second gRNA targeting a target site in a thioredoxin interacting protein (TXNIP) gene locus; and (d) a second vector comprising a nucleic acid, the nucleic acid comprising: (i) a nucleotide sequence encoding mesencephalic astrocyte derived neurotrophic factor (MANF) and a nucleotide sequence encoding HLA class I histocompatibility antigen, alpha chain E (HLA-E); (ii) a nucleotide sequence having sequence homology with a genomic region located left of the target site in the TXNIP gene locus; and (iii) a nucleotide sequence having sequence homology with a genomic region located right of the target site in the TXNIP gene locus, wherein (i) is flanked by (ii) and (iii); wherein the TXNIP gene locus is cleaved at the target site and the nucleic acid comprising the nucleotide sequences encoding MANF and HLA-E is inserted into the TXNIP gene locus, thereby disrupting the TXNIP gene; wherein the universal donor cell expresses TNFAIP3, PD-L-1, MANF and HLA-E and has disrupted expression of B2M and TXNIP.

In another method, Method 145, the present disclosure provides an in vitro method as provided in Method 144, wherein disrupted expression of B2M and TXNIP comprises reduced or eliminated expression of B2M and/or TXNIP.

In another method, Method 146, the present disclosure provides an in vitro method as provided in Method 144 or 145, wherein the nucleotide sequence of (b)(i) comprises the nucleotide sequence encoding TNFAIP3 linked to a nucleotide sequence encoding P2A linked to the nucleotide sequence encoding PD-L-1.

In another method, Method 147, the present disclosure provides an in vitro method as provided in any one of Methods 144 to 146, wherein the nucleotide sequence of (b)(i) comprises SEQ ID NO: 54.

In another method, Method 148, the present disclosure provides an in vitro method as provided in any one of Methods 144 to 147, wherein the nucleotide sequence of (b)(i) is operably linked to an exogenous promoter.

In another method, Method 149, the present disclosure provides an in vitro method as provided in Method 148, wherein the exogenous promoter is a CMV, EF1α, PGK, CAG, or UBC promoter.

In another method, Method 150, the present disclosure provides an in vitro method as provided in any one of Methods 144 to 149, wherein the nucleotide sequence of (b)(ii) comprises or consists essentially of SEQ ID NO: 15.

In another method, Method 151, the present disclosure provides an in vitro method as provided in any one of Methods 144 to 150, wherein the nucleotide sequence of (b)(iii) comprises or consists essentially of SEQ ID NO: 22.

In another method, Method 152, the present disclosure provides an in vitro method as provided in any one of Methods 144 to 151, wherein the first RNA-guided nuclease and first gRNA are present in a ratio of about 1:1 to about 1:10.

In another method, Method 153, the present disclosure provides an in vitro method as provided in any one of Methods 144 to 152, wherein the first RNA-guided nuclease is a first Cas9 nuclease.

In another method, Method 154, the present disclosure provides an in vitro method as provided in Method 153, wherein the first Cas9 nuclease is linked to at least one nuclear localization signal.

In another method, Method 155, the present disclosure provides an in vitro method as provided in any one of Methods 144 to 154, wherein the nucleotide sequence encoding HLA-E comprises a sequence encoding a HLA-E trimer, the HLA-E trimer comprising a B2M signal peptide fused to an HLA-G presentation peptide fused to a B2M membrane protein fused to HLA-E without its signal peptide.

In another method, Method 156, the present disclosure provides an in vitro method as provided in any one of Methods 144 to 155, wherein the nucleotide sequence of (d)(i) comprises the nucleotide sequence encoding MANF linked to a nucleotide sequence encoding P2A linked to the nucleotide sequence encoding HLA-E.

In another method, Method 157, the present disclosure provides an in vitro method as provided in any one of Methods 144 to 156, wherein the nucleotide sequence of (d)(i) comprises SEQ ID NO: 55.

In another method, Method 158, the present disclosure provides an in vitro method as provided in any one of Methods 144 to 157, wherein the nucleotide sequence of (d)(i) is operably linked to an exogenous promoter.

In another method, Method 159, the present disclosure provides an in vitro method as provided in Method 158, wherein the exogenous promoter is a CMV, EF1α, PGK, CAG, or UBC promoter.

In another method, Method 160, the present disclosure provides an in vitro method as provided in any one of Methods 144 to 159, wherein the nucleotide sequence of (d)(ii) consists essentially of SEQ ID NO: 42.

In another method, Method 161, the present disclosure provides an in vitro method as provided in any one of Methods 144 to 160, wherein the nucleotide sequence of (d)(iii) consists essentially of SEQ ID NO: 44.

In another method, Method 162, the present disclosure provides an in vitro method as provided in any one of Methods 144 to 161, wherein the second RNA-guided nuclease and second gRNA are present in a ratio of about 1:1 to about 1:10.

In another method, Method 163, the present disclosure provides an in vitro method as provided in any one of Methods 144 to 162, wherein the second RNA-guided nuclease is a second Cas9 nuclease.

In another method, Method 164, the present disclosure provides an in vitro method as provided in Method 163, wherein the second Cas9 nuclease is linked to at least one nuclear localization signal.

In another method, Method 165, the present disclosure provides an in vitro method as provided in any one of Methods 144 to 164, wherein the stem cell is an embryonic stem cell, an adult stem cell, an induced pluripotent stem cell, or a hematopoietic stem cell.

In another method, Method 166, the present disclosure provides an in vitro method as provided in any one of Methods 144 to 165, wherein the stem cell is a human stem cell.

In another method, Method 167, the present disclosure provides an in vitro method as provided in any one of Methods 144 to 166, wherein the universal donor cell has increased immune evasion and/or post-transplantation survival compared to a comparable cell without the nucleic acid insertion and gene disruption In another method, Method 168, the present disclosure provides an in vitro method for generating a universal donor cell, the method comprising delivering to a stem cell: (a) an RNA-guided nuclease and a guide RNA (gRNA) targeting a target site in a first target gene locus and a first nucleic acid comprising a nucleotide sequence encoding tumor necrosis factor alpha induced protein 3 (TNFAIP3), mesencephalic astrocyte derived neurotrophic factor (MANF), cluster of differentiation 39 (CD39) and/or cluster of differentiation 73 (CD73), wherein the first target gene locus is cleaved at the target site and the first nucleic acid comprising a nucleotide sequence encoding TNFAIP3, MANF, CD39 and/or CD73 is inserted into the target gene locus, thereby disrupting the target gene; and/or (b) an RNA-guided nuclease and a guide RNA (gRNA) targeting a target site in a beta-2 microglobulin (B2M) gene locus, wherein the B2M gene locus is cleaved at the target site, thereby disrupting the B2M gene; and/or (c) an RNA-guided nuclease and a guide RNA (gRNA) targeting a target site in a thioredoxin interacting protein (TXNIP) gene locus, wherein the TXNIP gene locus is cleaved at the target site, thereby disrupting the TXNIP gene; and/or (d) an RNA guided nuclease and a guide RNA (gRNA) targeting a target site in a class II transactivator (CIITA) gene locus, wherein the CIITA gene locus is cleaved at the target site, thereby disrupting the CIITA gene; and/or (e) an RNA guided nuclease and a guide RNA (gRNA) targeting a target site in a transforming growth factor beta (TGFβ) gene locus, wherein the TGFβ gene locus is cleaved at the target site, thereby disrupting the TGFβ gene.

In another method, Method 169, the present disclosure provides an in vitro method as provided in Method 168, wherein the target gene locus of (a) is selected from a beta-2 microglobulin (B2M) gene locus, a thioredoxin interacting protein (TXNIP) gene locus, a class II transactivator (CIITA) gene locus and/or a transforming growth factor beta (TGFβ) gene locus, and the universal donor cell has disrupted expression of B2M, TXNIP, CIITA and/or TGFβ.

In another method, Method 170, the present disclosure provides an in vitro method as provided in Method 168 or 169, wherein disrupted expression of B2M, TXNIP, CIITA and/or TGFβ comprises reduced or eliminated expression of B2M, TXNIP, CIITA and/or TGFβ.

In another method, Method 171, the present disclosure provides an in vitro method as provided in Method 169 or 170, wherein the target gene locus of (a) is the B2M gene locus and the nucleic acid further comprises (i) a nucleotide sequence having sequence homology with a genomic region located left of the target site in the B2M gene locus; and (ii) a nucleotide sequence having sequence homology with a genomic region located right of the target site in the B2M gene locus, wherein the nucleotide sequence encoding TNFAIP3, MANF, CD39 and/or CD73 is flanked by (i) and (ii), and the universal donor cell has disrupted expression of B2M.

In another method, Method 172, the present disclosure provides an in vitro method as provided in Method 171, wherein the nucleotide sequence of (i) comprises or consists essentially of SEQ ID NO: 15.

In another method, Method 173, the present disclosure provides an in vitro method as provided in any one of Methods 171 or 172, wherein the nucleotide sequence of (ii) comprises or consists essentially of SEQ ID NO: 22.

In another method, Method 174, the present disclosure provides an in vitro method as provided in Method 169, wherein the target gene locus of (a) is the TXNIP gene locus and the nucleic acid further comprises (i) a nucleotide sequence having sequence homology with a genomic region located left of the target site in the TXNIP gene locus; and (ii) a nucleotide sequence having sequence homology with a genomic region located right of the target site in the TXNIP gene locus, wherein the nucleotide sequence encoding TNFAIP3, MANF, CD39 and/or CD73 is flanked by (i) and (ii), and the universal donor cell has disrupted expression of TXNIP.

In another method, Method 175, the present disclosure provides an in vitro method as provided Method 174, wherein the nucleotide sequence of (i) comprises or consists essentially of SEQ ID NO: 42.

In another method, Method 176, the present disclosure provides an in vitro method as provided in Method 174 or 175, wherein the nucleotide sequence of (ii) comprises or consists essentially of SEQ ID NO: 44.

In another method, Method 177, the present disclosure provides an in vitro method as provided in Method 169, wherein the target gene locus of (a) is the CIITA gene locus and the nucleic acid further comprises (i) a nucleotide sequence having sequence homology with a genomic region located left of the target site in the CIITA gene locus; and (ii) a nucleotide sequence having sequence homology with a genomic region located right of the target site in the CIITA gene locus, wherein the nucleotide sequence encoding TNFAIP3, MANF, CD39 and/or CD73 is flanked by (i) and (ii), and the universal donor cell has disrupted expression of CIITA.

In another method, Method 178, the present disclosure provides an in vitro method as provided in Method 177, wherein the nucleotide sequence of (i) comprises or consists essentially of SEQ ID NO: 26.

In another method, Method 179, the present disclosure provides an in vitro method as provided in Method 177 or 178, wherein the nucleotide sequence of (ii) comprises or consists essentially of SEQ ID NO: 28.

In another method, Method 180, the present disclosure provides an in vitro method as provided in Method 169, wherein the target gene locus of (a) is the TGFβ gene locus and the nucleic acid further comprises (i) a nucleotide sequence having sequence homology with a genomic region located left of the target site in the TGFβ gene locus; and (ii) a nucleotide sequence having sequence homology with a genomic region located right of the target site in the TGFβ gene locus, wherein the nucleotide sequence encoding TNFAIP3, MANF, CD39 and/or CD73 is flanked by (i) and (ii) and the universal donor cell has disrupted expression of TGFβ.

In another method, Method 181, the present disclosure provides an in vitro method as provided in any one of Methods 168 to 180, wherein the target site of (b) comprises a nucleotide sequence consisting essentially of any one of SEQ ID NOs: 1 to 13.

In another method, Method 182, the present disclosure provides an in vitro method as provided in any one of Methods 168 to 181, wherein the target site of (c) comprises a nucleotide sequence consisting essentially of any one of SEQ ID NOs: 32-41.

In another method, Method 183, the present disclosure provides an in vitro method as provided in any one of Methods 168 to 182, wherein the target site of (d) comprises a nucleotide sequence consisting essentially of any one of SEQ ID NOs: 25 and 48-51.

In another method, Method 184, the present disclosure provides an in vitro method as provided in any one of Methods 168 to 183, wherein the target site of (e) comprises a nucleotide sequence consisting essentially of SEQ ID NO: 57.

In another method, Method 185, the present disclosure provides an in vitro method as provided in any one of Methods 168 to 184, further comprising delivering to the stem cell: (f) a RNA-guided nuclease and a guide RNA (gRNA) targeting a target site in a target gene locus and a nucleic acid comprising a nucleotide sequence encoding tumor necrosis factor alpha induced protein 3 (TNFAIP3), mesencephalic astrocyte derived neurotrophic factor (MANF), cluster of differentiation 39 (CD39), cluster of differentiation 73 (CD73), HLA class I histocompatibility antigen, alpha chain E (HLA-E) and/or programmed death-ligand 1 (PD-L-1) wherein the target gene locus is cleaved at the target site and the nucleic acid comprising the nucleotide sequence encoding TNFAIP3, MANF, CD39, CD73, HLA-E, and/or PD-L-1 is inserted into the target gene locus, thereby disrupting the target gene.

In another method, Method 186, the present disclosure provides an in vitro method as provided in Method 185, wherein the target gene locus of (f) is selected from a beta-2 microglobulin (B2M) gene locus, a thioredoxin interacting protein (TXNIP) gene locus, a class II transactivator (CIITA) gene locus and/or a transforming growth factor beta (TGFβ) gene locus.

In another method, Method 187, the present disclosure provides an in vitro method as provided in Method 186, wherein the target gene locus of (f) is the B2M gene locus and the nucleic acid of (f) further comprises (i) a nucleotide sequence having sequence homology with a genomic region located left of the target site in the B2M gene locus; and (ii) a nucleotide sequence having sequence homology with a genomic region located right of the target site in the B2M gene locus, wherein the nucleotide sequence encoding TNFAIP3, MANF, CD39, CD73, HLA-E, and/or PD-L-1 is flanked by (i) and (ii).

In another method, Method 188, the present disclosure provides an in vitro method as provided in Method 187, wherein the nucleotide sequence of (i) comprises or consists essentially of SEQ ID NO: 15.

In another method, Method 189, the present disclosure provides an in vitro method as provided in any one of Methods 187 or 188, wherein the nucleotide sequence of (ii) comprises or consists essentially of SEQ ID NO: 22.

In another method, Method 190, the present disclosure provides an in vitro method as provided in Method 186, wherein the target gene locus of (f) is the TXNIP gene locus and the nucleic acid of (f) further comprises (i) a nucleotide sequence having sequence homology with a genomic region located left of the target site in the TXNIP gene locus; and (ii) a nucleotide sequence having sequence homology with a genomic region located right of the target site in the TXNIP gene locus, wherein the nucleotide sequence encoding TNFAIP3, MANF, CD39, CD73, HLA-E, and/or PD-L-1 is flanked by (i) and (ii).

In another method, Method 191, the present disclosure provides an in vitro method as provided in any one of Methods 190, wherein the nucleotide sequence of (i) comprises or consists essentially of SEQ ID NO: 42.

In another method, Method 192, the present disclosure provides an in vitro method as provided in Method 190 or 191, wherein the nucleotide sequence of (ii) comprises or consists essentially of SEQ ID NO: 44.

In another method, Method 193, the present disclosure provides an in vitro method as provided in Method 186, wherein the target gene locus of (f) is the CIITA gene locus and the nucleic acid of (f) further comprises (i) a nucleotide sequence having sequence homology with a genomic region located left of the target site in the CIITA gene locus; and (ii) a nucleotide sequence having sequence homology with a genomic region located right of the target site in the CIITA gene locus, wherein the nucleotide sequence encoding TNFAIP3, MANF, CD39, CD73, HLA-E, and/or PD-L-1 is flanked by (i) and (ii).

In another method, Method 194, the present disclosure provides an in vitro method as provided in Method 193, wherein the nucleotide sequence of (i) comprises or consists essentially of SEQ ID NO: 26.

In another method, Method 195, the present disclosure provides an in vitro method as provided in Method 193 or 195, wherein the nucleotide sequence of (ii) comprises or consists essentially of SEQ ID NO: 28.

In another method, Method 196, the present disclosure provides an in vitro method as provided in Method 186, wherein the target gene locus of (f) is the TGFβ gene locus and the nucleic acid of (f) further comprises (i) a nucleotide sequence having sequence homology with a genomic region located left of the target site in the TGFβ gene locus; and (ii) a nucleotide sequence having sequence homology with a genomic region located right of the target site in the TGFβ gene locus, wherein the nucleotide sequence encoding TNFAIP3, MANF, CD39, CD73, HLA-E, and/or PD-L-1 is flanked by (i) and (ii).

In another method, Method 197, the present disclosure provides an in vitro method as provided in any one of Methods 185 to 196, wherein the target gene locus of (f) is the same as the target gene locus of (a).

In another method, Method 198, the present disclosure provides an in vitro method as provided in any one of Methods 185 to 197, wherein the target gene locus of (f) is different than the target gene locus of (a).

In another method, Method 199, the present disclosure provides an in vitro method as provided in any one of Methods 168 to 198, further comprising delivering to the stem cell: (g) a RNA-guided nuclease and a guide RNA (gRNA) targeting a target site in a target gene locus and a nucleic acid comprising a nucleotide sequence encoding tumor necrosis factor alpha induced protein 3 (TNFAIP3), mesencephalic astrocyte derived neurotrophic factor (MANF), cluster of differentiation 39 (CD39), cluster of differentiation 73 (CD73), HLA-E and/or PD-L-1 wherein the target gene locus is cleaved at the target site and the nucleic acid comprising a nucleotide sequence encoding TNFAIP3, MANF, CD39, CD73, HLA-E, and/or PD-L-1 is inserted into the target gene locus, thereby disrupting the target gene.

In another method, Method 200, the present disclosure provides an in vitro method as provided in Method 199, wherein the target gene locus of (g) is selected from a beta-2 microglobulin (B2M) gene locus, a thioredoxin interacting protein (TXNIP) gene locus, a class II transactivator (CIITA) gene locus and/or a transforming growth factor beta (TGFβ) gene locus.

In another method, Method 201, the present disclosure provides an in vitro method as provided in Method 200, wherein the target gene locus of (g) is the B2M gene locus and the nucleic acid of (g) further comprises (i) a nucleotide sequence having sequence homology with a genomic region located left of the target site in the B2M gene locus; and (ii) a nucleotide sequence having sequence homology with a genomic region located right of the target site in the B2M gene locus, wherein the nucleotide sequence encoding TNFAIP3, MANF, CD39, CD73, HLA-E, and/or PD-L-1 is flanked by (i) and (ii).

In another method, Method 202, the present disclosure provides an in vitro method as provided in Method 201, wherein the nucleotide sequence of (i) comprises or consists essentially of SEQ ID NO: 15.

In another method, Method 203, the present disclosure provides an in vitro method as provided in Method 201 or 202, wherein the nucleotide sequence of (ii) comprises or consists essentially of SEQ ID NO: 22.

In another method, Method 204, the present disclosure provides an in vitro method as provided in Method 200, wherein the target gene locus of (g) is the TXNIP gene locus and the nucleic acid of (g) further comprises (i) a nucleotide sequence having sequence homology with a genomic region located left of the target site in the TXNIP gene locus; and (ii) a nucleotide sequence having sequence homology with a genomic region located right of the target site in the TXNIP gene locus, wherein the nucleotide sequence encoding TNFAIP3, MANF, CD39, CD73, HLA-E, and/or PD-L-1 is flanked by (i) and (ii).

In another method, Method 205, the present disclosure provides an in vitro method as provided in Method 204, wherein the nucleotide sequence of (i) comprises or consists essentially of SEQ ID NO: 42.

In another method, Method 206, the present disclosure provides an in vitro method as provided in Method 204 or 205, wherein the nucleotide sequence of (ii) comprises or consists essentially of SEQ ID NO: 44.

In another method, Method 207, the present disclosure provides an in vitro method as provided in Method 200, wherein the target gene locus of (g) is the CIITA gene locus and the nucleic acid of (g) further comprises (i) a nucleotide sequence having sequence homology with a genomic region located left of the target site in the CIITA gene locus; and (ii) a nucleotide sequence having sequence homology with a genomic region located right of the target site in the CIITA gene locus, wherein the nucleotide sequence encoding TNFAIP3, MANF, CD39, CD73, HLA-E, and/or PD-L-1 is flanked by (i) and (ii).

In another method, Method 208, the present disclosure provides an in vitro method as provided in Method 207, wherein the nucleotide sequence of (i) comprises or consists essentially of SEQ ID NO: 26.

In another method, Method 209, the present disclosure provides an in vitro method as provided in Method 207 or 208, wherein the nucleotide sequence of (ii) comprises or consists essentially of SEQ ID NO: 28.

In another method, Method 210, the present disclosure provides an in vitro method as provided in Method 200, wherein the target gene locus of (g) is the TGFβ gene locus and the nucleic acid of (g) further comprises (i) a nucleotide sequence having sequence homology with a genomic region located left of the target site in the TGFβ gene locus; and (ii) a nucleotide sequence having sequence homology with a genomic region located right of the target site in the TGFβ gene locus, wherein the nucleotide sequence encoding TNFAIP3, MANF, CD39, CD73, HLA-E, and/or PD-L-1 is flanked by (i) and (ii).

In another method, Method 211, the present disclosure provides an in vitro method as provided in any one of Methods 199 to 210, wherein the target gene locus of (g) is the same as the target gene locus of (a) and/or (f).

In another method, Method 212, the present disclosure provides an in vitro method as provided in any one of Methods 199 to 211, wherein the target gene locus of (g) is different than the target gene locus of (a) and/or (f).

In another method, Method 213, the present disclosure provides an in vitro method as provided in any one of Methods 168 to 212, further comprising delivering to the stem cell: (h) a RNA-guided nuclease and a guide RNA (gRNA) targeting a target site in a target gene locus and a nucleic acid comprising a nucleotide sequence encoding tumor necrosis factor alpha induced protein 3 (TNFAIP3), mesencephalic astrocyte derived neurotrophic factor (MANF), cluster of differentiation 39 (CD39), cluster of differentiation 73 (CD73), HLA-E and/or PD-L-1 wherein the target gene locus is cleaved at the target site and the nucleic acid comprising a nucleotide sequence encoding TNFAIP3, MANF, CD39, CD73, HLA-E, and/or PD-L-1 is inserted into the target gene locus, thereby disrupting the target gene.

In another method, Method 214, the present disclosure provides an in vitro method as provided in Method 213, wherein the target gene locus of (h) is selected from a beta-2 microglobulin (B2M) gene locus, a thioredoxin interacting protein (TXNIP) gene locus, a class II transactivator (CIITA) gene locus and/or a transforming growth factor beta (TGFβ) gene locus.

In another method, Method 215, the present disclosure provides an in vitro method as provided in Method 214, wherein the target gene locus of (h) is the B2M gene locus and the nucleic acid of (h) further comprises (i) a nucleotide sequence having sequence homology with a genomic region located left of the target site in the B2M gene locus; and (ii) a nucleotide sequence having sequence homology with a genomic region located right of the target site in the B2M gene locus, wherein the nucleotide sequence encoding TNFAIP3, MANF, CD39, CD73, HLA-E, and/or PD-L-1 is flanked by (i) and (ii).

In another method, Method 216, the present disclosure provides an in vitro method as provided in Method 215, wherein the nucleotide sequence of (i) comprises or consists essentially of SEQ ID NO: 15.

In another method, Method 217, the present disclosure provides an in vitro method as provided in Methods 215 or 216, wherein the nucleotide sequence of (ii) comprises or consists essentially of SEQ ID NO: 22.

In another method, Method 218, the present disclosure provides an in vitro method as provided in Method 214, wherein the target gene locus of (h) is the TXNIP gene locus and the nucleic acid of (h) further comprises (i) a nucleotide sequence having sequence homology with a genomic region located left of the target site in the TXNIP gene locus; and (ii) a nucleotide sequence having sequence homology with a genomic region located right of the target site in the TXNIP gene locus, wherein the nucleotide sequence encoding TNFAIP3, MANF, CD39, CD73, HLA-E, and/or PD-L-1 is flanked by (i) and (ii).

In another method, Method 219, the present disclosure provides an in vitro method as provided in Method 218, wherein the nucleotide sequence of (i) comprises or consists essentially of SEQ ID NO: 42.

In another method, Method 220, the present disclosure provides an in vitro method as provided in Method 218 or 219, wherein the nucleotide sequence of (ii) comprises or consists essentially of SEQ ID NO: 44.

In another method, Method 221, the present disclosure provides an in vitro method as provided in Method 214, wherein the target gene locus of (h) is the CIITA gene locus and the nucleic acid of (h) further comprises (i) a nucleotide sequence having sequence homology with a genomic region located left of the target site in the CIITA gene locus; and (ii) a nucleotide sequence having sequence homology with a genomic region located right of the target site in the CIITA gene locus, wherein the nucleotide sequence encoding TNFAIP3, MANF, CD39, CD73, HLA-E, and/or PD-L-1 is flanked by (i) and (ii).

In another method, Method 222, the present disclosure provides an in vitro method as provided in Method 221, wherein the nucleotide sequence of (i) comprises or consists essentially of SEQ ID NO: 26.

In another method, Method 223, the present disclosure provides an in vitro method as provided in Method 221 or 222, wherein the nucleotide sequence of (ii) comprises or consists essentially of SEQ ID NO: 28.

In another method, Method 224, the present disclosure provides an in vitro method as provided in Method 214, wherein the target gene locus of (h) is the TGFβ gene locus and the nucleic acid of (h) further comprises (i) a nucleotide sequence having sequence homology with a genomic region located left of the target site in the TGFβ gene locus; and (ii) a nucleotide sequence having sequence homology with a genomic region located right of the target site in the TGFβ gene locus, wherein the nucleotide sequence encoding TNFAIP3, MANF, CD39, CD73, HLA-E, and/or PD-L-1 is flanked by (i) and (ii).

In another method, Method 225, the present disclosure provides an in vitro method as provided in any one of Methods 213 to 224, wherein the target gene locus of (h) is the same as target gene locus of (a), (f) and/or (g).

In another method, Method 226, the present disclosure provides an in vitro method as provided in any one of Methods 213 to 225, wherein the target gene locus of (h) is different than the target gene locus of (a), (f) and/or (g).

In another method, Method 227, the present disclosure provides an in vitro method as provided in any one of Methods 168 to 226, wherein the nucleic acid of (a), the nucleic acid of (f), the nucleic acid of (g) and/or the nucleic acid of (h) comprises the nucleotide sequence encoding MANF and the universal donor cell expresses MANF.

In another method, Method 228, the present disclosure provides an in vitro method as provided in Method 227, wherein the nucleotide sequence encoding MANF consists essentially of SEQ ID NO: 17.

In another method, Method 229, the present disclosure provides an in vitro method as provided in any one of Methods 168 to 228, wherein the nucleic acid of (a), the nucleic acid of (f), the nucleic acid of (g) and/or the nucleic acid of (h) comprises the nucleotide sequence encoding TNFAIP3 and the universal donor cell expresses TNFAIP3.

In another method, Method 230, the present disclosure provides an in vitro method as provided in Method 229, wherein the nucleotide sequence encoding TNFAIP3 consists essentially of SEQ ID NO: 19.

In another method, Method 231, the present disclosure provides an in vitro method as provided in any one of Methods 168 to 230, wherein the nucleic acid of (a), the nucleic acid of (f), the nucleic acid of (g) and/or the nucleic acid of (h) comprises the nucleotide sequence encoding CD39 and the universal donor cell expresses CD39.

In another method, Method 232, the present disclosure provides an in vitro method as provided in Method 231, wherein the nucleotide sequence encoding CD39 consists essentially of SEQ ID NO: 27.

In another method, Method 233, the present disclosure provides an in vitro method as provided in any one of Methods 168 to 232, wherein the nucleic acid of (a), the nucleic acid of (f), the nucleic acid of (g) and/or the nucleic acid of (h) comprises the nucleotide sequence encoding CD73 and the universal donor cell expresses CD73.

In another method, Method 234, the present disclosure provides an in vitro method as provided in Method 233, wherein the nucleotide sequence encoding CD73 consists essentially of SEQ ID NO: 46.

In another method, Method 235, the present disclosure provides an in vitro method as provided in any one of Methods 168 to 234, wherein the nucleic acid of (a) further comprises a nucleotide sequence encoding HLA class I histocompatibility antigen, alpha chain E (HLA-E) and the universal donor cell further expresses HLA-E.

In another method, Method 236, the present disclosure provides an in vitro method as provided in any one of Methods 168 to 235, wherein the nucleic acid of (f), the nucleic acid of (g) and/or the nucleic acid of (h) comprises the nucleotide sequence encoding HLA class I histocompatibility antigen, alpha chain E (HLA-E) and the universal donor cell expresses HLA-E.

In another method, Method 237, the present disclosure provides an in vitro method as provided in Method 168 to 236, wherein the nucleotide sequence encoding HLA-E comprises a sequence encoding a HLA-E trimer, the HLA-E trimer comprising a B2M signal peptide fused to an HLA-G presentation peptide fused to a B2M membrane protein fused to HLA-E without its signal peptide.

In another method, Method 238, the present disclosure provides an in vitro method as provided in any one of Methods 235 to 237, wherein the nucleotide sequence encoding HLA-E consists essentially of SEQ ID NO: 43.

In another method, Method 239, the present disclosure provides an in vitro method as provided in any one of Methods 235 to 238, wherein the nucleic acid of (a), the nucleic acid of (f), the nucleic acid of (g) and/or the nucleic acid of (h) comprises a nucleotide sequence encoding MANF and a nucleotide sequence encoding HLA-E and the universal donor cell expresses MANF and HLA-E.

In another method, Method 240, the present disclosure provides an in vitro method as provided in Method 239, wherein the nucleic acid of (a), the nucleic acid of (f), the nucleic acid of (g) and/or the nucleic acid of (h) comprises the nucleotide sequence encoding MANF linked to a nucleotide sequence encoding a P2A peptide linked to the nucleotide sequence encoding HLA-E.

In another method, Method 241, the present disclosure provides an in vitro method as provided in Method 240, wherein the nucleic acid of (a), the nucleic acid of (f), the nucleic acid of (g) and/or the nucleic acid of (h) comprises a nucleotide sequence consisting of SEQ ID NO: 55.

In another method, Method 242, the present disclosure provides an in vitro method as provided in any one of Methods 168 to 241 wherein the nucleic acid of (a) further comprises a nucleotide sequence encoding programmed death-ligand 1 (PD-L-1) and the universal donor cell further expresses PD-L-1.

In another method, Method 243, the present disclosure provides an in vitro method as provided in any one of Methods 168 to 242, wherein the nucleic acid of (f), the nucleic acid of (g) and/or the nucleic acid of (h) comprises the nucleotide sequence encoding PD-L-1 and the universal donor cell expresses PD-L-1.

In another method, Method 244, the present disclosure provides an in vitro method as provided in Method 242 or 243, wherein the nucleotide sequence encoding for PD-L-1 consists essentially of SEQ ID NO: 20.

In another method, Method 245, the present disclosure provides an in vitro method as provided in Methods 242 to 244, wherein the nucleic acid of (a), the nucleic acid of (f), the nucleic acid of (g), and/or the nucleic acid of (h) comprises a nucleotide sequence encoding TNFAIP3 and a nucleotide sequence encoding PD-L-1 and the universal donor cell expresses TNFAIP3 and PD-L-1.

In another method, Method 246, the present disclosure provides an in vitro method as provided in any one of Methods 242 to 245, wherein the nucleic acid of (a), the nucleic acid of (f), the nucleic acid of (g), and/or the nucleic acid of (h) comprises the nucleotide sequence encoding TNFAIP3 linked to a nucleotide sequence encoding a P2A peptide linked to the nucleotide sequence encoding PD-L-1.

In another method, Method 247, the present disclosure provides an in vitro method as provided in Method 246, wherein the nucleic acid of (a), the nucleic acid of (f), the nucleic acid of (g), and/or the nucleic acid of (h) comprises a nucleotide sequence consisting essentially of SEQ ID NO: 54.

In another method, Method 248, the present disclosure provides an in vitro method as provided in any one of Methods 242 to 247, wherein the nucleic acid of (a), the nucleic acid of (f), the nucleic acid of (g), and/or the nucleic acid of (h) comprises a nucleotide sequence of CD39 and a nucleotide sequence encoding PD-L-1 and the universal donor cell expresses CD39 and PD-L-1.

In another method, Method 249, the present disclosure provides an in vitro method as provided in Method 248, wherein the nucleic acid of (a), the nucleic acid of (f), the nucleic acid of (g), and/or the nucleic acid of (h) comprises the nucleotide sequence of CD39 linked to a nucleotide sequence encoding a P2A peptide linked to the nucleotide sequence encoding PD-L-1.

In another method, Method 250, the present disclosure provides an in vitro method as provided in Method 249, wherein the nucleic acid of (a), the nucleic acid of (f), the nucleic acid of (g), and/or the nucleic acid of (h) comprises a nucleotide sequence consisting essentially of SEQ ID NO: 53.

In another method, Method 251, the present disclosure provides an in vitro method as provided in any one of Methods 185 to 250, wherein the nucleic acid of (a), the nucleic acid of (f), the nucleic acid of (g), and/or the nucleic acid of (h) comprises the nucleotide sequence encoding MANF, the nucleotide sequence encoding TNFAIP3, and the nucleotide sequence encoding PD-L-1 and the universal donor cell expresses MANF, TNFAIP3 and PD-L-1.

In another method, Method 252, the present disclosure provides an in vitro method as provided in Method 251, wherein the nucleic acid of (a), the nucleic acid of (f), the nucleic acid of (g), and/or the nucleic acid of (h) comprises the nucleotide sequence encoding MANF linked to the nucleotide sequence encoding TNFAIP3 by a first nucleotide sequence encoding a P2A peptide and the nucleotide sequence encoding TNFAIP3 linked to the nucleotide sequence PD-L-1 by a second nucleotide sequence encoding a P2A peptide.

In another method, Method 253, the present disclosure provides an in vitro method as provided in Method 252, wherein the nucleic acid of (a), the nucleic acid of (f), the nucleic acid of (g), and/or the nucleic acid of (h) comprises a nucleotide sequence consisting essentially of SEQ ID NO: 52.

In another method, Method 254, the present disclosure provides an in vitro method as provided in any one of Methods 185 to 253, wherein the nucleic acid of (a), the nucleic acid of (f), the nucleic acid of (g), and/or the nucleic acid of (h) comprises the nucleotide sequence encoding CD39, the nucleotide sequence encoding CD73 and the nucleotide sequence encoding PD-L-1 and the universal donor cell expresses CD39, CD73 and PD-L-1.

In another method, Method 255, the present disclosure provides an in vitro method as provided in Method 254, wherein the nucleotide sequence encoding CD39 is linked to the nucleotide sequence encoding CD73 by a first nucleotide sequence encoding a P2A peptide and the nucleotide sequence encoding CD73 is linked to the nucleotide sequence encoding PD-L-1 by a second nucleotide sequence encoding a P2A peptide.

In another method, Method 256, the present disclosure provides an in vitro method as provided in Method 255, wherein the nucleic acid of (a), the nucleic acid of (f), the nucleic acid of (g), and/or the nucleic acid of (h) comprises a nucleotide sequence consisting essentially of SEQ ID NO: 56.

In another method, Method 257, the present disclosure provides an in vitro method as provided in any one of Methods 168 to 256, wherein the nucleic acid of (a), the nucleic acid of (f), the nucleic acid of (g), and/or the nucleic acid of (h) comprises the nucleotide sequence encoding CD39 and the nucleotide sequence encoding CD73 and the universal donor cell expresses CD39 and CD73.

In another method, Method 258, the present disclosure provides an in vitro method as provided in Method 257, wherein the nucleotide sequence encoding CD39 is linked to the nucleotide sequence encoding CD73 by a nucleotide sequence encoding a P2A peptide.

In another method, Method 259, the present disclosure provides an in vitro method as provided in Method 258, wherein the nucleic acid of (a), the nucleic acid of (f), the nucleic acid of (g), and/or the nucleic acid of (h) comprises a nucleotide sequence consisting essentially of SEQ ID NO: 58.

In another method, Method 260, the present disclosure provides an in vitro method as provided in any one of Methods 168 to 259, wherein the nucleotide sequence of any of the nucleic acids of (a), (f), (g), and/or (h) is operably linked to an exogenous promoter.

In another method, Method 261, the present disclosure provides an in vitro method as provided in Method 260, wherein the exogenous promoter is a CMV, EF1α, PGK, CAG, or UBC promoter.

In another method, Method 262, the present disclosure provides an in vitro method as provided in any one of Methods 168 to 261, wherein the RNA guided nuclease and the gRNA of (a), (b), (c), (d), (e), (f), (g) and/or (h) are present in a ratio of about 1:1 to about 1:10.

In another method, Method 263, the present disclosure provides an in vitro method as provided in any one of Methods 168 to 262, wherein the RNA guided nuclease and the gRNA of each of (a), (b), (c), (d), (e), (f), (g), and/or (h) are present in a ratio of about 1:1 to about 1:10.

In another method, Method 264, the present disclosure provides an in vitro method as provided in any one of Methods 168 to 263 wherein the RNA guided nuclease of each of (a), (b), (c), (d), (e), (f), (g), and/or (h) is a Cas9 nuclease.

In another method, Method 265, the present disclosure provides an in vitro method as provided in Method 264, wherein the Cas9 nuclease is linked to at least one nuclear localization signal.

In another method, Method 266, the present disclosure provides an in vitro method as provided in any one of Methods 168 to 264, wherein the stem cell is an embryonic stem cell, an adult stem cell, an induced pluripotent stem cell, or a hematopoietic stem cell.

In another method, Method 267, the present disclosure provides an in vitro method as provided in any one of Methods 168 to 266, wherein the stem cell is a human stem cell.

In another method, Method 268, the present disclosure provides an in vitro method as provided in any one of Methods 1 to 267, wherein the universal donor cell has increased immune evasion and/or post-transplantation survival compared to a comparable cell without the nucleic acid insertion and/or gene disruption.

In another method, Method 269, the present disclosure provides an in vitro method for generating a universal donor cell, the method comprising delivering to a stem cell: (a) a first RNA-guided nuclease and a first guide RNA (gRNA) targeting a target site in a beta-2 microglobulin (B2M) gene locus; (b) a first vector comprising a nucleic acid, the nucleic acid comprising: (i) a nucleotide sequence encoding tumor necrosis factor alpha induced protein 3 (TNFAIP3) and a nucleotide sequence encoding programmed death-ligand 1 (PD-L-1); (ii) a nucleotide sequence having sequence homology with a genomic region located left of the target site in the B2M gene locus; and (iii) a nucleotide sequence having sequence homology with a genomic region located right of the target site in the B2M gene locus, wherein (i) is flanked by (ii) and (iii); wherein the B2M gene locus is cleaved at the target site and the nucleic acid comprising the nucleotide sequences encoding TNFAIP3 and PD-L-1 is inserted into the B2M gene locus, thereby disrupting the B2M gene; wherein the universal donor cell expresses TNFAIP3 and PD-L-1 and has increased immune evasion and/or post-transplantation survival compared to a comparable cell without the nucleic acid insertion and gene disruption.

In another method, Method 270, the present disclosure provides an in vitro method as provided in Method 269, wherein disrupting the B2M gene comprises reducing or eliminating expression of B2M.

In another method, Method 271, the present disclosure provides an in vitro method as provided in Method 269 or 270, wherein the nucleotide sequence of (b)(i) comprises the nucleotide sequence encoding TNFAIP3 linked to a nucleotide sequence encoding a P2A peptide linked to the nucleotide sequence encoding PD-L-1.

In another method, Method 272, the present disclosure provides an in vitro method as provided in any one of Methods 269 to 271, wherein the nucleotide sequence of (b)(i) comprises SEQ ID NO: 54.

In another method, Method 273, the present disclosure provides an in vitro method as provided in any one of Methods 269 to 272, wherein the nucleotide sequence of (b)(i) is operably linked to an exogenous promoter.

In another method, Method 274, the present disclosure provides an in vitro method as provided in Method 273, wherein the exogenous promoter is a CMV, EF1α, PGK, CAG, or UBC promoter.

In another method, Method 275, the present disclosure provides an in vitro method as provided in any one of Methods 269 to 274, wherein the nucleotide sequence of (b)(ii) comprises or consists essentially of SEQ ID NO: 15.

In another method, Method 276, the present disclosure provides an in vitro method as provided in any one of Methods 269 to 275, wherein the nucleotide sequence of (b)(iii) comprises or consists essentially of SEQ ID NO: 22.

In another method, Method 277, the present disclosure provides an in vitro method as provided in any one of Methods 269 to 276, wherein the first RNA-guided nuclease and first gRNA are present in a ratio of about 1:1 to about 1:10.

In another method, Method 278, the present disclosure provides an in vitro method as provided in any one of Methods 269 to 277, wherein the first RNA-guided nuclease is a first Cas9 nuclease.

In another method, Method 279, the present disclosure provides an in vitro method as provided in Method 278, wherein the first Cas9 nuclease is linked to at least one nuclear localization signal.

In another method, Method 280, the present disclosure provides an in vitro method as provided in any one of Methods 269 to 279, further comprising: (c) a second RNA-guided nuclease and a second gRNA targeting a target site in a thioredoxin interacting protein (TXNIP) gene locus; and (d) a second vector comprising a nucleic acid, the nucleic acid comprising: (i) a nucleotide sequence encoding mesencephalic astrocyte derived neurotrophic factor (MANF) and a nucleotide sequence encoding HLA class I histocompatibility antigen, alpha chain E (HLA-E); (ii) a nucleotide sequence having sequence homology with a genomic region located left of the target site in the TXNIP gene locus; and (iii) a nucleotide sequence having sequence homology with a genomic region located right of the target site in the TXNIP gene locus, wherein (i) is flanked by (ii) and (iii); wherein the TXNIP gene locus is cleaved at the target site and the nucleic acid comprising the nucleotide sequences encoding MANF and HLA-E is inserted into the TXNIP gene locus, thereby disrupting the TXNIP gene; wherein the universal donor cell further expresses MANF and HLA-E.

In another method, Method 281, the present disclosure provides an in vitro method as provided in Method 280, wherein disrupting the TXNIP gene comprises reducing or eliminating expression of TXNIP.

In another method, Method 282, the present disclosure provides an in vitro method as provided in Method 280 or 281, wherein the nucleotide sequence encoding HLA-E comprises a sequence encoding a HLA-E trimer, the HLA-E trimer comprising a B2M signal peptide fused to an HLA-G presentation peptide fused to a B2M membrane protein fused to HLA-E without its signal peptide.

In another method, Method 283, the present disclosure provides an in vitro method as provided in any one of Methods 280 to 282, wherein the nucleotide sequence of (d)(i) comprises the nucleotide sequence encoding MANF linked to a nucleotide sequence encoding a P2A peptide linked to the nucleotide sequence encoding HLA-E.

In another method, Method 284, the present disclosure provides an in vitro method as provided in any one of Methods 280 to 283, wherein the nucleotide sequence of (d)(i) comprises SEQ ID NO: 55.

In another method, Method 285, the present disclosure provides an in vitro method as provided in any one of Methods 280 to 284, wherein the nucleotide sequence of (d)(i) is operably linked to an exogenous promoter.

In another method, Method 286, the present disclosure provides an in vitro method as provided in Method 285, wherein the exogenous promoter is a CMV, EF1α, PGK, CAG, or UBC promoter.

In another method, Method 287, the present disclosure provides an in vitro method as provided in any one of Methods 280 to 286, wherein the nucleotide sequence of (d)(ii) consists essentially of SEQ ID NO: 42.

In another method, Method 288, the present disclosure provides an in vitro method as provided in any one of Methods 280 to 287, wherein the nucleotide sequence of (d)(iii) consists essentially of SEQ ID NO: 44.

In another method, Method 289, the present disclosure provides an in vitro method as provided in any one of Methods 280 to 288 wherein the second RNA-guided nuclease and second gRNA are present in a ratio of about 1:1 to about 1:10.

In another method, Method 290, the present disclosure provides an in vitro method as provided in any one of Methods 280 to 289, wherein the second RNA-guided nuclease is a second Cas9 nuclease.

In another method, Method 291, the present disclosure provides an in vitro method as provided in Method 290, wherein the second Cas9 nuclease is linked to at least one nuclear localization signal.

In another method, Method 292, the present disclosure provides an in vitro method as provided in any one of Methods 269 to 291 wherein the stem cell is an embryonic stem cell, an adult stem cell, an induced pluripotent stem cell, or a hematopoietic stem cell.

In another method, Method 293, the present disclosure provides an in vitro method as provided in any one of Methods 269 to 292 wherein the stem cell is a human stem cell.

In another composition, Composition 294, the present disclosure provides a composition comprising a genetically modified cell comprising a nucleotide sequence encoding mesencephalic astrocyte derived neurotrophic factor (MANF), a nucleotide sequence encoding tumor necrosis factor alpha induced protein 3 (TNFAIP3), a nucleotide sequence encoding cluster of differentiation 73 (CD73), and/or a nucleotide sequence encoding cluster of differentiation 39 (CD39) inserted within or near a gene encoding beta-2-microglobulin (B2M), thioredoxin interacting protein (TXNIP), or class II transactivator (CIITA), wherein the genetically modified cell expresses MANF, TNFAIP3, CD73, and/or CD39 and has disrupted expression of B2M, TXNIP, and/or CIITA.

In another composition, Composition 295, the present disclosure provides a composition according to composition 294, wherein the disrupted expression of B2M, TXNIP, and/or CIITA comprises reduced or eliminated expression of B2M, TXNIP, and/or CIITA.

In another composition, Composition 296, the present disclosure provides a composition according to compositions 294 or 295, further comprising a nucleotide sequence encoding programmed death-ligand 1 (PD-L-1) and/or a nucleotide sequence encoding HLA class I histocompatibility antigen, alpha chain E (HLA-E) inserted within or near the B2M, TXNIP, or CIITA gene.

In another composition, Composition 297, the present disclosure provides a composition according to composition 296, wherein the nucleotide sequence encoding HLA-E comprises a sequence encoding a HLA-E trimer, the HLA-E trimer comprising a B2M signal peptide fused to an HLA-G presentation peptide fused to a B2M membrane protein fused to HLA-E without its signal peptide.

In another composition, Composition 298, the present disclosure provides a composition according to composition 296 or 297, wherein the genetically modified cell comprises the nucleotide sequence encoding MANF and the nucleotide sequence encoding HLA-E inserted within or near the TXNIP gene.

In another composition, Composition 299, the present disclosure provides a composition according to composition 298, wherein the nucleotide sequence encoding MANF and the nucleotide sequence encoding HLA-E are operably linked to an exogenous promoter.

In another composition, Composition 300, the present disclosure provides a composition according to compositions 298 or 299, wherein the nucleotide sequence encoding MANF is linked to the nucleotide sequence HLA-E by a nucleotide sequence encoding a ribosome skip.

In another composition, Composition 301, the present disclosure provides a composition according to composition 300, wherein the ribosome skip is a 2A sequence family member.

In another composition, Composition 302, the present disclosure provides a composition according to any one of compositions 294 to 301, wherein the genetically modified cell comprises the nucleotide sequence encoding TNFAIP3 and the nucleotide sequence encoding PD-L-1 inserted within or near the B2M gene.

In another composition, Composition 303, the present disclosure provides a composition according to composition 302, wherein the nucleotide sequence encoding TNFAIP3 and the nucleotide sequence encoding PD-L-1 are operably linked to an exogenous promoter.

In another composition, Composition 304, the present disclosure provides a composition according to compositions 302 or 303, wherein the nucleotide sequence encoding TNFAIP3 is linked to the nucleotide sequence encoding PD-L-1 by a nucleotide sequence encoding a ribosome skip.

In another composition, Composition 305, the present disclosure provides a composition according to composition 304, wherein the ribosome skip is a 2A sequence family member.

In another composition, Composition 306, the present disclosure provides a composition according to compositions 296 or 297, wherein the genetically modified cell comprises the nucleotide sequence encoding TNFAIP3, the nucleotide sequence encoding MANF, and the nucleotide sequence encoding PD-L-1 inserted within or near the B2M gene.

In another composition, Composition 307, the present disclosure provides a composition according to composition 306, wherein the nucleotide sequence encoding TNFAIP3, the nucleotide sequence encoding MANF, and the nucleotide sequence encoding PD-L-1 are operably linked to an exogenous promoter.

In another composition, Composition 308, the present disclosure provides a composition according to compositions 306 or 307, wherein the nucleotide sequence encoding TNFAIP3 is linked to the nucleotide sequence encoding MANF by a nucleotide sequence encoding a ribosome skip and the nucleotide sequence encoding MANF is linked to the nucleotide sequence PD-L-1 by a nucleotide sequence encoding a ribosome skip.

In another composition, Composition 309, the present disclosure provides a composition according to composition 308, wherein the ribosome skip is a 2A sequence family member.

In another composition, Composition 310, the present disclosure provides a composition according to any one of compositions 294 to 309, wherein the genetically modified cell comprises the nucleotide sequence encoding CD39 inserted within or near the CIITA gene.

In another composition, Composition 311, the present disclosure provides a composition according to composition 310, wherein the nucleotide sequence encoding CD39 is operably linked to an exogenous promoter.

In another composition, Composition 312, the present disclosure provides a composition according to composition 296 or 297, wherein the genetically modified cell comprises the nucleotide sequence encoding CD39 and the nucleotide sequence encoding PD-L-1 inserted within or near the B2M gene.

In another composition, Composition 313, the present disclosure provides a composition according to composition 312, wherein the nucleotide sequence encoding CD39 and the nucleotide sequence encoding PD-L-1 are operably linked to an exogenous promoter.

In another composition, Composition 314, the present disclosure provides a composition according to compositions 312 or 313, wherein the nucleotide sequence encoding CD39 is linked to the nucleotide sequence encoding PD-L-1 by a nucleotide sequence encoding a ribosome skip.

In another composition, Composition 315, the present disclosure provides a composition according to composition 314, wherein the ribosome skip is a 2A sequence family member.

In another composition, Composition 316, the present disclosure provides a composition comprising a nucleotide sequence encoding PD-L-1 inserted within or near the B2M gene, a nucleotide sequence encoding HLA-E inserted within or near the TXNIP gene, and/or a nucleotide sequence encoding CD39 inserted within or near the CIITA gene or the B2M gene, wherein the genetically modified cell expresses PD-L-1, HLA-E, and/or CD39 and has disrupted expression of B2M, TXNIP, and/or CIITA.

In another composition, Composition 317, the present disclosure provides a composition according to composition 316, wherein the disrupted expression of B2M, TXNIP, and/or CIITA comprises reduced or eliminated expression of B2M, TXNIP, and/or CIITA.

In another composition, Composition 318, the present disclosure provides a composition according to any one of compositions 294 to 317, wherein the cell is a stem cell.

In another composition, Composition 319, the present disclosure provides a composition according to composition 318, wherein the stem cell is an embryonic stem cell, an adult stem cell, an induced pluripotent stem cell, or a hematopoietic stem cell.

In another composition, Composition 320, the present disclosure provides a composition according to any one of compositions 294 to 319, wherein the cell is a differentiated cell or a somatic cell.

In another composition, Composition 321, the present disclosure provides a composition according to composition 320, wherein the cell is differentiated into lineage-restricted progenitor cells or fully differentiated somatic cells.

In another composition, Composition 322, the present disclosure provides a composition according to composition 321, wherein the lineage-restricted progenitor cells are definitive endoderm cells, primitive gut tube cells, posterior foregut cells, pancreatic endoderm progenitors, pancreatic endocrine progenitors, or pancreatic endocrine cells, and the fully differentiated somatic cells are immature beta cells or mature beta cells.

In another composition, Composition 323, the present disclosure provides a composition comprising a plurality of genetically modified cells according to any one of claims 294 to 322.

In another composition, Composition 324, the present disclosure provides a composition according to composition 323, wherein at least about 50% of the cells express MANF, HLA-E, TNFAIP3, PD-L-1, and/or CD39.

In another composition, Composition 325, the present disclosure provides a composition comprising a population of lineage-restricted progenitor cells or fully differentiated somatic cells derived from the plurality of genetically modified cells of compositions 323 or 324.

In another composition, Composition 326, the present disclosure provides a composition according to composition 325, wherein the lineage-restricted progenitor cells are definitive endoderm cells, primitive gut tube cells, posterior foregut cells, pancreatic endoderm progenitors, pancreatic endocrine progenitors, or pancreatic endocrine cells, and the fully differentiated somatic cells are immature beta cells or mature beta cells.

In another composition, Composition 327, the present disclosure provides a composition according to composition 325 or 326, wherein at least about 50% of the cells express MANF, HLA-E, TNFAIP3, PD-L-1, and/or CD39.

In another composition, Composition 328, the present disclosure provides a composition comprising the plurality of cells of compositions 323 or 324 or the population of cells of any one of compositions 325 to 327.

In another composition, Composition 329, the present disclosure provides a composition according to composition 328 further comprising at least one pharmaceutically acceptable excipient.

In another composition, Composition 330, the present disclosure provides a composition according to composition 328 or 329 for use in treating a subject in need thereof.

In another composition, Composition 331, the present disclosure provides a composition according to composition 330, wherein the subject has, is suspected of having, or is at risk for a disease or disorder.

In another composition, Composition 332, the present disclosure provides a composition according to composition 330 or 331, wherein the disease or disorder is a genetically inheritable disease, such as type I diabetes.

In another composition, Composition 333, the present disclosure provides a composition according to composition 332, wherein the disease or disorder is type II diabetes or a pancreactomy.

In another composition, Composition 334, the present disclosure provides a composition according to any one of compositions 328 to 333, wherein the subject is human In another method, Method 335, the present disclosure provides a method for treating a pancreatic disease or disorder in a subject in need thereof, the method comprising: (a) obtaining or having obtained the plurality of genetically modified cells of any one of claims 294 to 322 following differentiation into pancreatic endoderm cells, pancreatic endocrine cells, immature beta cells, or mature beta cells; and (b) administering the pancreatic endoderm cells, pancreatic endocrine cells, immature beta cells, or mature beta cells to the subject.

In another method, Method 336, the present disclosure provides a method as provided in Method 335, wherein administering comprises implanting a device comprising the pancreatic endoderm cells, pancreatic endocrine cells, immature beta cells, or mature beta cells into the subject.

In another method, Method 337, the present disclosure provides a method as provided in Methods 335 or 336, wherein the pancreatic disease or disorder is type I diabetes, type II diabetes, or a pancreactomy.

In another method, Method 338, the present disclosure provides a method as provided in any one of Methods 335 to 337, wherein the subject is human.

In another method, Method 339, the present disclosure provides a an in vitro method for generating a universal donor cell, the method comprising delivering to a stem cell: (a) a ribonucleoprotein (RNP) complex comprising an RNA-guided nuclease and a guide RNA (gRNA) targeting a target site in a beta-2 microglobulin (B2M) gene locus; (b) a vector comprising a nucleic acid, the nucleic acid comprising: (i) a nucleotide sequence encoding tumor necrosis factor alpha induced protein 3 (TNFAIP3) and a nucleotide sequence encoding programmed death-ligand 1 (PD-L-1); (ii) a nucleotide sequence consisting essentially of SEQ ID NO: 15 and having sequence homology with a genomic region located left of the target site in the B2M gene locus; and (iii) a nucleotide sequence consisting essentially of SEQ ID NO: 22 and having sequence homology with a genomic region located right of the target site in the B2M gene locus, wherein (i) is flanked by (ii) and (iii); wherein the B2M gene locus is cleaved at the target site and the nucleic acid comprising the nucleotide sequences encoding TNFAIP3 and PD-L-1 is inserted into the B2M gene locus, thereby disrupting the B2M gene; wherein the universal donor cell has increased immune evasion and/or post-transplantation survival compared to a comparable cell without the nucleic acid insertion and gene disruption.

In another method, Method 340, the present disclosure provides an in vitro method as provided in Method 339, wherein the nucleotide sequence of (b)(i) comprises the nucleotide sequence encoding TNFAIP3 linked to a nucleotide sequence encoding a ribosome skip linked to the nucleotide sequence encoding PD-L-1.

In another method, Method 341, the present disclosure provides a an in vitro method for generating a universal donor cell, the method comprising delivering to a stem cell: (a) a RNP complex comprising an RNA-guided nuclease and a gRNA targeting a target site in a thioredoxin interacting protein (TXNIP) gene locus; and (b) a vector comprising a nucleic acid, the nucleic acid comprising: (i) a nucleotide sequence encoding mesencephalic astrocyte derived neurotrophic factor (MANF) and a nucleotide sequence encoding HLA class I histocompatibility antigen, alpha chain E (HLA-E); (ii) a nucleotide sequence consisting essentially of SEQ ID NO: 42 and having sequence homology with a genomic region located left of the target site in the TXNIP gene locus; and (iii) a nucleotide sequence consisting essentially of SEQ ID NO: 44 and having sequence homology with a genomic region located right of the target site in the TXNIP gene locus, wherein (i) is flanked by (ii) and (iii); wherein the TXNIP gene locus is cleaved at the target site and the nucleic acid comprising the nucleotide sequences encoding MANF and HLA-E is inserted into the TXNIP gene locus, thereby disrupting the TXNIP gene and generating a universal donor cell, wherein the universal donor cell has increased immune evasion and/or post-transplantation survival compared to a comparable cell without the nucleic acid insertion and gene disruption.

In another method, Method 342, the present disclosure provides an in vitro method as provided in Method 341, wherein the nucleotide sequence encoding HLA-E comprises a sequence encoding a HLA-E trimer, the HLA-E trimer comprising a B2M signal peptide fused to an HLA-G presentation peptide fused to a B2M membrane protein fused to HLA-E without its signal peptide.

In another method, Method 343, the present disclosure provides an in vitro method as provided in Method 341 or 342, wherein the nucleotide sequence of (b)(i) comprises the nucleotide sequence encoding MANF linked to a nucleotide sequence encoding a ribosome skip linked to the nucleotide sequence encoding HLA-E.

In another method, Method 344, the present disclosure provides an in vitro method as provided in Method 340 or 343, wherein the ribosome skip of (b)(i) is a 2A sequence family member.

In another method, Method 345, the present disclosure provides a an in vitro method for generating a universal donor cell, the method comprising delivering to a stem cell: (a) a RNP complex comprising an RNA-guided nuclease and a gRNA targeting a target site in a class II transactivator (CIITA) gene locus; and (b) a vector comprising a nucleic acid, the nucleic acid comprising: (i) a nucleotide sequence encoding cluster of differentiation 39 (CD39); (ii) a nucleotide sequence consisting essentially of SEQ ID NO: 26 and having sequence homology with a genomic region located left of the target site in the CIITA gene locus; and (iii) a nucleotide sequence consisting essentially of SEQ ID NO: 28 and having sequence homology with a genomic region located right of the target site in the CIITA gene locus, wherein (i) is flanked by (ii) and (iii); wherein the CIITA gene locus is cleaved at the target site and the nucleic acid comprising the nucleotide sequence encoding CD39 is inserted into the CIITA gene locus, thereby disrupting the CIITA gene and generating a universal donor cell, wherein the universal donor cell has increased immune evasion and/or post-transplantation survival compared to a comparable cell without the nucleic acid insertion and gene disruption.

In another method, Method 346, the present disclosure provides an in vitro method as provided in any one of Methods 339 to 345, wherein the nucleotide sequence of (b)(i) is operably linked to an exogenous promoter.

In another method, Method 347, the present disclosure provides an in vitro method as provided in Method 346, wherein the exogenous promoter is a CMV, EF1α, PGK, CAG, or UBC promoter.

In another method, Method 348, the present disclosure provides a an in vitro method for generating a universal donor cell, the method comprising delivering to a stem cell: (a) a first ribonucleoprotein (RNP) complex comprising an RNA-guided nuclease and a guide RNA (gRNA) targeting a target site in a beta-2 microglobulin (B2M) gene locus; (b) a first vector comprising a nucleic acid, the nucleic acid comprising: (i) a nucleotide sequence encoding tumor necrosis factor alpha induced protein 3 (TNFAIP3) and a nucleotide sequence encoding programmed death-ligand 1 (PD-L-1); (ii) a nucleotide sequence consisting essentially of SEQ ID NO: 15 and having sequence homology with a genomic region located left of the target site in the B2M gene locus; and (iii) a nucleotide sequence consisting essentially of SEQ ID NO: 22 and having sequence homology with a genomic region located right of the target site in the B2M gene locus, wherein (i) is flanked by (ii) and (iii); wherein the B2M gene locus is cleaved at the target site and the nucleic acid comprising the nucleotide sequences encoding TNFAIP3 and PD-L-1 is inserted into the B2M gene locus, thereby disrupting the B2M gene; (c) a second RNP complex comprising an RNA-guided nuclease and a gRNA targeting a target site in a thioredoxin interacting protein (TXNIP) gene locus; and (d) a second vector comprising a nucleic acid, the nucleic acid comprising: (i) a nucleotide sequence encoding mesencephalic astrocyte derived neurotrophic factor (MANF) and a nucleotide sequence encoding HLA class I histocompatibility antigen, alpha chain E (HLA-E); (ii) a nucleotide sequence consisting essentially of SEQ ID NO: 42 and having sequence homology with a genomic region located left of the target site in the TXNIP gene locus; and (iii) a nucleotide sequence consisting essentially of SEQ ID NO: 44 and having sequence homology with a genomic region located right of the target site in the TXNIP gene locus, wherein (i) is flanked by (ii) and (iii); wherein the TXNIP gene locus is cleaved at the target site and the nucleic acid comprising the nucleotide sequences encoding MANF and HLA-E is inserted into the TXNIP gene locus, thereby disrupting the TXNIP gene and generating a universal donor cell, wherein the universal donor cell has increased immune evasion and/or post-transplantation survival compared to a comparable cell without the nucleic acid insertions and gene disruptions.

In another method, Method 349, the present disclosure provides an in vitro method as provided in Method 348, further comprising delivering to the stem cell: (e) a third RNP complex comprising an RNA-guided nuclease and a gRNA targeting a target site in a class II transactivator (CIITA) gene locus; and (f) a third vector comprising a nucleic acid, the nucleic acid comprising: (i) a nucleotide sequence encoding cluster of differentiation 39 (CD39); (ii) a nucleotide sequence consisting essentially of SEQ ID NO: 26 and having sequence homology with a genomic region located left of the target site in the CIITA gene locus; and (iii) a nucleotide sequence consisting essentially of SEQ ID NO: 28 and having sequence homology with a genomic region located right of the target site in the CIITA gene locus, wherein (i) is flanked by (ii) and (iii); wherein the CIITA gene locus is cleaved at the target site and the nucleic acid comprising the nucleotide sequence encoding CD39 is inserted into the CIITA gene locus, thereby disrupting the CIITA gene.

In another method, Method 350, the present disclosure provides an in vitro method as provided in Methods 294 to 349, wherein the nucleotide sequence encoding HLA-E comprises a sequence encoding a HLA-E trimer, the HLA-E trimer comprising a B2M signal peptide fused to an HLA-G presentation peptide fused to a B2M membrane protein fused to HLA-E without its signal peptide.

In another method, Method 351, the present disclosure provides an in vitro method as provided in any one of Methods 294 to 350, wherein the nucleotide sequence of (b)(i) comprises sequence encoding TNFAIP3 linked to sequence encoding a ribosome skip linked to sequence encoding PD-L-1; and the nucleotide sequence of (d)(i) comprises sequence encoding MANF linked to sequence encoding a ribosome skip linked to sequence encoding HLA-E.

In another method, Method 352, the present disclosure provides an in vitro method as provided in Method 351, wherein the ribosome skip of each of (b)(i) and (d)(i) is a 2A sequence family member.

In another method, Method 353, the present disclosure provides an in vitro method as provided in any one of Methods 294 to 352, wherein the nucleotide sequence of each of (b)(i), (d)(i), and (f)(i) is operably linked to an exogenous promoter.

In another method, Method 354, the present disclosure provides an in vitro method as provided in Method 353, wherein the exogenous promoter is a CMV, EF1α, PGK, CAG, or UBC promoter.

In another method, Method 355, the present disclosure provides a an in vitro method for generating a universal donor cell, the method comprising delivering to a stem cell: (a) a first ribonucleoprotein (RNP) complex comprising an RNA-guided nuclease and a guide RNA (gRNA) targeting a target site in a beta-2 microglobulin (B2M) gene locus; (b) a first vector comprising a nucleic acid, the nucleic acid comprising: (i) a nucleotide sequence encoding tumor necrosis factor alpha induced protein 3 (TNFAIP3), a nucleotide sequence encoding MANF, and a nucleotide sequence encoding programmed death-ligand 1 (PD-L-1); (ii) a nucleotide sequence consisting essentially of SEQ ID NO: 15 and having sequence homology with a genomic region located left of the target site in the B2M gene locus; and (iii) a nucleotide sequence consisting essentially of SEQ ID NO: 22 and having sequence homology with a genomic region located right of the target site in the B2M gene locus, wherein (i) is flanked by (ii) and (iii); wherein the B2M gene locus is cleaved at the target site and the nucleic acid comprising the nucleotide sequences encoding TNFAIP3, MANF, and PD-L-1 is inserted into the B2M gene locus, thereby disrupting the B2M gene; and generating a universal donor cell, wherein the universal donor cell has increased immune evasion and/or post-transplantation survival compared to a comparable cell without the nucleic acid insertions and gene disruptions.

In another method, Method 356, the present disclosure provides an in vitro method as provided in Method 355, further comprising delivering to the stem cell: (c) a second RNP complex comprising an RNA-guided nuclease and a gRNA targeting a target site in a class II transactivator (CIITA) gene locus; and (d) a second vector comprising a nucleic acid, the nucleic acid comprising: (i) a nucleotide sequence encoding cluster of differentiation 39 (CD39); (ii) a nucleotide sequence consisting essentially of SEQ ID NO: 26 and having sequence homology with a genomic region located left of the target site in the CIITA gene locus; and (iii) a nucleotide sequence consisting essentially of SEQ ID NO: 28 and having sequence homology with a genomic region located right of the target site in the CIITA gene locus, wherein (i) is flanked by (ii) and (iii); wherein the CIITA gene locus is cleaved at the target site and the nucleic acid comprising the nucleotide sequence encoding CD39 is inserted into the CIITA gene locus, thereby disrupting the CIITA gene.

In another method, Method 357, the present disclosure provides an in vitro method as provided in Method 355 or 356, wherein the nucleotide sequence of (b)(i) comprises the nucleotide sequence encoding TNFAIP3 linked to the nucleotide sequence encoding MANF by a nucleotide sequence encoding a ribosome skip and the nucleotide sequence encoding MANF linked to the nucleotide sequence PD-L-1 by a nucleotide sequence encoding a ribosome skip.

In another method, Method 358, the present disclosure provides an in vitro method as provided in Method 357, wherein the ribosome skip is a 2A sequence family member.

In another method, Method 359, the present disclosure provides an in vitro method as provided in any one of Methods 357 to 358, wherein the nucleotide sequence of (b)(i) is operably linked to an exogenous promoter.

In another method, Method 360, the present disclosure provides an in vitro method as provided in any one of Methods 356 to 359, wherein the nucleotide sequence of (d)(i) is operably linked to an exogenous promoter In another method, Method 361, the present disclosure provides an in vitro method as provided in Method 359 or 360, wherein the exogenous promoter is a CMV, EFla, PGK, CAG, or UBC promoter.

In another method, Method 362, the present disclosure provides an in vitro method as provided in any one of Methods 339 to 361, wherein each RNP complex comprises a molar ratio of RNA-guided nuclease to gRNA of about 1:1 to about 1:10.

In another method, Method 363, the present disclosure provides an in vitro method as provided in any one of Methods 339 to 362, wherein the RNA-guided nuclease of each RNP complex is a Cas9 nuclease.

In another method, Method 364, the present disclosure provides an in vitro method as provided in Method 363, wherein the Cas9 nuclease is linked to at least one nuclear localization signal.

In another method, Method 365, the present disclosure provides an in vitro method as provided in any one of Methods 339 to 362, wherein the stem cell is an embryonic stem cell, an adult stem cell, an induced pluripotent stem cell, or a hematopoietic stem cell.

In another method, Method 366, the present disclosure provides an in vitro method as provided in any one of Methods 339 to 365 wherein the stem cell is a human stem cell.

In another composition, Composition 367, the present disclosure provides a composition comprising a plurality of universal donor cells generated by any one of Methods 339 to 366.

In another composition, Composition 368, the present disclosure provides a composition according to composition 367, wherein at least about 50% of the cells express MANF, HLA-E, TNFAIP3, PD-L-1, and/or CD39.

In another composition, Composition 369, the present disclosure provides a composition comprising a population of lineage-restricted progenitor cells or fully differentiated somatic cells derived from the plurality of universal donor cells of composition 367 or 368

In another composition, Composition 370, the present disclosure provides a composition according to composition 369, wherein the lineage-restricted progenitor cells are definitive endoderm cells, primitive gut tube cells, posterior foregut cells, pancreatic endoderm progenitors, pancreatic endocrine progenitors, pancreatic endocrine cells, immature beta cells, or maturing beta cells, and the fully differentiated somatic cells are pancreatic beta cells.

In another composition, Composition 371, the present disclosure provides a composition according to composition 369 to 370, wherein at least about 50% of the cells express MANF, HLA-E, TNFAIP3, PD-L-1, and/or CD39.

In another composition, Composition 372, the present disclosure provides a composition comprising the plurality of cells of any one of compositions 367 or 368 or the population of cells of any one of compositions 369 to 371.

In another composition, Composition 373, the present disclosure provides a composition according to composition 372 further comprising at least one pharmaceutically acceptable excipient.

In another composition, Composition 374, the present disclosure provides a composition according to composition 372 to 373 for use in treating a subject in need thereof.

In another composition, Composition 375, the present disclosure provides a composition according to composition claim 374, wherein the subject has, is suspected of having, or is at risk for a disease or disorder.

In another composition, Composition 376, the present disclosure provides a composition according to composition 375, wherein the disease or disorder is a genetically inheritable disease, such as type I diabetes.

In another composition, Composition 377, the present disclosure provides a composition according to composition 375, wherein the disease or disorder is type II diabetes or a pancreactomy.

In another composition, Composition 378, the present disclosure provides a composition according to composition 374 to 377, wherein the subject is human.

In another method, Method 379, the present disclosure provides a method for treating a pancreatic disease or disorder in a subject in need thereof, the method comprising: (c) obtaining or having obtained the plurality of universal donor cells of claim 367 or 368 following differentiation into pancreatic endoderm cells, pancreatic endocrine cells, immature beta cells, or mature beta cells; and (d) administering the pancreatic endoderm cells, pancreatic endocrine cells, immature beta cells, or mature beta cells to the subject.

In another method, Method 380, the present disclosure provides a method as provided in Method 379, wherein administering comprises implanting a device comprising the pancreatic endoderm cells, pancreatic endocrine cells, immature beta cells, or mature beta cells into the subject.

In another method, Method 381, the present disclosure provides a method as provided in Methods 379 to 380, wherein the pancreatic disease or disorder is type I diabetes, type II diabetes, or a pancreactomy.

In another method, Method 382, the present disclosure provides a method as provided in any one of Methods 379 to 381, wherein the subject is human.

In another composition, Composition 383, the present disclosure provides a composition as provided in any one of Compositions 294 to 296 wherein the genetically modified cell comprises the nucleotide sequence encoding CD39 and the nucleotide sequence encoding PD-L-1 inserted within or near the B2M gene.

In another composition, Composition 384, the present disclosure provides a composition according to composition 383, wherein the nucleotide sequence encoding CD39 is linked to the nucleotide sequence encoding PD-L-1 by a nucleotide sequence encoding a 2A sequence family member.

In another composition, Composition 385, the present disclosure provides a composition according to compositions 383 or 384, wherein the nucleotide sequence encoding CD39 and the nucleotide sequence encoding PD-L-1 are operably linked to an exogenous promoter.

In another composition, Composition 386, the present disclosure provides a composition as provided in any one of Compositions 294 to 296, wherein the genetically modified cell comprises the nucleotide sequence encoding CD39, the nucleotide sequence encoding CD73, and the nucleotide sequence encoding PD-L-1 inserted within or near the B2M gene.

In another composition, Composition 387, the present disclosure provides a composition according to composition 386, wherein the nucleotide sequence encoding CD39 is linked to the nucleotide sequence encoding CD73 by a nucleotide sequence encoding a 2A sequence family member, and the nucleotide sequence encoding CD73 is linked to the nucleotide sequence encoding PD-L-1 by a nucleotide sequence encoding a 2A sequence family member.

In another composition, Composition 388, the present disclosure provides a composition according to compositions 386 or 387, wherein the nucleotide sequence encoding CD39, the nucleotide sequence encoding CD73, and the nucleotide sequence encoding PD-L-1 are operably linked to an exogenous promoter.

In another composition, Composition 389, the present disclosure provides a composition comprising a genetically modified cell comprising (a) a first polynucleotide sequence encoding mesencephalic astrocyte derived neurotrophic factor (MANF) and a second polynucleotide encoding HLA class I histocompatibility antigen, alpha chain E (HLA-E) inserted within or near a gene encoding thioredoxin interacting protein (TXNIP) and (b) a third polynucleotide sequence encoding tumor necrosis factor alpha induced protein 3 (TNFAIP3) and a fourth polynucleotide encoding programmed death-ligand 1 (PD-L-1) inserted within or near a gene encoding beta-2-microglobulin (B2M), wherein the genetically modified cell expresses MANF, HLA-E, TNFAIP3, and PD-L-1 and has disrupted expression of TXNIP and B2M.

In another method, Method 390, the present disclosure provides an in vitro method for preparing a universal donor cell, the method comprising delivering to a stem cell: (a) a first RNA-guided nuclease and a first guide RNA (gRNA) targeting a target site in a beta-2 microglobulin (B2M) gene locus; (b) a first vector comprising a nucleic acid, the nucleic acid comprising: (i) a nucleotide sequence encoding tumor necrosis factor alpha induced protein 3 (TNFAIP3) and a nucleotide sequence encoding programmed death-ligand 1 (PD-L-1); (ii) a nucleotide sequence having sequence homology with a genomic region located left of the target site in the B2M gene locus; and (iii) a nucleotide sequence having sequence homology with a genomic region located right of the target site in the B2M gene locus, wherein (i) is flanked by (ii) and (iii); wherein the B2M gene locus is cleaved at the target site and the nucleic acid comprising the nucleotide sequences encoding TNFAIP3 and PD-L-1 is inserted into the B2M gene locus, thereby disrupting the B2M gene; wherein the universal donor cell expresses TNFAIP3 and PD-L-1 and has increased immune evasion and/or post-transplantation survival compared to a comparable cell without the nucleic acid insertion and gene disruption.

In another method, Method 391, the present disclosure provides an in vitro method according to Method 390, wherein disrupting the B2M gene comprises reducing or eliminating expression of B2M.

In another method, Method 392, the present disclosure provides an in vitro method according to Method 390 or 391, wherein the nucleotide sequence of (b)(i) comprises the nucleotide sequence encoding TNFAIP3 linked to a nucleotide sequence encoding P2A linked to the nucleotide sequence encoding PD-L-1.

In another method, Method 393, the present disclosure provides an in vitro method according to any one of Methods 390 to 392, wherein the nucleotide sequence of (b)(i) comprises SEQ ID NO: 54.

In another method, Method 394, the present disclosure provides an in vitro method according to any one of Methods 390 to 393, wherein the nucleotide sequence of (b)(i) is operably linked to an exogenous promoter.

In another method, Method 395, the present disclosure provides an in vitro method according to any one of Methods 390 to 394, wherein the exogenous promoter is a CMV, EF1α, PGK, CAG, or UBC promoter.

In another method, Method 396, the present disclosure provides an in vitro method according to any one of Methods 390 to 395, wherein the nucleotide sequence of (b)(ii) comprises or consists essentially of SEQ ID NO: 15.

In another method, Method 397, the present disclosure provides an in vitro method according to any one of Methods 390 to 396, wherein the nucleotide sequence of (b)(iii) comprises or consists essentially of SEQ ID NO: 22.

In another method, Method 398, the present disclosure provides an in vitro method according to any one of Methods 390 to 397, wherein the first RNA-guided nuclease and first gRNA are present in a ratio of about 1:1 to about 1:10.

In another method, Method 399, the present disclosure provides an in vitro method according to any one of Methods 390 to 398, wherein the first RNA-guided nuclease is a first Cas9 nuclease.

In another method, Method 400, the present disclosure provides an in vitro method according to Method 399, wherein the first Cas9 nuclease is linked to at least one nuclear localization signal.

In another method, Method 401, the present disclosure provides an in vitro method according to any one of Method 390 to 400, further comprising delivering to the stem cell: (c) a second RNA-guided nuclease and a second gRNA targeting a target site in a thioredoxin interacting protein (TXNIP) gene locus; and (d) a second vector comprising a nucleic acid, the nucleic acid comprising: (i) a nucleotide sequence encoding mesencephalic astrocyte derived neurotrophic factor (MANF) and a nucleotide sequence encoding HLA class I histocompatibility antigen, alpha chain E (HLA-E); (ii) a nucleotide sequence having sequence homology with a genomic region located left of the target site in the TXNIP gene locus; and (iii) a nucleotide sequence having sequence homology with a genomic region located right of the target site in the TXNIP gene locus, wherein (i) is flanked by (ii) and (iii); wherein the TXNIP gene locus is cleaved at the target site and the nucleic acid comprising the nucleotide sequences encoding MANF and HLA-E is inserted into the TXNIP gene locus, thereby disrupting the TXNIP gene; wherein the universal donor cell further expresses MANF and HLA-E.

In another method, Method 402, the present disclosure provides an in vitro method according to Method 401, wherein disrupting the TXNIP gene comprises reducing or eliminating expression of TXNIP.

In another method, Method 403, the present disclosure provides an in vitro method according to Method 401 or 402, wherein the nucleotide sequence encoding HLA-E comprises a sequence encoding a HLA-E trimer, the HLA-E trimer comprising a B2M signal peptide fused to an HLA-G presentation peptide fused to a B2M membrane protein fused to HLA-E without its signal peptide.

In another method, Method 404, the present disclosure provides an in vitro method according to any one of Methods 401 to 403, wherein the nucleotide sequence of (d)(i) comprises the nucleotide sequence encoding MANF linked to a nucleotide sequence encoding P2A linked to the nucleotide sequence encoding HLA-E.

In another method, Method 405, the present disclosure provides an in vitro method according to any one of Methods 401 to 404, wherein the nucleotide sequence of (d)(i) comprises SEQ ID NO: 55.

In another method, Method 406, the present disclosure provides an in vitro method according to any one of Methods 401 to 405, wherein the nucleotide sequence of (d)(i) is operably linked to an exogenous promoter.

In another method, Method 407, the present disclosure provides an in vitro method according to Method 406, wherein the exogenous promoter is a CMV, EF1α, PGK, CAG, or UBC promoter.

In another method, Method 408, the present disclosure provides an in vitro method according to any one of Methods 401 to 407, wherein the nucleotide sequence of (d)(ii) consists essentially of SEQ ID NO: 42.

In another method, Method 409, the present disclosure provides an in vitro method according to any one of Methods 401 to 408, wherein the nucleotide sequence of (d)(iii) consists essentially of SEQ ID NO: 44.

In another method, Method 410, the present disclosure provides an in vitro method according to any one of Methods 401 to 409, wherein the second RNA-guided nuclease and second gRNA are present in a ratio of about 1:1 to about 1:10.

In another method, Method 411 the present disclosure provides an in vitro method according to any one of Methods 401 to 410, wherein the second RNA-guided nuclease is a second Cas9 nuclease.

In another method, Method 412, the present disclosure provides an in vitro method according to Method 411, wherein the second Cas9 nuclease is linked to at least one nuclear localization signal.

In another method, Method 413, the present disclosure provides an in vitro method according to any one of Methods 401 to 412, further comprising delivering to the stem cell: (e) a third RNA-guided nuclease and a third gRNA targeting a target site in class II transactivator (CIITA) gene locus; and (f) a second vector comprising a nucleic acid, the nucleic acid comprising: (i) a nucleotide sequence encoding CD39; (ii) a nucleotide sequence having sequence homology with a genomic region located left of the target site in the CIITA gene locus; and (iii) a nucleotide sequence having sequence homology with a genomic region located right of the target site in the CIITA gene locus, wherein (i) is flanked by (ii) and (iii); wherein the TXNIP gene locus is cleaved at the target site and the nucleic acid comprising the nucleotide sequences encoding CD39 is inserted into the CIITA gene locus, thereby disrupting the CIITA gene; wherein the universal donor cell further expresses CD39.

In another method, Method 414, the present disclosure provides an in vitro method according to Method 413 wherein the nucleotide sequence of (e)(i) comprises SEQ ID NO: 27.

In another method, Method 415, the present disclosure provides an in vitro method according to Method 413 or 414, wherein the nucleotide sequence of (f)(i) is operably linked to an exogenous promoter.

In another method, Method 416, the present disclosure provides an in vitro method according to Method 415, wherein the exogenous promoter is a CMV, EF1α, PGK, CAG, or UBC promoter.

In another method, Method 417, the present disclosure provides an in vitro method according to any one of Methods 413 to 416, wherein the nucleotide sequence of (f)(ii) consists essentially of SEQ ID NO: 26.

In another method, Method 418, the present disclosure provides an in vitro method according to any one of Methods 413 to 417, wherein the nucleotide sequence of (f)(iii) consists essentially of SEQ ID NO: 28.

In another method, Method 419, the present disclosure provides an in vitro method according to any one of Methods 413 to 418, wherein the third RNA-guided nuclease and third gRNA are present in a ratio of about 1:1 to about 1:10.

In another method, Method 420, the present disclosure provides an in vitro method according to any one of Methods 413 to 419, wherein the third RNA-guided nuclease is a third Cas9 nuclease.

In another method, Method 421, the present disclosure provides an in vitro method according to Method 420, wherein the third Cas9 nuclease is linked to at least one nuclear localization signal.

In another method, Method 422, the present disclosure provides an in vitro method according to any one of methods 390 to 421, further comprising delivering to the stem cell: (g) a fourth RNA-guided nuclease and a fourth gRNA targeting a target site in TGFβ gene locus, thereby disrupting the TGFβ gene.

In another method, Method 423, the present disclosure provides an in vitro method according to Method 422, wherein the fourth gRNA targets a nucleotide sequence consisting essentially of SEQ ID NO: 57.

In another method, Method 424, the present disclosure provides an in vitro method according to any one of Methods 390 to 423, wherein the stem cell is an embryonic stem cell, an adult stem cell, an induced pluripotent stem cell, or a hematopoietic stem cell.

In another method, Method 425, the present disclosure provides an in vitro method according to any one of Methods 390 to 424, wherein the stem cell is a human stem cell.

In another composition, Composition 426, the present disclosure provides a composition comprising a genetically modified cell comprising: (a) a disrupted B2M gene and a first insertion of a first polynucleotide encoding mesencephalic astrocyte derived neurotrophic factor (MANF) into the disrupted B2M gene; (b) a disrupted TXNIP gene and a second insertion of a second polynucleotide encoding tumor necrosis factor alpha induced protein 3 (TNFAIP3) into the disrupted TXNIP gene; (c) a disrupted CIITA gene and a third insertion of a third polynucleotide encoding CD39, wherein the cell expresses MANF, TNFAIP3 and CD39 and has disrupted expression of B2M, TXNIP and CIITA.

In another composition, Composition 427, the present disclosure further provides a composition according to Composition 426, wherein the third polynucleotide comprises a nucleotide sequence consisting essentially of SEQ ID NO: 27.

In another composition, Composition 428, the present disclosure provides a composition according to any one of compositions 426 to 427, wherein the disrupted expression of B2M, TXNIP and/or CIITA comprises reduced or eliminated expression of the B2M protein, the TXNIP protein and/or the CIITA protein.

In another composition, Composition 429, the present disclosure further provides a composition according to any one of Compositions 426 to 428, wherein the genetically modified cell further comprises (d) a disrupted TGFβ gene and wherein the cell has disrupted expression of a TGFβ protein.

In another composition, Composition 430, the present disclosure provides a composition according to composition 429, wherein the disrupted expression of the TGFβ protein comprises reduced or eliminated expression of the TGFβ protein.

In another composition, Composition 431, the present disclosure provides a composition according to any one of compositions 426 to 430, wherein the universal donor cell has increased immune evasion and/or post-transplantation survival compared to a comparable cell without the polynucleotide insertion and gene disruption.

In another composition, Composition 432, the present disclosure provides a composition according to any one of compositions 426 to 431, wherein the cell is a stem cell.

In another composition, Composition 433, the present disclosure provides a composition according to composition 432, wherein the stem cell is an embryonic stem cell, an adult stem cell, an induced pluripotent stem cell, or a hematopoietic stem cell.

In another composition, Composition 434, the present disclosure provides a composition according to any one of compositions 426 to 431, wherein the cell is a differentiated cell or a somatic cell.

In another composition, Composition 435, the present disclosure provides a composition according to composition 434, wherein the cell is differentiated into lineage-restricted progenitor cells or fully differentiated somatic cells.

In another composition, Composition 436, the present disclosure provides a composition according to composition 435, wherein the lineage-restricted progenitor cells are definitive endoderm cells, primitive gut tube cells, posterior foregut cells, pancreatic endoderm progenitors, pancreatic endocrine progenitors, or immature beta cells, and the fully differentiated somatic cells are pancreatic beta cells.

In another composition, Composition 437, the present disclosure provides a composition comprising a plurality of genetically modified cells according to any one of Compositions 1 to 436.

In another composition, Composition 438, the present disclosure provides a composition comprising population of lineage-restricted progenitor cells or fully differentiated somatic cells derived from the plurality of genetically modified cells of composition 437.

In another composition, Composition 439, the present disclosure provides a composition according to composition 438, wherein the population comprises definitive endoderm cells, primitive gut tube cells, posterior foregut cells, pancreatic endoderm cells, pancreatic endocrine precursor cells, immature beta cells, and/or pancreatic beta cells.

In another composition, Composition 440, the present disclosure provides a composition comprising the plurality of cells of composition 437 or the population of cells of composition 438 or 439 and at least one pharmaceutically acceptable excipient.

In another method, Method 441, the present disclosure provides a method for treating a pancreatic disease or disorder in a subject in need thereof, the method comprising: (a) obtaining or having obtained the population of lineage restricted progenitor cells or fully differentiated somatic cells of claim 438, wherein the lineage restricted progenitor cells or fully differentiated somatic cells comprise pancreatic endoderm cells, pancreatic endocrine precursor cells, immature beta cells, and/or pancreatic beta cells; and (b) administering the pancreatic endoderm cells, pancreatic endocrine cells, immature beta cells, and/or beta cells to the subject.

In another method, Method 442, the present disclosure provides a method for treating a pancreatic disease or disorder in a subject in need thereof, the method comprising (a) obtaining or having obtained the plurality of genetically modified cells of claim 437, wherein the plurality of genetically modified cells comprises stem cells; (b) differentiating the genetically modified cells into pancreatic endoderm cells, pancreatic endocrine precursor cells, immature beta cells, and/or pancreatic beta cells; and (c) administering the pancreatic endoderm cells, pancreatic endocrine precursor cells, immature beta cells, and/or pancreatic beta cells to the subject.

In another method, Method 443, the present disclosure provides a method as provided in Method 441 or 442, wherein the pancreatic disease or disorder is Type I diabetes, Type II diabetes or a pancreactomy.

In another method, Method 444, the present disclosure provides an in vitro method for preparing a universal donor cell, the method comprising delivering to a stem cell: (a) a RNA-guided nuclease and a gRNA targeting a target site in a thioredoxin interacting protein (TXNIP) gene locus; and (b) a vector comprising a nucleic acid, the nucleic acid comprising: (i) a nucleotide sequence encoding mesencephalic astrocyte derived neurotrophic factor (MANF) and a nucleotide sequence encoding HLA class I histocompatibility antigen, alpha chain E (HLA-E); (ii) a nucleotide sequence having sequence homology with a genomic region located left of the target site in the TXNIP gene locus; and (iii) a nucleotide sequence having sequence homology with a genomic region located right of the target site in the TXNIP gene locus, wherein (i) is flanked by (ii) and (iii); wherein the TXNIP gene locus is cleaved at the target site and the nucleic acid comprising the nucleotide sequences encoding MANF and HLA-E is inserted into the TXNIP gene locus, thereby disrupting the TXNIP gene; wherein the universal donor cell expresses MANF and HLA-E.

In another method, Method 445, the present disclosure provides an in vitro method according to Method 444, wherein disrupting the TXNIP gene comprises reducing or eliminating expression of TXNIP.

In another method, Method 446, the present disclosure provides an in vitro method according to Method 444 or 445, wherein the nucleotide sequence encoding HLA-E comprises a sequence encoding a HLA-E trimer, the HLA-E trimer comprising a B2M signal peptide fused to an HLA-G presentation peptide fused to a B2M membrane protein fused to HLA-E without its signal peptide.

In another method, Method 447, the present disclosure provides an in vitro method according to any one of Methods 444 to 446, wherein the nucleotide sequence of (b)(i) comprises the nucleotide sequence encoding MANF linked to a nucleotide sequence encoding P2A linked to the nucleotide sequence encoding HLA-E.

In another method, Method 448, the present disclosure provides an in vitro method according to any one of Methods 444 to 447, wherein the nucleotide sequence of (b)(i) comprises SEQ ID NO: 55.

In another method, Method 449, the present disclosure provides an in vitro method according to any one of Methods 444 to 448, wherein the nucleotide sequence of (b)(i) is operably linked to an exogenous promoter.

In another method, Method 450, the present disclosure provides an in vitro method according to Method 449, wherein the exogenous promoter is a CMV, EF1α, PGK, CAG, or UBC promoter.

In another method, Method 451, the present disclosure provides an in vitro method according to any one of Methods 444 to 450, wherein the nucleotide sequence of (b)(ii) consists essentially of SEQ ID NO: 42.

In another method, Method 452, the present disclosure provides an in vitro method according to any one of Methods 444 to 451, wherein the nucleotide sequence of (b)(iii) consists essentially of SEQ ID NO: 44.

In another method, Method 453, the present disclosure provides an in vitro method according to any one of Methods 444 to 452, wherein the RNA-guided nuclease and gRNA are present in a ratio of about 1:1 to about 1:10.

In another method, Method 454 the present disclosure provides an in vitro method according to any one of Methods 444 to 453, wherein the RNA-guided nuclease is a Cas9 nuclease.

In another method, Method 455, the present disclosure provides an in vitro method according to Method 454, wherein the Cas9 nuclease is linked to at least one nuclear localization signal.

EXAMPLES

The examples below describe generation and characterization of specific universal donor cells according to the present disclosure.

Example 1: Cell Maintenance and Expansion

Maintenance of hESC/hiPSCs. Human embryonic stem cells (hESC) and human induced pluripotent stem cells (hiPSCs) were maintained in StemFlex Complete (Life Technologies, A3349401) on BIOLAMININ 521 CTG (BioLamina Cat #CT521) or laminin 511 coated tissue culture plates. The cells were fed daily with StemFlex media. For plating of the cells as single cells, the cells were plated with 1% RevitaCell™ Supplement (100×) (ThermoFisher Cat #A2644501) in StemFlex on BIOLAMININ or laminin 511 coated plates. For passaging, 1% REVITACELL™ Supplement (100×) was added.

Single cell cloning of hPSCs. For single cell cloning, hPSCs (hESCs or hiPSCs) were fed with StemFlex Complete (Life Technologies, A3349401) with 1% RevitaCell™ Supplement (100×) (ThermoFisher Cat #A2644501). Following dissociation with ACCUTASE®, the cells were sorted as a single cell per well of a pre-coated plate. The 96 well plates were pre-coated with a 1:10 or a 1:20 dilution of BIOLAMININ 521 CTG (BioLamina Cat #CT521) in DPBS, calcium, magnesium (Life Technologies, 14040133) for 2 hours at 37° C. The WOLF FACS-sorter (Nanocellect) was used to sort single cells into the wells. The plates were pre-filled with 100-200 μL of StemFlex Complete with RevitaCell™ and 4 μL/mL of Recombinant Laminin iMatrix-511 E8 (AMSBIO, AMS.892 011). Three days post cell seeding, the cells were fed with fresh StemFlex and continued to be fed every other day with 100-200 μL of media. After 10 days of growth, the cells were fed daily with StemFlex until day 12-14. At this time, the plates were dissociated with ACCUTASE® and the collected cell suspensions were split 1:2 with half going into a new 96 well plate for maintenance and half going into a DNA extraction solution QuickExtract™ DNA Extraction Solution (Lucigen). Following DNA extraction, PCR was performed to assess presence or absence of desired gene edits at the targeted DNA locus. Sanger sequencing was used to verify desired edits.

Expansion of single cell derived hPSCs clones. For hESCs, successfully targeted clones were passaged from 96-well plates to 24-well plates using StemFlex and BIOLAMININ 521 or Recombinant Laminin iMatrix-511 E8. Following expansion in 24-well plates, the cells were passaged onto 6-well plates and a transition to KSR A10H10 media was begun the day after plating in StemFlex. The first day post plating, the cells were fed with a 50:50 mix of KSR A10H10 and StemFlex. The next day the cells were fed with 100% KSR A10H10. After 2 days in 100% KSR A10H10, the cells could be passaged using 10% XF in KSR A10H10. If the cells had not had 2 days of 100% KSR A10H10, the cells received BIOLAMININ 521 or Recombinant Laminin iMatrix-511 E8 to enable attachment and survival, followed by additional growth in KSR A10H10 and full transition to culture with laminin. Following the full transition to KSR A10H10, hESCs clones were passaged as described in Schulz et al. (2012) PLoS ONE 7(5): e37004.

For hiPSCs, cells are maintained in StemFlex Complete throughout the cloning and regular maintenance processes on BIOLAMININ-coated plates with RevitaCell™ at the passaging stages.

Example 2: Generation of B2M Knock Out (KO) with MANF-P2A-TNFAIP3-P2A-PD-L-1 Knock In (KI) Human Pluripotent Stem Cells This example describes the generation and characterization of specific universal donor cells with additional edits to improve survival (MANF) and immune evasion (TNFAIP3, also known as A20) according to the present disclosure. Cells were generated in which a transgene encoding MANF-P2A-TNFAIP3-P2A-PD-L-1 was inserted into the B2M gene locus, thereby knocking out the B2M gene.

B2M targeting gRNAs were designed for targeting exon 1 of the B2M coding sequence. These gRNAs had predicted low off-target scores based on sequence homology prediction using gRNA design software. The target sequences of the gRNAs are presented in Table 2. A gRNA comprises RNA sequence corresponding to the target DNA sequence.

TABLE 2

B2M gRNA Target Sequences

| Name | Target Sequence (5'-3') | SEQ ID NO: | PAM |
|---|---|---|---|
| B2M-1 gRNA (Exon 1_T12) | GCTACTCTCTCTTTCTGGCC | 1 | TGG |
| B2M-2 gRNA (Exon 1_T2) | GGCCGAGATGTCTCGCTCCG | 2 | TGG |
| B2M-3 gRNA (Exon 1_T8) | CGCGAGCACAGCTAAGGCCA | 3 | CGG |
| Exon 1_T1 | TATAAGTGGAGGCGTCGCGC | 4 | TGG |
| Exon 1_T3 | GAGTAGCGCGAGCACAGCTA | 5 | AGG |
| Exon 1_T4 | ACTGGACGCGTCGCGCTGGC | 6 | GGG |
| Exon 1_T5 | AAGTGGAGGCGTCGCGCTGG | 7 | CGG |
| Exon 1_T6 | GGCCACGGAGCGAGACATCT | 8 | CGG |
| Exon 1_T7 | GCCCGAATGCTGTCAGCTTC | 9 | AGG |
| Exon 1_T9 | CTCGCGCTACTCTCTCTTTC | 10 | TGG |
| Exon 1_T10 | TCCTGAAGCTGACAGCATTC | 11 | GGG |

TABLE 2-continued

B2M gRNA Target Sequences

| Name | Target Sequence (5'-3') | SEQ ID NO: | PAM |
|---|---|---|---|
| Exon 1_T11 | TTCCTGAAGCTGACAGCATT | 12 | CGG |
| Exon 1_T13 | ACTCTCTCTTTCTGGCCTGG | 13 | AGG |

Plasmid design to insert a transgene encoding MANF-P2A-TNFAIP3-P2A-PD-L-1 into the B2M locus was made such that the starting codon of B2M was removed after undergoing homology directed repair (HDR) to insert the transgene, nullifying any chance of partial B2M expression. Successful HDR resulted in the insertion of the 3 genes of MANF, TNFAIP3, and PD-L-1 (CD274) into the genome. The three coding sequences were linked by P2A peptide coding sequences to allow for expression of the three separate proteins from a single transcript. The coding sequence of MANF-P2A-TNFAIP3-P2A-PD-L-1 comprises the nucleotide sequence of SEQ ID NO: 52. FIG. 1 presents a schematic of the B2M-CAGGS-MANF-P2A-TNFAIP3-P2A-PD-L-1 donor plasmid and Table 3 identifies the elements and locations therein. The donor plasmid contained a CAGGS promoter (i.e., comprising a CMV enhancer, a chicken 3-actin promoter, and a chimeric intron) driven cDNA of MANF-P2A-TNFAIP3-P2A-PD-L-1 flanked by 800 base pair homology arms with identical sequence to the B2M locus around exon 1. The complete sequence of the plasmid comprises the nucleotide sequence of SEQ ID NO: 24.

TABLE 3

Elements of B2M-CAGGS-MANF-P2A-TNFAIP3-P2A-PD-L-1 Donor Plasmid

| Element | Location (size in bp) | SEQ ID NO: |
|---|---|---|
| Left ITR | 1-130 (130) | 14 |
| LHA-B2M | 145-944 (800) | 15 |
| CAGGS promoter | 973-2639 (1667) | 16 |
| MANF | 2684-3229 (546) | 17 |
| P2A | 3239-3295 (57) | 18 |
| TNFAIP3 | 3296-5665 (2370) | 19 |
| P2A | 5675-5731 (57) | 18 |
| PD-L-1 | 5732-6604 (873) | 20 |
| bGH poly(A) signal | 6622-6846 (225) | 21 |
| RHA-B2M | 6853-7652 (800) | 22 |
| Right ITR | 7694-7834 (141) | 23 |
| Entire plasmid | 10,181 bp | 24 |

Human ESCs were electroporated using the Neon Electroporator (Neon Transfection System ThermoFisher Cat #MIPK5000) with 4 μg of plasmid DNA per million hESCs, along with a ribonucleoprotein (RNP) mixture of Cas9 protein and B32M-2 gRNA (SEQ TD NO: 2). To form the RNP complex, gRNA and Cas9 were combined in one vessel with R-buffer (Neon Transfection System 100 μL Kit ThermoFisher Cat #MPK10096) to a total volume of 25-50 μL and incubated for 15 min at RT. Cells were dissociated using ACCUTASE®, then resuspended in DMVEM/F12 media (Gibco, cat #11320033), counted using an NC-200 (Chemometec) and centrifuged. A total of 1×106 cells were resuspended with the plasmid, the RNP complex, and R-buffer. This mixture was then electroporated. Following electroporation, the cells were pipetted out into an Eppendorf tube or a well of a 6-well plate filled with StemFlex media with RevitaCell™. This cell suspension was then plated into pre-coated tissue culture dishes. Cells were cultured in a normoxia incubator (37° C., 800 $CO_2$).

Seven to ten days post electroporation, the cells were enriched for PD-L-1 expressing cells via magnetic assisted cell sorting (MACS) using anti-mouse IgG Dynabeads (ThermoFisher, CELLection™ Pan Mouse IgG Kit, 1153D. These enriched cells (L1V008 cell line) represented a bulk KI population that was highly PD-L-1 positive. The enriched cells were then FACS-sorted for PD-L-1 surface expression using the WOLF FACS-sorter (Nanocellect) into BIOLAMININ 521 CTG coated 96-well plates with StemFlex and RevitaCell™. To detect the PD-L-1 surface expression, anti-PD-L-1 fluorescent antibodies were used (see Table 4). For FACS-sorting, unedited cells served as a negative control. PD-L-1 positive cells were selected for sorting and single cell cloning.

TABLE 4

Antibodies for Flow Cytometry

| Antigen | Clone | Fluorophore | Manufacturer | Catalog # |
|---|---|---|---|---|
| B2M | 2M2 | PE | Biolegend | 316305 |
| HLA-ABC | W6/32 | Alexa 488 | Biolegend | 311415 |
| mIgG1 kappa | N/A | PE | BD Bioscience | 555749 |
| PD-L-1 | B7-H1 | Alexa-488 | ThermoFisher | 53-5983-42 |
| HLA-E | 3D12 | PE | ThermoFisher | 12-9953-42 |

Plated single cells were grown in a normoxia incubator (37° C., 8% $CO_2$) with every other day media changes until colonies were large enough to be re-seeded as single cells. When confluent, samples were split for maintenance and genomic DNA extraction. Correctly targeted clones were identified via PCR for the MANF-TNFAIP3-PD-L-1 KI insertion using primers that amplify from outside the plasmid homology arms at the site of insertion into the B2M locus, enabling amplification of the KI integrated DNA only. The B2M KO state of clones was confirmed via PCR and Sanger sequencing. The correct KI and KO clones were expanded in increasing tissue culture formats until a population size of 30 million cells was reached.

Example 3: Generation of B2M KO with MANF-P2A-TNFAIP3-P2A-PD-L-1 KI and CIITA KO with CD39 KI Human Pluripotent Stem Cells Cells will be generated in which a transgene encoding MANF-P2A-TNFAIP3-P2A-PD-L-1 is inserted into the B2M gene locus and a transgene encoding CD39 is inserted into the CIITA gene locus, thereby knocking out the B2M and CIITA genes.

Human pluripotent stem cells will be electroporated essentially as described above in Example 2 with the B2M-CAGGS-MANF-P2A-TNFAIP3-P2A-PD-L-1 donor plasmid (SEQ ID NO: 24, Table 3) and an RNP comprising Cas9 and B2M-2 gRNA (SEQ ID NO: 2). Seven to ten days post electroporation, the cells will be enriched for PD-L-1 expressing (positive) cells via MACS using Miltenyi reagents or ThermoFisher reagents. After the enriched PD-L-1 positive population is expanded, the cells will be electroporated essentially as described above in Example 2 with a CIITA-CAGGS-CD39 donor plasmid, as detailed below in Table 5, and an RNP comprising Cas9 and a gRNA directed to exon 3 of CIITA, e.g., CIITA Ex3_T6 gRNA (target sequence is 5'-GGTCCATCTGGTCATAGAAG-3' SEQ ID NO: 25; PAM is TGG).

Figure 2:
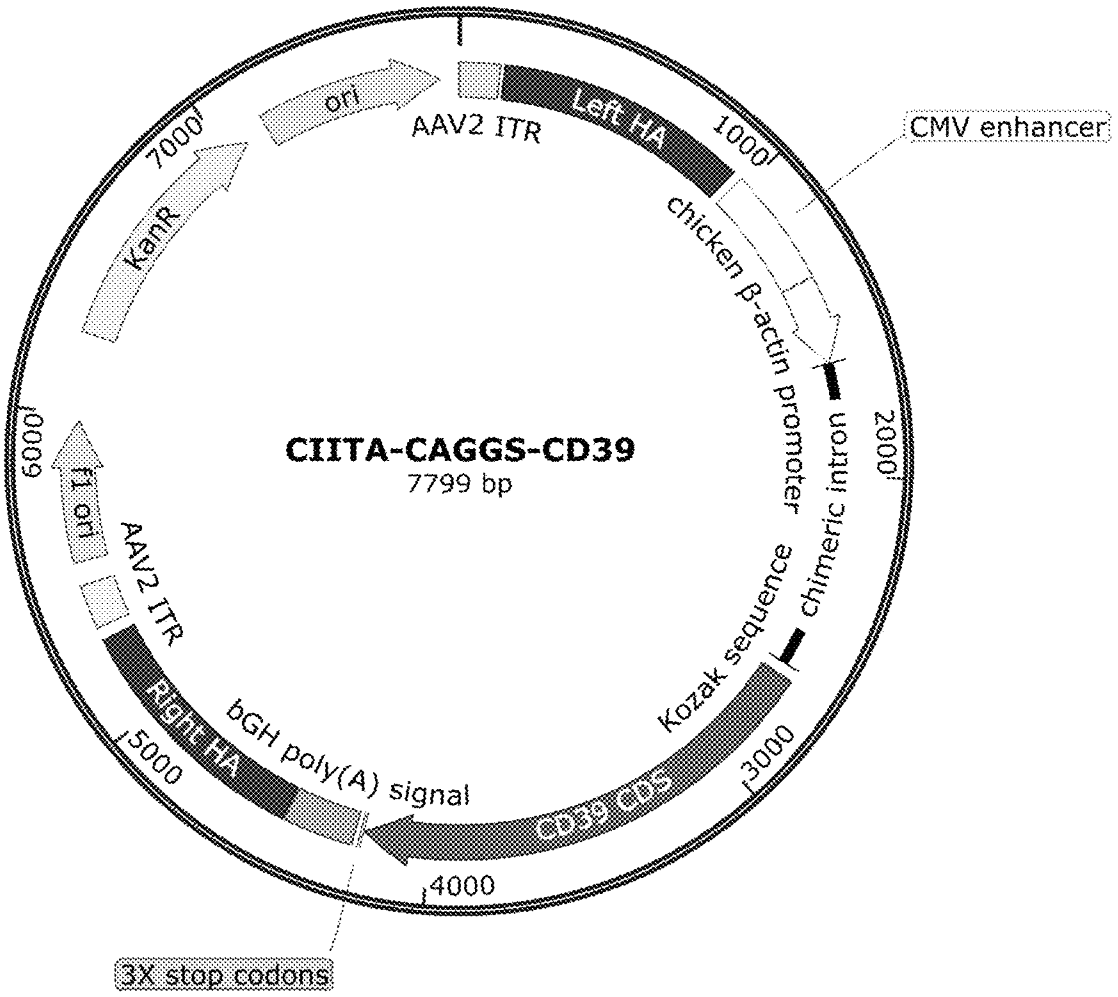
FIG. 2 presents the plasmid map of CIITA-CAGGS-CD39 donor vector.

FIG. 2 presents a schematic of the CIITA-CAGGS-CD39 donor plasmid and Table 5 identifies the elements and locations therein. The CIITA-CAGGS-CD39 donor plasmid comprises a CAGGS promoter (comprising a CMV enhancer, a chicken j-actin promoter, and a chimeric intron) to drive expression of cDNA of CD39 flanked by 800 base pair homology arms with identical sequence to the CIITA locus around exon 3. The complete sequence of the plasmid comprises the nucleotide sequence of SEQ ID NO: 29.

TABLE 5

Elements of CIITA-CAGGS-CD39 Donor Plasmid

| Element | Location (size in bp) | SEQ ID NO: |
|---|---|---|
| Left ITR | 1-130 (130) | 14 |
| LHA-CIITA | 145-944 (800) | 26 |
| CAGGS promoter | 973-2639 (1667) | 16 |
| CD39 | 2684-4213 (1530) | 27 |
| bGH poly(A) signal | 4240-4464 (225) | 21 |
| RHA-CIITA | 4471-5270 (800) | 28 |
| Right ITR | 5312-5452 (141) | 23 |
| Entire plasmid | 7799 | 29 |

Seven to ten days post electroporation, the cells will be enriched for PD-L-1 and/or CD39 expressing cells via MACS using Miltenyi reagents (Anti-Mouse IgG MicroBeads Cat #130-048-401, LS Columns Cat #130-042-401, and MidiMACS Separator Cat #130-042-302) or ThermoFisher reagents (DynaMag™-15 Magnet Cat #12301D, CELLection™ Pan Mouse IgG Kit Cat #11531D, Dynabeads™ Pan Mouse IgG Cat #11042). Post PD-L-1 and/or CD39 enrichment, the enriched cells will be FACS sorted for PD-L-1 and/or CD39 expression using the WOLF FACS-sorter (Nanocellect) into BIOLAMININ 521 CTG coated 96-well plates with StemFlex and RevitaCell™ with gating set for PD-L-1 and CD39 double positive cells. For FACS-sorting, unedited cells served as a negative control. Positive cells will be selected for sorting and single cell cloning.

Plated single cells will be grown in a normoxia incubator (37° C., 8% $CO_2$) with every other day media changes until colonies were large enough to be re-seeded as single cells. When confluent, samples will be split for maintenance and genomic DNA extraction. Correctly targeted clones will be identified via PCR for the PD-L-1 KI insertion and the CD39 KI insertion using primers that amplify a region from outside the plasmid homology arms at each insertion site, enabling amplification of the KI integrated DNA only. The B2M and CIITA KO state of clones will be confirmed via PCR and Sanger sequencing.

Example 4: Generation of B2M KO with CD39-P2A-PD-L-1 KI Human Pluripotent Stem Cells Cells were generated in which a transgene encoding CD39-P2A-PD-L-1 was inserted into the B2M gene locus, thereby knocking out the B2M gene.

Human pluripotent stem cells were electroporated essentially as described above in Example 2 with a B2M-CAGGS-CD39-P2A-PD-L-1 donor plasmid, as detailed below in Table 6, and an RNP comprising Cas9 and a B2M-2 gRNA (SEQ ID NO: 2).

Figure 3:
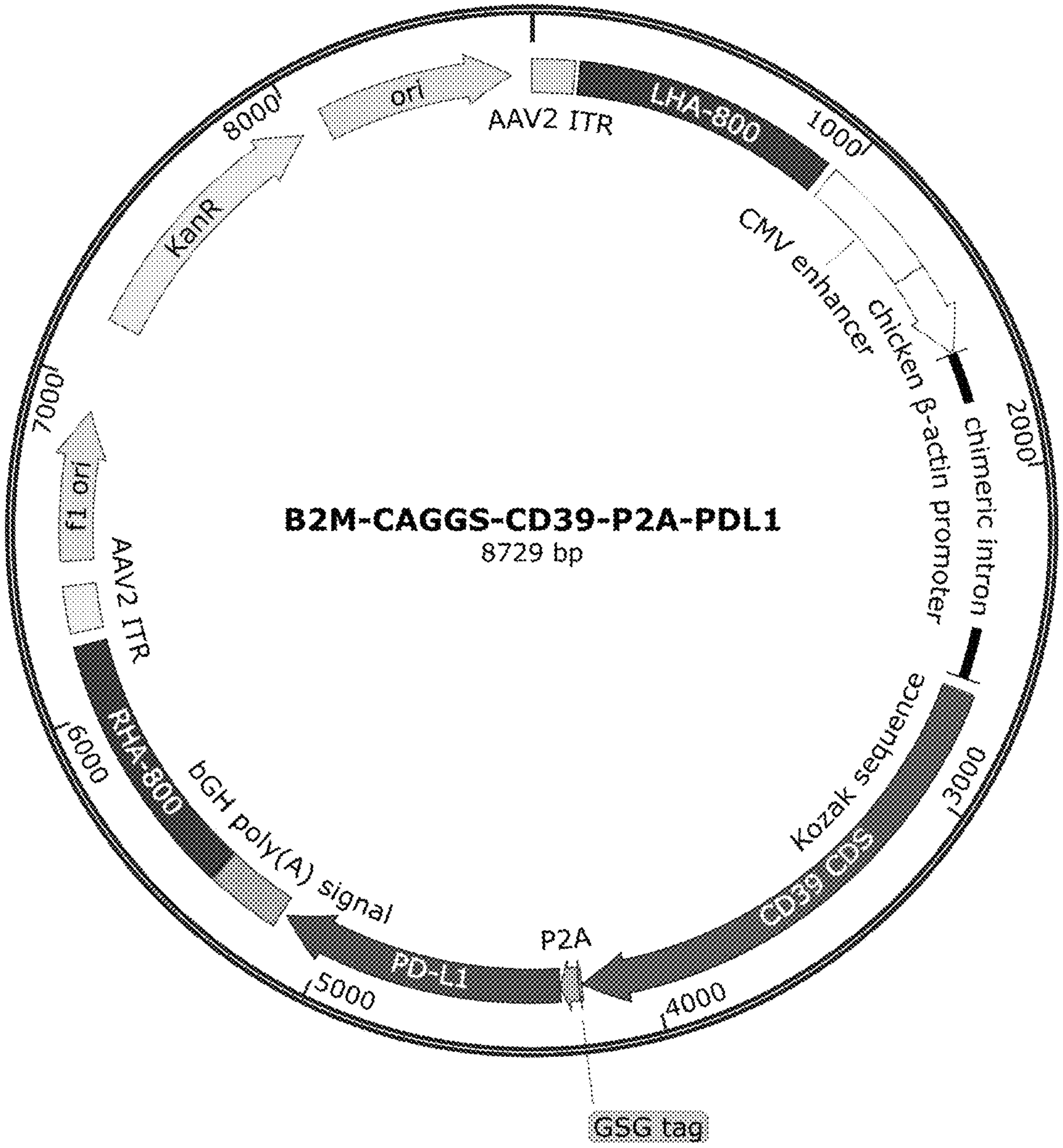
FIG. 3 presents the plasmid map of B2M-CAGGS-CD39-P2A-PD-L-1 donor vector.

FIG. 3 presents a schematic of the B2M-CAGGS-CD39-P2A-PD-L-1 donor plasmid and Table 6 identifies the elements and locations therein. The B2M-CAGGS-CD39-P2A-PD-L-1 donor plasmid comprises a CAGGS promoter (comprising a CMV enhancer, a chicken 3-actin promoter, and a chimeric intron) to drive expression of cDNA of CD39-P2A-PD-L-1 (SEQ ID NO: 53) flanked by 800 base pair homology arms with identical sequence to the B2M locus around exon 1. The complete sequence of the B2M-CAGGS-CD39-P2A-PD-L-1 donor plasmid comprises the nucleotide sequence of SEQ ID NO: 30.

TABLE 6

Elements of B2M-CAGGS-CD39-P2A-PD-L-1 Donor Plasmid

| Element | Location (size in bp) | SEQ ID NO: |
|---|---|---|
| Left ITR | 1-130 (130) | 14 |
| LHA-B2M | 145-944 (800) | 15 |
| CAGGS promoter | 973-2639 (1667) | 16 |
| CD39 | 2684-4213 (1530) | 27 |
| P2A | 4223-4279 (57) | 18 |
| PD-L-1 | 4280-5152 (873) | 20 |
| bGH poly(A) signal | 5170-5394 (225) | 21 |
| RHA-B2M | 5401-6200 (800) | 22 |
| Right ITR | 6242-6382 (141) | 23 |
| Entire plasmid | 8729 bp | 30 |

Seven to ten days post electroporation, the cells were enriched for PD-L-1 expressing cells via magnetic assisted cell sorting (MACS) using anti-mouse IgG Dynabeads (ThermoFisher, CELLection™ Pan Mouse IgG Kit, 11531D. These enriched cells represented a bulk KI population that was highly PD-L-1 positive. The enriched cells were then FACS-sorted for PD-L-1 surface expression using the WOLF FACS-sorter (Nanocellect) into BIOLAMININ 521 CTG coated 96-well plates with StemFlex and RevitaCell™. To detect the PD-L-1 surface expression, anti-PD-L-1 fluorescent antibodies were used (see Table 4). For FACS-sorting, unedited cells served as a negative control. PD-L-1 positive cells were selected for sorting and single cell cloning.

Plated single cells were grown in a normoxia incubator (37° C., 8% $CO_2$) with every other day media changes until colonies were large enough to be re-seeded as single cells. When confluent, samples were split for maintenance and genomic DNA extraction. Correctly targeted clones were identified via PCR for the CD39-PD-L-1 KI insertion using primers that amplify from outside the plasmid homology arms at the site of insertion into the B2M locus, enabling amplification of the KI integrated DNA only. The B2M KO state of clones was confirmed via PCR and Sanger sequencing. The correct KI and KO clones (L1V017 cell line) were expanded in increasing tissue culture formats until a population size of 30 million cells was reached.

Example 5: Generation of B2M KO with MANF-P2A-TNFAIP3-P2A-PD-L-1 KI and B2M KO with CD39-P2A-PD-L-1 KI Human Pluripotent Stem Cells Cells will be generated in which a transgene encoding MANF-P2A-TNFAIP3-P2A-PD-L-1 is inserted into the B2M gene locus at a first target site and a transgene encoding CD39-P2A-PD-L-1 is inserted into another location in the B2M gene locus at a second target site, thereby knocking out the B2M gene.

Human pluripotent stem cells will be electroporated essentially as described above in Example 2 with the B2M-CAGGS-MANF-P2A-TNFAIP3-P2A-PD-L-1 donor plasmid (SEQ ID NO: 24, Table 3) and an RNP comprising Cas9 and B2M-2 gRNA (SEQ ID NO: 3). After PD-L-1 enrichment and expansion, the cells will be electroporated with a B2M-CAGGS-CD39-P2A-PD-L-1 donor plasmid (SEQ ID NO: 30. Table 6), and an RNP comprising Cas9 and a second B2M gRNA chosen from SEQ ID NO: 1 or 3-13 (see Table 2 above). The cells will be enriched, expanded, selected, and characterized as described above.

Example 6: Generation of B2M KO with TNFAIP3-P2A-PD-L-1 KI and TXNIP KO with MANF-P2A-HLA-E KI Human Pluripotent Stem Cells ("X1" Cells)

Cells were generated in which a transgene encoding TNFAIP3-P2A-PD-L-1 was inserted into the B2M gene locus and a transgene encoding MANF-P2A-HLA-E was inserted into a TXNIP, thereby knocking out the B2M and TXNIP genes.

Figure 4:
FIG. 4 presents the plasmid map of B2M-CAGGS-TNFAIP3-P2A-PD-L-1 donor vector.

Human pluripotent stem cells were electroporated essentially as described above in Example 2 with a B2M-CAGGS-TNFAIP3-P2A-PD-L-1 donor plasmid (see below) and an RNP comprising Cas9 and B2M-2 gRNA (SEQ ID NO: 2). FIG. 4 presents a schematic of the B2M-CAGGS-TNFAIP3-P2A-PD-L-1 donor plasmid (also called X1-1 cassette) and Table 7 identifies the elements and locations therein. The B2M-CAGGS-TNFAIP3-P2A-PD-L-1 donor plasmid comprises a CAGGS promoter (comprising a CMV enhancer, a chicken 3-actin promoter, and a chimeric intron) to drive expression of cDNA of TNFAIP3-P2A-PD-L-1 (SEQ ID NO: 54) flanked by 800 base pair homology arms with identical sequence to the B2M locus around exon 1. The complete sequence of the B2M-CAGGS-TNFAIP3-P2A-PD-L-1 donor plasmid comprises the nucleotide sequence of SEQ ID NO: 31.

TABLE 7

Elements of B2M-CAGGS-TNFAIP3-P2A-PD-L-1 Donor Plasmid

| Element | Location (size in bp) | SEQ ID NO: |
|---|---|---|
| Left ITR | 1-130 (130) | 14 |
| LHA-B2M | 145-944 (800) | 15 |
| CAGGS promoter | 973-2639 (1667) | 16 |
| TNFAIP3 | 2684-5053 (2370) | 19 |
| P2A | 5063-5119 (57) | 18 |
| PD-L-1 | 5120-5992 (873) | 20 |
| bGH poly(A) signal | 6010-6234 (225) | 21 |
| RHA-B2M | 6241-7040 (800) | 22 |
| Right ITR | 7082-7222 (141) | 23 |
| Entire plasmid | 9569 bp | 31 |

Seven to ten days post electroporation, the cells were enriched for PD-L-1 expressing cells via MACS essentially as described in Example 2. Post PD-L-1 enrichment, the enriched cells were electroporated with a TXNIP-CAGGS-MANF-P2A-HLA-E donor plasmid, as detailed below, and an RNP comprising Cas9 and a gRNA targeting exon 1 of the TXNIP gene (i.e., TXNIP_Exon 1_T5 gRNA, SEQ ID NO: 37). Table 8 presents the target sequences of additional gRNAs that target exon 1 or exon 2 of the TXNIP gene. These gRNAs had predicted low off-target scores based on sequence homology prediction using gRNA design software.

TABLE 8

| TXNIP gRNA Target Sequences | | | |
|---|---|---|---|
| Name | Target Sequence (5'-3') | SEQ ID NO: | PAM |
| TXNIP_Exon 1_T1 | GAAGCGTGTCTTCATAGCGC | 32 | AGG |
| TXNIP_Exon 1_T21 | TTACTCGTGTCAAAGCCGTT | 33 | AGG |
| TXNIP_Exon 1_T22 | TGTCAAAGCCGTTAGGATCC | 34 | TGG |
| TXNIP_Exon 1_T23 | GCCGTTAGGATCCTGGCTTG | 35 | CGG |
| TXNIP_Exon 1_T25 | GCGGAGTGGCTAAAGTGCTT | 36 | TGG |
| TXNIP_Exon 1_T5 | TCCGCAAGCCAGGATCCTAA | 37 | CGG |
| TXNIP_Exon 2_T4 | GTTCGGCTTTGAGCTTCCTC | 38 | AGG |
| TXNIP_Exon 2_T2 | GAGATGGTGATCATGAGACC | 39 | TGG |
| TXNIP_Exon 2_T1 | TTGTACTCATATTTGTTTCC | 40 | AGG |
| TXNIP_Exon 2_T3 | AACAAATATGAGTACAAGTT | 41 | CGG |

Figure 5:
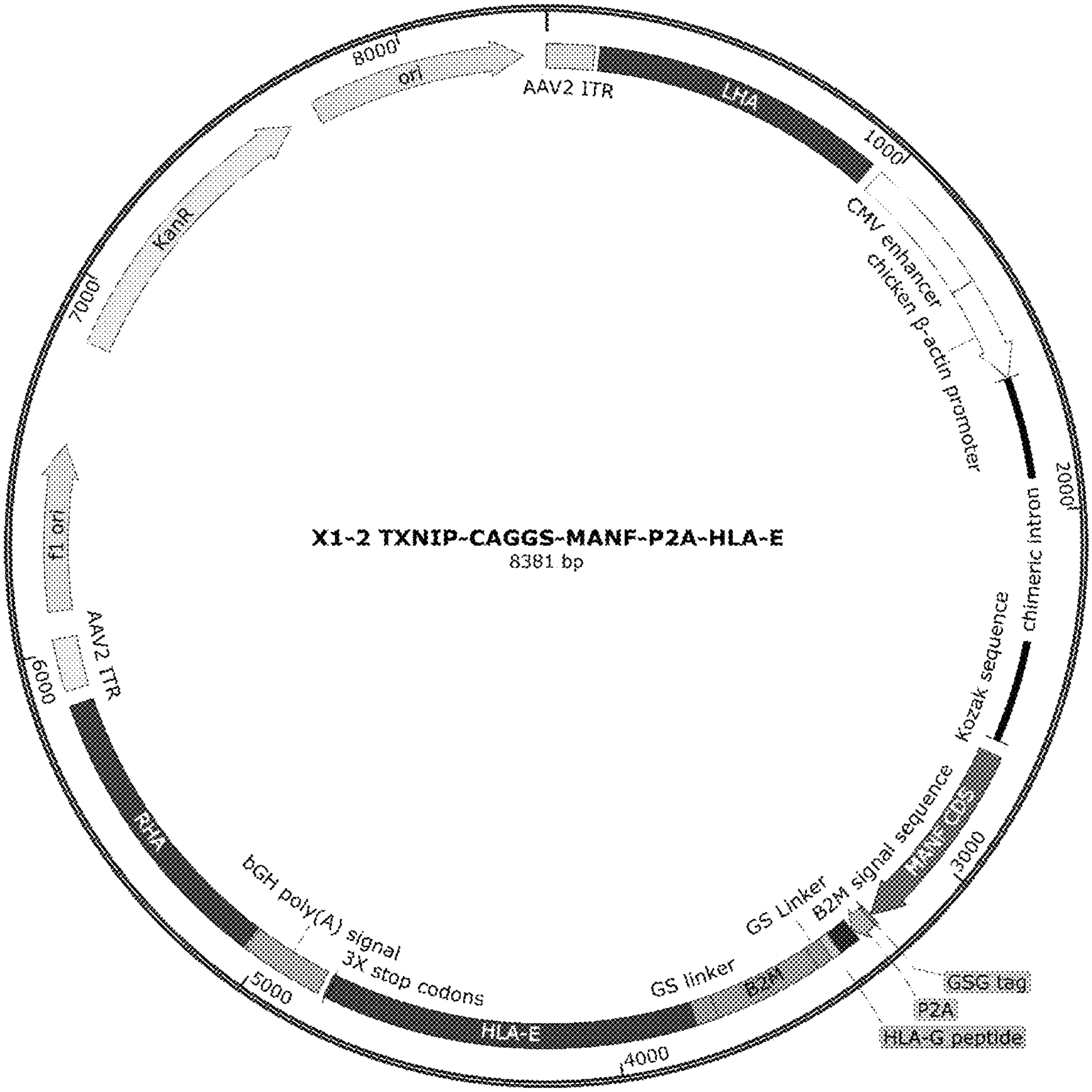
FIG. 5 presents the plasmid map of TXNIP-CAGGS-MANF-P2A-HLA-E donor vector.

FIG. 5 presents a schematic of the TXNIP-CAGGS-MANF-P2A-HLA-E donor plasmid (also called X1-2 cassette) and Table 9 identifies the elements and locations therein. The TXNIP-CAGGS-MANF-P2A-HLA-E donor plasmid comprises a CAGGS promoter (comprising a CMV enhancer, a chicken 3-actin promoter, and a chimeric intron) to drive expression of cDNA of MANF-P2A-HLA-E (SEQ ID NO: 55) flanked by 800 base pair homology arms with identical sequence to the TXNIP locus around exon 1. The HLA-E sequence (SEQ ID NO: 43) encodes a HLA-E trimer, which comprises a B2M signal peptide fused to an HLA-G presentation peptide fused to a GS linker fused to the B2M membrane protein fused to a GS linker fused to the HLA-E protein without its signal peptide. This trimer design has been previously published (Gornalusse et al. (2017) Nat. Biotechnol. 35(8): 765-772). The complete sequence of the TXNIP-CAGGS-MANF-P2A-HLA-E donor plasmid comprises the nucleotide sequence of SEQ ID NO: 45.

TABLE 9

| Elements of TXNIP-CAGGS-MANF-P2A-HLA-E Donor Plasmid | | |
|---|---|---|
| Element | Location (size in bp) | SEQ ID NO: |
| Left ITR | 1-130 (130) | 14 |
| LHA-TXNIP | 145-944 (800) | 42 |
| CAGGS promoter | 973-2639 (1667) | 16 |
| MANF | 2684-3229 (546) | 17 |
| P2A | 3239-3295 (57) | 18 |
| HLA-E | 3296-4795 (1500) | 43 |
| bGH poly(A) signal | 4822-5046 (225) | 21 |
| RHA-TXNIP | 5053-5852 (800) | 44 |
| Right ITR | 5894-6034 (141) | 23 |
| Entire plasmid | 8381 bp | 45 |

Seven to ten days post electroporation, the cells were enriched for HLA-E expressing cells via MACS using Miltenyi reagents or ThermoFisher reagents. These enriched cells were then FACS sorted using the WOLF FACS-sorter (Nanocellect) into BIOLAMININ 521 CTG coated 96-well plates with StemFlex and RevitaCell™ with gating set for PD-L-1 and HLA-E double positive cells. To detect the PD-L-1 surface expression and HLA-E surface expression, anti-PD-L-1 and anti-HLA-E fluorescent antibodies were used (see Table 4). For FACS-sorting, unedited cells served as a negative control. PD-L-1 and HLA-E double positive cells (L1V028 cell line) were selected for sorting and single cell cloning.

Plated single cells were grown in a normoxia incubator (37° C., 8% $CO_2$) with every other day media changes until colonies were large enough to be re-seeded as single cells. When confluent, samples were split for maintenance and genomic DNA extraction. Correctly targeted clones were identified via PCR for the PD-L-1 KI insertion and the HLA-E KI insertion using primers that amplify from outside the plasmid homology arms at each insertion site, thereby enabling amplification of the KI integrated DNA only. The B2M and TXNIP KO state of clones were confirmed via PCR and Sanger sequencing. The correct KI and KO clones were expanded in increasing tissue culture formats until a population size of 30 million cells was reached. These cells are referred to as X1 cells hereafter.

Example 7: Generation of B2M KO with TNFAIP3-P2A-PD-L-1 KI, TXNIP KO with MANF-P2A-HLA-E KI, and CIITA KO with CD39 KI Human Pluripotent Stem Cells Cells were generated in which a transgene encoding TNFAIP3-P2A-PD-L-1 was inserted into the B2M gene locus, a transgene encoding MANF-P2A-HLA-E was inserted into the TXNIP gene locus, and a transgene encoding CD39 was inserted into the CIITA gene locus, thereby knocking out the B2M, TXNIP, and CIITA genes.

Human pluripotent stem cells were electroporated essentially as described above in Example 2 with the B2M-CAGGS-TNFAIP3-P2A-PD-L-1 donor plasmid (SEQ ID NO: 31, Table 7) and an RNP comprising Cas9 and B2M-2 gRNA (SEQ ID NO: 2). Seven to ten days post electroporation, the cells were enriched for PD-L-1 expressing (positive) cells via MACS essentially as described in Example 2. After the enriched PD-L-1 positive population is expanded, the cells were electroporated essentially as described above in Example 2 with the TXNIP-CAGGS-MANF-P2A-HLA-E donor plasmid (SEQ ID NO: 45, Table 9) and an RNP comprising Cas9 and TXNIP_Exon 1_T5 gRNA (SEQ ID NO: 37). After enrichment for HLA-E positive cells and expansion of PD-L-1 and HLA-E cells, the double positive cells were used for further insertion of CD39 into the CIITA locus.

The CIITA-CAGGS-CD39 donor plasmid (SEQ ID NO: 29, Table 5) was introduced along with the ribonucleoprotein (RNP) complex made up of the CIITA targeting gRNA (CIITA Ex3_T6 gRNA (SEQ ID NO: 25)) and Cas9 protein. In particular, a clone of X1, described in Example 7, was transfected with the CIITA-CAGGS-CD39 donor plasmid along with the RNP made up of the CIITA targeting gRNA (CIITA Ex3_T6 gRNA (SEQ ID NO: 25)) and Cas9 protein. Per 2 million of hESC cells, 4 μg of plasmid DNA was delivered along with the RNP via electroporation. Electroporation was carried out in hESC cells using the Neon Electroporator with the RNP mixture of Cas9 protein (Biomay) and guide RNA (Biospring) at a molar ratio of 5:1 (gRNA: Cas9) with absolute values of 125 pmol Cas9 and 625 pmol gRNA per 2 million cells. To form the RNP complex, gRNA and Cas9 were combined in one vessel with R-buffer (Neon Transfection Kit) to a total volume of 25-50 μL and incubated for 15 min at room temperature (RT). Cells were dissociated using ACCUTASE®, then resuspended in StemFlex media, counted using an NC-200 (Chemometec) and centrifuged. A total of 2×106 cells were resuspended with the RNP complex and R-buffer was added to a total volume of ~115 μL. This mixture was then electroporated with 3 pulses for 30 ms at 1000 V. Two electroporations were performed. Following electroporation, the cells were pipetted out into a well of a 6 well plate filled with StemFlex media with RevitaCell and laminin 511. The plates were pre-coated with BIOLAMININ 521 CTG at 1:10 dilution. Cells were cultured in a normoxia incubator (37° C., 8% $CO_2$).

Figure 6:
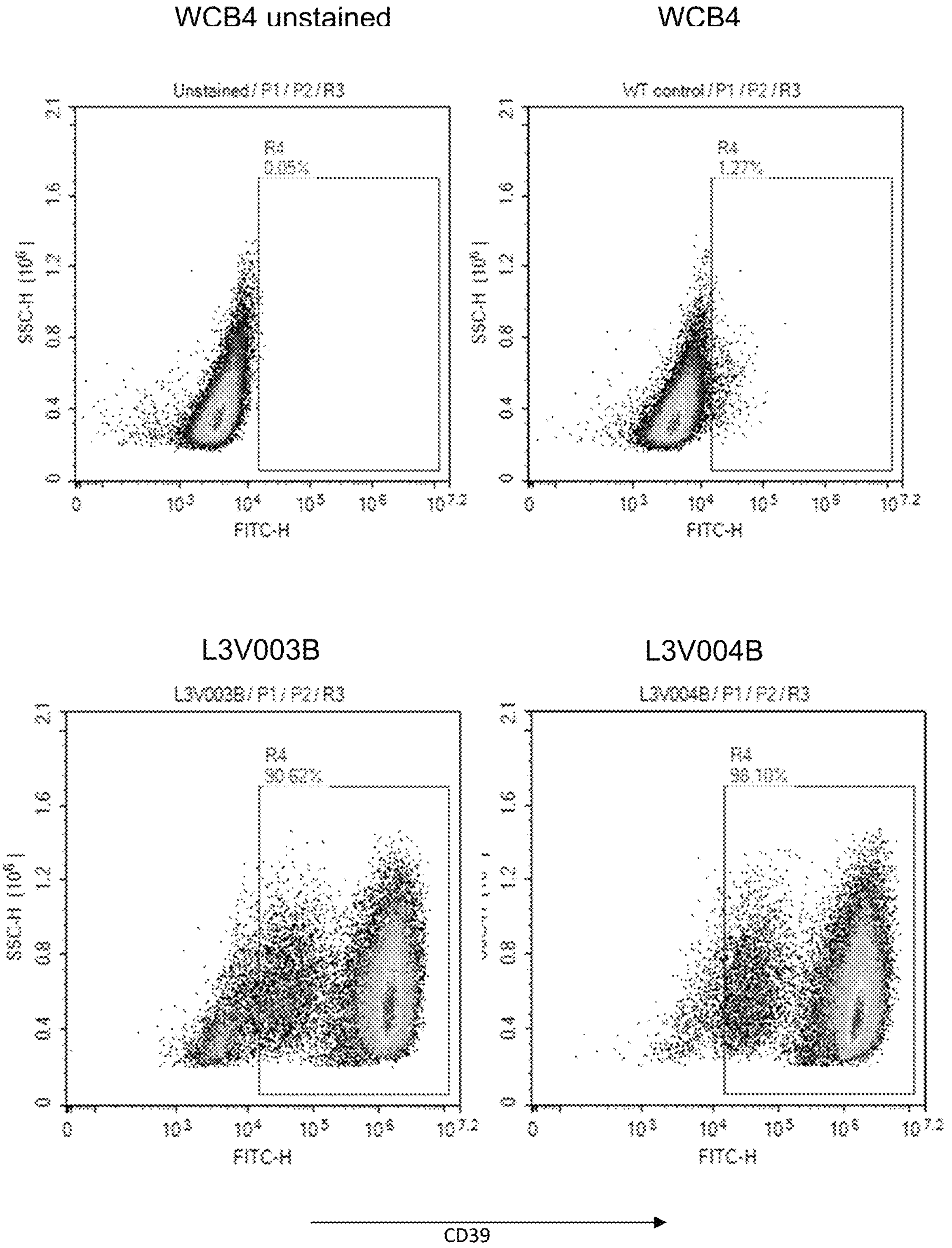
FIG. 6. shows flow cytometry of L3V003B and L3V004B cell lines for CD39 expression.

Two days post electroporation, the cells were enriched for transfected CD39 expressing cells using an antibody against CD39 via fluorescence assisted cell sorting (FACS). These enriched cells were then expanded and sorted again 7 to 10 days post electroporation to enrich for CD39 knock in. These enriched cells, generated from the clone of X1, represent a bulk transfected population of CD39 positive cells ("L3V003B," also referred to as "X4"). A guide targeting the TGF-β2 gene was also used to edit the clone of X1 having the CD39 KI to generate a bulk transfected population of CD39 positive cells and TGF-β2 negative cells ("L3V004B," also referred to as "X4+TGF-β2 KO." These populations were assessed for CD39 expression by flow cytometry, however the overall percentage was lower than expected so the bulk cells were enriched a third time for CD39 expressing cells and showed >90% CD39 expression by flow cytometry (FIG. 6).

Example 8: Generation of B2M KO with TNFAIP3-P2A-PD-L-1 KI, TXNIP KO with MANF-P2A-HLA-E KI, and B2M KO with CD39-P2A-PD-L-1 KI Human Pluripotent Stem Cells Cells will be generated in which a transgene encoding TNFAIP3-P2A-PD-L-1 is inserted into the B2M gene locus at a first target site, a transgene encoding MANF-P2A-HLA-E is inserted into the TXNIP gene locus, and a transgene encoding CD39-P2A-PD-L-1 is inserted into another location in the B2M gene locus at a second target site, thereby knocking out the B2M and TXNIP genes.

Human pluripotent stem cells will be electroporated essentially as described above in Example 2 with the B2M-CAGGS-TNFAIP3-P2A-PD-L-1 donor plasmid (SEQ ID NO: 31, Table 7) and an RNP comprising Cas9 and B2M-2 gRNA (SEQ ID NO: 2). Seven to ten days post electroporation, the cells will be enriched for PD-L-1 expressing (positive) cells via MACS using Miltenyi reagents or ThermoFisher reagents. After the enriched PD-L-1 positive population is expanded, the cells will be electroporated essentially as described above in Example 2 with the TXNIP-CAGGS-MANF-P2A-HLA-E donor plasmid (SEQ ID NO: 45, Table 9) and an RNP comprising Cas9 and TXNIP_Exon 1_T5 gRNA (SEQ ID NO: 37). After enrichment for HLA-E positive cells and expansion of PD-L-1 and HLA-E cells, the double positive cells will be electroporated with a B2M-CAGGS-CD39-P2A-PD-L-1 donor plasmid (SEQ ID NO: 30, Table 6) and an RNP comprising Cas9 and a B2M gRNA chosen from SEQ ID NO: 1 or 3-13. The cells will be enriched for CD39 positive cells, expanded, and selected for PD-L-1, HLA-E, and CD39 triple positive cells, which will be characterized as described above.

In some embodiments, in the B2M-CAGGS-CD39-P2A-PD-L-1 donor plasmid, the cDNA of CD39-P2A-PD-L-1 is flanked by 800 base pair homology arms with sequence identity to genomic sequence on either side of the second B2M target site.

Example 9: G-Band Karyotype Analysis of Edited Clones 1 million edited ES cells (see Examples 2 and 6) were passaged into a T-25 culture flask with culture media (DMEM/F12+10% Xeno-free KSR with 10 ng/mL Activin and 10 ng/mL Heregulin). After culturing overnight, three T25 culture flasks were shipped to Cytogenetics Laboratory (Cell Line Genetics, Inc.) for Karyotyping analysis; FISH analysis for Chromosome 1, 12, 17, 20; and array comparative genomic hybridization (aCGH) analysis with standard 8×60K array. The G-banding results of selected B2M KO with MANF-TNFAIP3(A20)-PD-L-1 KI clones (L1V008 cell lines; Example 2) and TXNIP KO with MANF-P2A-HLA-E KI/B2M KO with TNFAIP3(A20)-P2A-PD-L-1 KI clones (L1V028 cell lines; Example 6) are shown in Table 10.

TABLE 10

G-band Karyotyping Results

| Cell Line | Type | Passage | Karyotyping analysis | FISH analysis | aCGH array analysis |
|---|---|---|---|---|---|
| L1V008-C1 | B2M KO with MANF-TNFAIP3(A20)-PD-L-1 KI | P34 | Normal | 3.5% Trisomy 1qp32.3 | PASS |
| L1V008-C3 | B2M KO with MANF-TNFAIP3(A20)-PD-L-1 KI | P34 | Normal | Normal | PASS |
| L1V028-C2 | TXNIP KO with MANF-P2A-HLA-E KI; B2M KO with A20-P2A-PD-L-1 KI | P37 | Normal | Normal | PASS |
| L1V028-C3 | TXNIP KO with MANF-P2A-HLA-E KI; B2M KO with A20-P2A-PD-L-1 KI | P36 | Normal | 8.5% duplication of MDM4 | PASS |
| L1V028-C17 | TXNIP KO with MANF-P2A-HLA-E KI; B2M KO with A20-P2A-PD-L-1 KI | P36 | Normal | Normal | PASS |
| L1V028-C18 | TXNIP KO with MANF-P2A-HLA-E KI; B2M KO with A20-P2A-PD-L-1 KI | P38 | Normal | Normal | PASS |
| L1V028-C21 | TXNIP KO with MANF-P2A-HLA-E KI; B2M KO with A20-P2A-PD-L-1 KI | P38 | Normal | 8.5% duplication of MDM4 | PASS |

TABLE 10-continued

| G-band Karyotyping Results | | | | | |
|---|---|---|---|---|---|
| Cell Line | Type | Passage | Karyotyping analysis | FISH analysis | aCGH array analysis |
| L1V028-C24 | TXNIP KO with MANF-P2A-HLA-E KI; B2M KO with A20-P2A-PD-L-1 KI | P36 | Normal | Normal | PASS |

Example 10: Differentiation of Edited Human Embryonic Stem Cells to Pancreatic Endoderm Cells (PECs)

Maintenance of edited human embryonic stem cells (ES). The edited human pluripotent stem cells at various passages (P38-42) were maintained by seeding at 33,000 cells/cm$^2$ for a 4-day passage or 50,000 cells/cm$^2$ for a 3-day passage with hESM medium (DMEM/F12+10% KSR+10 ng/mL Activin A and 10 ng/mL Heregulin) and final 10% human AB serum.

Aggregation of edited human embryonic stem cells for PECs differentiation. The edited cells were dissociated into single cells with ACCUTASE® and then centrifuged and resuspended in 2% StemPro (Cat #A1000701, Invitrogen, CA) in DMEM/F12 medium at 1 million cells per ml, and total 350-400 million of cells were seeded in one 850 cm$^2$ roller bottle (Cat #431198, Corning, N.Y.) with rotation speed at 8 RPM±0.5 RPM for 18-20 hours before differentiation. The aggregates from edited human pluripotent stem cells were differentiated into pancreatic lineages using in roller bottles as described in Schulz et al. (2012) PLoS ONE 7(5): e37004. Aggregates from edited human pluripotent stems cells were differentiated into pancreatic lineages as described in Rezania et al. (2014) Nat. Biotechnol. 32(11): 1121-1133 and US20200208116.

Figure 7:
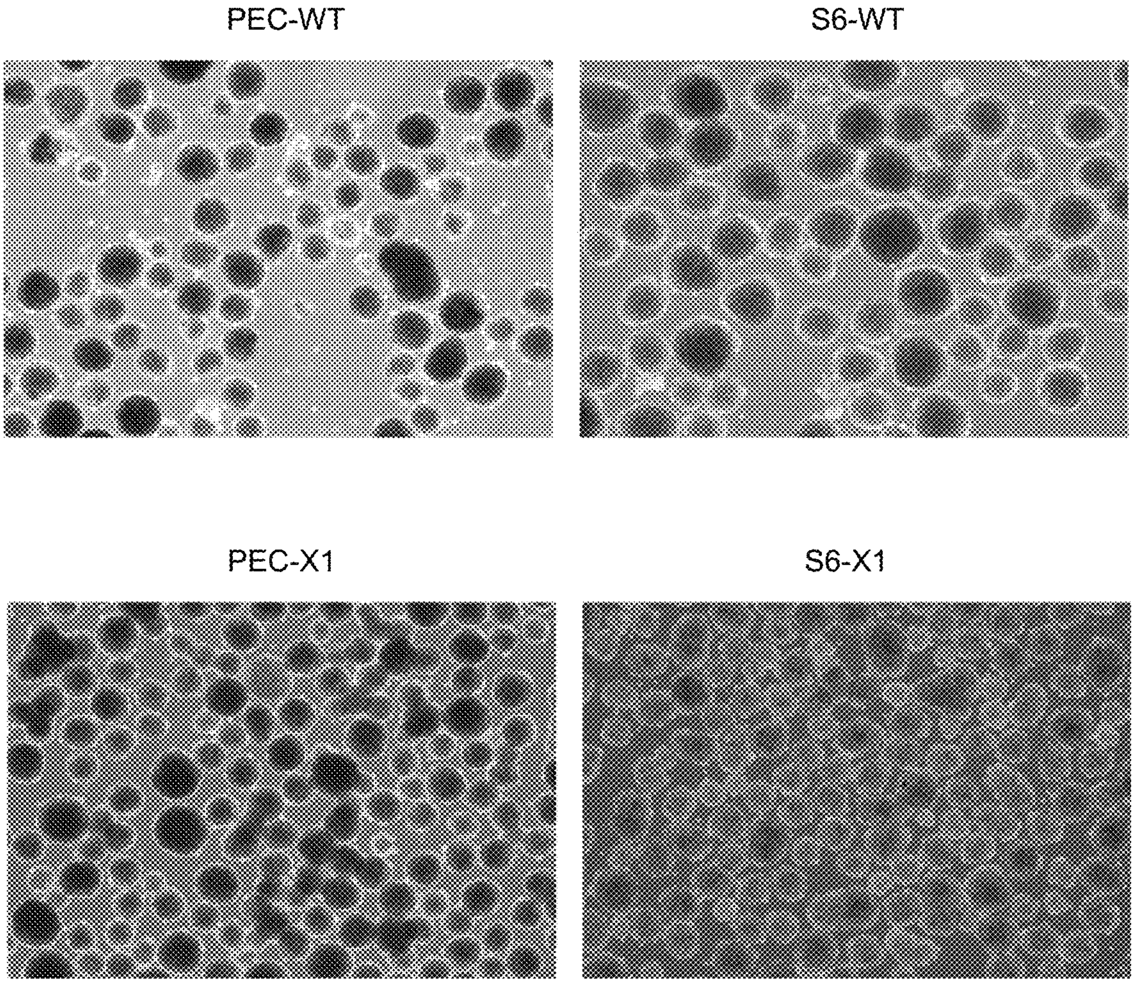
FIG. 7 shows the morphology of PEC and Stage 6 (S6) cells differentiated from wild type (WT) cells (upper panels) or X1 cells (i.e., TXNIP KO/MANF-P2A-HLA-E KI & B2M KO/TNFAIP3(A20)-P2A-PD-L-1 KI).

FIG. 7 shows similar morphology among TXNIP KO/MANF-P2A-HLA-E KI & B2M KO/TNFAIP3(A20)-P2A-PD-L-1 KI clones (“X1” or L1V028 cell line) at PEC stage and Stage 6 (S6) and those differentiated from wild-type cells.

Example 11: Gene Expression at PEC Stage and Stage 6

Targeted RNAseq for gene expression analysis was performed using Illumina TruSeq and a custom panel of oligos targeting 111 genes. The panel primarily contained genes that are markers of the developmental stages during pancreatic differentiation. At end of PEC stage and Stage 6, 10 μL APV (aggregated pellet volume) was collected and extracted using the Qiagen RNeasy or RNeasy 96 spin column protocol, including on-column DNase treatment. Quantification and quality control were performed using either the TapeStation combined with Qubit, or by using the Qiagen QIAxcel. 50-200 ng of RNA was processed according to the Illumina TruSeq library preparation protocol, which consists of cDNA synthesis, hybridization of the custom oligo pool, washing, extension, ligation of the bound oligos, PCR amplification of the libraries, and clean-up of the libraries, prior to quantification and quality control of the resulting dsDNA libraries using either the TapeStation combined with Qubit, or by using the Qiagen QIAxcel. The libraries were subsequently diluted to a concentration of 4 nM and pooled, followed by denaturing, spike in of PhiX control, and further dilution to 10-12 pM prior to loading on the Illumina MiSeq sequencer. Following the sequencing run, initial data analysis was performed automatically through BaseSpace, generating raw read counts for each of the custom probes. For each gene, these read counts were then summed for all probes corresponding to that gene, with the addition of 1 read count (to prevent downstream divisions by 0). Normalization was performed to the gene SF3B2, and the reads were typically visualized as fold change vs. Stage 0. When the data was processed for principal component analysis, normalization was performed using the DEseq method.

Figure 8:
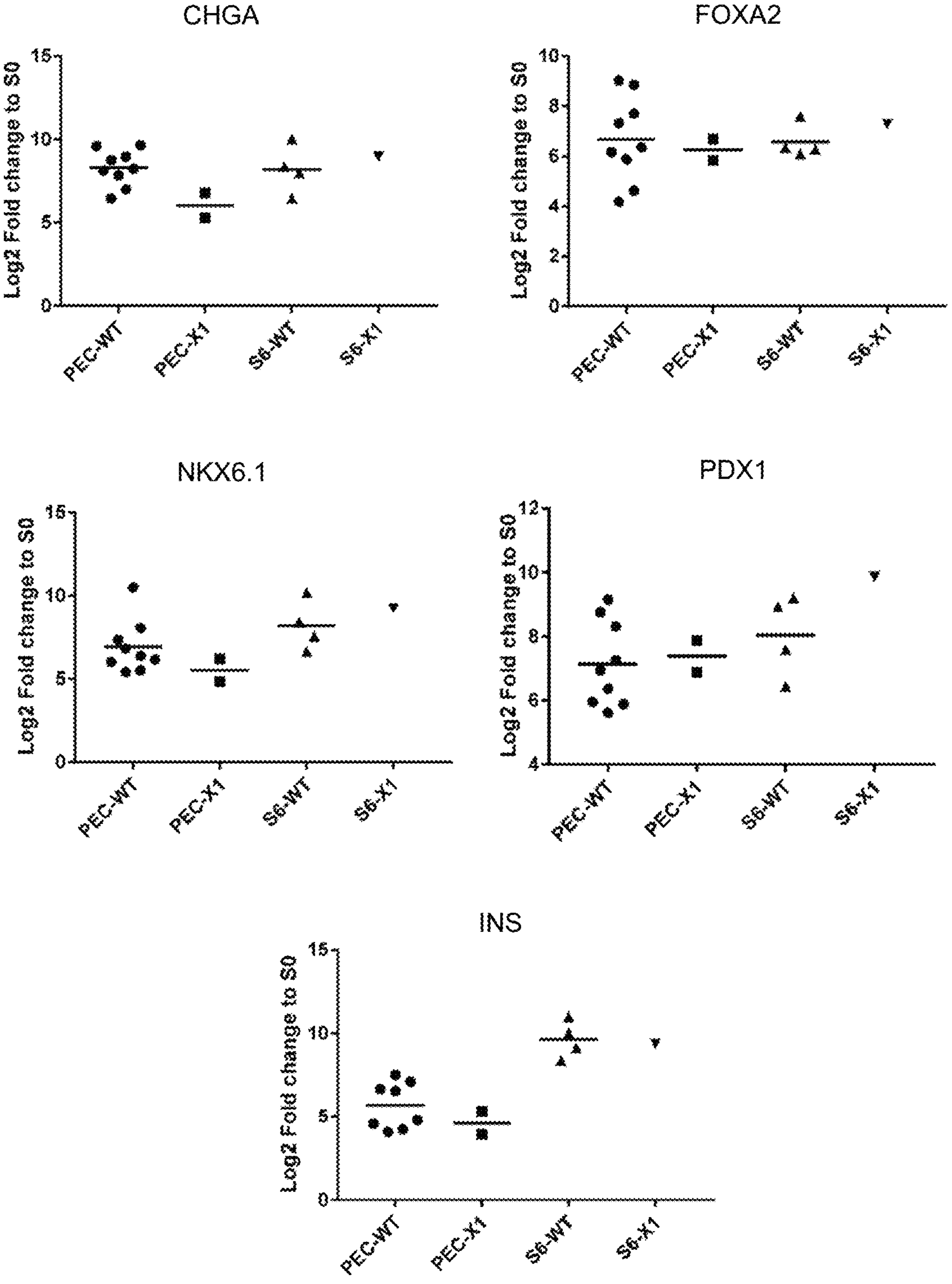
FIG. 8 shows selected gene expression in PEC and Stage 6 (S6) cells differentiated from wild type (WT) cells (upper panels) or X1 ("X1") cells (i.e., TXNIP KO/MANF-P2A-HLA-E KI & B2M KO/TNFAIP3(A20)-P2A-PD-L-1 KI).

Selected gene expression is shown in FIG. 8. The expression pattern of CHGA, FOXA2, NKX6.1, PDX1 and INS from the “X1” clones, i.e., TXNIP KO/MANF-P2A-HLA-E KI & B2M KO/TNFAIP3(A20)-P2A-PD-L-1 KI (X1), at PEC stage and Stage 6 (S6) was similar to that of cells differentiated from wild-type cells.

Example 12: Flow Cytometry for CHGA, PDX1 and NKX6.1 at PEC Stage and Stage 6

PEC stage and stage 6 aggregates were washed with PBS and then enzymatically dissociated to single cells suspension at 37° C. using ACCUMAX™ (Catalog #A7089, Sigma, MO). MACS Separation Buffer (Cat #130-091-221, Miltenyi Biotec, North Rhine-Westphalia, Germany) was added and the suspension was passed through a 40 μm filter and pelleted. For intracellular marker staining, cells were fixed for 30 mins in 4% (wt/v) paraformaldehyde, washed in FACS Buffer (PBS, 0.1% (wt/v) BSA, 0.1% (wt/v) NaN3) and then cells were permeabilized with Perm Buffer (PBS, 0.2% (v/v) Triton X-100 (Cat #A16046, Alfa Aesar, MA), 5% (v/v) normal donkey serum, 0.1% (wt/v) NaN3) for 30 mins on ice and then washed with washing buffer (PBS, 1% (wt/v) BSA, 0.1% (wt/v) NaN3). Cells were incubated with primary antibodies (Table 11) diluted with Block Buffer (PBS, 0.1% (v/v) Triton X-100, 5% (v/v) normal donkey serum, 0.1% (wt/v) NaN3) overnight at 4° C. Cells were washed in IC buffer and then incubated with appropriate secondary antibodies for 60 mins at 4° C. Cells were washed in IC buffer and then in FACS Buffer. Flow cytometry data were acquired with NovoCyte Flow Cytometer (ACEA Biosciences, Brussels). Data were analyzed using FlowJo software (Tree Star, Inc.). Intact cells were identified based on forward (low angle) and side (orthogonal, 90°) light scatter. Background was estimated using antibody controls and undifferentiated cells. In the figures, a representative flow cytometry plot is shown for one of the sub-populations. Numbers reported in the figures represent the percentage of total cells from the intact cells gate.

TABLE 11

| Antibodies for flow cytometry | | | |
|---|---|---|---|
| Antigen | Fluorophore | Source | Dilution |
| PDX1 | PE | BD Bioscience (Cat#562161) | 1:2.5 |
| NKX6.1 | AF647 | BD Bioscience (Cat#563338) | 1:2.5 |
| CHGA | AF405 | Novus (Cat#NBP2-33198AF405) | 1:1000 |

Figure 9:
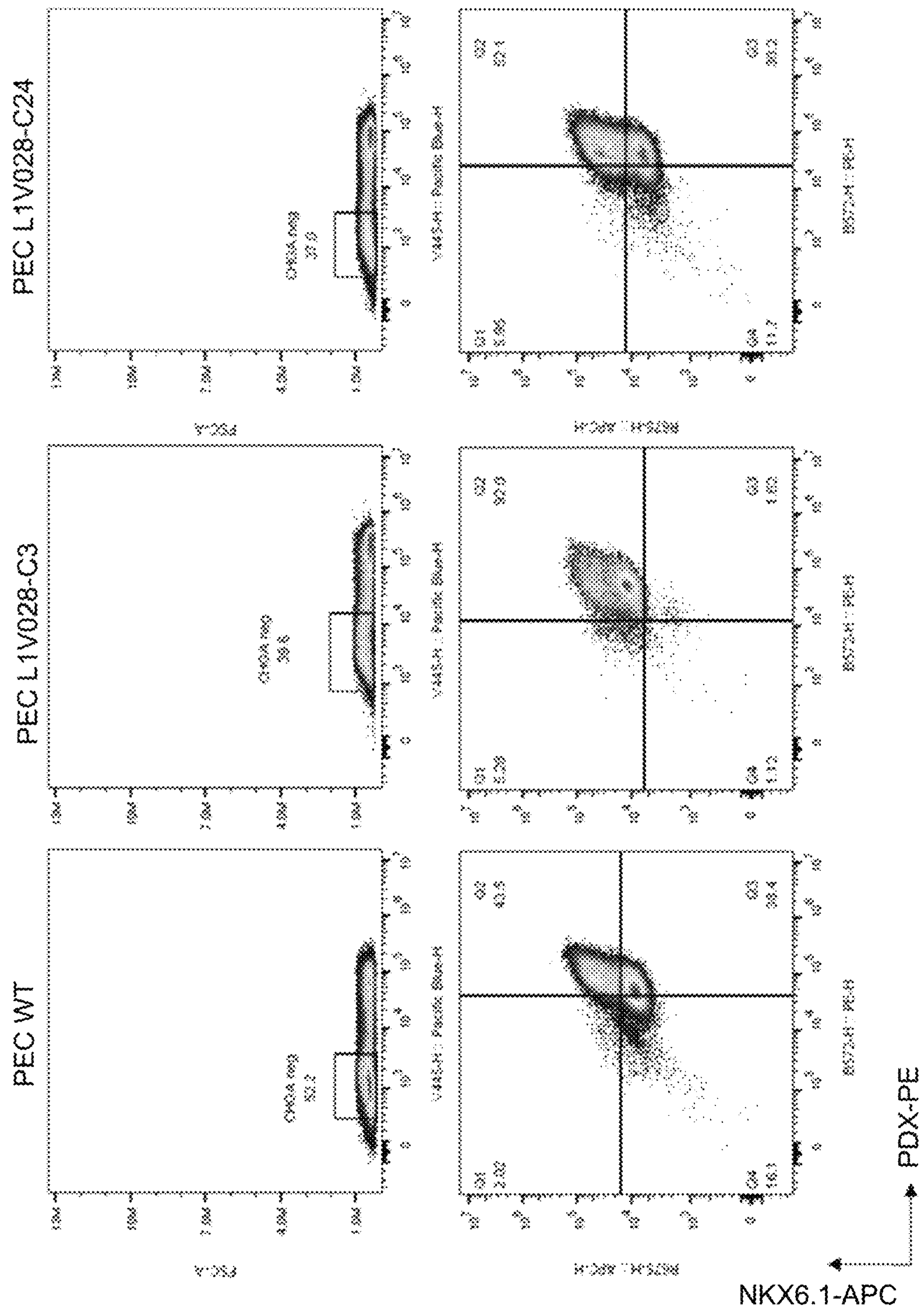
FIG. 9 shows flow cytometry of CHGA, PDX1 and NKX6.1 in PEC cells differentiated from wild type (WT) cells or TXNIP KO/MANF-P2A-HLA-E KI & B2M KO/TNFAIP3(A20)-P2A-PD-L-1 KI cells (L1V028-C3, L1V028-24).
Figure 10A:
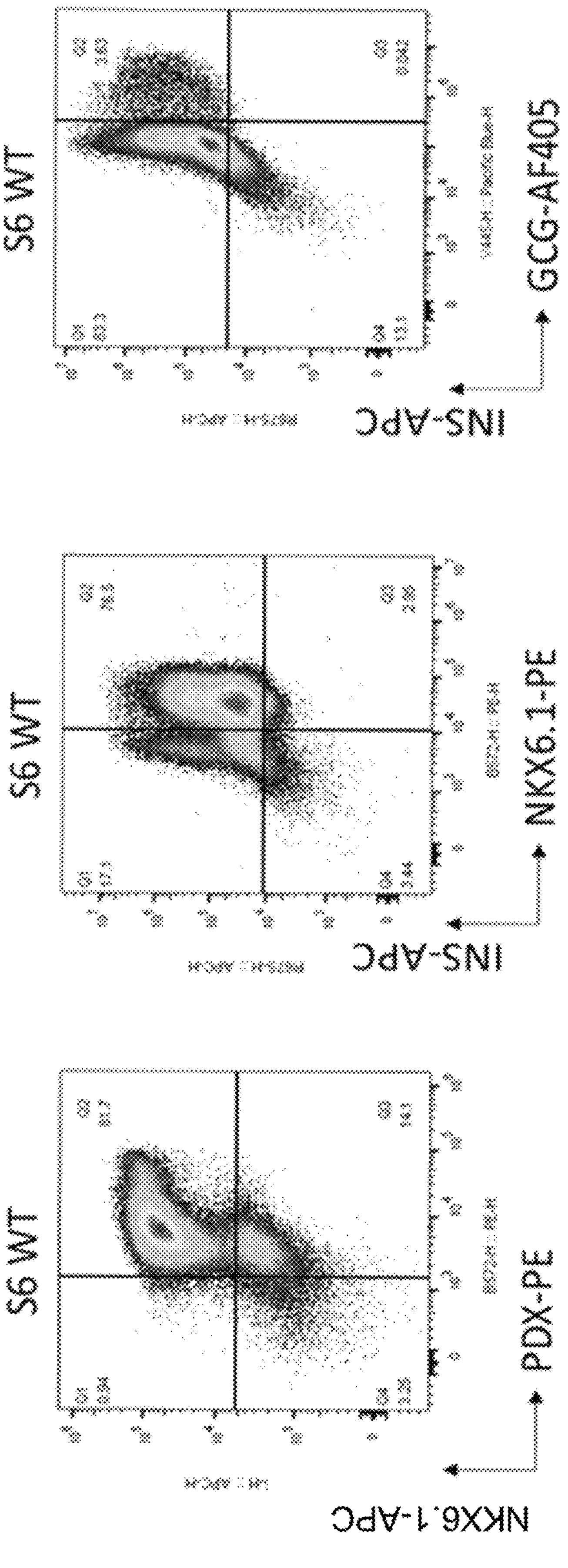
FIG. 10A shows flow cytometry of CHGA, PDX1 and NKX6.1 in Stage 6 (S6) cells differentiated from wild type (WT) cells
Figure 10B:
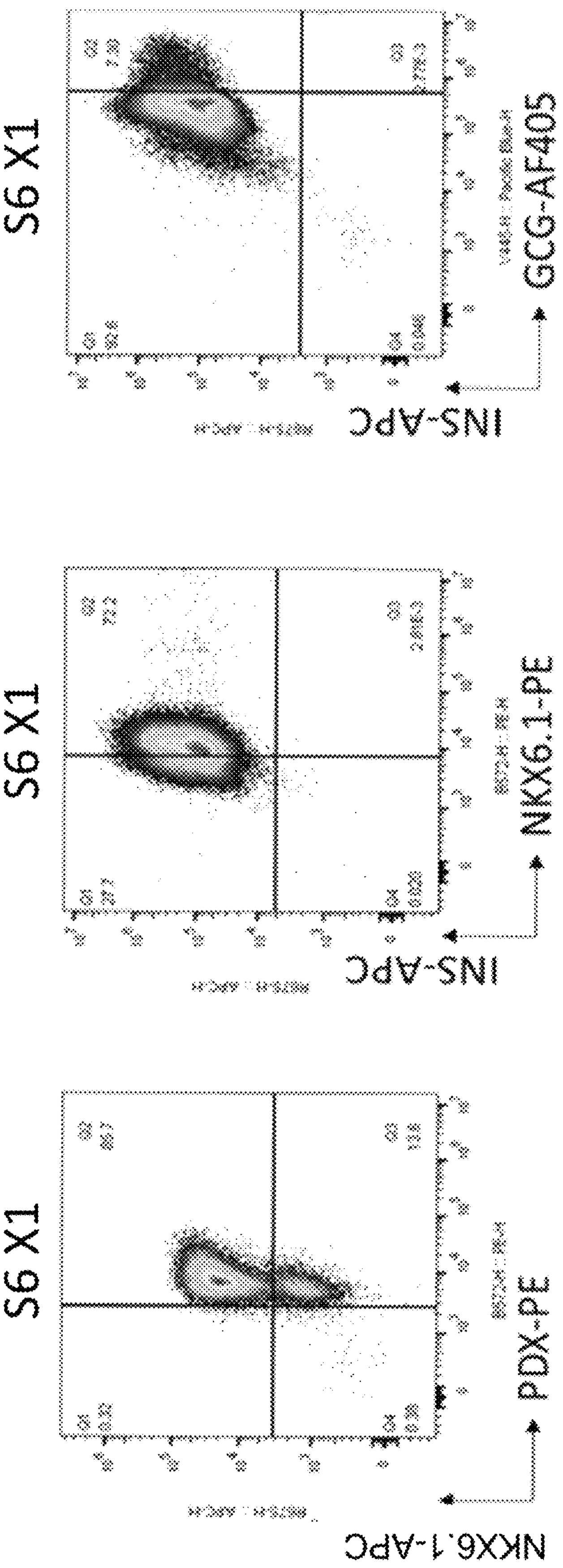
FIG. 10B shows flow cytometry of CHGA, PDX1 and NKX6.1 in Stage 6 (S6) cells differentiated from X1 cells (i.e., TXNIP KO/MANF-P2A-HLA-E KI & B2M KO/TNFAIP3(A20)-P2A-PD-L-1 KI).

FIG. 9 presents flow cytometry for CHGA, PDX1 and NKX6.1 in PEC cells differentiated from wild type cells or two L1V028 clones generated in Example 6 (i.e., TXNIP KO/MANF-P2A-HLA-E KI & B2M KO/TNFAIP3(A20)-P2A-PD-L-1 KI). FIGS. 10A and 10B presents flow cytometry for CHGA, PDX1 and NKX6.1 in Stage 6 (S6) cells differentiated from wild type cells (FIG. 10A) or X1 cells (i.e., TXNIP KO/MANF-P2A-HLA-E KI & B2M KO/TNFAIP3(A20)-P2A-PD-L-1 KI) (FIG. 10B).

Example 13: In Vivo Efficacy Study of B2M KO/MANF-P2A-TNFAIP3-P2A-PD-L-1 KI Cells Pancreatic endoderm cells were generated from the B2M KO/MANF-P2A-TNFAIP3(A20)-P2A-PD-L-1 KI (L1V008) cell line described above in Example 2 and a clonal unmodified cell line obtained from transfection with a non-cutting guide-RNA (NCG).

Pancreatic endoderm aggregates derived from the indicated clonal lines were loaded into perforated devices (PD) to produce test or control articles. The PDs permitted direct vascularization upon subcutaneous transplantation, and the encapsulated pancreatic progenitor cells matured in vivo into functional pancreatic endocrine cells including glucose-responsive, insulin-producing cells.

As summarized in Table 12, the L1V008 and control cells were tested in four groups of athymic nude rats in which each was implanted subcutaneously with two articles, each containing approximately $7\times10^6$ cells.

TABLE 12

| Study Design | | | | | |
|---|---|---|---|---|---|
| | | Genetic Modification | | | GSIS |
| Group Number | Group ID | Knock-out (Loss of | Knock-in (Gain of Function | Number of Animals | Test Time Points |
| 1 | L1V009B (Bulk) | B2M | MANF, TNFAIP3, PD-L-1 | 8 per Group | Week 12, 16, 20, 24 |
| 2 | L1V008-C1 | B2M | MANF, TNFAIP3, PD-L-1 | | |
| 3 | L1V008-C3 | B2M | MANF, TNFAIP3, PD-L-1 | | |
| 4 | Control | None | None | | |

Starting at 12 weeks all surviving animals were subjected to efficacy evaluation through glucose stimulated insulin secretion (GSIS) testing. Blood samples were obtained from non-fasted animals prior to and after intraperitoneal administration of 3 g/kg glucose. Serum concentrations of human C-peptide were determined through standard enzyme linked immunosorbent assays. The C-peptide reading for the control group (GRP 4) was taken 60 min after intraperitoneal administration of glucose, while the readings for the experimental groups were taken 90 min post administration.

Figure 11:
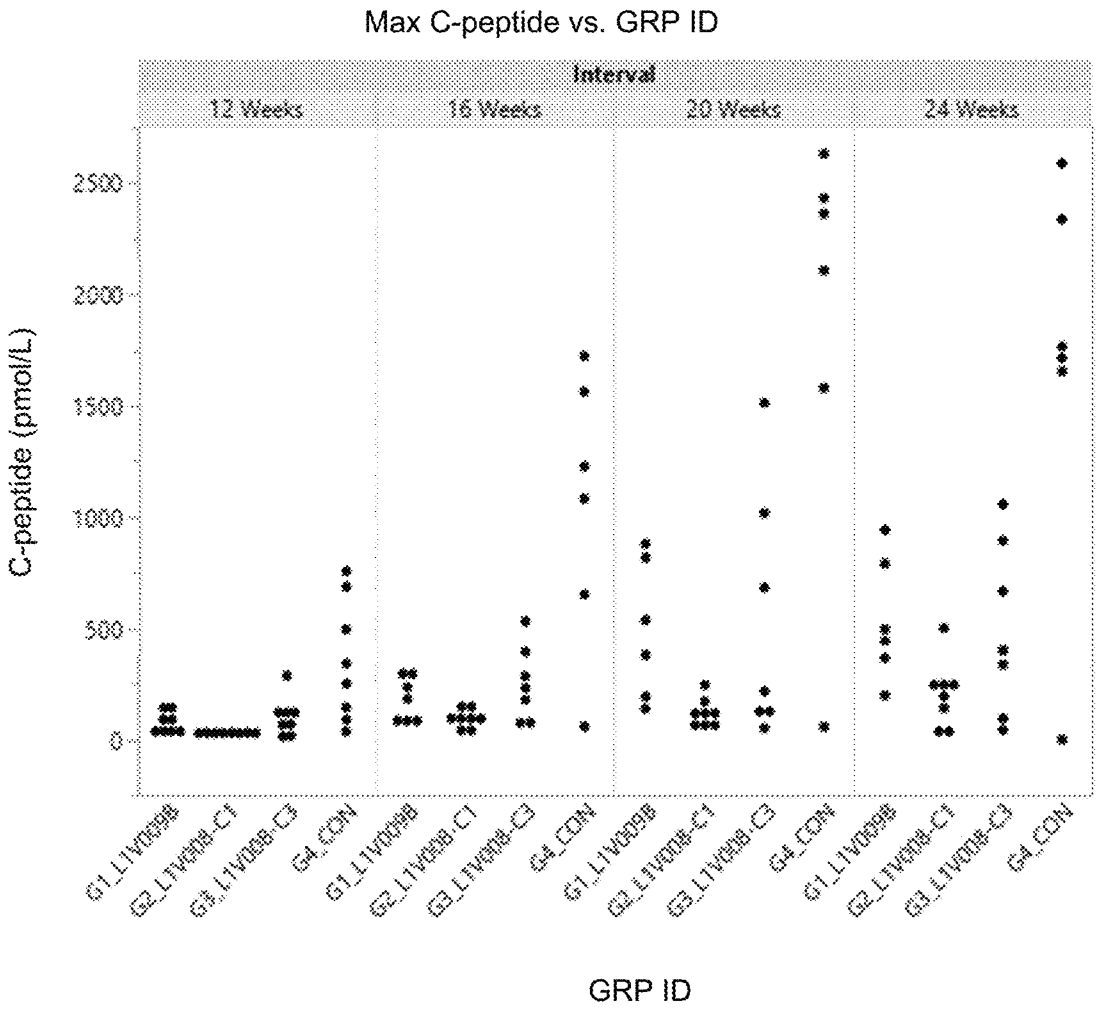
FIG. 11 shows C-peptide levels at 12, 16, 20, 24 weeks in blood samples obtained from athymic nude rats transplanted with cell aggregates of L1V009B bulk cells (GRP 1) or L1V008 clonal isolates (B2M KO/MANF-P2A-TNFAIP3-P2A-PD-L-1 KI; GRP 2 and GRP 3) or control cells (GRP 4), 90 min after intraperitoneal administration of 3 g/kg glucose for GRP 1-3 and 60 min after administration for GRP 4.

FIG. 11 presents the C-peptide levels for the four groups at 12, 16, 20 and 24 weeks. Results indicated there were no substantial differences between experimental groups. These results indicated that neither the genetic modifications that were introduced nor the manipulations required to generate clonal lines affected the ability for the cell lines in question to differentiate into pancreatic endoderm cells in vitro and subsequently generate functional beta cells in vivo.

Example 14: In Vivo Efficacy Study of B2M KO/CD39-P2A-PD-L-1 KI Cells

Pancreatic endoderm aggregates derived from the B2M KO/CD39-P2A-PD-L-1 KI (L1V017) cell line prepared in Example 4 or from control cells were loaded into perforated devices and implanted into animals for GSIS testing as described above in Example 13. Table 13 presents the study design.

TABLE 13

| Study Design | | | | | |
|---|---|---|---|---|---|
| | | Genetic Modification | | | GSIS |
| Group Number | Group ID | Knock-out (Loss of Function) | Knock-in (Gain of Function | Number of Animals | Test Time Points |
| 1 | L1V017B (Bulk) | B2M | CD39, PD-L-1 | 6 per group | Week 12, 16, 20, 24 |
| 2 | Control | None | None | | |

Figure 12:
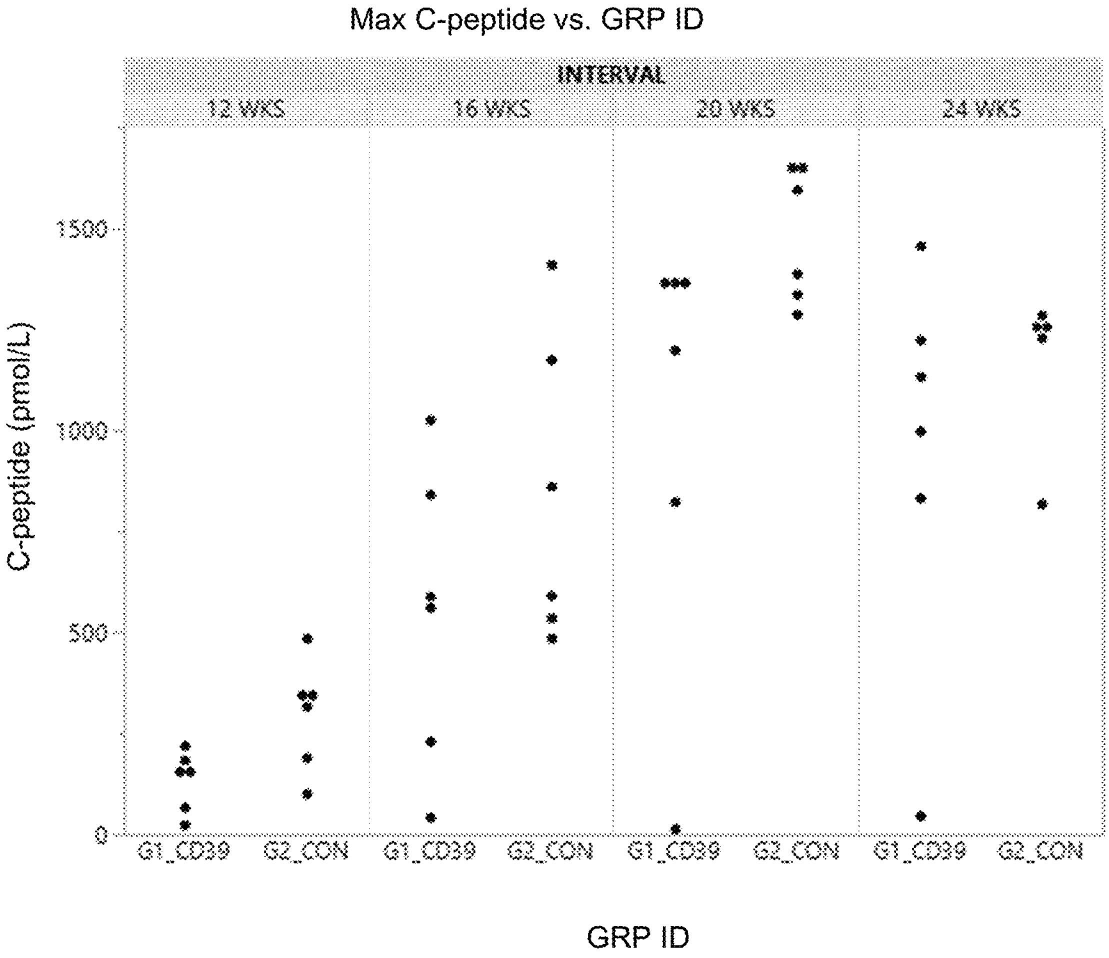
FIG. 12 shows C-peptide levels at 12, 16, 20, 24 weeks in blood samples obtained from athymic nude rats transplanted with cell aggregates from B2M KO/CD39-P2A-PD-L-1 KI or control cells 90 min (60 min for the 24 week reading) after intraperitoneal administration of 3 g/kg glucose.

As shown in FIG. 12, the genetic modifications and manipulations required to generate this cell line did not affect the cells ability cells to differentiate into pancreatic endoderm cells in vitro and subsequently generate functional beta cells in vivo.

Example 15: In Vivo Efficacy Study of TXNIP KO/MANF-P2A-HLA-E KI & B2M KO/TNFAIP3(A20)-P2A-PD-L-1 KI Cells PEC stage and stage 6 cells differentiated from control cells (NCG) or a L1V028 clone generated in Example 6 (i.e., TXNIP KO/MANF-P2A-HLA-E KI & B2M KO/TNFAIP3 (A20)-P2A-PD-L-1 KI; "X1") were tested for in vivo efficacy. Test or control capsules were transplanted into the left kidney of NSG mice (Jackson Laboratory Stock No: 005557). Table 14 presents the study design.

TABLE 14

| Study Design | | | | | | | |
|---|---|---|---|---|---|---|---|
| | | Genetic Modification | | | | | Read out |
| Group Number | Group ID | Knock-out (Loss of Function) | Knock-in (Gain of Function) | Stage | Number of Animals | Transplantation site | of C-peptide serum |
| 1 | NCG | None | None | PEC | 5 per Group | Kidney capsule (left Side) | Week 12,16,20,24 |
| 2 | L1V028-C24 (X1) | TXNIP B2M | PD-L-1 HLA-E MANF TNFAIP3 | PEC | | | |
| 3 | NCG | None | None | S6 | | | |
| 4 | L1V028-C24 (X1) | TXNIP B2M | PD-L-1 HLA-E MANF TNFAIP3 | S6 | | | |
| 5 | V1B-H9 | TXNIP B2M | PD-L-1 HLA-E | S6 | | | |

Figure 13:
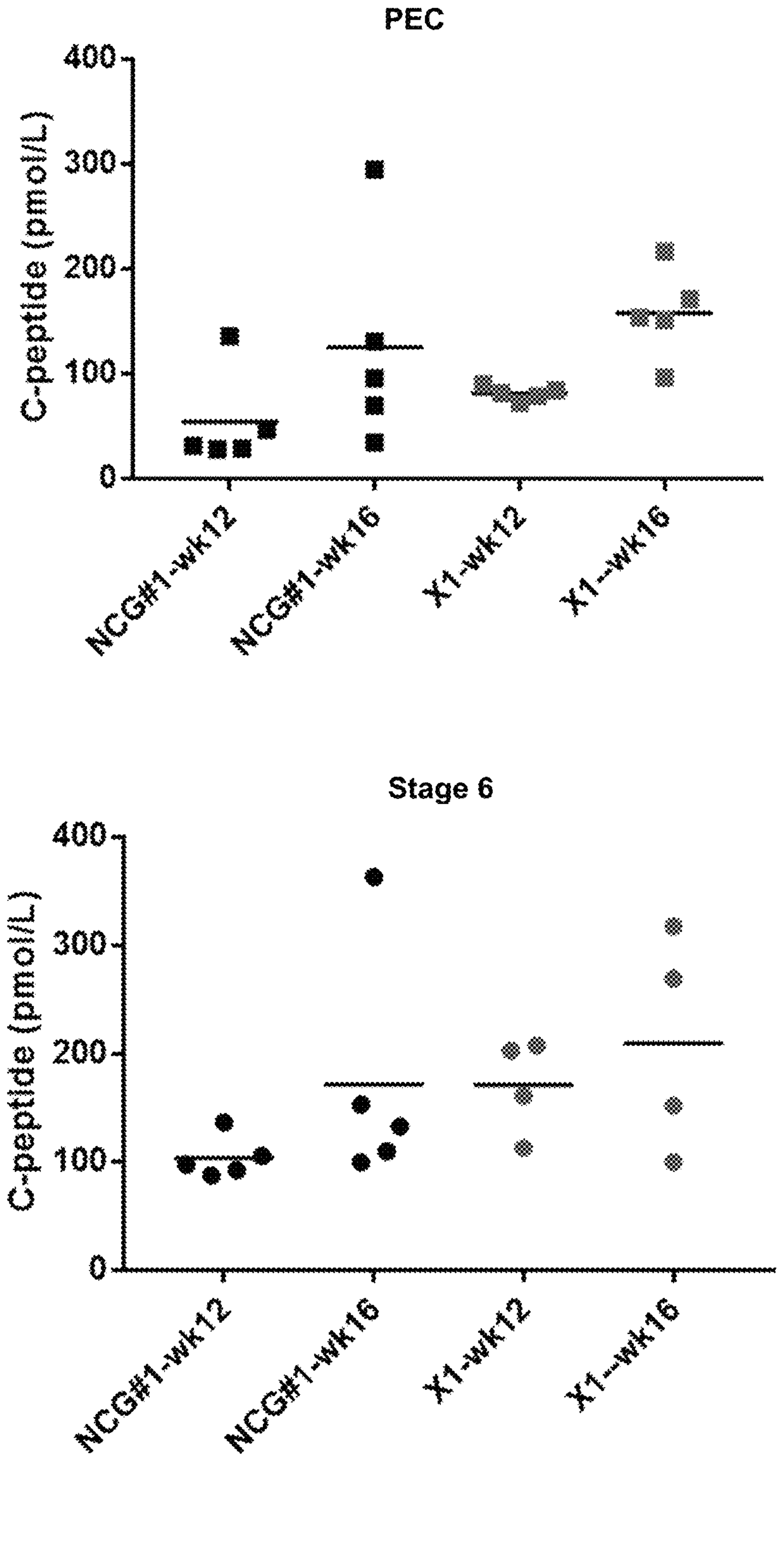
FIG. 13 shows C-peptide levels at 12 and 16 weeks in blood samples obtained from NSG mice transplanted with capsules containing PEC stage or Stage 6 (S6) differentiated cell aggregates of unmodified (NCG) or B2M KO/TNFAIP3-P2A-PD-L-1 KI & TXNIP KO/MANF-P2A-HLA-E KI (X1) after glucose stimulation.
Figure 14:
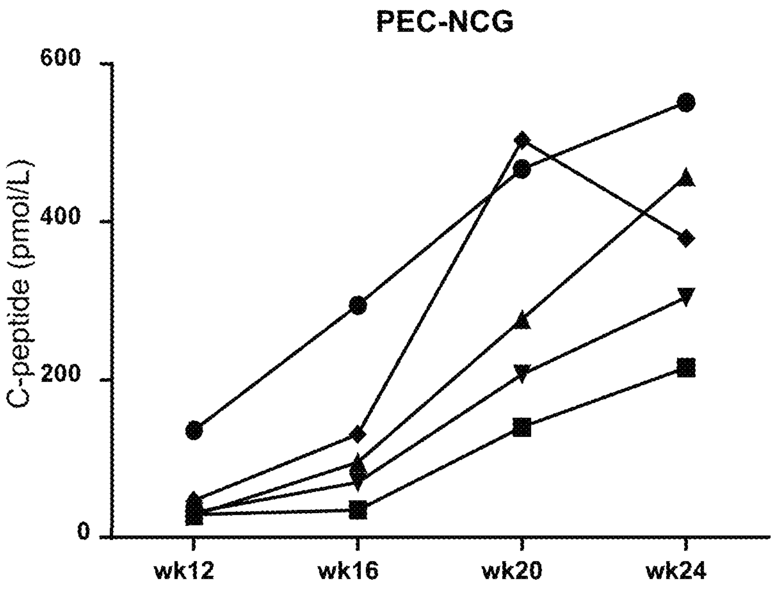
FIG. 14 presents the average C-peptide levels at 12, 16, 20, 24 weeks after glucose stimulation in the PEC-control (NCG) and PEC-X1 (B2M KO/TNFAIP3-P2A-PD-L-1 KI and TXNIP KO/MANF-P2A-HLA-E KI) groups of mice.
Figure 14:
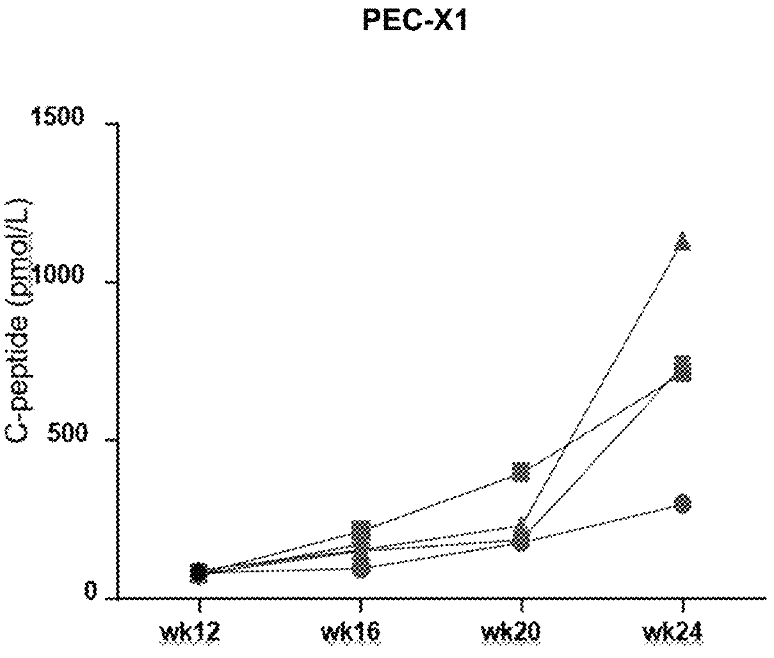

GSIS testing was performed at 12, 16, 20 and 24 weeks. FIG. 13 presents the C-peptide levels at weeks 12 and 16 for individual animals in the PEC-control, PEC-X1, S6-control, and S6-X1 groups. FIG. 14 presents a time course of the mean C-peptide levels from week 12 to week 24 for PEC-control and PEC-X1 groups. These results show that the X1 cells are able to differentiate into pancreatic endoderm cells in vitro and subsequently generate functional beta cells in vivo.

At 26 weeks, after GSIS testing, animals were euthanized and explanted test articles were fixed in neutral buffered formalin, processed to slides, and stained with H&E and by immunohistochemistry for insulin and glucagon.

Figure 15:
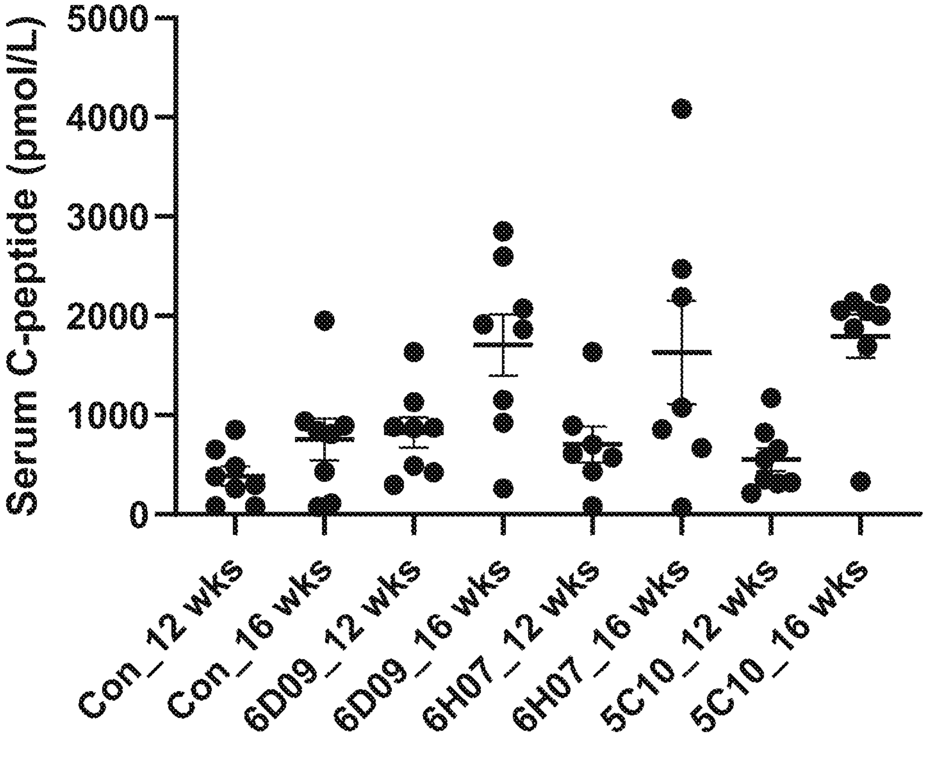
FIG. 15 presents C-peptide levels at 12, 16, and 20 weeks in NSG mice transplanted with capsules containing cells differentiated from unmodified (CON) or clones (i.e., 6D09, 6H07, and 5C10) of B2M KO/TNFAIP3-P2A-PD-L-1 KI & TXNIP KO/MANF-P2A-HLA-E KI (X1) cells.

Several seed run clones from the "X1" cell line (i.e., L1V028) were also tested in vivo. The clones were selected based on whole genome sequencing. They had Het/Hom on-site genotypes, exhibited no unintended plasmid insertions, and did not exhibit any variants that may have functionally altered oncogenes. Clone 6D09 had no putative off-target insertions, whereas clones 6H07 and 5C10 has at least one putative off-target insertion. GSIS testing was performed at weeks 12 and 16. FIG. 15 presents C-peptides levels for each animal and group mean levels at 12 weeks, 16 weeks, and 20 weeks. Clones 6D09, 6H07, and 5C10 exhibited good in vivo efficiency.

Example 16: Generation of B2M Knock Out (KO) with CD39-P2A-CD73-P2A-PD-L-1 KI Human Pluripotent Stem Cells Cells were generated in which a transgene encoding CD39-P2A-CD73-P2A-PD-L-1 was inserted into the B2M gene locus thereby knocking out the B2M gene.

Human pluripotent stem cells were electroporated essentially as described above in Example 2 with a B2M-CAGGS-CD39-P2A-CD73-P2A-PD-L-1 donor plasmid, as detailed below in Table 15, and an RNP comprising Cas9 and a B2M-2 gRNA (SEQ ID NO: 2).

Figure 16:
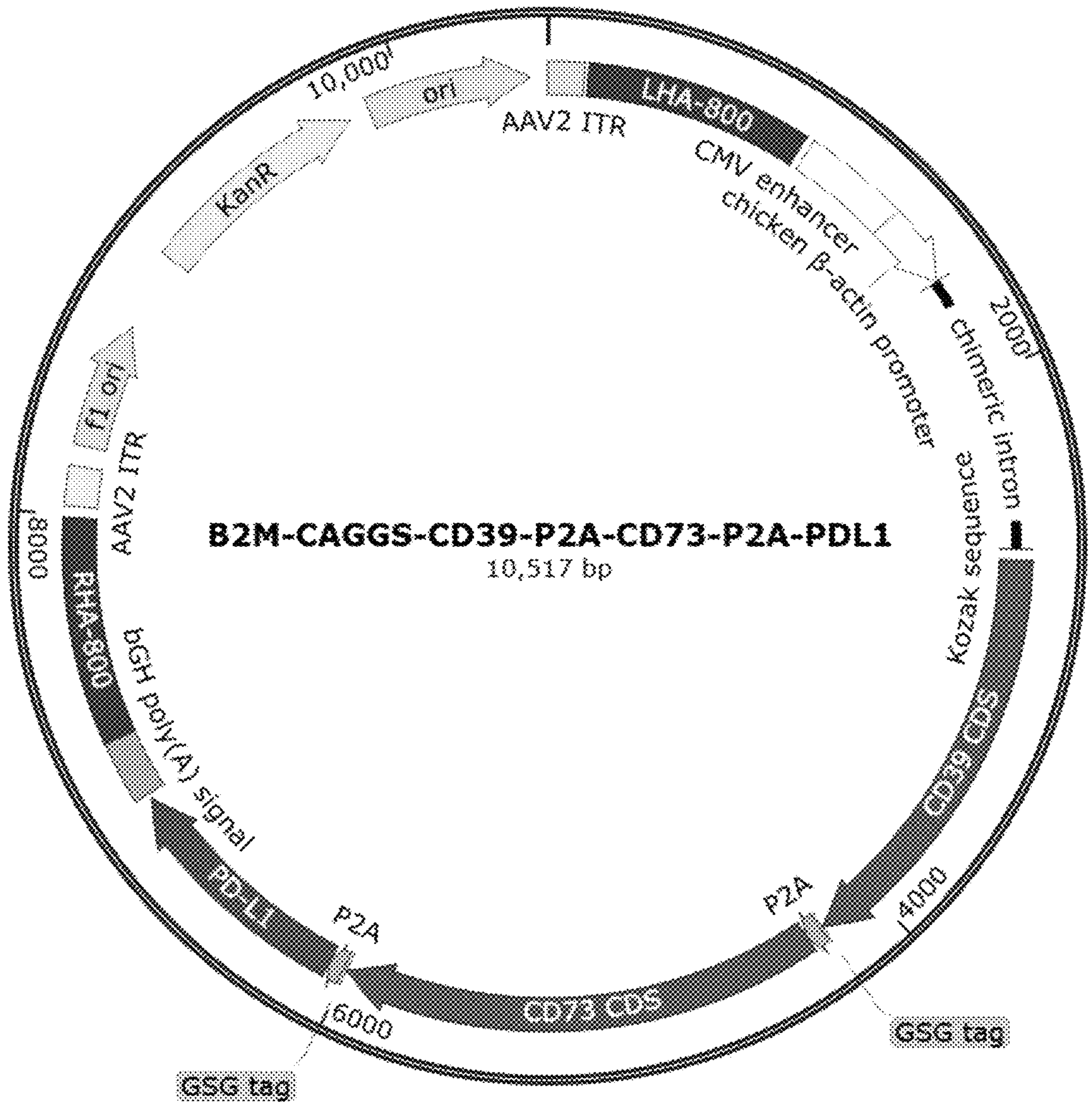
FIG. 16 presents the plasmid map of B2M-CAGGS-CD39-P2A-CD73-P2A-PD-L-1 donor vector.

FIG. 16 presents a schematic of the B2M-CAGGS-CD39-P2A-CD73-P2A-PD-L-1 plasmid and Table 15 identifies the elements and locations therein. The B2M-CAGGS-CD39-P2A-CD73-P2A-PD-L-1 donor plasmid comprises a CAGGS promoter to drive expression of cDNA of CD39-P2A-CD73-P2A-PD-L-1 (SEQ ID NO: 56) flanked by 800 base pair homology arms with identical sequence to the B2M locus around exon 1. The complete sequence of the B2M-CAGGS-CD39-P2A-CD73-P2A-PD-L-1 donor plasmid comprises the nucleotide sequence of SEQ ID NO: 47.

TABLE 15

Elements of B2M-CAGGS-CD39-P2A-CD73-P2A-PD-L-1 Donor Plasmid

| Element | Location (size in bp) | SEQ ID NO: |
|---|---|---|
| Left ITR | 1-130 (130) | 14 |
| LHA-B2M | 145-944 (800) | 15 |
| CAGGS promoter | 973-2639 (1667) | 16 |
| CD39 | 2684-4213 (1530) | 27 |
| P2A | 4223-4279 (57) | 18 |
| CD73 | 4280-6001 (1722) | 46 |
| P2A | 6011-6067 (57) | 18 |
| PD-L-1 | 6068-6940 (873) | 20 |
| bGH poly(A) signal | 6958-7182 (225) | 21 |
| RHA-B2M | 7189-7988 (800) | 22 |
| Right ITR | 8030-8170 (141) | 23 |
| Entire plasmid | 10,517 bp | 47 |

Seven to ten days post electroporation, the cells were enriched for PD-L-1 expressing cells via magnetic assisted cell sorting (MACS) using anti-mouse IgG Dynabeads (ThermoFisher, CELLection™ Pan Mouse IgG Kit, 11531D. These enriched cells represented a bulk KI population that was highly PD-L-1 positive. The enriched cells were then FACS-sorted for PD-L-1 surface expression using the WOLF FACS-sorter (Nanocellect) into BIOLAMININ 521 CTG coated 96-well plates with StemFlex and RevitaCell™. To detect the PD-L-1 surface expression, anti-PD-L-1 fluorescent antibodies were used (see Table 4). For FACS-sorting, unedited cells served as a negative control. PD-L-1 positive cells were selected for sorting and single cell cloning.

Plated single cells were grown in a normoxia incubator (37° C., 8% $CO_2$) with every other day media changes until colonies were large enough to be re-seeded as single cells. When confluent, samples were split for maintenance and genomic DNA extraction. Correctly targeted clones were identified via PCR for the CD39-P2A-CD73-P2A-PD-L-1 KI insertion using primers that amplify from outside the plasmid homology arms at the site of insertion into the B2M locus, enabling amplification of the KI integrated DNA only. The B2M KO state of clones was confirmed via PCR and Sanger sequencing. The correct KI and KO clones (L1V018B cell line) were expanded in increasing tissue culture formats until a population size of 30 million cells was reached.

Example 17. Generation of B2M KO with TNFAIP3 (A20)-P2A-PD-L-1 KI Human Pluripotent Stem Cells Human pluripotent stem cells were electroporated essentially as described above in Example 2 with a B2M-CAGGS-TNFAIP3 (A20)-P2A-PD-L-1 donor plasmid (SEQ ID NO: 31, Table 7) and an RNP comprising Cas9 and B2M-2 gRNA (SEQ ID NO: 2) to generate a L1V019B cell line. FIG. 4 presents a schematic of the B2M-CAGGS-TNFAIP3-P2A-PD-L-1 donor plasmid (also called X1-1 cassette).

Seven to ten days post electroporation, the cells were enriched for PD-L-1 expressing cells via magnetic assisted cell sorting (MACS) using anti-mouse IgG Dynabeads (ThermoFisher, CELLection™ Pan Mouse IgG Kit, 11531D. These enriched cells represented a bulk KI population that was highly PD-L-1 positive. The enriched cells were then FACS-sorted for PD-L-1 surface expression using the WOLF FACS-sorter (Nanocellect) into BIOLAMININ 521 CTG coated 96-well plates with StemFlex and RevitaCell™. To detect the PD-L-1 surface expression, anti-PD-L-1 fluorescent antibodies were used (see Table 4). For FACS-sorting, unedited cells served as a negative control. PD-L-1 positive cells were selected for sorting and single cell cloning.

Plated single cells were grown in a normoxia incubator (37° C., 8% $CO_2$) with every other day media changes until colonies were large enough to be re-seeded as single cells. When confluent, samples were split for maintenance and genomic DNA extraction. Correctly targeted clones were identified via PCR for the A20-P2A-PD-L-1 KI insertion using primers that amplify from outside the plasmid homology arms at the site of insertion into the B2M locus, enabling amplification of the KI integrated DNA only. The B2M KO state of clones was confirmed via PCR and Sanger sequencing. The correct KI and KO clones (L1V019B cell line) were expanded in increasing tissue culture formats until a population size of 30 million cells was reached.

Example 18: Differentiation and Characterization of Additional Edited Cell Lines Cells from the L1V017B cell line (i.e., CD39-P2A-PD-L-1 KI and B2M KO) prepared above in Example 4, the L1V018B cell line (i.e., CD39-P2A-CD73-P2A-PD-L-1 KI and B2M KO) prepared above in Example 16, and the L1V019B cell line (i.e., TNFAIP3 (A20)-P2A-PD-L-1 KI and B2M KO) prepared above in Example 17 were differentiated essentially as described above in Example 10.

Figure 17:
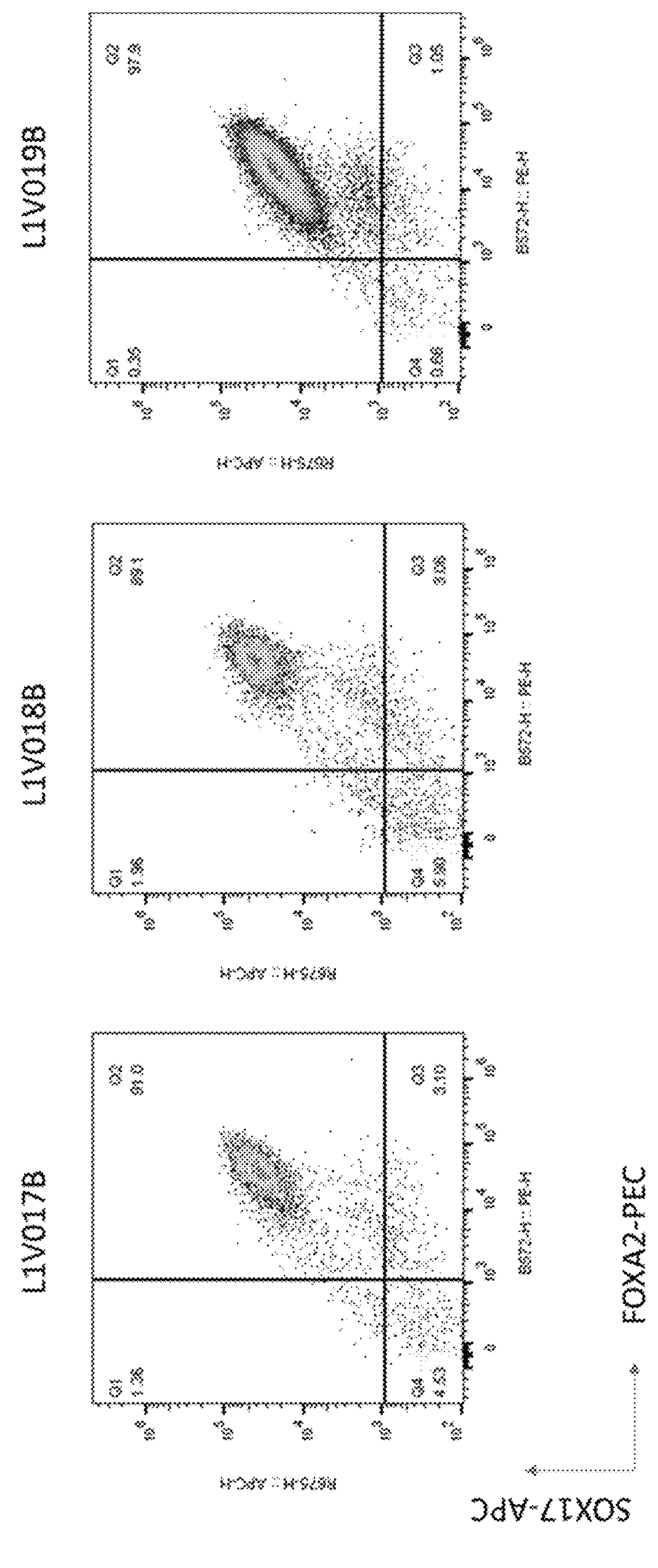
FIG. 17 shows flow cytometry of SOX17 and FOXA2 expression in L1V017B cells (i.e., CD39-P2A-PD-L-1 KI and B2M KO), L1V018B cells (i.e., CD39-P2A-CD73-P2A-PD-L-1 KI and B2M KO), and L1V019B cells (i.e., TNFAIP3 (A20)-P2A-PD-L-1 KI and B2M KO).
Figure 18:
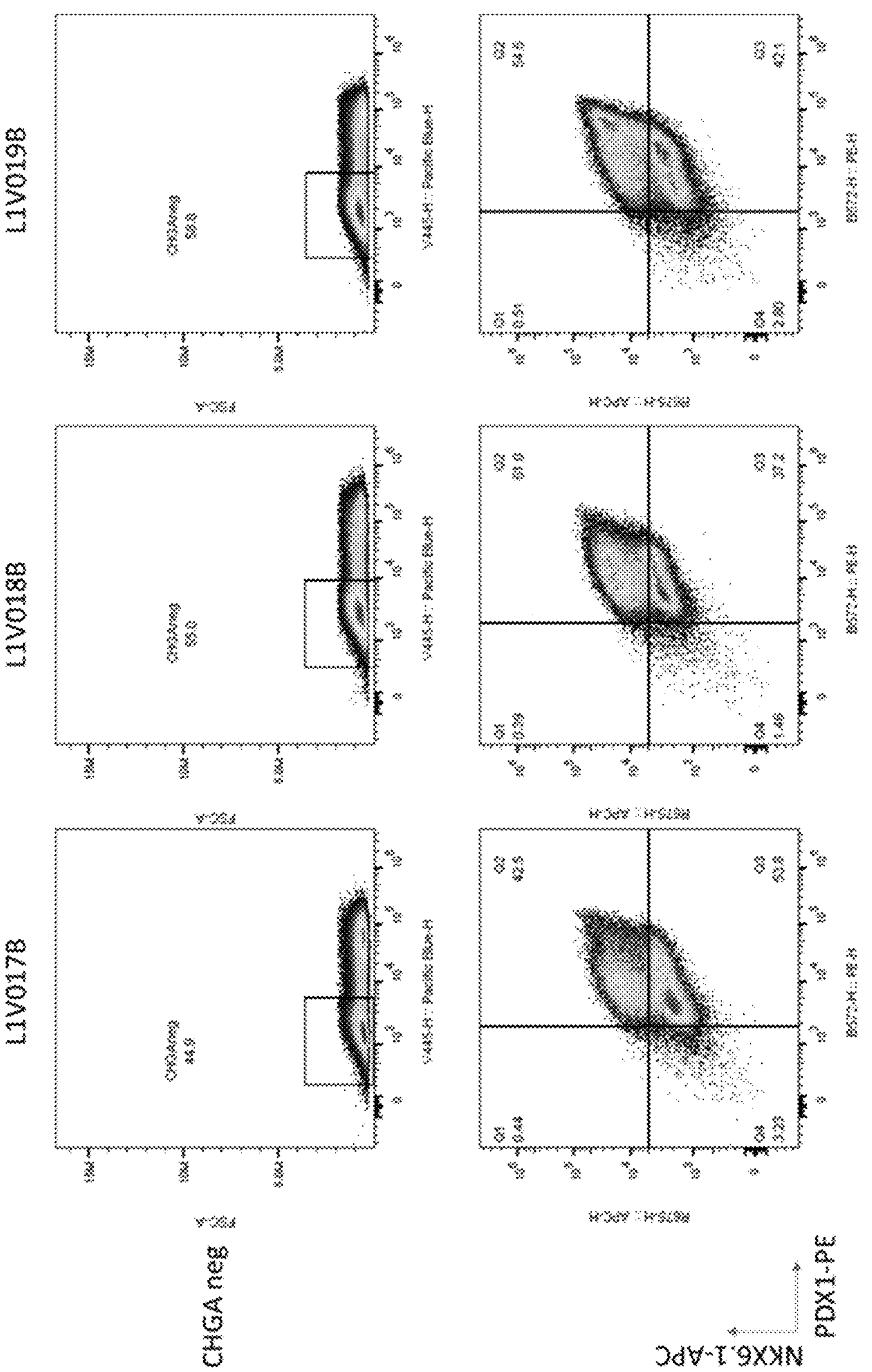
FIG. 18 shows flow cytometry of CHGA, NKX6.1, and PDX1 expression in L1V017B cells (i.e., CD39-P2A-PD-L-1 KI and B2M KO), L1V018B cells (i.e., CD39-P2A-CD73-P2A-PD-L-1 KI and B2M KO), and L1V019B cells (i.e., TNFAIP3 (A20)-P2A-PD-L-1 KI and B2M KO).
Figure 19:
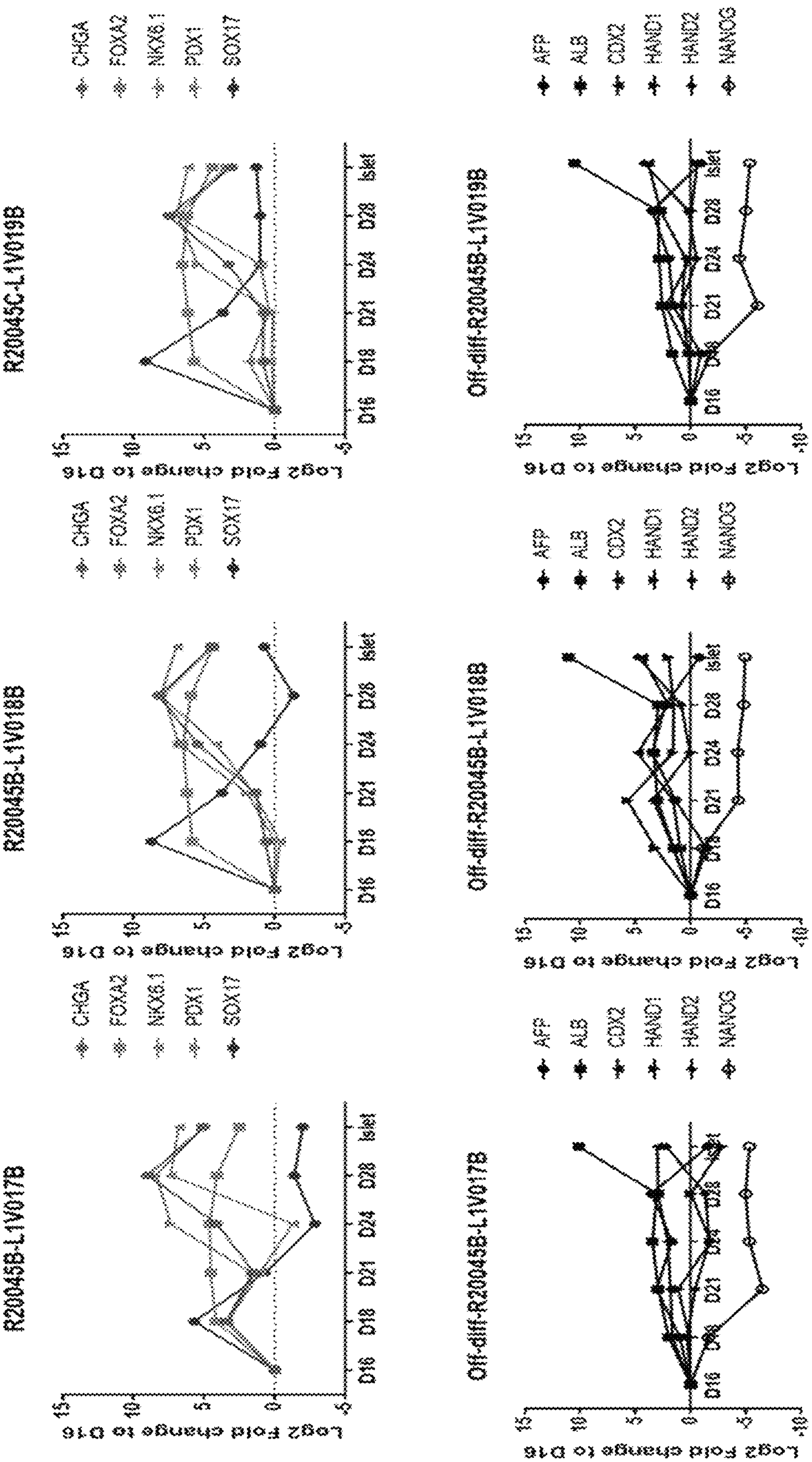
FIG. 19 presents a time course of gene expression of various markers in L1V017B cells (i.e., CD39-P2A-PD-L-1 KI and B2M KO), L1V018B cells (i.e., CD39-P2A-CD73-P2A-PD-L-1 KI and B2M KO), and L1V019B cells (i.e., TNFAIP3 (A20)-P2A-PD-L-1 KI and B2M KO).

Gene expression was examined at various time points during the differentiation process essentially described above in Examples 11 and 12. FIG. 17 presents flow cytometry for SOX17 and FOXA2 expression at day 18 to confirm presence of DE (definitive endoderm) cells. Presence of differentiated pancreatic endodermal cells (PEC) was further confirmed by flow cytometry by the presence of a CHGA negative and PDX1 and NKX6.1 positive predominant population (see FIG. 18). The time course of expression from day 16 to islets cells of various makers (e.g., CHGA, FOXA2, NKX6.1, PDX1, SOX17, AFP, ALB, CDX2, HAND1, HAND2, NANOG) is shown in FIG. 19.

Example 19: Generation of B2M KO with PD-L-1 KI, TXNIP KO with HLA-E KI, and CIITA KO with CD39 KI Human Pluripotent Stem Cells Cells will be generated in which a polynucleotide encoding PD-L-1 is inserted into the B2M gene locus, a polynucleotide encoding HLA-E is inserted into the TXNIP gene locus, and a polynucleotide encoding CD39 is inserted into the CIITA gene locus, thereby knocking out the B2M, TXNIP, and CIITA genes.

Human pluripotent stem cells will be electroporated essentially as described above in Example 2 with a B2M-CAGGS-PD-L-1 donor plasmid in which the PD-L-1 sequence (SEQ ID NO: 20) is flanked by 800 bp homology arms (SEQ ID NOS: 15 and 22) having sequence homolog to genomic sequence located to the left and right, respectively, of the target site in the B2M gene locus and an RNP comprising Cas9 and B2M-2 gRNA (SEQ ID NO: 2). Seven to ten days post electroporation, the cells will be enriched for PD-L-1 expressing (positive) cells via MACS essentially as described in Example 2. After the enriched PD-L-1 positive population is expanded, the cells will be electroporated essentially as described above in Example 2 with a TXNIP-CAGGS-HLA-E donor plasmid in which the HLA-E sequence (SEQ ID NO:43) is flanked by 800 bp arms (SEQ ID NOS: 42 and 44) having sequence homolog to genomic sequence located to the left and right, respectively, of the target site in the TXNIP gene locus and an RNP comprising Cas9 and TXNIP_Exon 1_T5 gRNA (SEQ ID NO: 37). After enrichment for HLA-E positive cells and expansion of PD-L-1 and HLA-E cells, the double positive cells will be electroporated with the CIITA-CAGGS-CD39 donor plasmid (Table 5) and an RNP comprising Cas9 and CIITA Ex3_T6 gRNA (SEQ ID NO: 25). The cells will be enriched for CD39 expressing cells, expanded, and selected for PD-L-1, HLA-E, and CD39 triple positive cells, which will be characterized as described above.

Example 20: Generation of B2M KO with TNFAIP3-P2A-PD-L-1 KI, TXNIP KO with MANF-P2A-HLA-E KI, and B2M KO with CD39-P2A-PD-L-1 KI Human Pluripotent Stem Cells Cells will be generated in which a polynucleotide encoding PD-L-1 is inserted into the B2M gene locus at a first target site, a polynucleotide encoding HLA-E is inserted into the TXNIP gene locus, and a polynucleotide encoding CD39 is inserted into another location in the B2M gene locus at a second target site, thereby knocking out the B2M and TXNIP genes.

Double positive cells expressing PD-L-1 and HLA-E will be generated essentially as described above in Example 16. The double positive cells will be electroporated with a B2M-CAGGS-CD39 donor plasmid in which the CD39 sequence (SEQ ID NO: 27) is flanked by 800 bp homology arms having sequence identity to genomic sequence around the second B2M target site and an RNP comprising Cas9 and a B2M gRNA chosen from SEQ ID NO: 1 or 3-13. The cells will be enriched for CD39 positive cells, expanded, and selected for PD-L-1, HLA-E, and CD39 triple positive cells, which will be characterized as described above.

Example 21: Differentiation of Edited Human Embryonic Stem Cells to Pancreatic Endoderm Cells (PECs)

Maintenance of edited human embryonic stem cells (ES). The edited human pluripotent stem cells comprising a B2M KO with TNFAIP3-P2A-PD-L-1 KI, TXNIP KO with MANF-P2A-HLA-E KI, CIITA KO with CD39 KI ("X4"; see Example 7) at various passages (P38-42) were maintained by seeding at about 33,000 cells/$cm^2$ for a 4-day passage or about 50,000 cells/$cm^2$ for a 3-day passage with hESM medium (DMEM/F12+10% KSR+10 ng/mL Activin A and 10 ng/mL Heregulin) and final 10% human AB serum.

Aggregation of edited human embryonic stem cells for PECs differentiation. The edited cells were dissociated into single cells with ACCUTASE® and then centrifuged and resuspended in 2% StemPro (Cat #A1000701, Invitrogen, CA) in DMEM/F12 medium at 1 million cells per ml, and total 350-400 million of cells were seeded in one 850 $cm^2$ roller bottle (Cat #431198, Corning, N.Y.) with rotation speed at 8 RPM±0.5 RPM for 18-20 hours before differentiation. The aggregates from edited human pluripotent stem cells were differentiated into pancreatic lineages using in roller bottles as described in Schulz et al. (2012) PLoS ONE 7(5): e37004 and shown for X1 cells. Aggregates from edited human pluripotent stems cells were differentiated into pancreatic lineages as described in Rezania et al. (2014) Nat. Biotechnol. 32(11): 1121-1133 and US20200208116.

The expression pattern of CHGA, FOXA2, NKX6.1, PDX1 and INS from the "X4" clones, i.e., TXNIP KO/MANF-P2A-HLA-E KI, B2M KO/TNFAIP3(A20)-P2A-PD-L-1 KI, and CIITA KO/CD39 KI, at PEC stage and Stage 6 (S6) was determine to confirm differentiation.

EXAMPLE 22: In Vivo Efficacy Study of Txnip Ko/Manf-P2a-Hla-E Ki & B2M KO/TNFAIP3(A20)-P2A-PD-L-1 KI, CIITA KO/CD39 KI Cells PEC stage and stage 6 cells differentiated from control cells (NCG) or X4 (i.e., TXNIP KO/MANF-P2A-HLA-E KI & B2M KO/TNFAIP3(A20)-P2A-PD-L-1 KI, CIITA KO/CD39 KI) will also be tested for in vivo efficacy. Test or control capsules will be transplanted into the left kidney of NSG mice (Jackson Laboratory Stock No: 005557).

GSIS testing will performed at 12, 16, 20 and 24 weeks, as described in Example 15 for the X1 cells. At 26 weeks, after GSIS testing, animals will be euthanized and explanted test articles will be fixed in neutral buffered formalin, processed to slides, and stained with H&E and by immunohistochemistry for insulin and glucagon.

Example 23: Generation of X1 Human Pluripotent Stem Cells with TGF-β2 KO

Cells were generated in which a transgene encoding TNFAIP3-P2A-PD-L-1 was inserted into the B2M gene locus, a transgene encoding MANF-P2A-HLA-E was inserted into the TXNIP gene locus, a transgene encoding CD39 was inserted into the CIITA gene locus, and the TGF-β2 gene was knocked out thereby the cells had knock outs of the B2M, TXNIP, CIITA and TGF-β2 genes.

Human pluripotent stem cells were electroporated essentially as described above in Example 2 with the B2M-CAGGS-TNFAIP3-P2A-PD-L-1 donor plasmid (SEQ ID NO: 31, Table 7) and an RNP comprising Cas9 and B2M-2 gRNA (SEQ ID NO: 2). Seven to ten days post electroporation, the cells were enriched for PD-L-1 expressing (positive) cells via MACS essentially as described in Example 2. After the enriched PD-L-1 positive population was expanded, the cells were electroporated essentially as described above in Example 2 with the TXNIP-CAGGS-MANF-P2A-HLA-E donor plasmid (SEQ ID NO: 45, Table 9) and an RNP comprising Cas9 and TXNIP_Exon 1_T5 gRNA (SEQ ID NO: 37). After enrichment for HLA-E positive cells and expansion of PD-L-1 and HLA-E cells, the double positive cells were electroporated with the CIITA-CAGGS-CD39 donor plasmid (SEQ ID NO: 29, Table 5) and an RNP comprising Cas9 and CIITA Ex3_T6 gRNA (SEQ ID NO:25). The cells were enriched for CD39 expressing cells, expanded, and selected for PD-L-1, HLA-E, and CD39 triple positive cells, which were characterized as described above.

Confirmed triple positive cells, which also had B2M, TXNIP, and CIITA genes knocked out, were electroporated with RNP comprising Cas9 and a TGF-β2 gRNA to generate a TGF-β2 knock out. The TGF-β2 gRNA1 (5'-GTT-CATGCGCAAGAGGATCG-3' (SEQ ID NOS: 57), the PAM is AGG) was used to knock-out the TGF-β2 protein in an X1 clone and an X4 bulk cell lines by causing a frameshift mutation in the TGF-β2 gene exon 1. Electroporation was carried out in these enriched hESC cells using the Neon Electroporator with the RNP mixture of Cas9 protein (Biomay) and guide RNA (IDT) at a molar ratio of 5:1 (gRNA:Cas9) with absolute values of 125 pmol Cas9 and 625 pmol gRNA per 1 million cells. To form the RNP complex, gRNA and Cas9 were combined in one vessel with R-buffer (Neon Transfection Kit) to a total volume of 25-50 μL and incubated for 15 min at room temperature (RT). This mixture was then combined with the cells to a total volume of ~115 μL using R-buffer. This mixture was then electroporated with 1 pulse for 20 ms at 1500 V. Following electroporation, the cells were pipetted out into a 6 well plate filled with STEMFLEX™ media with REVITACELL™ Supplement (100×) and laminin 511. Cells were cultured in a normoxia incubator (37° C., 8% $CO_2$). The L3V003B ("X4") population targeted with the TGF-β2 gRNA was name L3V004B ("X4+TGF-β2 KO") while the X1 clone population targeted with the TGF-β2 gRNA was named L3V002B ("X1+TGF-β2 KO"). This process was repeated once more for L3V004B population and two times for L3V002B to ensure a high efficiency of TGF-02 KO.

Plated single cells were grown in a normoxia incubator (37° C., 8% $CO_2$) with every other day media changes until colonies are large enough to be re-seeded as single cells. When confluent, samples were split for maintenance and genomic DNA extraction. Correctly targeted clones were confirmed by PCR and Sanger sequencing.

Figure 20A:
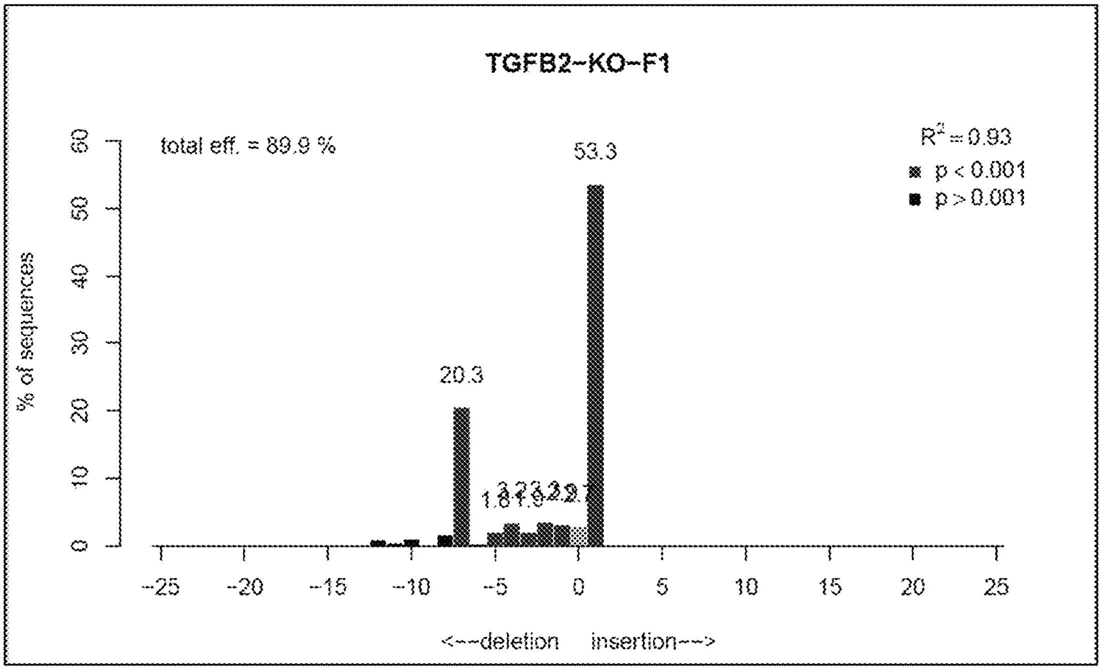
FIG. 20A shows TIDE analysis showing a 90% KO of the TGF-β2 gene in X1 (B2M KO/TNFAIP3-P2A-PD-L-1 KI & TXNIP KO/MANF-P2A-HLA-E KI)+TGF-β2 KO cells ("L3V002B") with prominent edits of +1 and −7 causing a frame shift in the coding region.
Figure 20B:
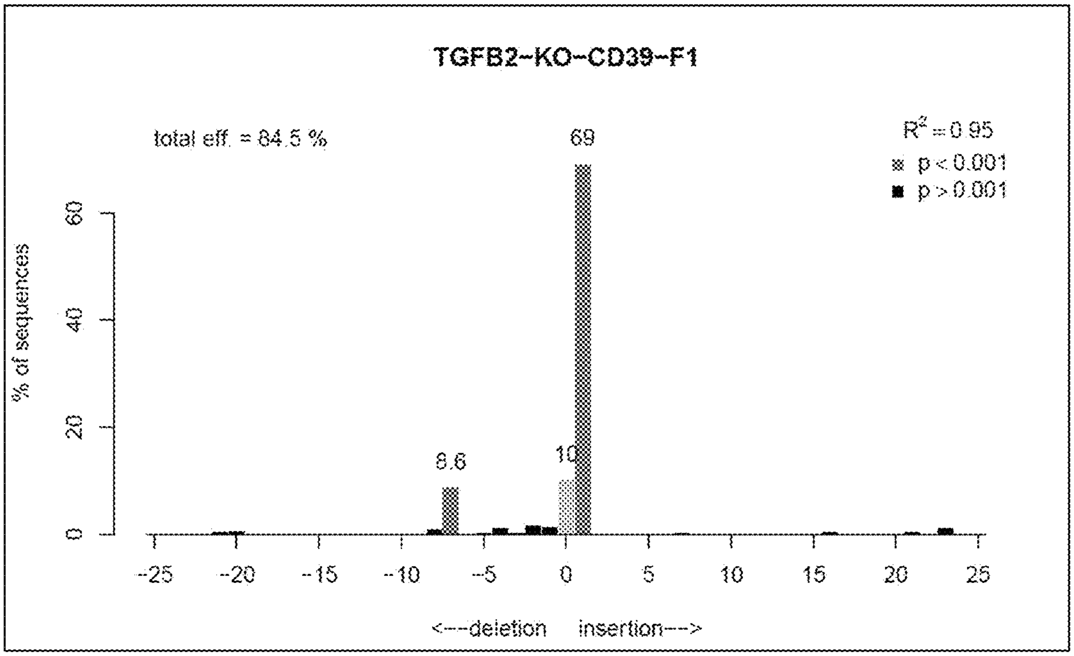
FIG. 20B shows TIDE analysis showing a 90% KO of the TGF-β2 gene in X4 (B2M KO/TNFAIP3-P2A-PD-L-1 KI & TXNIP KO/MANF-P2A-HLA-E KI & CIITA KO/CD39 KI)+TGF-β2 cells ("L3V004B") with prominent edits of +1 and −7 causing a frame shift in the coding region.

PCR for the target TGF-β2 sequence was performed and the resulting amplified DNA was assessed for cutting efficiency by TIDE analysis. PCR for relevant regions was performed using Platinum Taq Supermix (Invitrogen, cat #125320176 and Cat #11495017). The sequence of the PCR primers are presented in Table 16. FIGS. 20A and 20B show the TGF-β2 KO editing efficiencies for two bulk edited lines L3V002 ("TGFB2-KO-F1") and L3V004 ("TGFB2-KO-CD39-F1"). Both populations had over 80% KO which was above the desired threshold with +1 and −7 indels being the most prominent edits.

TABLE 16

TGF-β2 KO Primers

| Name | Type | Sequence (5'-3') | SEQ ID NO: |
|---|---|---|---|
| TGF-β2 F1 | forward | AGGATACGTTTTTCTGTTGGGC | 59 |
| TGF-β2 R1 | reverse | GGAGAACGGGAAAAGAGCGA | 60 |

Example 24: Differentiation of Edited Human Embryonic Stem Cells to Pancreatic Endoderm Cells (PECs)

Maintenance of edited human embryonic stem cells (ES). The edited human pluripotent stem cells comprising a B2M KO with TNFAIP3-P2A-PD-L-1 KI, TXNIP KO with MANF-P2A-HLA-E KI, CIITA KO with CD39 KI, and TGF-β2 KO ("X4+TGF-β2 KO") at various passages (P38-42) were maintained by seeding at about 33,000 cells/$cm^2$ for a 4-day passage or about 50,000 cells/$cm^2$ for a 3-day passage with hESM medium (DMEM/F12+10% KSR+10 ng/mL Activin A and 10 ng/mL Heregulin) and final 10% human AB serum.

Aggregation of edited human embryonic stem cells for PECs differentiation. The edited cells were dissociated into single cells with ACCUTASE® and then centrifuged and resuspended in 2% StemPro (Cat #A1000701, Invitrogen, CA) in DMEM/F12 medium at 1 million cells per ml, and total 350-400 million of cells were seeded in one 850 $cm^2$ roller bottle (Cat #431198, Corning, N.Y.) with rotation speed at 8 RPM±0.5 RPM for 18-20 hours before differentiation. The aggregates from edited human pluripotent stem cells were differentiated into pancreatic lineages using in roller bottles as described in Schulz et al. (2012) PLoS ONE 7(5): e37004 and shown for X1 cells. Aggregates from edited human pluripotent stems cells were differentiated into pancreatic lineages as described in Rezania et al. (2014) Nat. Biotechnol. 32(11): 1121-1133 and US20200208116.

The expression pattern of CHGA, FOXA2, NKX6.1, PDX1 and INS from the "X4+TGF-β2 KO" clones, i.e., TXNIP KO/MANF-P2A-HLA-E KI & B2M KO/TNFAIP3 (A20)-P2A-PD-L-1 KI (X1) CIITA KO/CD39 KI and TGF-β2 KO, at PEC stage and Stage 6 (S6) was determined to confirm differentiation.

Example 25: Immune Evasion Assay with B2M KO and X1 PEC Cells

Figure 21:
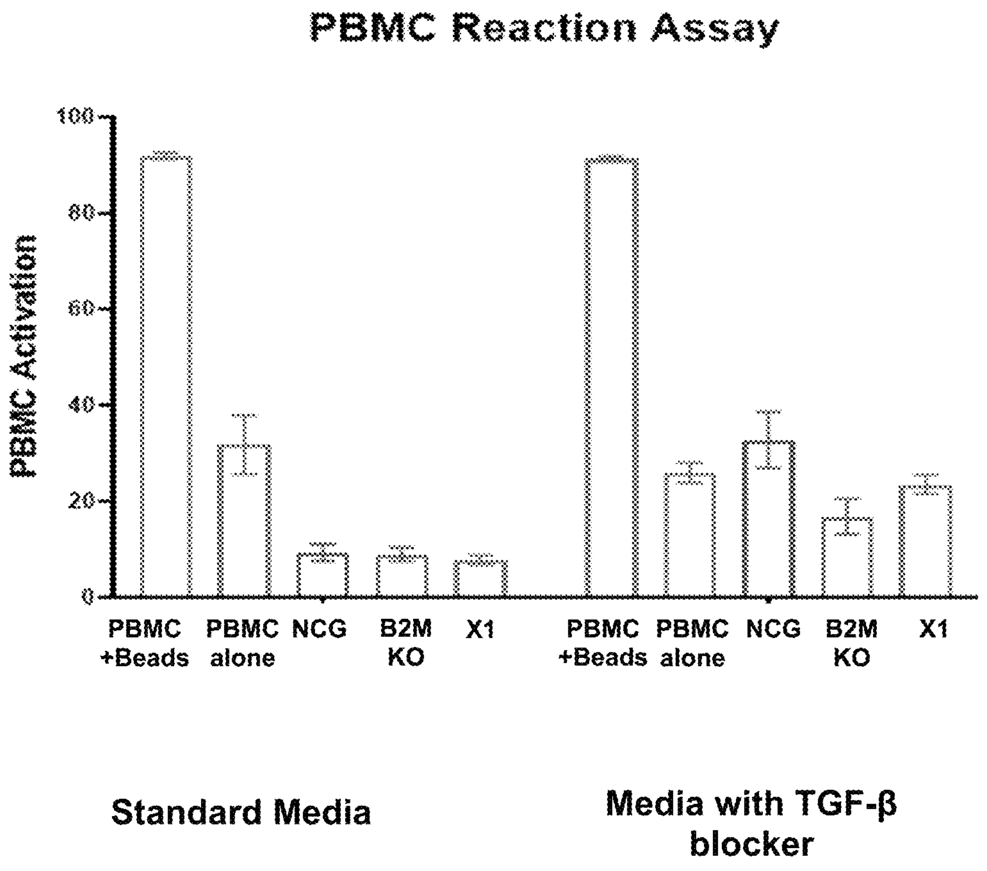
FIG. 21 presents immune evasion assay data using peripheral blood mononuclear cells proliferation assay in the presence of X1 and B2M KO edited cells with or without the presence of TGF-β blockers in the medium.

The capacity of B2M KO and TXNIP KO/MANF-P2A-HLA-E KI & B2M KO/TNFAIP3(A20)-P2A-PD-L-1 KI ("X1") cells to evade the immune response with and in the absence of TGF-β signaling in the media was tested using an immune evasion assay using peripheral blood mononuclear cell (PBMC) proliferation assay. The assay was conducted as per the manufacturer's instruction provided for the CellTrace™ CFSE Cell Proliferation Kit. Briefly fluorescently labelled PBMCs were added to X-VIVO-15 media comprising edited or non-cutting control PEC cells, IL-2 and human serum with or without TGF-β blocking antibodies. Antibodies were used against TGF-β1, TGF-β2 and TGF-β3 to block the proteins from signaling in the media and inhibit TGFβ-mediated immune evasion. PBMC cell proliferation was monitored using the dye-dilution CFSE Cell Proliferation kit over a period of 5-days. The PBMC activation data without or with the TGF-β blocker is provided in FIG. 21. The results show that without TGF-β blocking, all PECs was "immune evasive" as no T-cell activation was induced for any of the samples. With TGF-β blocking, there was more T-cell activation. The NCG (non-cutting control that had normal B2M) drove T-cell activation responses above the PBMCs alone control, but both B2M KO and X1 (which also has a B2M KO) PECs were below the baseline, which suggested that X1 and B2M KO PECs were immune evasive while NCG PECs were mildly immunogenic to allogenic PBMCs.

Example 26: Characterization of Edited and Differentiated PEC Cells for TGF-β2 Secretion The TGF-β1 and TGF-β2 secretion level profiles in edited and differentiated cells were tested in 72 hr condition media using an ELISA based assay using anti-TGF-β1 and anti-TGF-β2 antibodies. The antibodies used are provided in the Table below.

| ELISA target | Vendor | Cat# |
|---|---|---|
| TGF-b1 | ThermoFisher | BMS249 |
| TGF-b2 | R&D | DB250 |
| S100A8/A9-Calprotein 9 | FisherScientific | 501656476 |
| GDF9 | LifeSpan | LS-526-1 |
| PDGF-AA | ThermoFisher | EHPDGFA |
| PDGF-BB | ThermoFisher | EHPDGFB |

Figure 22A:
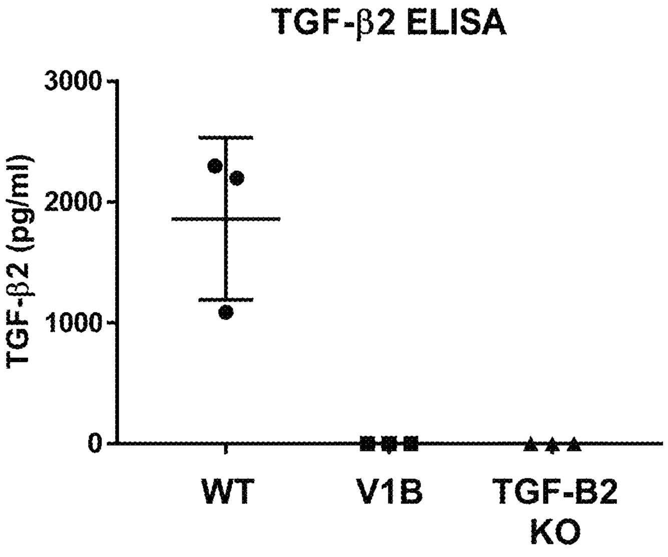
FIG. 22A shows data from an ELISA assay against secreted TGF-β2 in condition media harboring differentiated wild-type, V1B (HLA-E KI, TXNIP KO, PD-L-1 KI, B2M KO) and TGF-β2 KO PEC cells for 72 hrs.
Figure 22B:
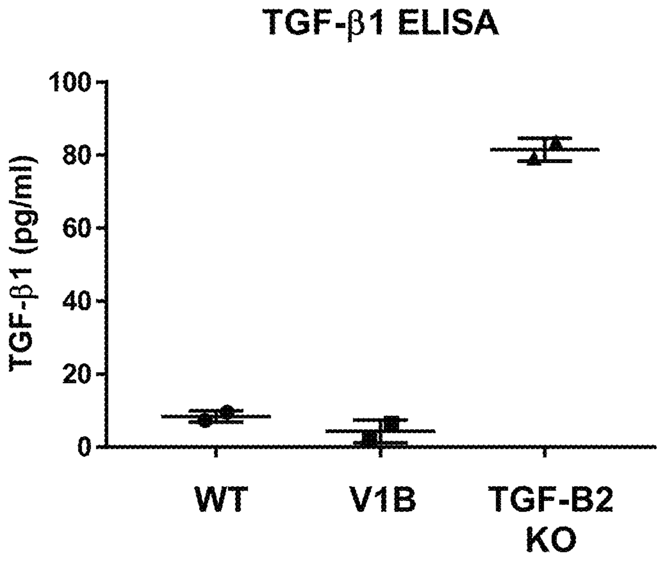
FIG. 22B shows data from an ELISA assay against secreted TGF-β1 in condition media harboring differentiated wild-type, V1B (HLA-E KI, TXNIP KO, PD-L-1 KI, B2M KO) and TGF-β2 KO PEC cells for 72 hrs.

The TGF-β2 and TGF-β1 secretion profiles were determined in a TGF-β2 KO cell and an edited cell having HLA-E KI, TXNIP KO, PD-L-1 KI, and B2M KO ("V1B"). Results show that both V1B and TGF-β2 KO cells exhibited undetectable levels of TGF-β2 in the condition media (see FIG. 22A). However, interestingly conditioned media from TGF-β2 KO cells exhibited higher levels of TGF-β1 secretion (see FIG. 22B).

Example 27: Characterization of Chemoattractants Secreted by TGF-β82 KO Cells

Figure 23A:
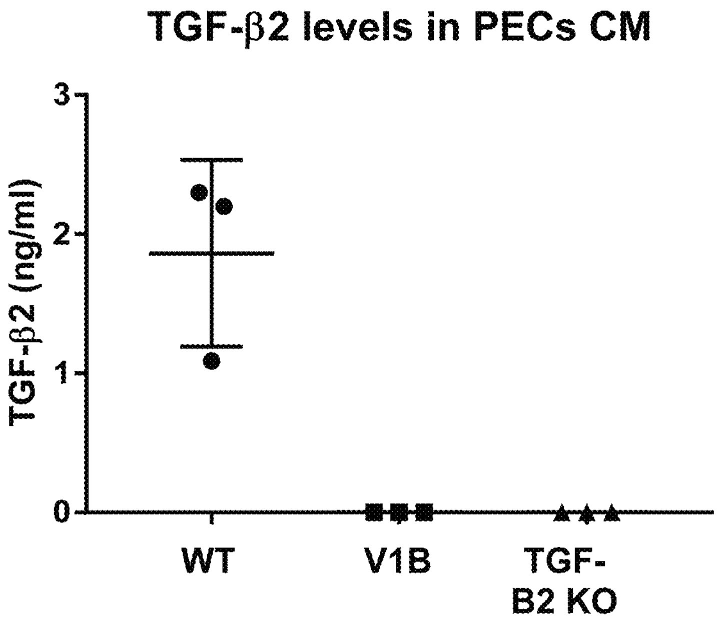
FIG. 23A provides data for TGF-β secreted from V1B and TGF-β2 KO PEC cells.
Figure 23B:
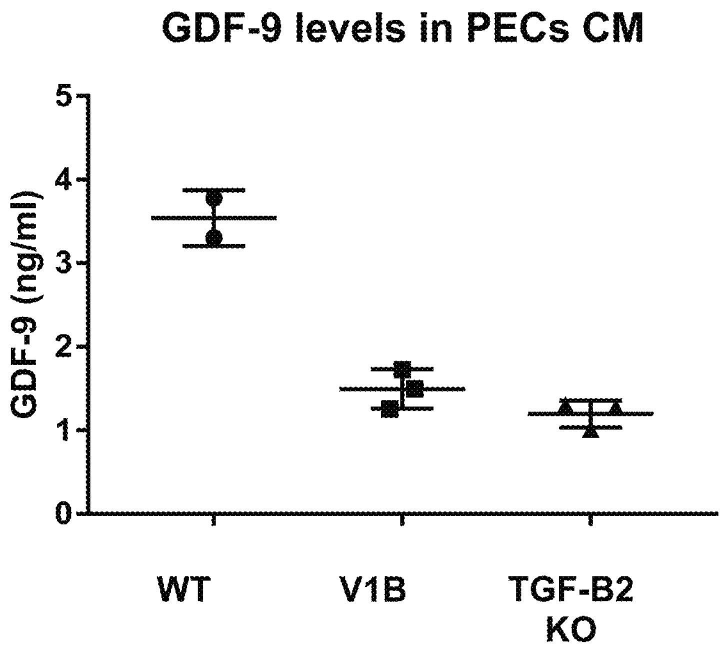
FIG. 23B provides data for GDF-9 secreted from V1B and TGF-β2 KO PEC cells.
Figure 23C:
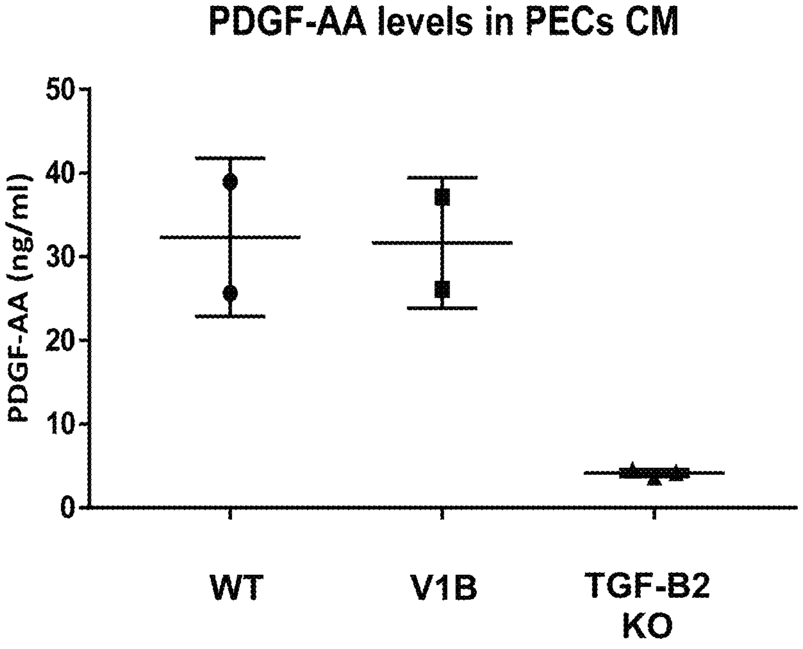
FIG. 23C provides data for PDGF-AA secreted from V1B and TGF-β2 KO PEC cells.

Fibroblast migration and resulting fibrosis is directed by chemoattractants secreted by the engrafted cells. An ELISA based approach was used to check if the TGF-β2 KO cells have reduced secretion of chemoattractants as compared to V1B cells (HLA-E KI, TXNIP KO, PD-L-1 KI, B2M KO) and X1 (antibodies provided in Table in Example 26). The tested chemoattractants included TGF-β2 (see FIG. 23A), growth differentiation factor (GDF-9, see FIG. 23B), and platelet derived growth factor-AA (PDGF-AA, see FIG. 23C).

Results suggest that both V1B and TGF-β2 KO cells showed greatly reduced secretion of TGF-β2 and GDF-9. However, only TGF-β2 KO cells showed reduced secretion of PDGF-AA.

Example 28: In-Vitro Fibroblast Migration Assay

Figure 24A:
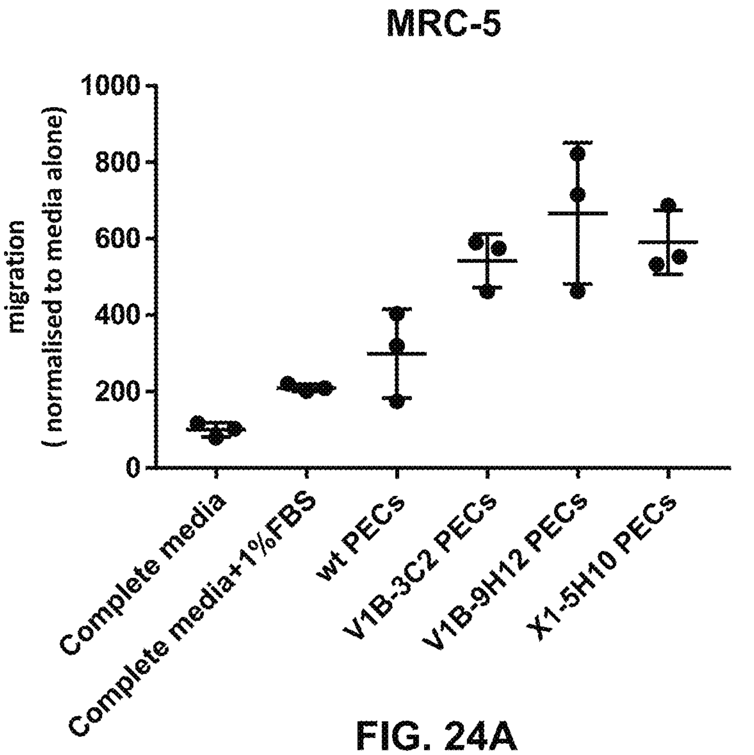
FIGS. 24A-24B show fibroblast migration assays using human lung fibroblasts (MRC-5) cells with condition media from WT, V1B, and X1 PEC cells (FIG. 24A) and WT and TGF-β2 KO PEC cells (FIG. 24B).
Figure 24B:
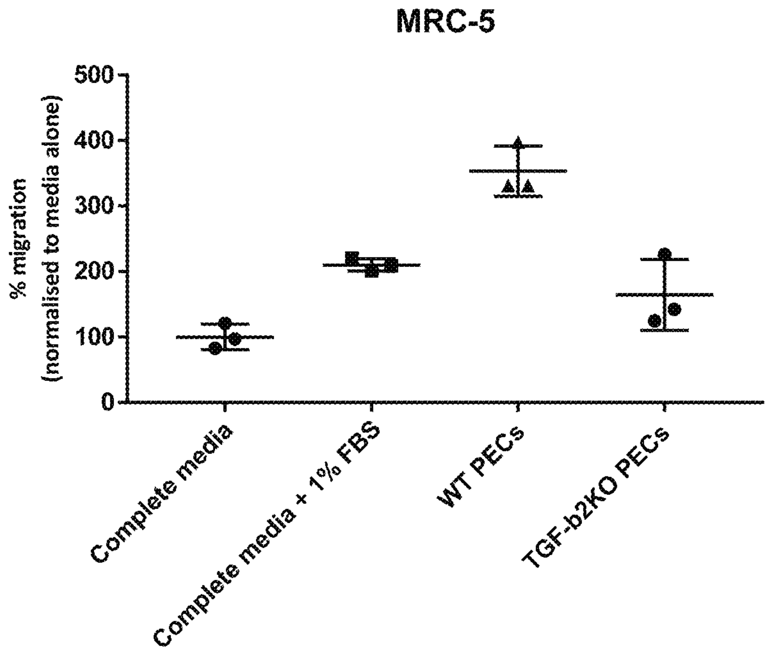
Figure 25A:
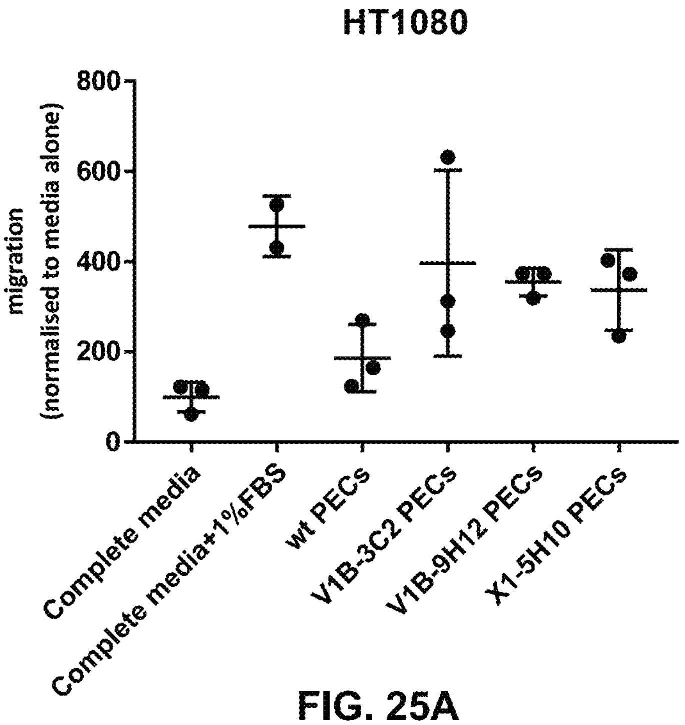
FIGS. 25A-25C show fibroblast migration assays using human fibrosarcoma (HT1080) cells with condition media from WT, V1B, and X1 PEC cells (FIG. 25A), WT and TGF-β2 KO PEC cells (FIG. 25B), and WT, X4 (L3V003B), and X4+TGF-β2 KO (L3V004B) PEC cells (FIG. 25C).
Figure 25B:
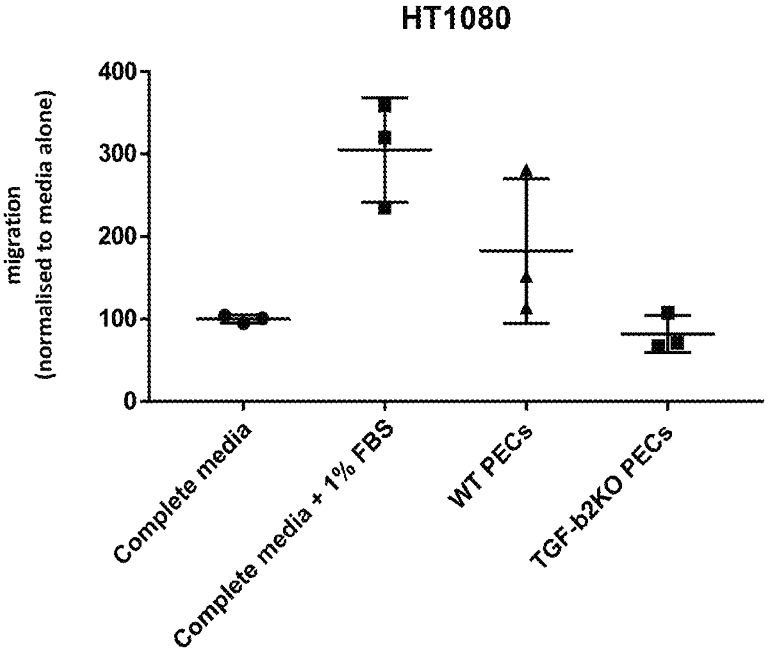
Figure 25C:
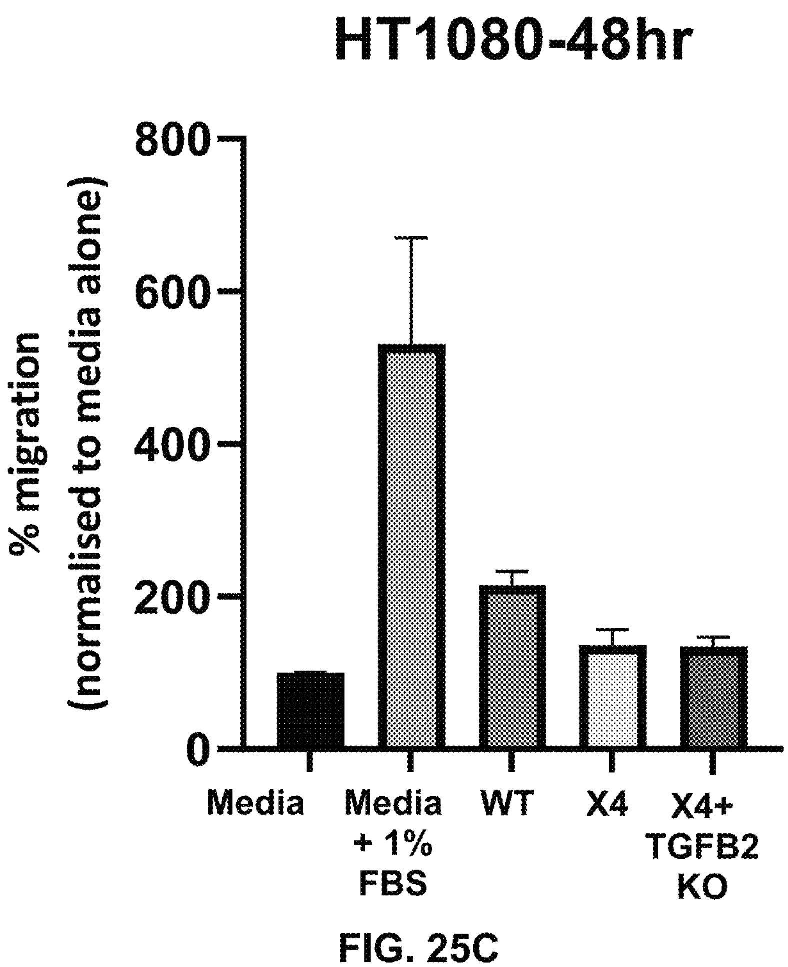

In-vitro fibroblast migration assays were conducted using the QCM chemotaxis cell migration assay kit from Millipore/Sigma (cat #ECM509) as per the manufacturer's instructions. Briefly, cell suspensions comprising MRC-5 (human lung fibroblast) or HT1080 (human fibrosarcoma) cells were placed in the upper chamber of an assay cell that is separated from the outer chamber comprising 72-hr condition media from wild-type, V1B, TGF-β2 KO, X1, X4, and/or X4+TGF-β2 KO PEC cells by a 8 μm pore size polycarbonate membrane. Cells were allowed to migrate through the polycarbonate membrane for 2-24 hrs. Migrated cells clung to the bottom of membrane. Migrated cells were dissociated from the membrane and lyzed. The cells were quantified using the CyQuant GR Dye. FIGS. 24A-24B show fibroblast migration assay results performed using human lung fibroblasts (MRC-5) cells with condition media from WT, V1B, and X1 cells (FIG. 24A) and WT and TGF-β2 KO cells (FIG. 24B). FIGS. 25A-25C show fibroblast migration assay results performed using human fibrosarcoma (HT1080) cells with condition media from WT, V1B, and X1 cells (FIG. 25A), WT and TGF-β2 KO cells (FIG. 25B), and WT, X4, and X4+TGF-β2 KO cells (FIG. 25C). As seen from the data presented, both the TGF-β2 KO edited PEC condition media supported reduced migration of fibroblasts compared to wild-type.

Example 29: In Vivo Efficacy Study of TXNIP KO/MANF-P2A-HLA-E KI & B2M KO/TNFAIP3(A20)-P2A-PD-L-1 KI, CIITA KO/CD39 KI and TGF-β2 KO Cells PEC stage and stage 6 cells differentiated from control cells (NCG) or X4+TGF-β2 KO cell lines generated in Example 24 (i.e., TXNIP KO/MANF-P2A-HLA-E KI, B2M KO/TNFAIP3(A20)-P2A-PD-L-1 KI, CIITA KO/CD39 KI, and TGF-β2 KO) will be tested for in vivo efficacy. Test or control capsules will be transplanted into the left kidney of NSG mice (Jackson Laboratory Stock No: 005557).

GSIS testing will be performed at 12, 16, 20 and 24 weeks, as described in Example 14 for X1 cells. At 26 weeks, after GSIS testing, animals will be euthanized and explanted test articles will be fixed in neutral buffered formalin, processed to slides, and stained with H&E and by immunohistochemistry for insulin and glucagon.

The invention claimed is:

1. A genetically modified stem cell comprising:

(a) a disrupted TXNIP gene and a first insertion of a first polynucleotide encoding mesencephalic astrocyte derived neurotrophic factor (MANF) into the disrupted TXNIP gene;

(b) a disrupted B2M gene and a second insertion of a second polynucleotide encoding tumor necrosis factor alpha induced protein 3 (TNFAIP3) into the disrupted B2M gene;

wherein the cell expresses MANF and TNFAIP3 and has disrupted expression of TXNIP and B2M and the cell has increased immune evasion and/or post-transplantation survival compared to a stem cell without the polynucleotide insertion and gene disruption.

2. The genetically modified stem cell of claim 1, wherein the first insertion further comprises a third polynucleotide encoding HLA class I histocompatibility antigen, alpha chain E (HLA-E).

3. The genetically modified stem cell of claim 2, wherein the nucleotide sequence encoding HLA-E comprises a sequence encoding a HLA-E trimer, the HLA-E trimer comprising a B2M signal peptide fused to an HLA-G presentation peptide fused to a B2M membrane protein fused to HLA-E without its signal peptide.

4. The genetically modified stem cell of claim 2, wherein the first polynucleotide encoding MANF is linked to the third polynucleotide HLA-E by a polynucleotide encoding a P2A peptide such that the first insertion comprises a MANF-P2A-HLA-E construct.

5. The genetically modified stem cell of claim 4, wherein the MAN F-P2A-HLA-E construct comprises a polynucleotide sequence consisting essentially of SEQ ID NO: 55.

6. The genetically modified stem cell of claim 5, wherein the MANF-P2A-HLA-E construct is operably linked to an exogenous promoter.

7. The genetically modified stem cell of claim 1, wherein the second insertion further comprises a fourth polynucleotide encoding programmed death-ligand 1 (PD-L1).

8. The genetically modified stem cell of claim 7, wherein the second nucleotide sequence encoding TNFAIP3 is linked to the fourth nucleotide sequence encoding PD-L1 by a nucleotide sequence encoding a P2A peptide such that the second insertion comprises a TNFAIP3-P2A-PD-L1 construct.

9. The genetically modified stem cell of claim 8, wherein the TNFAIP3-P2A-PD-L1 construct comprises a nucleotide sequence consisting essentially of SEQ ID NO: 54.

10. The genetically modified stem cell of claim 8, wherein the TNFAIP3-P2A-PD-L1 construct is operably linked to an exogenous promoter.

11. The genetically modified stem cell of claim 1, wherein the disrupted expression of B2M and TXNIP comprises reduced or eliminated expression of B2M and/or TXNIP.

12. The genetically modified stem cell of claim 1, wherein the stem cell is an embryonic stem cell, an adult stem cell, an induced pluripotent stem cell, or a hematopoietic stem cell.

13. A plurality of genetically modified stem cells of claim 1.

14. A population of lineage-restricted progenitor cells or fully differentiated somatic cells derived from the plurality of genetically modified cells of claim 13.

15. The population of lineage-restricted progenitor cells or fully differentiated somatic cells of claim 14, wherein the population comprises definitive endoderm cells, primitive gut tube cells, posterior foregut cells, pancreatic endoderm cells, pancreatic endocrine precursor cells, immature beta cells, and/or pancreatic beta cells.

16. A composition comprising the population of lineage-restricted progenitor cells or fully differentiated somatic cells of claim 14 and at least one pharmaceutically acceptable excipient.

* * * * *